United States Patent
Martin et al.

(10) Patent No.: US 11,319,318 B2
(45) Date of Patent: May 3, 2022

(54) PYRIDINONES AND ISOQUINOLINONES AS INHIBITORS OF THE BROMODOMAIN BRD9

(71) Applicant: Boehringer Ingelheim International GmbH, Ingelheim am Rhein (DE)

(72) Inventors: Laetitia Martin, Vienna (AT); Steffen Steurer, Vienna (AT); Xiao-Ling Cockcroft, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/554,440

(22) PCT Filed: Mar. 4, 2016

(86) PCT No.: PCT/EP2016/054713
§ 371 (c)(1),
(2) Date: Aug. 30, 2017

(87) PCT Pub. No.: WO2016/139361
PCT Pub. Date: Sep. 9, 2016

(65) Prior Publication Data
US 2018/0044335 A1 Feb. 15, 2018

(30) Foreign Application Priority Data

Mar. 5, 2015 (EP) ..................................... 15157879
Dec. 10, 2015 (EP) ..................................... 15199403

(51) Int. Cl.
| | | |
|---|---|---|
| C07D 471/04 | (2006.01) |
| C07D 217/24 | (2006.01) |
| C07D 401/10 | (2006.01) |
| C07D 519/00 | (2006.01) |
| C07D 237/28 | (2006.01) |
| C07D 471/08 | (2006.01) |
| C07D 401/12 | (2006.01) |
| C07D 487/08 | (2006.01) |
| C07D 401/04 | (2006.01) |
| C07D 213/64 | (2006.01) |
| C07D 237/32 | (2006.01) |
| C07D 401/06 | (2006.01) |

(52) U.S. Cl.
CPC ......... *C07D 471/04* (2013.01); *C07D 213/64* (2013.01); *C07D 217/24* (2013.01); *C07D 237/28* (2013.01); *C07D 237/32* (2013.01); *C07D 401/04* (2013.01); *C07D 401/06* (2013.01); *C07D 401/10* (2013.01); *C07D 401/12* (2013.01); *C07D 471/08* (2013.01); *C07D 487/08* (2013.01); *C07D 519/00* (2013.01)

(58) Field of Classification Search
CPC .................................................... C07D 471/04

USPC ........................................................ 546/276.4
See application file for complete search history.

(56) References Cited

U.S. PATENT DOCUMENTS

| | | | | |
|---|---|---|---|---|
| 5,466,697 A | * | 11/1995 | Wilhelm .............. | C07D 471/04 514/300 |
| 5,716,954 A | * | 2/1998 | Wilhelm ................ | C07C 69/76 514/234.2 |
| 9,034,900 B2 | * | 5/2015 | Bennett ................ | C07D 498/04 514/309 |

FOREIGN PATENT DOCUMENTS

| | | | | |
|---|---|---|---|---|
| WO | WO 2005049581 | * | 6/2005 | .......... C07D 237/22 |
| WO | WO 2008033854 | * | 8/2008 | .......... C07D 237/22 |
| WO | WO 2009039397 | * | 3/2009 | .......... C07D 237/22 |
| WO | 2010069504 A1 | | 6/2010 | |
| WO | WO 2010069504 | * | 6/2010 | .......... C07D 237/22 |
| WO | WO 2013142390 | * | 9/2013 | .......... C07D 21/22 |
| WO | WO 2014201173 | * | 12/2014 | .......... C07D 21/22 |
| WO | 2015004533 A2 | | 1/2015 | |
| WO | 2015018203 A1 | | 2/2015 | |
| WO | 2015058160 A1 | | 4/2015 | |
| WO | WO 2015058160 | * | 4/2015 | .......... C07D 237/22 |
| WO | 2015081203 A1 | | 6/2015 | |
| WO | 2015081246 A1 | | 6/2015 | |
| WO | WO 2016077378 | * | 5/2016 | .......... C07D 471/04 |
| WO | 2016077380 A1 | | 5/2019 | |

OTHER PUBLICATIONS

Venkatesh et al., J. Pharm. Sci. 89, 145-54 (2000).*
Dorwald F. A. Side Reactions in Organic Synthesis, 2005, Wiley: VCH, Weinheim p. IX of Preface p. 1-15.*
Venkatesh, J. Pharm. Sci. 89, 145-54 (2000) (p. 146, left column).*

(Continued)

*Primary Examiner* — Nizal S Chandrakumar
(74) *Attorney, Agent, or Firm* — Andrea V. Lockenour

(57) ABSTRACT

The present invention encompasses compounds of general formula (I) wherein the groups $R^1$ to $R^9$, $X_1$ and $X_2$ have the meanings given in the claims and in the specification. The compounds of the invention are suitable for the treatment of diseases characterized by excessive or abnormal cell proliferation, e.g. cancer, pharmaceutical preparations containing such compounds and their uses as a medicament.

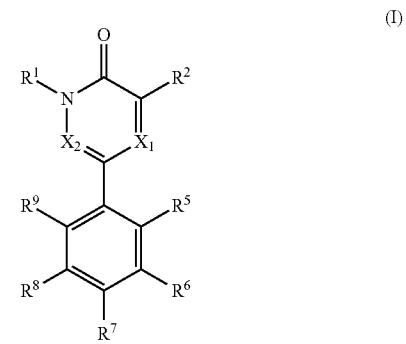

6 Claims, No Drawings

(56) References Cited

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802, 784.*
International Search report, for PCT/EP2016054713, Form PCT/ISA/210, dated Jun. 15, 2016.
Filippakapoulos, Panagis et al. "Histone Recognition and Large-Scale Structural Analysis of the Human Bromodomain Family" (2012) Cell, 149, 214-231.
Ho, Lena et al. "Chromatin remodelling during development" (2010) Nature, 463(7280): 474-484.
Kadoch, Cigall et al. "Proteomic and Bioinformatic Analysis of mSWI/SNF (BAF) Complexes Reveals Extensive Roles in Human Malignancy" (2013) Nat Genet. 45(6) 592-601.
Kang, Ji Un et al. "Gain at chromosomal region 5p15.33, containing TERT, is the most frequent genetic event in early stages of non-small cell lung cancer" (2008) Cancer Genetics and Cytogenetics, 182, 1-11.
Middeljans, Evelien et al. "SS18 Together with Animal-Specific Factors Defines Human BAF-Type SWI-SNF Complexes" (2012) PLOS One, vol. 7, Issue 3, e33834, 10 pgs.
Scotto, Luigi et al. "Integrative genomics analysis of chromosome 5p gain in cervical cancer reveals target over-expressed genes, including Drosha" (2008) Molecular Cancer, 7:58, 10 pgs.
Venkatesh, Srini et al. "Role of the Development Scientist in Compound Lead Selection and Optimization" (2000) Journal of Pharmaceutical Sciences, vol. 89, No. 2, 145-154.
Wilson, Boris G. et al. "SWI/SNF nucleosome remodellers and cancer" (2011) Nature Reviews | Cancer, vol. 11, 481-492.

* cited by examiner

PYRIDINONES AND ISOQUINOLINONES AS INHIBITORS OF THE BROMODOMAIN BRD9

This invention relates to compounds of the general formula (I)

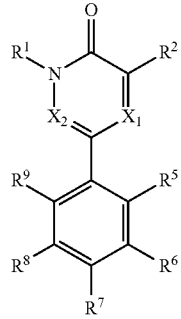

wherein the groups $R^1$ to $R^9$, $X_1$ and $X_2$ have the meanings given in the claims and in the specification. The compounds of the invention are suitable for the treatment of diseases characterized by excessive or abnormal cell proliferation, pharmaceutical preparations containing such compounds and their uses as a medicament. The compounds of the invention are BRD9 inhibitors.

BACKGROUND OF THE INVENTION

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell (Filippakopoulos et al., 2012, Cell 149, 214-231).

BRD9 and BRD7 are two related proteins that have been shown to be part of the chromatin-remodelling BAF (also known as SWI/SNF) complex (Kadoch et al., 2013, Nat. Genet. 45, 592-601; Middeljans et al., 2012, PLoS. One. 7, e33834). Both proteins harbor a bromodomain in the amino-terminal half of the sequence, as well as a domain of unknown function (DUF3512) carboxy-terminally to it. Recurrent amplifications of the BRD9 locus have been observed in ovarian and breast cancer (Kang et al., 2008, Cancer Genet. Cytogenet. 182, 1-11; Scotto et al., 2008, Mol. Cancer 7, 58). However, in most cases these amplifications are broad, not of a high copy number and contain numerous genes, such that direct conclusions to a role of BRD9 in cancer are not possible. The function of the BAF complex is in remodeling of chromatin (Ho and Crabtree, 2010, Nature 463, 474-484). Numerous subunits of the BAF complex are recurrently mutated in cancer (Wilson and Roberts, 2011, Nat. Rev. Cancer 11, 481-492). The functions of BRD9 and BRD7 in this complex are not known.

Thus, there is the need to provide BRD9 inhibitors useful for the prevention and/or treatment of diseases characterized by excessive or abnormal cell proliferation, such as cancer.

DETAILED DESCRIPTION OF THE INVENTION

The present invention relates to compounds of formula (I)

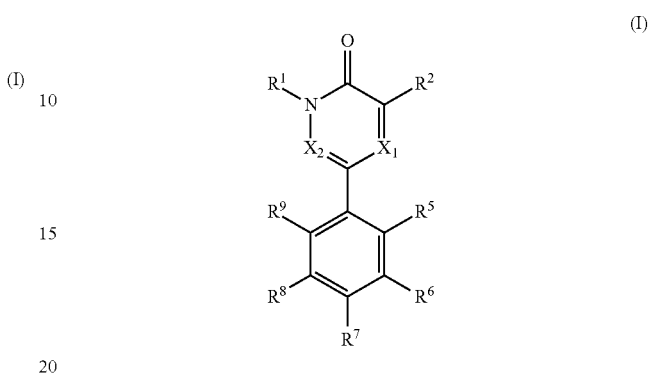

wherein,
$R^1$ is —$C_{1-3}$alkyl or -cyclopropyl;
$R^2$ is selected from halogen, —$C_{1-3}$alkyl, —$C_{1-3}$haloalkyl, —$NH_2$, —$NHC_{1-3}$alkyl and —OH,
$X_1$ is N or $CR^3$
$X_2$ is N or $CR^4$
wherein $X_1$ and $X_2$ cannot be both N in the same molecule
$R^3$ is H or —$C_{1-3}$alkyl;
$R^4$ is H or —$C_{1-3}$alkyl;
  wherein $R^3$ and $R^4$ cannot be both —$C_{1-3}$alkyl in the same molecule;
alternatively, $R^2$ and $R^3$ taken together form a benzene ring or a 5-6 membered heteroarene ring, each of which rings can be optionally and independently substituted with one or more groups selected from halogen,
—OH, —$NH_2$, —NH—$C_{1-3}$alkyl and —$C_{1-3}$alkyl, wherein the —$C_{1-3}$alkyl group can be optionally substituted with 5-6 membered heteroaryl or phenyl,
$R^5$ and $R^9$ can be the same or different and are independently selected from —H, —O—$C_{1-3}$alkyl and —$C_{1-3}$alkyl;
$R^6$ and $R^8$ can be the same or different and are independently selected from —H, —OH, halogen, —$NH_2$, —$C_{1-3}$alkyl, —O—$C_{1-3}$alkyl, —O—$C_{1-3}$haloalkyl, —$C_{1-3}$alkyl-O—$C_{1-3}$alkyl, 4-7 membered heterocycloalkyl, —$C_{1-3}$alkyl-$SO_2$—$C_{1-3}$alkyl, —$C_{1-3}$alkyl-$NH_2$, —$C_{1-3}$alkyl-N(—$C_{1-3}$alkyl)$_2$, —N($C_{1-3}$alkyl)$_2$, —NH—$R^{13}$;
$R^{13}$ is selected from —$SO_2$—$C_{1-3}$alkyl and —$C_{1-3}$alkyl, wherein the —$C_{1-3}$alkyl groups can be optionally substituted with 5 to 6 membered heteroaryl;
alternatively, $R^5$ and $R^6$ taken together form a benzene ring;
alternatively, $R^7$ and $R^6$ or $R^7$ and $R^8$ taken together form a 5-7 membered heterocycloalkyl optionally substituted with —$C_{1-3}$alkyl;
$R^7$ is selected from —H, —$NH_2$, —Y—$R^{12}$, —$C_{1-3}$alkyl and 4-7 membered heterocycloalkyl;
Y is selected from —$CR^{10}R^{11}$—, —$SO_2$— and —CO—;
$R^{10}$ and $R^{11}$ can be the same or different and are independently selected from —H or —$C_{1-3}$alkyl;
or $R^{10}$ and $R^{11}$ taken together form a —$C_{3-4}$cycloalkyl,
$R^{12}$ is selected from —$NH_2$, —OH, —$C_{1-3}$alkyl, —N($R^{15}$, $R^{16}$), —O—$R^{17}$, aryl, 5-6 membered heteroaryl, wherein the aryl or heteroaryl is optionally and independently substituted with one or more halogen, 4-7 membered heterocycloalkyl, which heterocycloalkyl is optionally and independently substituted with one or more groups selected from halogen, —OH, —NH$_2$, —C$_{1-3}$alkyl, —NHC$_{1-3}$alkyl, —N(C$_{1-3}$alkyl)$_2$, —O—C$_{1-3}$alkyl and —CH$_2$—R$^{14}$;

R$^{14}$ is selected from 5-10 membered mono- or bicyclic aryl or heteroaryl, which is optionally substituted with —NH$_2$, —OH, halogen, —CN, C$_{1-3}$alkyl, —O—C$_{1-3}$alkyl;

R$^{15}$ is —H or —C$_{1-3}$alkyl

R$^{16}$ is selected from —C$_{1-3}$alkyl, —C$_{2-3}$alkyl-N(C$_{1-3}$alkyl)$_2$, —C$_{2-3}$alkyl-NHC$_{1-3}$alkyl and 4-7 membered heterocycloalkyl, which heterocycloalkyl is optionally substituted with —C$_{1-3}$alkyl;

R$^{17}$ is —C$_{1-3}$alkyl or 4-7 membered heterocycloalkyl, which heterocycloalkyl is optionally substituted with C$_{1-3}$alkyl;

wherein when R$^7$ is Y—R$^{12}$, R$^6$ and R$^8$ can be the same or different and are independently selected from —H, —OH, halogen, —NH$_2$, —CN, —C$_{1-3}$alkyl, —C$_{1-3}$haloalkyl, —O—C$_{1-3}$alkyl, —O—C$_{1-3}$haloalkyl and —C$_{1-3}$alkyl-O—C$_{1-3}$alkyl;

wherein at least one of the substituents R$^5$ to R$^9$ is not hydrogen;

wherein the compounds of formula (I) may be optionally be present in the form of salts.

The present invention relates to a compound according to formula I

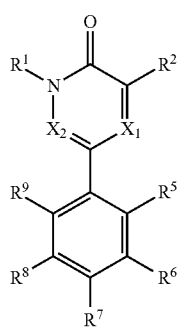

(I)

R$^1$ is —C$_{1-3}$alkyl or -cyclopropyl;

R$^2$ is selected from halogen, —C$_{1-3}$alkyl, —C$_{1-3}$haloalkyl, —NH$_2$, —NHC$_{1-3}$alkyl and —OH, X$_1$ is N or CR$^3$ X$_2$ is N or CR$^4$ wherein X$_1$ and X$_2$ cannot be both N in the same molecule R$^3$ is H or —C$_{1-3}$alkyl;

R$^4$ is H or —C$_{1-3}$alkyl;
  wherein R$^3$ and R$^4$ cannot be both —C$_{1-3}$alkyl in the same molecule;

alternatively, R$^2$ and R$^3$ taken together form a benzene ring or a 5-6 membered heteroarene ring, each of which rings can be optionally and independently substituted with one or more groups selected from halogen, —OH, —NH$_2$, —NH—C$_{1-3}$alkyl and —C$_{1-3}$alkyl, wherein the —C$_{1-3}$alkyl group can be optionally substituted with 5-6 membered heteroaryl or phenyl, R$^6$ is —OCH$_3$, R$^8$ is —OCH$_3$, R$^5$ is —H and R$^9$ is —H;

or wherein R$^6$ is —OCH$_3$, R$^9$ is —OCH$_3$, R$^5$ is —H and R$^8$ is —H;

or wherein R$^5$ is —OCH$_3$, R$^8$ is —OCH$_3$, R$^6$ is —H and R$^9$ is —H;

R$^7$ is selected from —H, —NH$_2$, —Y—R$^{12}$, —C$_{1-3}$alkyl and 4-7 membered heterocycloalkyl;

Y is selected from —CR$^{10}$R$^{11}$—, —SO$_2$— and —CO—;

R$^{10}$ and R$^{11}$ can be the same or different and are independently selected from —H or —C$_{1-3}$alkyl; or R$^{10}$ and R$^{11}$ taken together form a —C$_{3-4}$cycloalkyl, R$^{12}$ is selected from —NH$_2$, —OH, —C$_{1-3}$alkyl, —N(R$^{15}$,R$^{16}$), —O—R$^{17}$, aryl, 5-6 membered heteroaryl, wherein the aryl or heteroaryl is optionally and independently substituted with one or more halogen, 4-7 membered heterocycloalkyl, which heterocycloalkyl is optionally and independently substituted with one or more groups selected from halogen, —OH, —NH$_2$, —C$_{1-3}$alkyl, —NHC$_{1-3}$alkyl, —N(C$_{1-3}$alkyl)$_2$, —O—C$_{1-3}$alkyl and —CH$_2$—R$^{14}$;

R$^{14}$ is selected from 5-10 membered mono- or bicyclic aryl or heteroaryl, which is optionally substituted with —NH$_2$, —OH, halogen, —CN, C$_{1-3}$alkyl, —O—C$_{1-3}$alkyl;

R$^{15}$ is —H or —C$_{1-3}$alkyl

R$^{16}$ is selected from —C$_{1-3}$alkyl, —C$_{2-3}$alkyl-N(C$_{1-3}$alkyl)$_2$, —C$_{2-3}$alkyl-NHC$_{1-3}$alkyl and 4-7 membered heterocycloalkyl, which heterocycloalkyl is optionally substituted with —C$_{1-3}$alkyl;

R$^{17}$ is —C$_{1-3}$alkyl or 4-7 membered heterocycloalkyl, which heterocycloalkyl is optionally substituted with C$_{1-3}$alkyl wherein at least one of the substituents R$^5$ to R$^9$ is not hydrogen;

or a compound of Formula I, wherein

R$^1$ is —C$_{1-3}$alkyl or -cyclopropyl;

R$^2$ is selected from halogen, —C$_{1-3}$alkyl, —C$_{1-3}$haloalkyl, —NH$_2$, —NHC$_{1-3}$alkyl and —OH, X$_1$ is N or CR$^3$ X$_2$ is CR$^4$ R$^3$ is H or —C$_{1-3}$alkyl;

R$^4$ is H or —C$_{1-3}$alkyl;
  wherein R$^3$ and R$^4$ cannot be both —C$_{1-3}$alkyl in the same molecule;

alternatively, R$^2$ and R$^3$ taken together form a benzene ring or a 5-6 membered heteroarene ring, each of which rings can be optionally and independently substituted with one or more groups selected from halogen, —NH$_2$, —NH—C$_{1-3}$alkyl and —C$_{1-3}$alkyl, wherein the —C$_{1-3}$alkyl group can be optionally substituted with 5-6 membered heteroaryl or phenyl, R$^5$ and R$^9$ can be the same or different and are independently selected from —H, —O—C$_{1-3}$alkyl and —C$_{1-3}$alkyl;

R$^6$ and R$^8$ can be the same or different and are independently selected from —H, —OH, halogen, —NH$_2$, —C$_{1-3}$alkyl, —O—C$_{1-3}$alkyl, —O—C$_{1-3}$haloalkyl, —C$_{1-3}$alkyl-O—C$_{1-3}$alkyl, 4-7 membered heterocycloalkyl, —C$_{1-3}$alkyl-SO$_2$—C$_{1-3}$alkyl, —C$_{1-3}$alkyl-NH$_2$, —C$_{1-3}$alkyl-N(—C$_{1-3}$alkyl)$_2$, —N(C$_{1-3}$alkyl)$_2$, —NH—R$^{13}$;

R$^{13}$ is selected from —SO$_2$—C$_{1-3}$alkyl and —C$_{1-3}$alkyl, wherein the —C$_{1-3}$alkyl groups can be optionally substituted with 5 to 6 membered heteroaryl;

alternatively, R$^5$ and R$^6$ taken together form a benzene ring;

alternatively, R$^7$ and R$^6$ or R$^7$ and R$^8$ taken together form a 5-7 membered heterocycloalkyl optionally substituted with —C$_{1-3}$alkyl, R$^7$ is selected from —NH$_2$, —Y—R$^{12}$, —SO$_2$—C$_{1-3}$alkyl, —CO—C$_{1-3}$alkyl and 4-7 membered heterocycloalkyl;

Y is selected from —CR$^{10}$R$^{11}$—, —SO$_2$— and —CO—;
  R$^{10}$ and R$^{11}$ can be the same or different and are independently selected from —H or —C$_{1-3}$alkyl; or R$^{10}$ and R$^{11}$ taken together form a —C$_{3-4}$cycloalkyl,
R$^{12}$ is selected from —NH$_2$, —OH, —N(R$^{15}$,R$^{16}$), —O—R$^{17}$, aryl, 5-6 membered heteroaryl, wherein the aryl or heteroaryl is optionally and independently substituted with one or more halogen, 4-7 membered heterocycloalkyl, which heterocycloalkyl is optionally and independently substituted with one or more groups selected from halogen, —OH, —NH$_2$, —C$_{1-3}$alkyl, —NHC$_{1-3}$alkyl, —N(C$_{1-3}$alkyl)$_2$, —O—C$_{1-3}$alkyl and —CH$_2$—R$^{14}$;
R$^{14}$ is selected from 5-10 membered mono- or bicyclic aryl or heteroaryl, which is optionally substituted with —NH$_2$, —OH, halogen, —CN, C$_{1-3}$alkyl, —O—C$_{1-3}$alkyl;
R$^{15}$ is —H or —C$_{1-3}$alkyl
R$^{16}$ is selected from —C$_{1-3}$alkyl, —C$_{2-3}$alkyl-N(C$_{1-3}$alkyl)$_2$, —C$_{2-3}$alkyl-NHC$_{1-3}$alkyl and 4-7 membered heterocycloalkyl, which heterocycloalkyl is optionally substituted with —C$_{1-3}$alkyl;
R$^{17}$ is 4-7 membered heterocycloalkyl, which heterocycloalkyl is optionally substituted with C$_{1-3}$alkyl wherein at least one of the substituents R$^5$ to R$^9$ is not hydrogen;
wherein, the compounds of formula (I) may be optionally be present in the form of salts.

In a preferred embodiment, the invention relates to a compound or its salts according to formula I, wherein

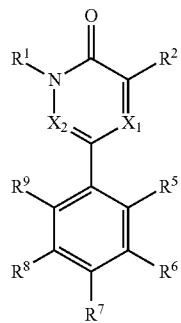

(I)

R$^1$ is —C$_{1-3}$alkyl or -cyclopropyl;
R$^2$ is selected from halogen, —C$_{1-3}$alkyl, —C$_{1-3}$haloalkyl, —NH$_2$, —NHC$_{1-3}$alkyl and —OH,
X$_1$ is N or CR$^3$
X$_2$ is N or CR$^4$
  wherein X$_1$ and X$_2$ cannot be both N in the same molecule
R$^3$ is H or —C$_{1-3}$alkyl;
R$^4$ is H or —C$_{1-3}$alkyl;
  wherein R$^3$ and R$^4$ cannot be both —C$_{1-3}$alkyl in the same molecule;
alternatively, R$^2$ and R$^3$ taken together form a benzene ring or a 5-6 membered heteroarene ring, each of which rings can be optionally and independently substituted with one or more groups selected from halogen, —OH, —NH$_2$, —NH—C$_{1-3}$alkyl and —C$_{1-3}$alkyl, wherein the —C$_{1-3}$alkyl group can be optionally substituted with 5-6 membered heteroaryl or phenyl, R$^6$ is —OCH$_3$, R$^8$ is —OCH$_3$, R$^5$ is —H and R$^9$ is —H;
or wherein R$^6$ is —OCH$_3$, R$^9$ is —OCH$_3$, R$^5$ is —H and R$^8$ is —H;
or wherein R$^5$ is —OCH$_3$, R$^8$ is —OCH$_3$, R$^6$ is —H and R$^9$ is —H;
R$^7$ is selected from —H, —NH$_2$, —Y—R$^{12}$, —C$_{1-3}$alkyl and 4-7 membered heterocycloalkyl;
  Y is selected from —CR$^{10}$R$^{11}$—, —SO$_2$— and —CO—;
    R$^{10}$ and R$^{11}$ can be the same or different and are independently selected from —H or —C$_{1-3}$alkyl; or R$^{10}$ and R$^{11}$ taken together form a —C$_{3-4}$cycloalkyl,
  R$^{12}$ is selected from —NH$_2$, —OH, —C$_{1-3}$alkyl, —N(R$^{15}$,R$^{16}$), —O—R$^{17}$, aryl, 5-6 membered heteroaryl, wherein the aryl or heteroaryl is optionally and independently substituted with one or more halogen, 4-7 membered heterocycloalkyl, which heterocycloalkyl is optionally and independently substituted with one or more groups selected from halogen, —OH, —NH$_2$, —C$_{1-3}$alkyl, —NHC$_{1-3}$alkyl, —N(C$_{1-3}$alkyl)$_2$, —O—C$_{1-3}$alkyl and —CH$_2$—R$^{14}$;
  R$^{14}$ is selected from 5-10 membered mono- or bicyclic aryl or heteroaryl, which is optionally substituted with —NH$_2$, —OH, halogen, —CN, C$_{1-3}$alkyl, —O—C$_{1-3}$alkyl;
  R$^{15}$ is —H or —C$_{1-3}$alkyl
  R$^{16}$ is selected from —C$_{1-3}$alkyl, —C$_{2-3}$alkyl-N(C$_{1-3}$alkyl)$_2$, —C$_{2-3}$alkyl-NHC$_{1-3}$alkyl and 4-7 membered heterocycloalkyl, which heterocycloalkyl is optionally substituted with —C$_{1-3}$alkyl;
  R$^{17}$ is —C$_{1-3}$alkyl or 4-7 membered heterocycloalkyl, which heterocycloalkyl is optionally substituted with C$_{1-3}$alkyl wherein at least one of the substituents R$^5$ to R$^9$ is not hydrogen.

In a preferred embodiment, a compound or its salts according to formula I

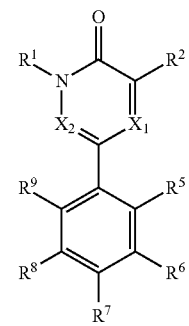

(I)

wherein
R$^1$ is —C$_{1-3}$alkyl or -cyclopropyl;
R$^2$ is selected from halogen, —C$_{1-3}$alkyl, —C$_{1-3}$haloalkyl, —NH$_2$, —NHC$_{1-3}$alkyl and —OH,
X$_1$ is N or CR$^3$
X$_2$ is CR$^4$
R$^3$ is H or —C$_{1-3}$alkyl;
R$^4$ is H or —C$_{1-3}$alkyl;
  wherein R$^3$ and R$^4$ cannot be both —C$_{1-3}$alkyl in the same molecule;

alternatively, $R^2$ and $R^3$ taken together form a benzene ring or a 5-6 membered heteroarene ring, each of which rings can be optionally and independently substituted with one or more groups selected from halogen, —$NH_2$, —NH—$C_{1-3}$alkyl and —$C_{1-3}$alkyl, wherein the —$C_{1-3}$alkyl group can be optionally substituted with 5-6 membered heteroaryl or phenyl, $R^5$ and $R^9$ can be the same or different and are independently selected from —H, —O—$C_{1-3}$alkyl and —$C_{1-3}$alkyl;

$R^6$ and $R^8$ can be the same or different and are independently selected from —H, —OH, halogen, —$NH_2$, —$C_{1-3}$alkyl, —O—$C_{1-3}$alkyl, —O—$C_{1-3}$haloalkyl, —$C_{1-3}$alkyl-O—$C_{1-3}$alkyl, 4-7 membered heterocycloalkyl, —$C_{1-3}$alkyl-$SO_2$—$C_{1-3}$alkyl, —$C_{1-3}$alkyl-$NH_2$, —$C_{1-3}$alkyl-N(—$C_{1-3}$alkyl)$_2$, —N($C_{1-3}$alkyl)$_2$, —NH—$R^{13}$;

$R^{13}$ is selected from —$SO_2$—$C_{1-3}$alkyl and —$C_{1-3}$alkyl, wherein the —$C_{1-3}$alkyl groups can be optionally substituted with 5 to 6 membered heteroaryl;

alternatively, $R^5$ and $R^6$ taken together form a benzene ring;

alternatively, $R^7$ and $R^6$ or $R^7$ and $R^8$ taken together form a 5-7 membered heterocycloalkyl optionally substituted with —$C_{1-3}$alkyl, $R^7$ is selected from —$NH_2$, —Y—$R^{12}$, —$SO_2$—$C_{1-3}$alkyl, —CO—$C_{1-3}$alkyl and 4-7 membered heterocycloalkyl;

Y is selected from —$CR^{10}R^{11}$—, —$SO_2$— and —CO—;

$R^{10}$ and $R^{11}$ can be the same or different and are independently selected from —H or —$C_{1-3}$alkyl; or $R^{10}$ and $R^{11}$ taken together form a —$C_{3-4}$cycloalkyl, $R^{12}$ is selected from —$NH_2$, —OH, —N($R^5$,$R^{16}$), —O—$R^{17}$, aryl, 5-6 membered heteroaryl, wherein the aryl or heteroaryl is optionally and independently substituted with one or more halogen, 4-7 membered heterocycloalkyl, which heterocycloalkyl is optionally and independently substituted with one or more groups selected from halogen, —OH, —$NH_2$, —$C_{1-3}$alkyl, —$NHC_{1-3}$alkyl, —N($C_{1-3}$alkyl)$_2$, —O—$C_{1-3}$alkyl and —$CH_2$—$R^{14}$;

$R^{14}$ is selected from 5-10 membered mono- or bicyclic aryl or heteroaryl, which is optionally substituted with —$NH_2$, —OH, halogen, —CN, $C_{1-3}$alkyl, —O—$C_{1-3}$alkyl;

$R^{15}$ is —H or —$C_{1-3}$alkyl $R^{16}$ is selected from —$C_{1-3}$alkyl, —$C_{2-3}$alkyl-N($C_{1-3}$alkyl)$_2$, —$C_{2-3}$alkyl-$NHC_{1-3}$alkyl and 4-7 membered heterocycloalkyl, which heterocycloalkyl is optionally substituted with —$C_{1-3}$alkyl;

$R^{17}$ is 4-7 membered heterocycloalkyl, which heterocycloalkyl is optionally substituted with $C_{1-3}$alkyl wherein at least one of the substituents $R^5$ to $R^9$ is not hydrogen.

In a preferred embodiment, the invention relates to compounds of formula (I), wherein when $R^7$ is Y—$R^{12}$, $R^6$ and $R^8$ can be the same or different and are independently selected from —H, —OH, halogen, —$NH_2$, —CN, —$C_{1-3}$alkyl, —$C_{1-3}$haloalkyl, —O—$C_{1-3}$alkyl, —O—$C_{1-3}$haloalkyl and —$C_{1-3}$alkyl-O—$C_{1-3}$alkyl.

In a preferred embodiment, the invention relates to compounds of formula (I) wherein $R^1$ is selected from —$CH_3$, —$CH_2CH_3$ and cyclopropyl.

In a preferred embodiment, the invention relates to compounds of formula, wherein $R^2$ is selected from —$CH_3$, —Br, —I, —$CHF_2$, —$NH_2$, —$NHCH_3$ and —OH.

In a preferred embodiment, the invention relates to compounds of formula (I), wherein $R^2$ is selected from —$CH_3$ and —I.

In a preferred embodiment, the invention relates to compounds of formula (I), wherein $X_1$ is —$CR^3$ and $R^3$ is selected from —H, —$CH_3$.

In a preferred embodiment, the invention relates to compounds of formula (I), wherein $X_2$ is —$CR^4$ and $R^4$ is selected from —H, —$CH_3$.

In a preferred embodiment, the invention relates to compounds of formula (I), wherein

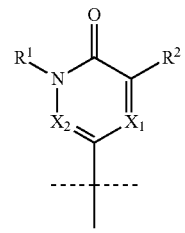

is selected from

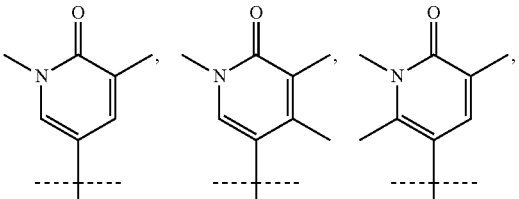

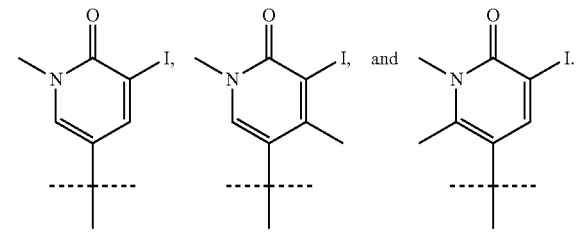

In a more preferred embodiment, the invention relates to compounds of formula (I), wherein

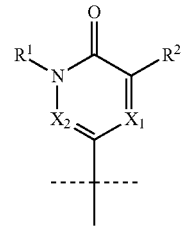

is selected from

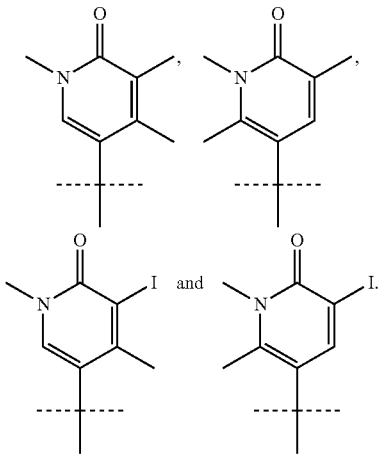

In a preferred embodiment, the invention relates to compounds of formula (I), wherein $R^2$ and $R^3$ taken together form a benzene or a 5-6 membered nitrogen containing heteroarene ring, each of which rings is optionally and independently substituted with one or two halogen, —OH, —NH$_2$, —NH—C$_{1-3}$alkyl and —C$_{1-3}$alkyl, wherein the —C$_{1-3}$alkyl group can be optionally substituted with a 6 membered aryl or 5-6 membered heteroaryl. More preferably, the benzene or a 5-6 membered nitrogen containing heteroarene ring of this embodiment are not substituted.

In a preferred embodiment, the invention relates to compounds of formula (I), wherein $X_1$ is $CR^3$ and $R^2$ and $R^3$ taken together form a benzene or a 5-6 membered nitrogen containing heteroarene ring, each of which rings is optionally and independently substituted with one or two halogen, —NH$_2$, —NH—C$_{1-3}$alkyl and —C$_{1-3}$alkyl, wherein the —C$_{1-3}$alkyl group can be optionally substituted with a 6 membered aryl or 5-6 membered heteroaryl. More preferably, the benzene or a 5-6 membered nitrogen containing heteroarene ring of this embodiment are not substituted.

In a preferred embodiment, the invention relates to compounds of formula (I), wherein

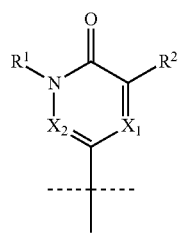

is selected from

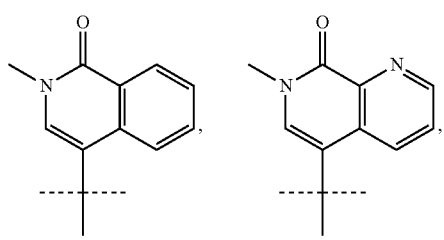

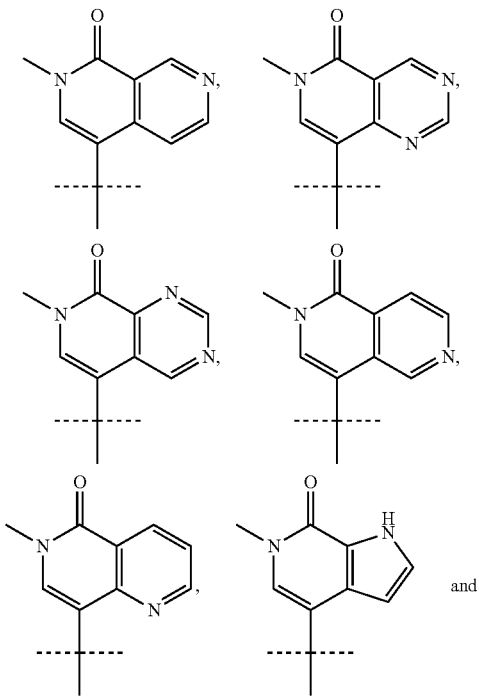

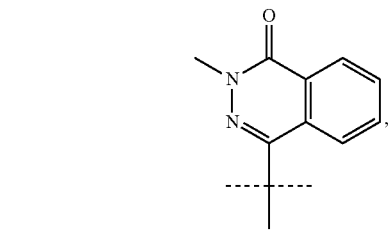

each of which groups are optionally and independently substituted with one or two —F, —CH$_3$, —OH, —NH$_2$, —NHCH$_3$ or

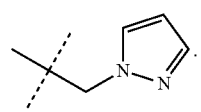

In a preferred embodiment, the invention relates to compounds of formula (I), wherein

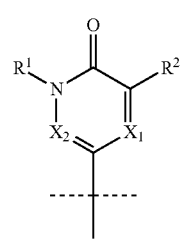

is selected from

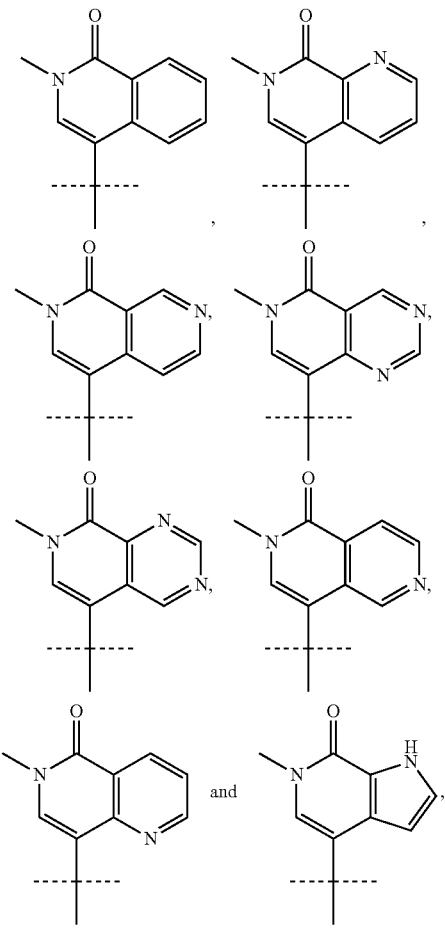

each of which groups are optionally and independently substituted with one or two —F, —CH$_3$, —OH, —NH$_2$, —NHCH$_3$ or

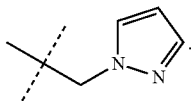

More preferably the groups of this embodiment are not substituted.

In a preferred embodiment, the invention relates to compounds of formula (I), wherein

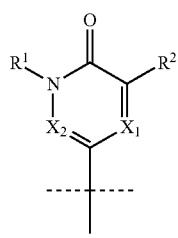

is selected from

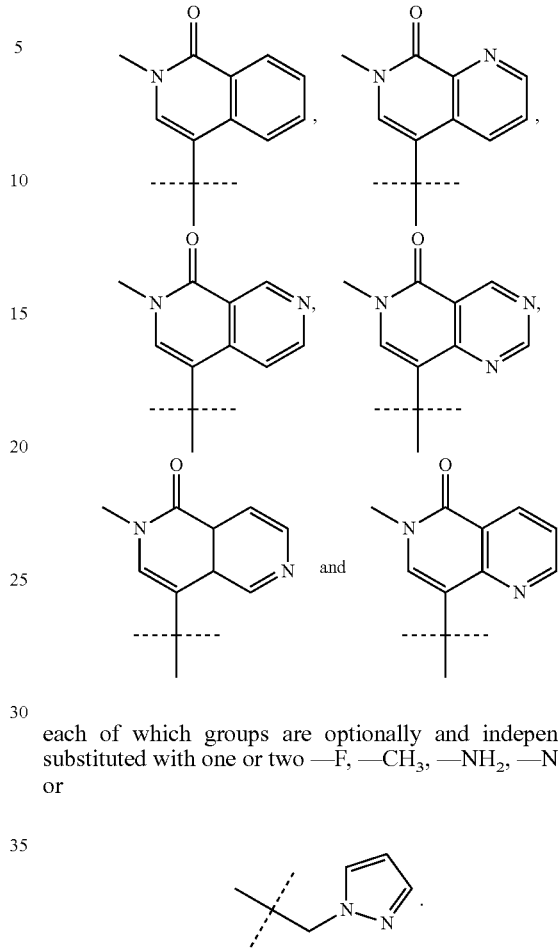

each of which groups are optionally and independently substituted with one or two —F, —CH$_3$, —NH$_2$, —NHCH$_3$ or

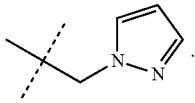

More preferably the groups of this embodiment are not substituted.

In a preferred embodiment, the invention relates to compounds of formula (I), wherein $R^6$ and $R^8$ can be the same or different and are independently selected from —H, —OH, —NH$_2$, —CH$_2$NH$_2$, halogen, —C$_{1-3}$alkyl, —O—C$_{1-3}$alkyl, —O—C$_{1-3}$haloalkyl, —C$_{1-3}$alkyl-O—C$_{1-3}$alkyl, 4-7 membered heterocycloalkyl, —CH$_2$—SO$_2$—C$_{1-3}$alkyl, —CH$_2$—N(—C$_{1-3}$alkyl)$_2$, —N(C$_{1-3}$alkyl)$_2$, —NH—R$^{13}$, wherein R$^{13}$ is selected from —SO$_2$—C$_{1-3}$alkyl and —C$_{1-3}$alkyl, wherein the —C$_{1-3}$alkyl group can be optionally substituted with 6 membered heteroaryl.

In a preferred embodiment, the invention relates to compounds of formula (I), wherein $R^6$ and $R^8$ can be the same or different and are independently selected from —H, —OH, —NH$_2$, —CH$_2$NH$_2$, —C$_{1-3}$alkyl, —O—C$_{1-3}$alkyl, —O—C$_{1-3}$haloalkyl, —C$_{1-3}$alkyl-O—C$_{1-3}$alkyl, 4-7 membered heterocycloalkyl, —CH$_2$—N(—C$_{1-3}$alkyl)$_2$, —N(C$_{1-3}$alkyl)$_2$, —NH—R$^{13}$, wherein R$^{13}$ is —C$_{1-3}$alkyl, wherein the —C$_{1-3}$alkyl group can be optionally substituted with 6 membered heteroaryl.

In a preferred embodiment, the invention relates to compounds of formula (I), wherein $R^6$ and $R^8$ can be the same or different and are independently selected from —H, —CH$_3$, —CH$_2$CH$_3$, —O—CF$_2$, —O—CF$_3$, —F, —Cl, —CH$_2$N(CH$_3$)$_2$, —NH$_2$, —CH$_2$NH$_2$, —OH, —OCH$_3$, —OCH$_2$CH$_3$, —NHSO$_2$CH$_3$, —NHSO$_2$CH$_2$CH$_3$,

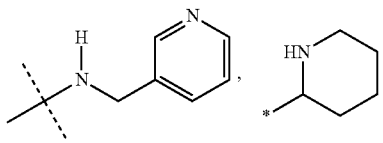

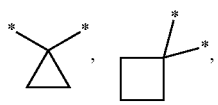

—SO$_2$— and —CO—.

In a preferred embodiment, the invention relates to compounds of formula (I), wherein Y is selected from —CH$_2$—, —C(CH$_3$)$_2$—, —CH(CH$_3$)—, —C(CH$_2$CH$_3$)$_2$ and —SO$_2$—

In a preferred embodiment, the invention relates to compounds of formula (I), wherein R$^7$ is selected from —H, —Y—R$^{12}$, —CH$_3$, —CH$_2$—O—CH$_3$, —CH(OH)—CH$_2$CH$_3$, —CH(CH$_3$)—NH$_2$CH$_2$, —CH$_2$NH$_2$ and —NH$_2$.

In a preferred embodiment, the invention relates to compounds of formula (I), wherein R$^7$ is selected from —Y—R$^{12}$, —CH$_2$—O—CH$_3$, —CH(OH)—CH$_2$CH$_3$, —CH(CH$_3$)—NHCH$_2$, —CH$_2$NH$_2$, —SO$_2$—CH$_3$, —SO$_2$—CH$_2$CH$_3$ and —NH$_2$.

In a preferred embodiment, the invention relates to compounds of formula (I), wherein R$^{12}$ is selected from 4-7 membered nitrogen containing heterocycloalkyl, which heterocycloalkyl is optionally and independently substituted with one or two groups selected from —OH, —NH$_2$, halogen, —C$_{1-3}$alkyl, —O—C$_{1-3}$alkyl, —NH—C$_{1-3}$alkyl, —N(C$_{1-3}$alkyl)$_2$ and —CH$_2$—R$^{14}$, wherein R$^{14}$ is selected from

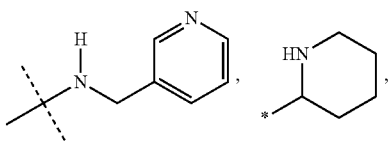

—N(CH$_3$)$_2$, —CH$_2$—SO$_2$CH$_2$CH$_3$, —CH$_2$SO$_2$CH$_3$, —O(CH$_2$)$_2$OCH$_3$, and —OCH(CH$_3$)$_2$.

In a preferred embodiment, the invention relates to compounds of formula (I), wherein R$^6$ and R$^8$ can be the same or different and are independently selected from —H, —CH$_3$, —CH$_2$CH$_3$, —O—CF$_2$, —O—CF$_3$, —CH$_2$N(CH$_3$)$_2$, —NH$_2$, —CH$_2$NH$_2$, —OH, —OCH$_3$, —OCH$_2$CH$_3$, —N(CH$_3$)$_2$, —O(CH$_2$)$_2$OCH$_3$, and —OCH(CH$_3$)$_2$.

In a preferred embodiment, the invention relates to compounds of formula (I), wherein R$^5$, R$^6$, R$^8$ and R$^9$ are —H.

In a preferred embodiment, the invention relates to compounds of formula (I), wherein one group selected from R$^5$, R$^6$, R$^8$ and R$^9$ is —O—CH$_3$, and the remaining groups are —H.

In a preferred embodiment, the invention relates to compounds of formula (I), wherein one group selected from R$^5$, R$^6$, R$^8$ and R$^9$ is —O—CH$_3$, a second group is selected from —O—C$_{1-3}$alkyl and —C$_{1-3}$alkyl and the remaining groups are —H.

In a preferred embodiment, the invention relates to compounds of formula (I), wherein R$^5$ and R$^9$ can be the same or different and are independently selected from —H, —O—CH$_3$, —O—CH$_2$CH$_3$ and —CH$_3$ In a preferred embodiment, the invention relates to compounds of formula (I), wherein R$^8$ is —O—CH$_3$, and R$^5$, R$^6$ and R$^9$ are —H.

In a preferred embodiment, the invention relates to compounds of formula (I), wherein R$^6$ is —OCH$_3$, R$^8$ is —OCH$_3$, R$^5$ is —H and R$^9$ is —H.

In a preferred embodiment, the invention relates to compounds of formula (I), wherein R$^6$ is —OCH$_3$, R$^9$ is —OCH$_3$, R$^5$ is —H and R$^8$ is —H.

In a preferred embodiment, the invention relates to compounds of formula (I), wherein R$^5$ is —OCH$_3$, R$^8$ is —OCH$_3$, R$^6$ is —H and R$^9$ is —H.

In a preferred embodiment, the invention relates to compounds of formula (I), wherein R$^7$ and R$^6$ or R$^7$ and R$^8$ taken together form a pyrrolidine or a piperidine ring, optionally substituted at the nitrogen atom with C$_{1-3}$alkyl.

In a preferred embodiment, the invention relates to compounds of formula (I), wherein R$^7$ is selected from —H, —NH$_2$, —Y—R$^{12}$ and —C$_{1-3}$alkyl.

In a preferred embodiment, the invention relates to compounds of formula (I), wherein R$^7$ is —Y—R$^{12}$.

In a preferred embodiment, the invention relates to compounds of formula (I), wherein Y is selected from —CH$_2$—, —C(CH$_3$)$_2$—, —CH(CH$_3$)—, —C(CH$_2$CH$_3$)$_2$, and phenyl, wherein the phenyl is optionally substituted with —OH or —NH$_2$;

or R$^{12}$ is selected from —O—R$^{17}$, wherein R$^{17}$ is 4-6 membered nitrogen containing heterocycloalkyl;

or R$^{12}$ is 5-6 membered heteroaryl, which heteroaryl group is optionally and independently substituted with two halogen, or R$^{12}$ is selected from —C$_{1-3}$alkyl, —NH$_2$, —N(R$^{15}$,R$^{16}$), wherein R$^{15}$ is —H or —C$_{1-3}$alkyl and R$^{16}$ is selected from —C$_{1-3}$alkyl, —C$_{1-3}$alkyl-N(C$_{1-3}$alkyl)$_2$, —C$_{1-3}$alkyl-NHC$_{1-3}$alkyl and 4-6 membered heterocycloalkyl, which heterocycloalkyl is optionally substituted with —C$_{1-3}$alkyl.

In a preferred embodiment, the invention relates to compounds of formula (I), wherein R$^{12}$ is selected from 4-7 membered nitrogen containing heterocycloalkyl, which heterocycloalkyl is optionally and independently substituted with one or two groups selected from —OH, —NH$_2$, halogen, —C$_{1-3}$alkyl, —O—C$_{1-3}$alkyl, —NH—C$_{1-3}$alkyl, —N(C$_{1-3}$alkyl)$_2$ and —CH$_2$—R$^{14}$, wherein R$^{14}$ is selected from

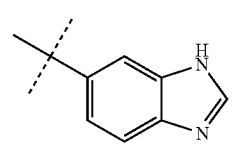

and phenyl, wherein the phenyl is optionally substituted with —OH or —NH$_2$;

or $R^{12}$ is selected from —$N(R^5,R^6)$, wherein $R^{15}$ is —H or —$C_{1-3}$alkyl and $R^{16}$ is selected from —$C_{1-3}$alkyl, —$C_{1-3}$alkyl-$N(C_{1-3}alkyl)_2$, —$C_{1-3}$alkyl-$NHC_{1-3}$alkyl and 4-6 membered heterocycloalkyl, which heterocycloalkyl is optionally substituted with —$C_{1-3}$alkyl.

In a preferred embodiment, the invention relates to compounds of formula (I), wherein $R^{12}$ is selected from 4-7 membered nitrogen containing heterocycloalkyl, which heterocycloalkyl is optionally and independently substituted with one or two groups selected from —OH, —$NH_2$, halogen, —$C_{1-3}$alkyl, —O—$C_{1-3}$alkyl, —NH—$C_{1-3}$alkyl, —$N(C_{1-3}alkyl)_2$ and —$CH_2$—$R^{14}$, wherein $R^{14}$ is selected from

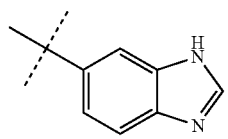

and phenyl, wherein the phenyl is optionally substituted with —OH or —$NH_2$.

In a preferred embodiment, the invention relates to compounds of formula (I), wherein $R^{12}$ is selected from 4-7 membered nitrogen containing heterocycloalkyl, which heterocycloalkyl is optionally and independently substituted with one or two groups selected from —OH, —$NH_2$, halogen, —$C_{1-3}$alkyl, —O—$C_{1-3}$alkyl, —NH—$C_{1-3}$alkyl, —$N(C_{1-3}alkyl)_2$.

In a preferred embodiment, the invention relates to compounds of formula (I), wherein $R^{12}$ is selected from —$N(R^{15},R^{16})$, wherein $R^{15}$ is —H or —$C_{1-3}$alkyl and $R^{16}$ is selected from —$C_{1-3}$alkyl, —$C_{1-3}$alkyl-$N(C_{1-3}alkyl)_2$, —$C_{1-3}$alkyl-$NHC_{1-3}$alkyl and 4-6 membered heterocycloalkyl, which heterocycloalkyl is optionally substituted with —$C_{1-3}$alkyl.

In a preferred embodiment, the invention relates to compounds of formula (I), wherein $R^7$ is selected from —H, —$CH_3$, —$NH_2$, —$CH_2NH_2$, —CO—$NH_2$,

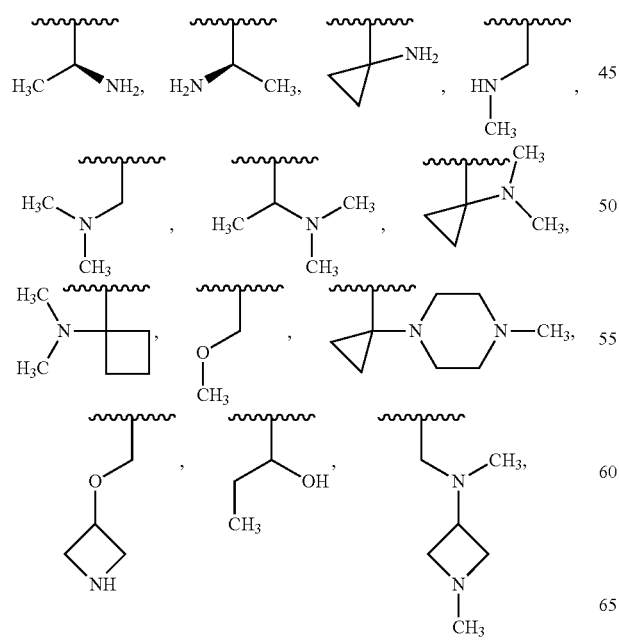

-continued

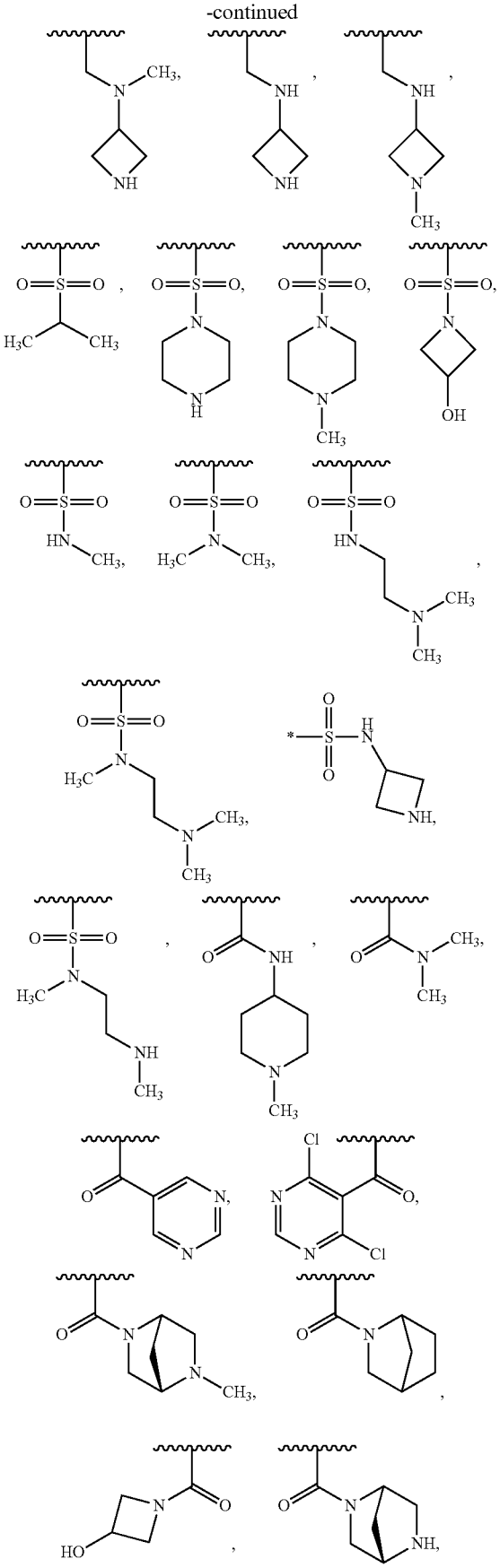

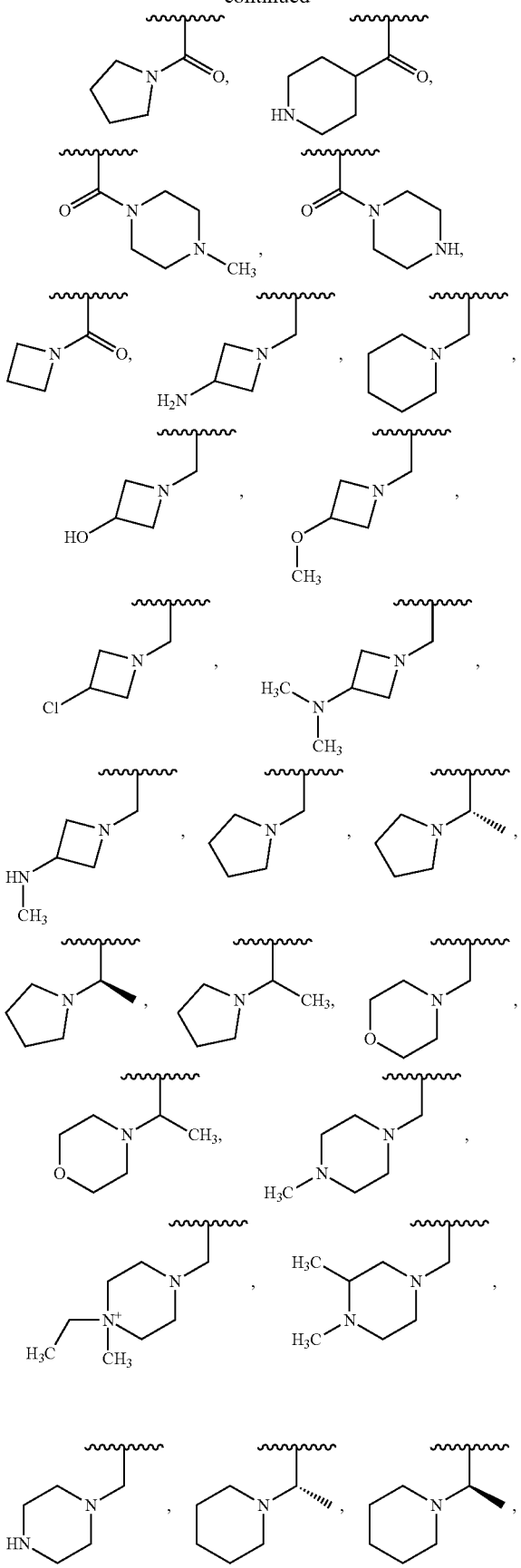
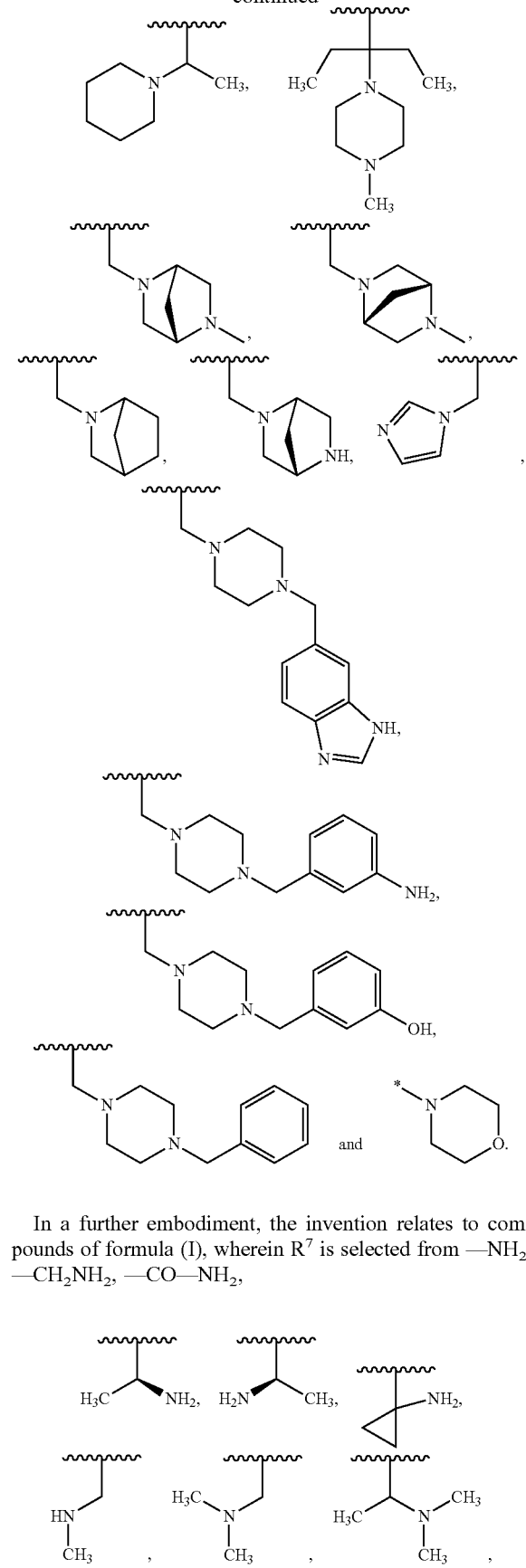
In a further embodiment, the invention relates to compounds of formula (I), wherein $R^7$ is selected from —$NH_2$, —$CH_2NH_2$, —CO—$NH_2$, 19
-continued
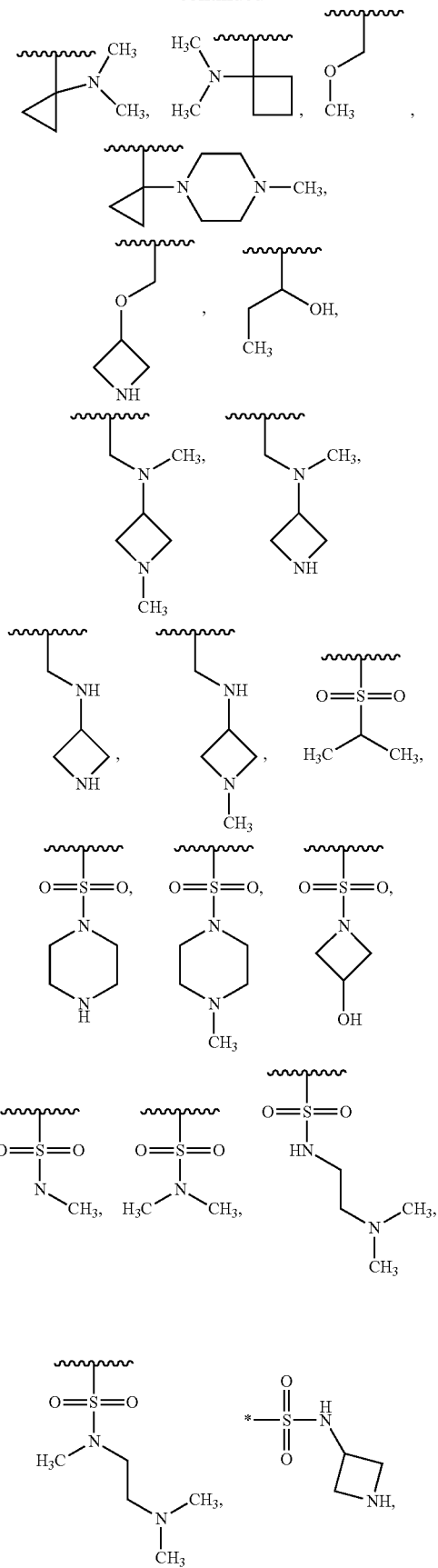
20
-continued
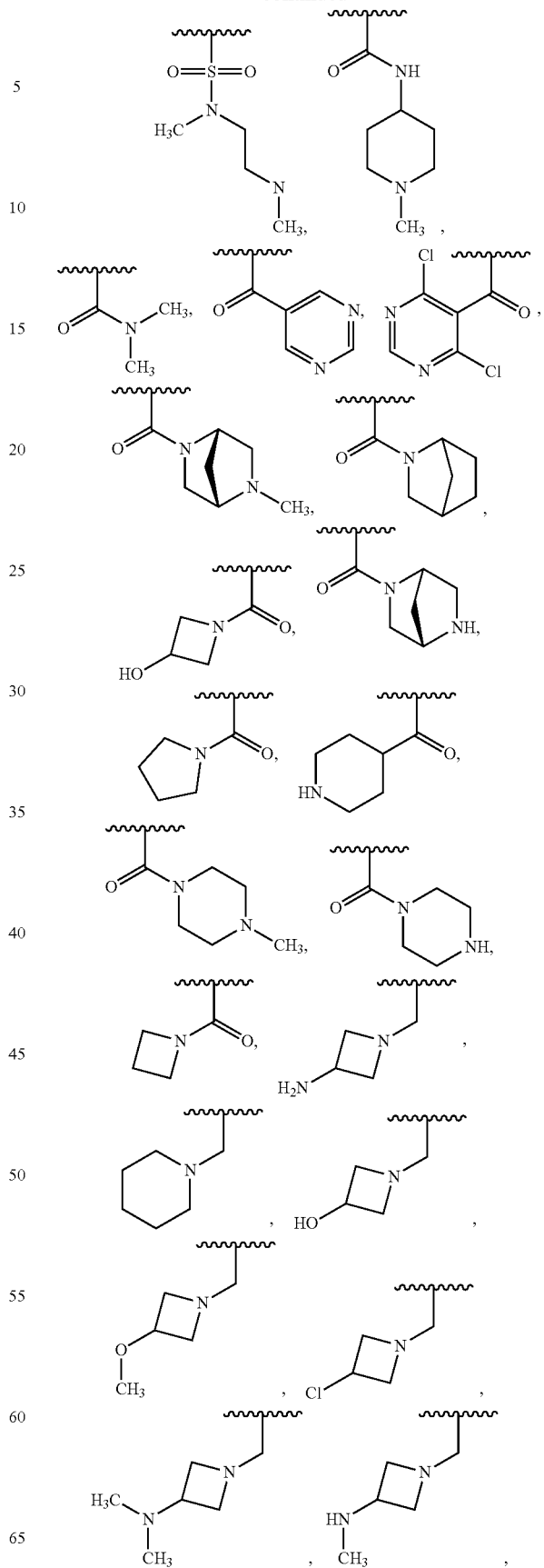

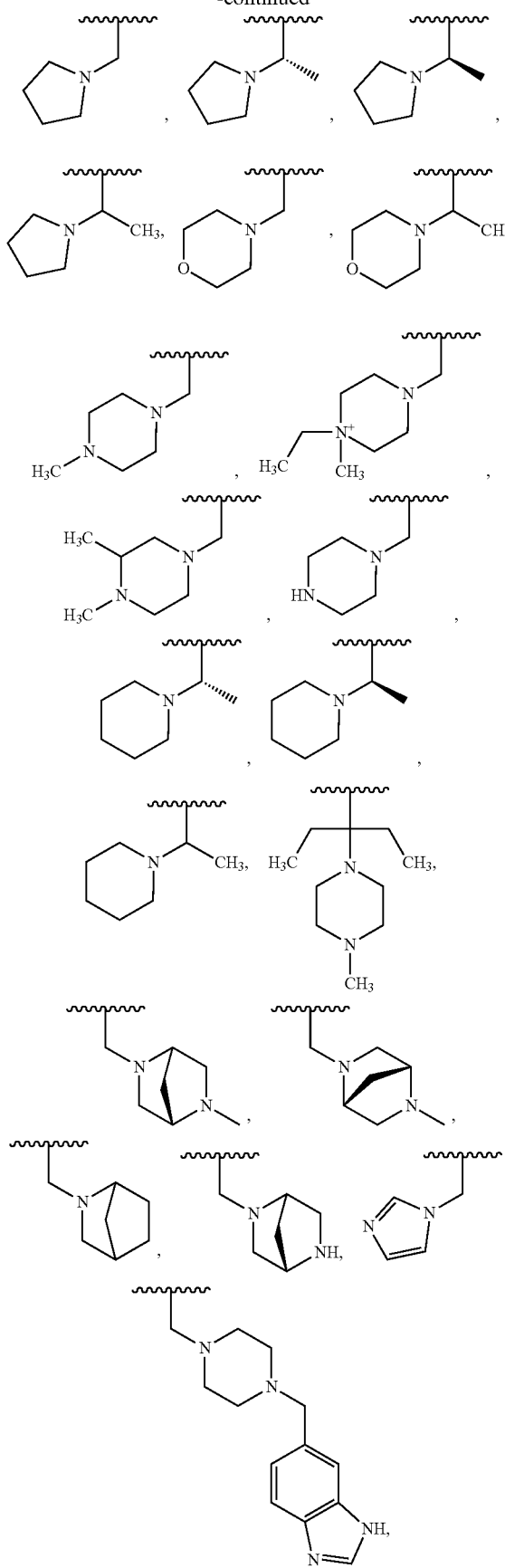
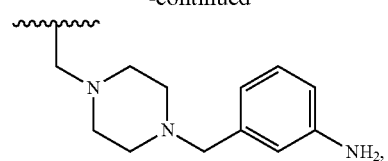
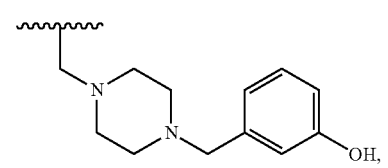
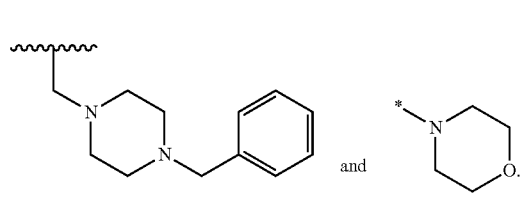
In a further embodiment, the invention relates to compounds of formula (I), wherein R⁷ is selected from —CH₂NH₂,
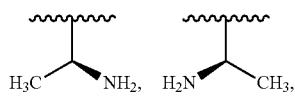
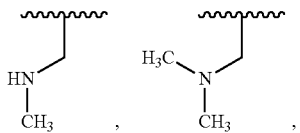
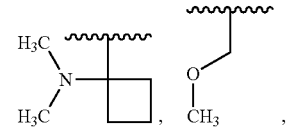
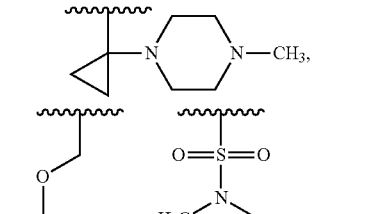
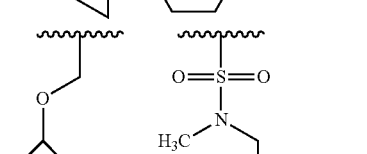
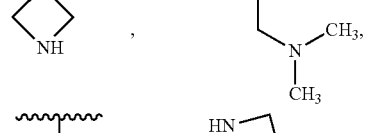
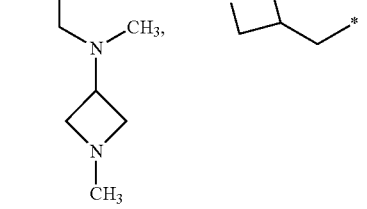

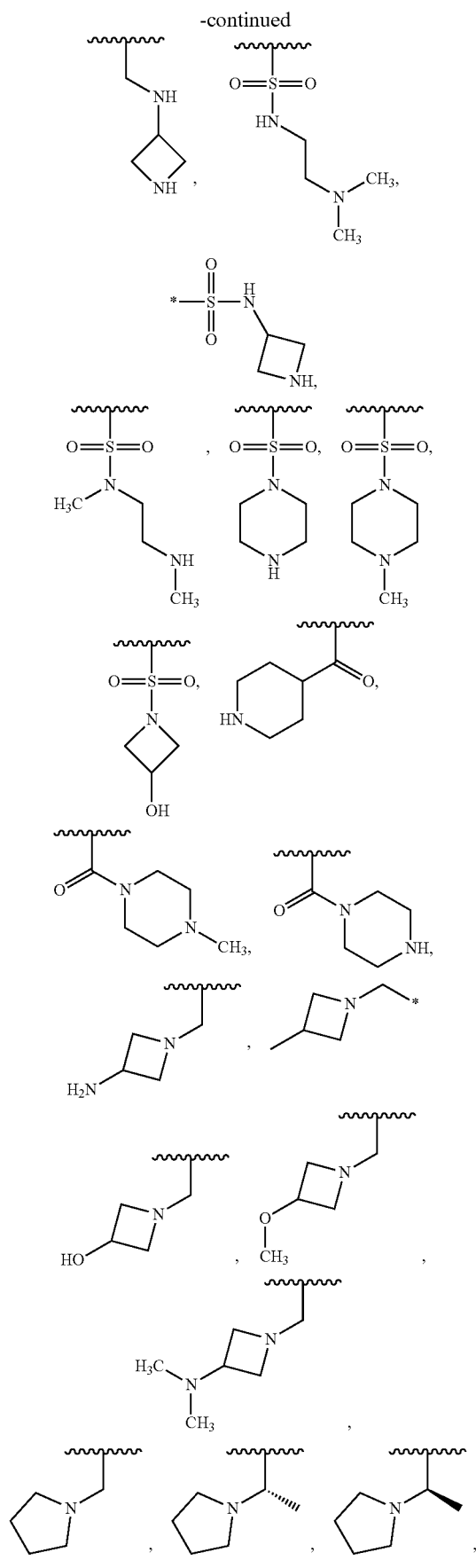
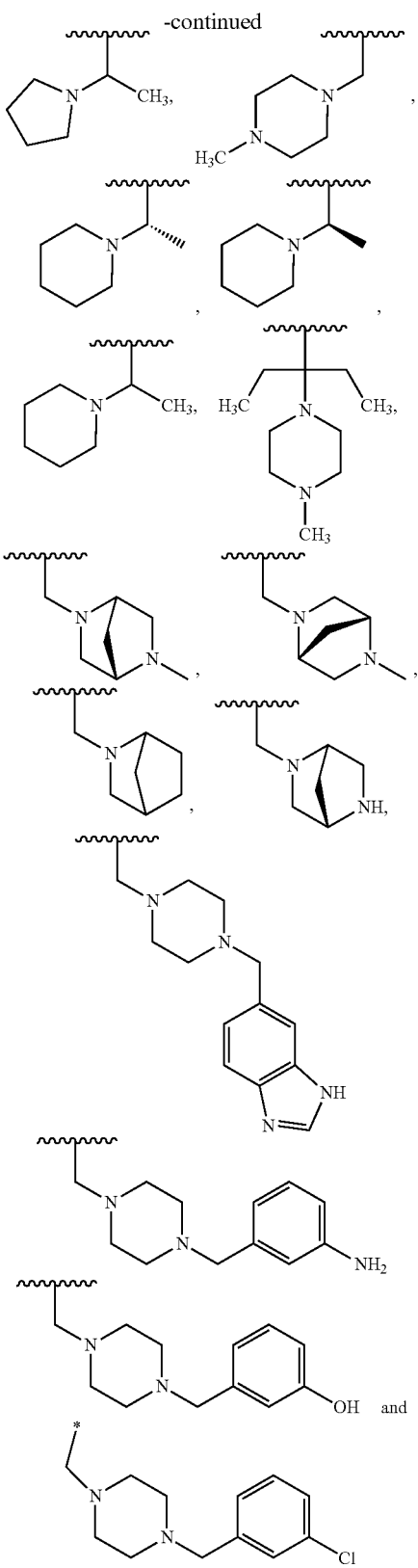
Or $R^7$ and $R^6$ together form a piperidine or a pyrrolidine.
In a preferred embodiment, the heterocycloalkyle is present in the compounds of formula (I) are nitrogen containing heterocycloalkyles.

In a further embodiment, the invention relates to compounds of formula (I) for use in the treatment of cancer.

In a further embodiment, the invention relates to compound of general formula (I) according to anyone of the embodiments described herein in the description and the claims—or the pharmaceutically acceptable salts thereof—for use in the treatment and/or prevention of cancer.

In a further embodiment, the invention relates to pharmaceutical preparation comprising as active substance one or more compounds of general formula (I) according to anyone of the embodiments described herein in the description and the claims optionally in combination with conventional excipients and/or carriers.

In a further embodiment, the invention relates to pharmaceutical preparation comprising a compound of general formula (I) according to anyone of the embodiments described herein in the description and the claims—or one of the pharmaceutically acceptable salts thereof—and at least one other cytostatic or cytotoxic active substance, different from formula (I).

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to compounds of general formula (I)—or the pharmaceutically acceptable salts thereof—for use in the treatment and/or prevention of cancer.

In another aspect the invention relates to the use of the compounds of general formula (I)—or the pharmaceutically acceptable salts thereof—in the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named subgroup is the radical attachment point, for example the substituent —$C_{1-5}$alkyl-$C_{3-10}$cycloalkyl, means a $C_{3-10}$cycloalkyl group which is bound to a $C_{1-5}$alkyl, the latter of which is bound to the core structure or to the group to which the substituent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$, —CH$_2$CH$_3$ and —CH$_2$CH$_2$ or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Other examples of alkylene are methylene, ethylene, propylene, 1-methylethylene, butylene, 1-methylpropylene, 1.1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H$_2$N—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or H$_2$N—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or H$_2$N—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms.

Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

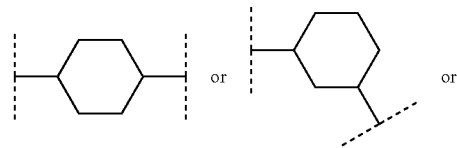

or

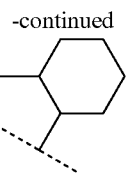

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

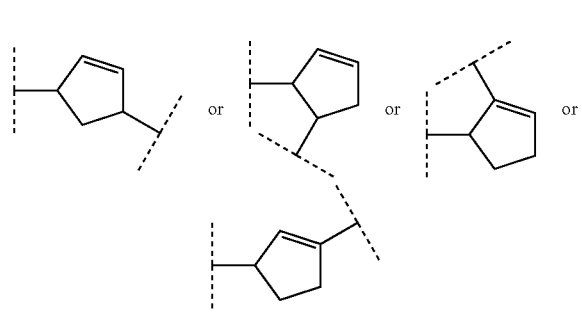

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.

phenyl and

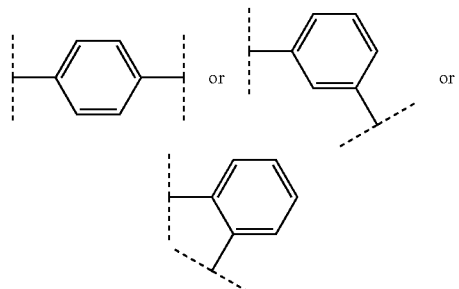

(o, m, p-phenylene), naphthyl and

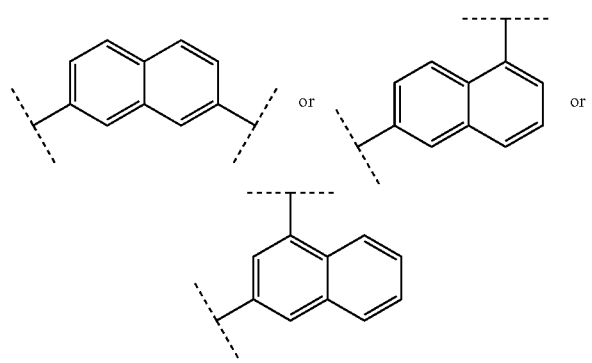

etc.

The above definition for arylene also applies when arylene is part of another group as in HO-aryleneamino or H₂N-aryleneoxy for example.

Heterocyclyl denotes ring systems, which are derived from the previously defined cycloalkyl, cycloalkenyl and aryl by replacing one or more of the groups —CH₂— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —SO₂—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-azabicyclo[3.2.1]octyl, 8-azabicyclo[5.1.0]octyl, 2-oxa-5-azabicyclo[2.2.1]-heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]-decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-di-aza-spiro[5.5]undecyl, 2.8-diaza-spiro[4.5]decyl etc.

Further examples are the structures illustrated below, which may be attached via each hydrogen-carrying atom (exchanged for hydrogen):

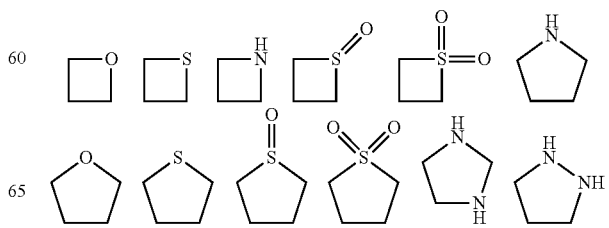

-continued
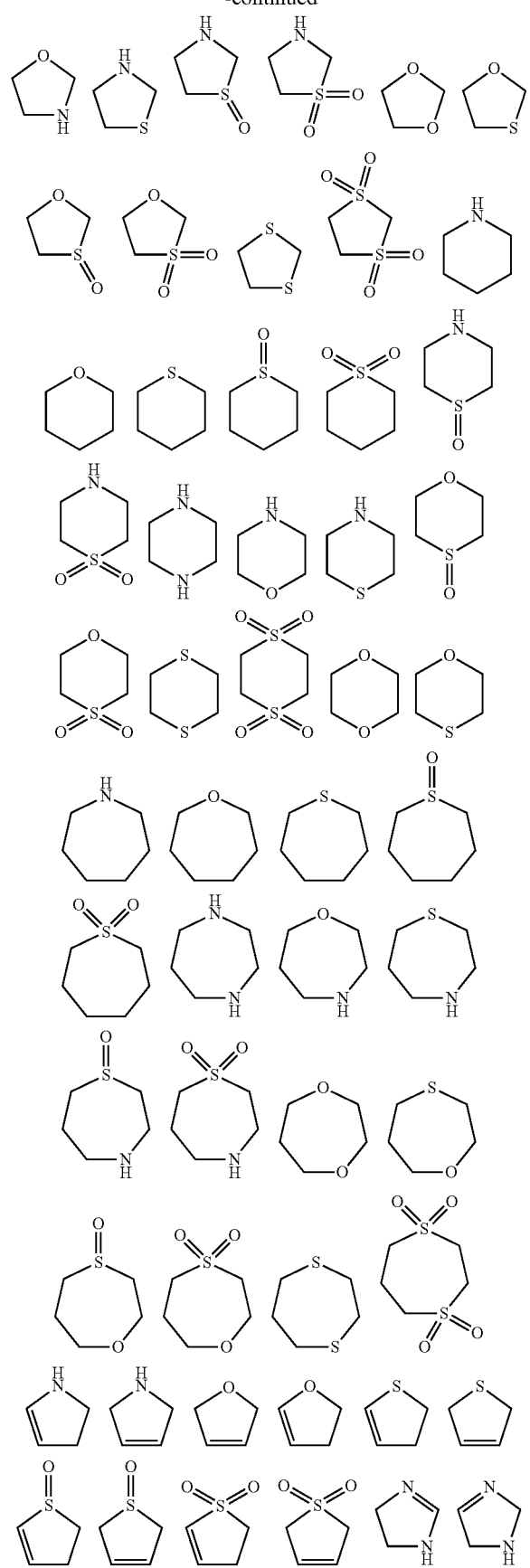
-continued
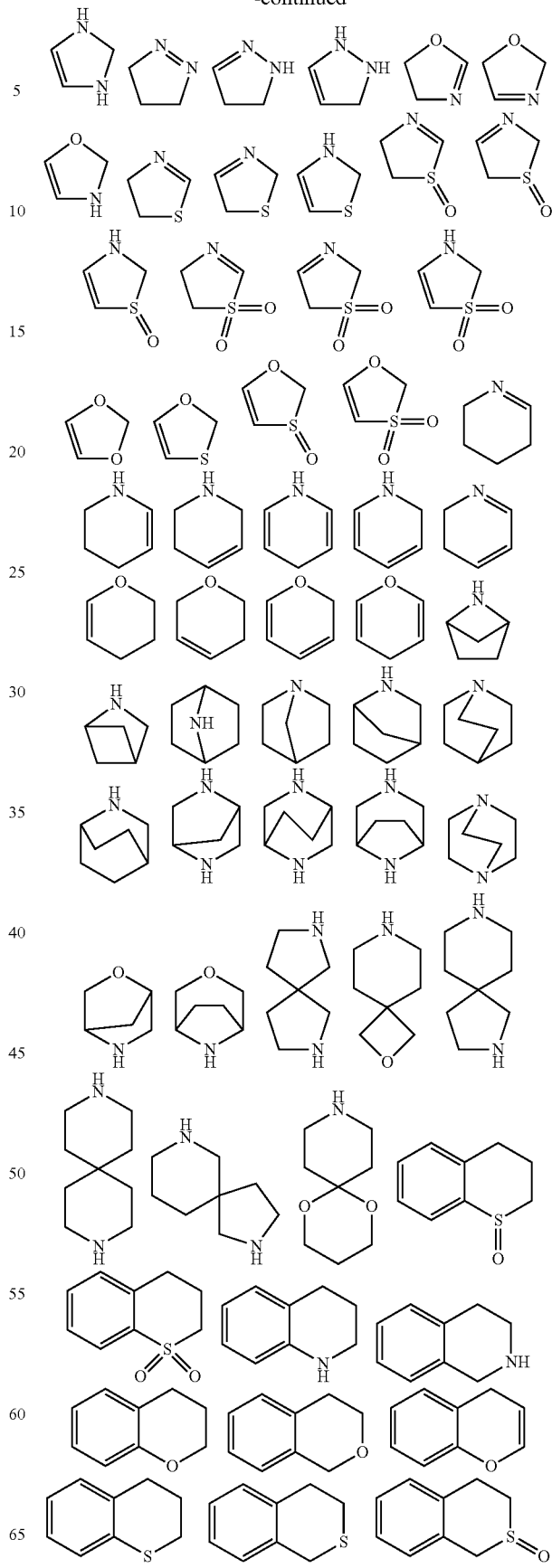

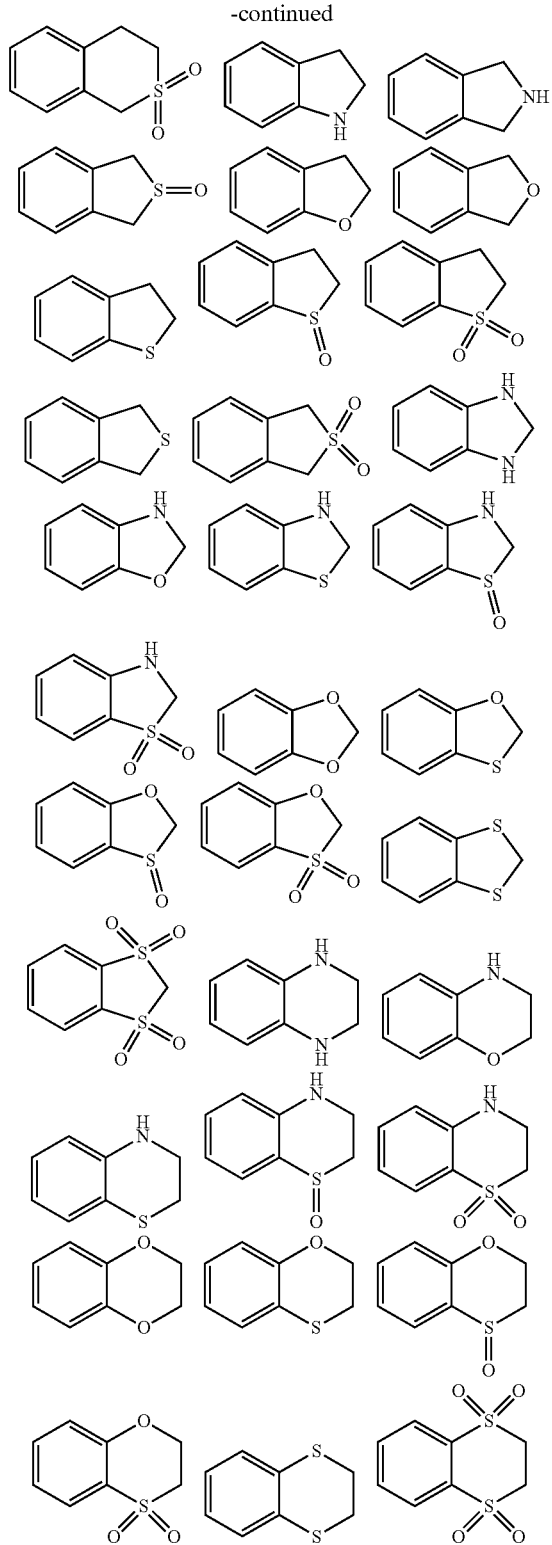

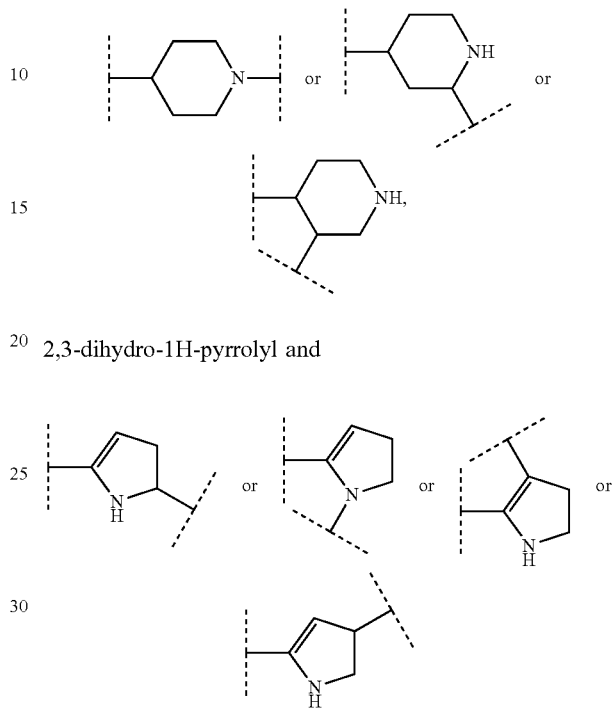

cyclyl, is bivalent and requires two binding partners. Formally, the second valency is obtained by removing a hydrogen atom from a heterocyclyl. Corresponding groups are for example piperidinyl and 2,3-dihydro-1H-pyrrolyl and etc.

The above definition of heterocyclylene also applies if heterocyclylene is part of another group as in HO-heterocyclyleneamino or H$_2$N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, The above definition of heterocyclyl also applies if heterocyclyl is part of another group as in heterocyclylamino or heterocyclyloxy for example.

If the free valency of a heterocyclyl is saturated, then a heterocyclic group is obtained.

The term heterocyclylene is also derived from the previously defined heterocyclyl. Heterocyclylene, unlike heteronaphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

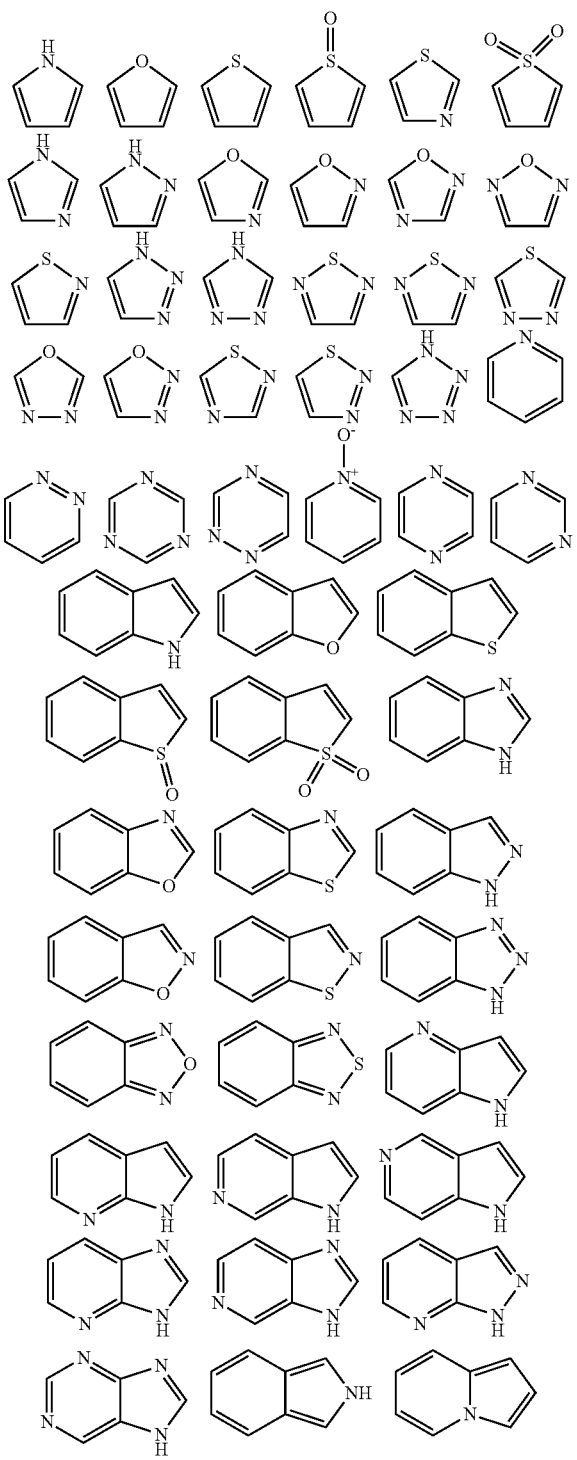

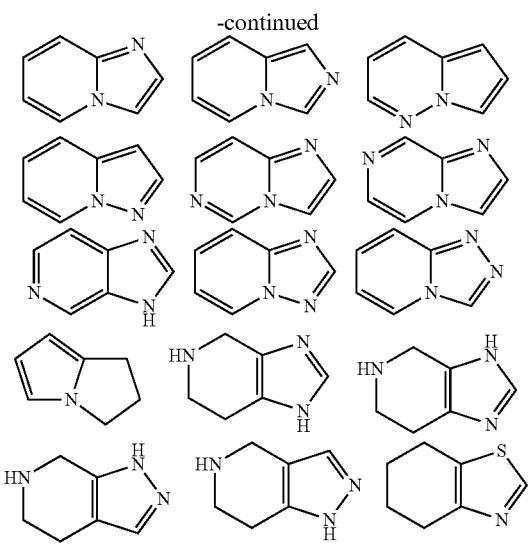

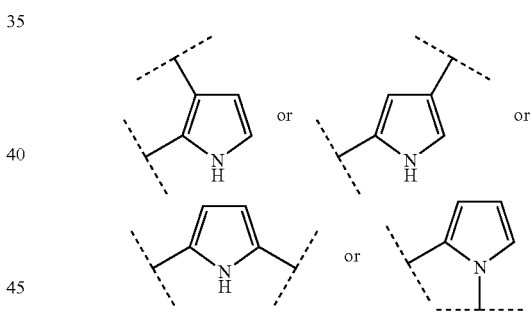

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and etc.

The above definition of heteroarylene also applies when heteroarylene is part of another group as in HO-heteroaryleneamino or H$_2$N-heteroaryleneoxy, for example.

The bivalent groups mentioned above (alkylene, alkenylene, alkynylene etc.) may also be part of composite groups (e.g. H$_2$N—C$_{1-4}$alkylene- or HO—C$_{1-4}$alkylene-). In this case one of the valencies is saturated by the attached group (here: —NH$_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

"Substituted with one or more groups" means that the group is substituted with one, two, three, four, five or more groups depending on the valency of the group which is substituted. The skilled person will have no difficulties to establish how many hydrogens can be substituted in a group. Preferably, the referred group is substituted with one, two or three further groups. More preferably, the group is substituted with one or two groups.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

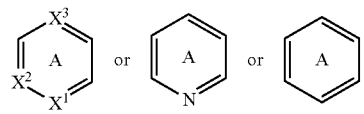

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

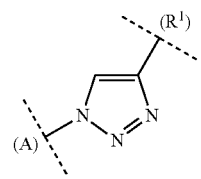

or (R$^2$)—C(O)NH— or (R$^2$)—NHC(O)—;

Groups or substituents are frequently selected from among a number of alternative groups/substituents with a corresponding group designation (e.g. R$^a$, R$^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| AcOH | Acetic acid |
| ACN, CH$_3$CN | Acetonitrile |
| BBr3 | Boron tribromide |
| Boc | tert.butoxy carbonyl; di-tert-butyl dicarbonate |
| Boc$_2$O | Boc anhydride |
| B$_2$pin$_2$ | Bis(pinacolato)diboron |
| Cs$_2$CO$_3$ | Cesium carbonate |
| CH$_2$Cl$_2$ | Dichloromethane |
| CH$_2$O | Formaldehyde |
| CO | Carbon monoxide |
| DCM | Dichloromethane |

| | |
|---|---|
| dppf | 1,1'-Bis(diphenylphosphino)ferrocene |
| DIAD | Diisopropyl azodicarboxylate |
| DIPEA | Diisopropylethyl amine |
| DME | 1,2-Dimethoxyethane |
| DMF | N,N-Dimethylformamide |
| DMSO | Dimethylsulphoxide |
| EDCI | N-(3-Dimethylaminopropyl)-N'-ethylcarbodiimide hydrochloride |
| EtOAc or EA | Ethyl acetate |
| EtOH | Ethanol |
| GST | Glutathione S-transferase |
| h or hrs | Hour(s) |
| $HCO_2H$ | Formic acid |
| $H_2O$ | Water |
| Hal | Halogen |
| HATU | N-[(Dimethylamino)-(1H-1,2,3-triazolo[4,5-b]pyridin-1-yl)-methylene]-N-methylmethan-amineium hexafluorophosphate N-oxide |
| HCl | Hydrochloric acid |
| HOBt | 1-Hydroxybenzotriazole |
| HPLC | High performance liquid chromatography |
| $K_2CO_3$ | Potassium carbonate |
| KOAc | Potassium acetate |
| LiHMDS | Lithium hexamethyl disilazide |
| LiOH | Lithium hydroxide |
| M | Molar (mol/L) |
| MeOH | Methanol |
| MeTi(OiPr)$_3$ | Methyltitanium(IV) triisopropoxide |
| μL | Microliter |
| Min or min | Minute(s) |
| mL | Milliliter |
| MS | Mass spectrometry |
| MsCl | Methanesulfonyl chloride |
| N | Normal |
| NaBH(OAc)$_3$ | Sodium triacetoxyborohydride |
| $Na_2CO_3$ | Sodium carbonate |
| NaOH | Sodium hydroxide |
| NIS | N-Iodosuccinimide |
| $Na_2SO_4$ | Sodium sulfate |
| $NH_3$ | Ammonia |
| $NH_4Cl$ | Ammonium chloride |
| $NH_4^+ HCO_2^-$ | Ammonium formate |
| NMP | N-Methyl-2-pyrrolidone |
| NMR | Nuclear magnetic resonance |
| $PBr_3$ | Phosphorus tribromide |
| Pd$_2$dba$_3$ | Tris(dibenzylideneacetone)dipalladium(0) |
| Pd(dppf)Cl$_2$ | [1,1'-Bis(diphenylphosphino)ferrocene]dichloro-palladium(II) |
| Pd(dppf)Cl$_2$•CH$_2$Cl$_2$ | [1,1'-Bis(diphenylphosphino)ferrocene]dichloro-palladium(II), dichloromethane |
| Pd(PtBu$_3$)$_2$ | Bis(tri-tert-butylphosphine)palladium(0) |
| Pd(PPh$_3$)$_4$ | Tetrakis(triphenylphosphine)palladium(0) |
| PE | Petrol ether |
| PPh$_3$ | Triphenylphosphine |
| RP | Reversed phase |
| RT or rt | Room temperature (20 to 25° C.) |
| SOCl$_2$ | Thionyl chloride |
| SPhos | Sodium 2'-dicyclohexylphosphino-2,6-dimethoxy-1,1'-biphenyl-3-sulfonate hydrate |
| TBTU | o-Benzotriazol-1-yl-N,N,N',N'-tetramethyl-uronium tetrafluoroborate |
| TEA | Triethylamine |
| tert | Tertiary |
| TFA | Trifluoroacetic acid |
| THF | Tetrahydrofuran |
| $t_R$ | Retention time [min] |
| sat. | Saturated |
| Ar | Aromatic |

Other features and advantages of the present invention will become apparent from the following more detailed Examples which exemplarily illustrate the principles of the invention without restricting its scope.

General

Unless stated otherwise, all the reactions are carried out in commercially obtainable apparatus using method s that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high-performance liquid chromatography (HPLC) of the example compounds according to the invention is carried out with columns made by Waters (names: Sunfire C18 OBD, 10 μm, 30×100 mm Part. No. 186003971; X-Bridge C18 OBD, 10 μm, 30×100 mm Part. No. 186003930). The compounds are eluted using different gradients of $H_2O$/ACN wherein 0.2% HCOOH is added to the water (acid conditions). For chromatography under basic conditions the water is made basic according to the following recipe: 5 mL of ammonium hydrogen carbonate solution (158 g to 1 L $H_2O$) and 2 mL 32% ammonia $_{(aq)}$ are made up to 1 L with $H_2O$.

The analytical HPLC (reaction monitoring) of intermediate compounds is carried out with columns made by Waters, Phenomenex, Merck, Halo and YMC Triart. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time $t_{Ret.}$=0.

HPLC Analytical Methods

Method 1 (M1)
    HPLC: Agilent 1100 Series
    MS: Agilent LC/MSD SL
    Column: Phenomenex Mercury Gemini C18, 3 μm, 2×20 mm, Part. No. 00M-4439-B0-CE
    Solvent: A: 5 mM NH$_4$HCO$_3$/20 mM NH$_3$ in H$_2$O; B: Acetonitrile (HPLC grade)
    Detection: MS: Positive and negative mode
    Mass range: 120-900 m/z
    Flow: 1.00 mL/min
    Column temperature: 40° C.
    Gradient: 0.00-2.50 min: 5%→95% B
    2.50-2.80 min: 95% B
    2.81-3.10 min: 95%→5% B Method 2 (M2)
    HPLC: Agilent 1100/1200 Series
    MS: Agilent LC/MSD SL
    Column: Waters X-Bridge C18, 2.5 μm, 2.1×30 mm
    Solvent: A: 0.1% NH$_4$HCO$_3$/0.1% NH$_3$ in H$_2$O; B: Acetonitrile (HPLC grade)
    Detection: MS: Positive mode
    Mass range: 150-750 m/z
    Flow: 1.40 mL/min
    Column temperature: 45° C.
    Gradient: 0.00-1.00 min: 15%→95% B
    1.00-1.30 min: 95% B Method 3 (M3)
    HPLC: Agilent 1100/1200 Series
    MS: Agilent LC/MSD SL
    Column: Waters X-Bridge C18, 2.5 μm, 2.1×30 mm
    Solvent: A: 0.1% NH$_4$HCO$_3$/0.1% NH$_3$ in H$_2$O; B: Acetonitrile (HPLC grade)
    Detection: MS: Positive mode
    Mass range: 50-500 m/z
    Flow: 1.40 mL/min Column temperature: 45° C.
Gradient: 0.00-1.00 min: 15%→95% B
1.00-1.30 min: 95% B
Method 4 (M4)
HPLC: Agilent 1100/1200 Series
MS: Agilent LC/MSD SL
Column: YMC Triart C18, 3.0 μm, 2.0×30 mm
Solvent: A: 0.1% formic acid in water; B: 0.1% formic acid in Acetonitrile (HPLC grade)
Detection: MS: Positive mode
Mass range: 150-750 m/z
Flow: 1.40 mL/min
Column temperature: 45° C.
Gradient: 0.00-1.00 min: 15%→100% B
1.00-1.1 min: 100% B
Method 5 (M5)
HPLC: 200, DAD 200-400 nm, Agilent
MS: 6120 MS, Agilent
Column: Luna C18(2) 3 μm, 30*2.0 mm
Solvent: A: water containing 0.0375% TFA; B: Acetonitrile containing 0.018% TFA
Detection: Positive
Mass range: 100-1000 m/z
Flow: 1.0 mL/min
Column temperature: 50° C.
Gradient: 0.00-0.30 min: 0 B %→0 B %
0.30-1.40 min: 0 B %→60 B %
1.40-1.55 min: 60 B %→60 B %
1.55-1.56 min: 60 B %→0 B %
1.56-2.00 min: 0 B %→0 B %
Method 6 (M6)
HPLC: 1200, DAD 200-400 nm, Agilent
MS: 6120 MS, Agilent
Column: Chromolith Flash RP-18 Endcapped 25-2 mm
Solvent: A: water containing 0.0375% TFA; B: Acetonitrile containing 0.018% TFA
Detection: Positive
Mass range: 100-1000 m/z
Flow: 1.5 mL/min
Column temperature: 40° C.
Gradient: 0.01-0.70 min: 5 B %→95 B %
0.70-1.15 min: 95 B %→95 B %
1.15-1.16 min: 95 B %→5 B %
1.16-1.60 min: 5 B %→5 B %
Method 7 (M7)
HPLC: 1200, DAD 200-400 nm, Agilent
MS: 6120 MS, Agilent
Column: Luna C18(2) 3 μm, 30*2.0 mm
Solvent: A: water containing 0.0375% TFA; B: Acetonitrile containing 0.018% TFA
Detection: Positive
Mass range: 100-1000 m/z
Flow: 1.0 mL/min
Column temperature: 50° C.
Gradient: 0.00-1.15 min: 10 B %→80 B %
1.15-1.55 min: 80 B %→80 B %
1.55-1.56 min: 80 B %→10 B %
1.56-2.00 min: 10 B %→10 B %
Method 8 (M8)
HPLC: LC-20AB, SPD-M20A 190-370 nm, SHAMADZU
Column: Luna C18(2) 5 μm, 50*2.0 mm
Solvent: A: water containing 0.0375% TFA; B: Acetonitrile containing 0.018% TFA
Flow: 0.8 mL/min
Column temperature: 40° C.
Gradient: 0.01-4.00 min: 10 B %→80 B %
4.00-4.90 min: 80 B %→80 B %
4.90-4.92 min: 80 B %→10 B %
4.92-5.50 min: 10 B %→10 B %
Method 9 (M9)
HPLC: LC-20AD, SPD-M20A 190-370 nm
MS: LCMS-2020EV MS, SHAMADZU
Column: Halo-C18, 2.7 μm, 2.1×30 mm
Solvent: A: water containing 0.0375% TFA; B: Acetonitrile containing 0.018% TFA
Detection: Positive
Mass range: 100-1000 m/z
Flow: 1.0 mL/min
Column temperature: 50° C.
Gradient: 0.00-1.15 min: 10 B %→90 B %
1.15-1.55 min: 90 B %→90 B %
1.55-1.56 min: 90 B %→10 B %
1.56-2.00 min: 10 B %→10 B %
Method 10 (M10)
HPLC: 1200, DAD 200-400 nm, Agilent
MS: 6120 MS, Agilent
Column: Luna C18(2) 5 μm, 50*2.0 mm
Solvent: A: water containing 0.0375% TFA; B: Acetonitrile containing 0.018% TFA
Detection: Positive
Mass range: 100-1000 m/z
Flow: 1.0 mL/min
Column temperature: 50° C.
Gradient: 0.00-0.40 min: 1 B %→1 B %
0.40-3.40 min: 1 B %→90 B %
3.40-3.85 min: 90 B %→100 B %
3.85-3.86 min: 100 B %→1 B %
3.86-4.50 min: 1 B %→1 B %
Method 11 (M11)
HPLC: 1200, DAD 200-400 nm, Agilent
MS: 6120 MS, Agilent
Column: Luna C18(2) 5 μm, 50*2.0 mm
Solvent: A: water containing 0.0375% TFA; B: Acetonitrile containing 0.018% TFA
Detection: Positive
Mass range: 100-1000 m/z
Flow: 1.0 mL/min
Column temperature: 50° C.
Gradient: 0.00-0.40 min: 10 B %→10 B %
0.40-3.40 min: 10 B %→90 B %
3.40-3.85 min: 90 B %→100 B %
3.85-3.86 min: 100 B %→10 B %
3.86-4.50 min: 10 B %→10 B %

Preparation of the Compounds According to the Invention

The compounds according to the invention are prepared by the methods of synthesis described hereinafter, in which the substituents of the general formula have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Unless otherwise specified, the substituents $R^1$ through $R^9$ and $X_1$ through $X_5$ of the following reaction schemes are as defined in the description and claims.

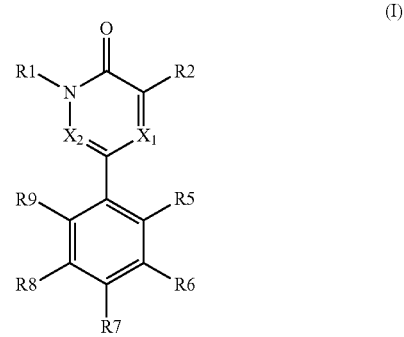

(I)

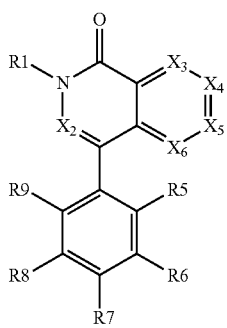

(II)

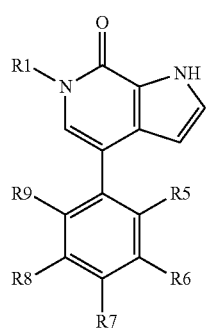

(III)

General Synthesis of Compounds of Type I:

The synthesis of key intermediate C from starting materials A and B is illustrated in Scheme 1.

Scheme 1

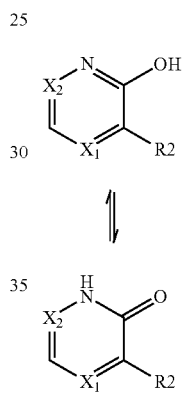

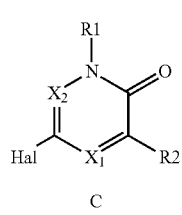

C

Starting materials A (e.g. $X_1$, $X_2$=CH, $G_1$=OH, Hal=Br), B (e.g. $X_1$,$X_2$=CH, $R_2$=CH$_3$, Hal=Br; $X_1$=CH, $X_2$=C—CH$_3$, $R_2$=CH$_3$, Hal=Br; $X_1$=C—CH$_3$, $X_2$=CH, $R_2$=CH$_3$, Hal=Br; $X_1$=N, $X_2$=CH, $R_2$=CH$_3$, Hal=Br; $X_1$, $X_2$=CH, $R_2$=CHF$_2$, Hal=Br; $X_1$, $X_2$=CH, $R_2$=CF$_3$, Hal=Br; $X_1$=CH, $X_2$=N, $R_2$=CH$_3$, Hal=Cl) or C (e.g. $R^2$=$X_1$,$X_2$=CH, $R_2$=H, Hal=Br; $X_1$=CH, $X_2$=N, $R_2$=H, Hal=Br) are commercially available.

Starting from A ($X_1$, $X_2$=CH, $G_1$=OH, Hal=Br), benzylation of alcohol G1 leads to intermediate B ($R_2$=OBn). Starting from B, alkylation of nitrogen amide leads to intermediate C (eg. introduction of $R_1$=CH$_3$ by deprotonation of the nitrogen amide with a base and reaction with CH$_3$I).

The synthesis of key intermediate C from starting materials D is illustrated in Scheme 2.

Scheme 2

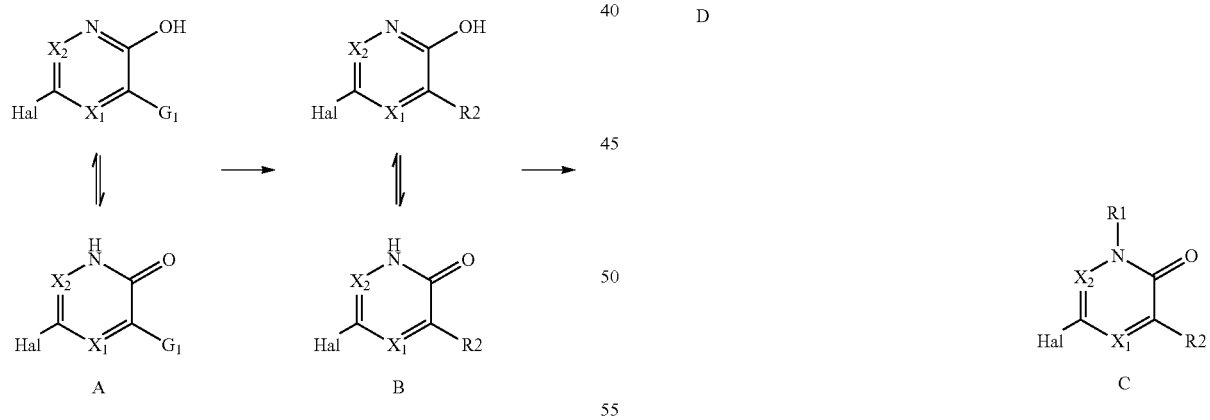

D

E

C

Starting materials D (e.g. $X_1$, $X_2$=CH, $R_2$=CH$_3$; $X_1$=CH, $X_2$=C—CH$_3$, $R_2$=H) are commercially available.

Starting from D, alkylation leads to E (eg. introduction of $R_1$=CH$_3$ by deprotonation of the nitrogen amide with a base and reaction with CH$_3$I). Compound C can be synthesized by electrophilic halogenation of intermediate E (eg. introduction of Br using NBS or introduction of I using NIS).

The synthesis of key intermediate C from starting materials F is illustrated in Scheme 3.

Scheme 3

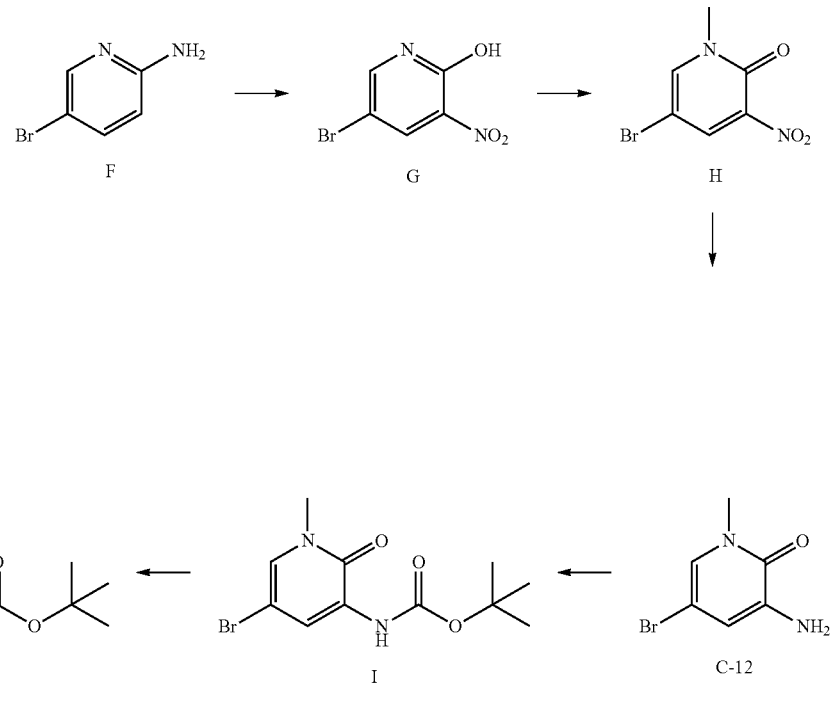

Starting material F is commercially available

Starting from F, nitration leads to intermediate G, alkylation of nitrogen amide gives compound H (eg. introduction of $R_1=CH_3$ by deprotonation of the nitrogen amide with a base and reaction with $CH_3I$). Reduction of the nitro group gives intermediate C12. Di-Boc protection followed by mono-Boc cleavage leads to intermediate I, which is then alkylated to give intermediate C13.

The synthesis of key intermediate J from intermediate C is illustrated in Scheme 4.

Scheme 4

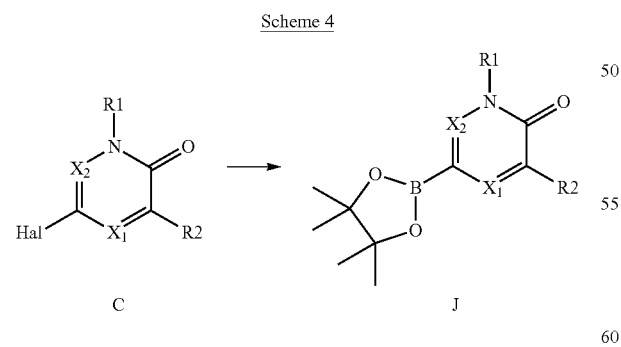

Compound J can be synthesized by palladium catalyzed borylation of the corresponding halogenated starting material C.

The synthesis of compounds of formula (I) from key intermediate C, J, K and L is illustrated in Scheme 5 and Scheme 6.

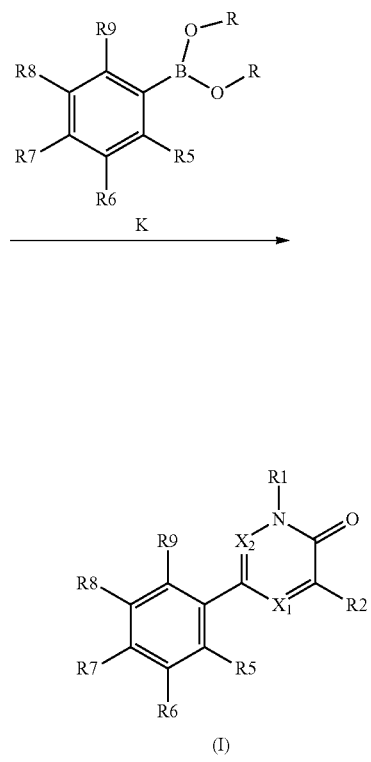

Scheme 6

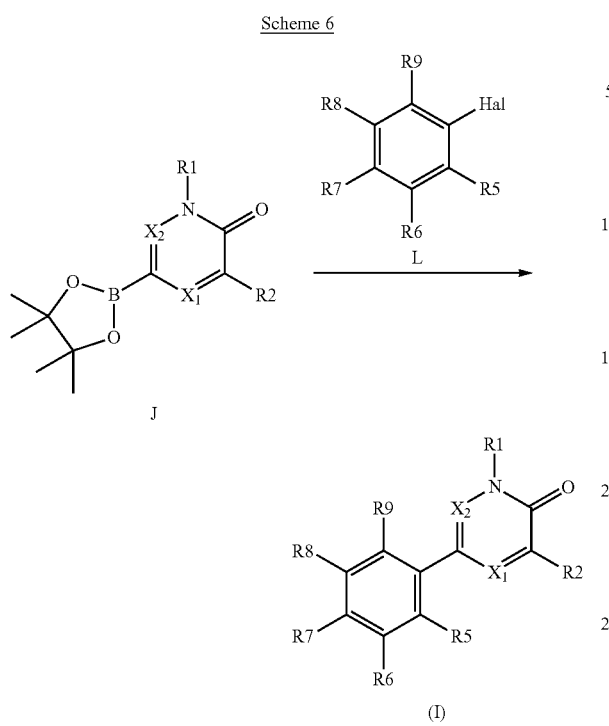

Compound (I) can be synthesized by metal catalyzed Suzuki cross-coupling of the corresponding halogenated starting material C and L with the boronic acid or ester K and J, respectively.

General Synthesis of Compounds of Type II

The synthesis of key intermediate Q from starting materials O and P is illustrated in Scheme 7.

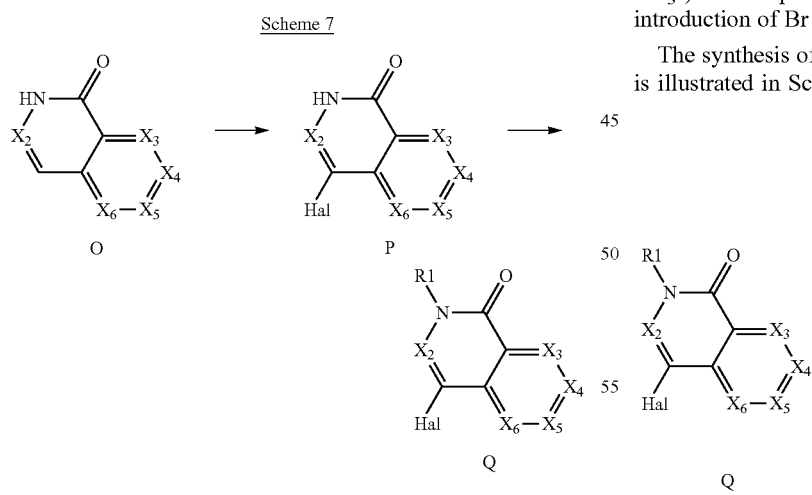

Starting materials O (e.g. $X_2$, $X_3$, $X_4$, $X_5$=CH, $X_6$=C—CH$_3$; $X_2$, $X_3$, $X_4$, $X_6$=CH, $X_5$=N; $X_2$, $X_3$, $X_4$, $X_5$=CH, $X_6$=C—F), P (e.g. $X_2$, $X_3$, $X_4$, $X_5$, $X_6$=CH, Hal=Br; $X_3$, $X_4$, $X_5$, $X_6$=CH, $X_2$=N, Hal=Br; $X_2$, $X_4$, $X_5$, $X_6$=CH, $X_3$=N, Hal=Br; $X_2$, $X_3$, $X_5$, $X_6$=CH, $X_4$=N, Hal=Br; $X_2$, $X_3$, $X_4$, $X_5$=CH, $X_6$=N, Hal=Br; $X_2$, $X_3$, $X_5$=CH, $X_4$, $X_6$=N, Hal=Br) are commercially available.

Starting from O, electrophilic halogenation leads to intermediate P (eg. introduction of Br using PyHBr$_3$ or NBS, introduction of I using I$_2$). Alkylation of nitrogen amide leads to intermediate Q (eg. introduction of R$_1$=CH$_3$ by deprotonation of the nitrogen amide with a base and then reaction with CH$_3$I).

The synthesis of key intermediate Q from starting materials O and R is illustrated in Scheme 8.

Scheme 8

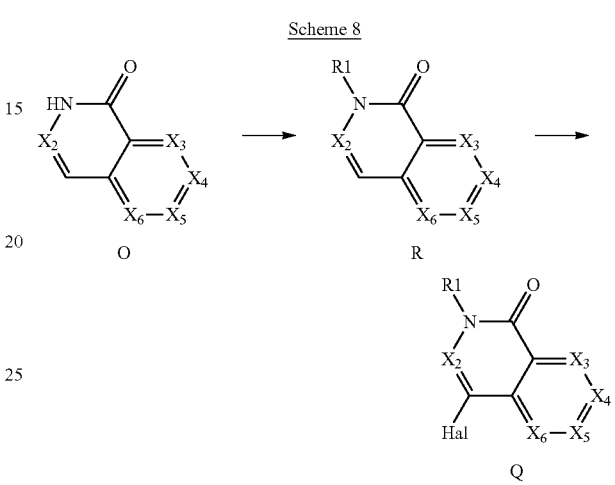

Starting materials O (e.g. $X_2$, $X_3$, $X_4$, $X_5$, $X_6$=CH; $X_2$, $X_3$, $X_4$, $X_5$=CH, $X_6$=C—OCH$_3$; $X_2$, $X_3$, $X_5$, $X_6$=CH, $X_4$=C—NO$_2$), R (e.g. $X_2$, $X_3$, $X_4$, $X_5$=CH, $X_6$=C—NO$_2$; R$_1$=CH$_3$; $X_2$, $X_3$, $X_4$, $X_6$=CH, $X_5$=C—Br; R$_1$=CH$_3$) are commercially available.

Starting from O, alkylation of nitrogen amide leads to intermediate R (eg. introduction of R$_1$=CH$_3$ by deprotonation of the nitrogen amide with a base and then reaction with CH$_3$I). Electrophilic halogenation of intermediate R (eg. introduction of Br using NBS or Br$_2$) gives intermediate Q.

The synthesis of key intermediate S from intermediate Q is illustrated in Scheme 9.

Scheme 9

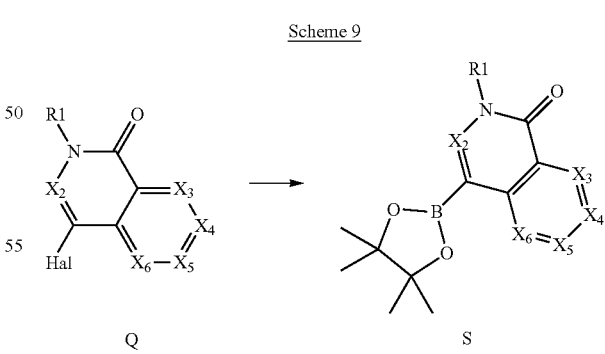

Compound S can be synthesized by palladium catalyzed borylation of the corresponding halogenated starting material Q.

The synthesis of compounds of formula (II) from key intermediate Q, S, K and L is illustrated in Scheme 10 and Scheme 11.

Scheme 10
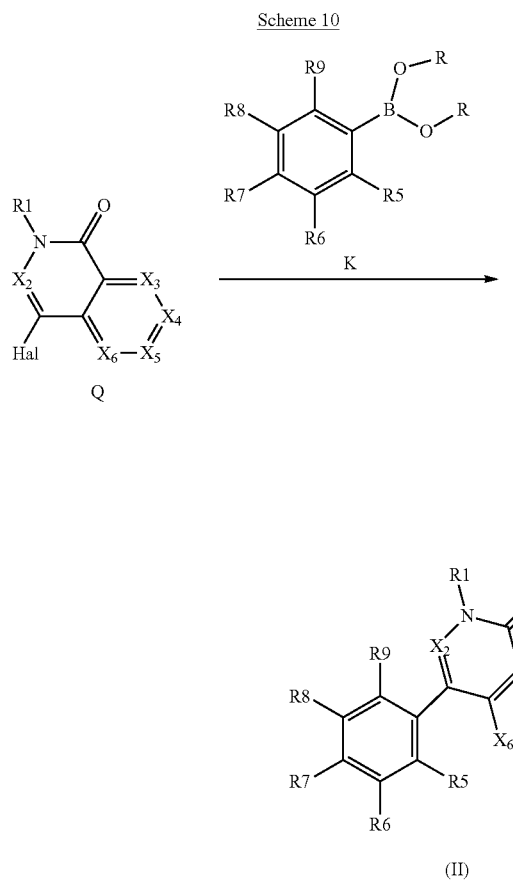
Scheme 11
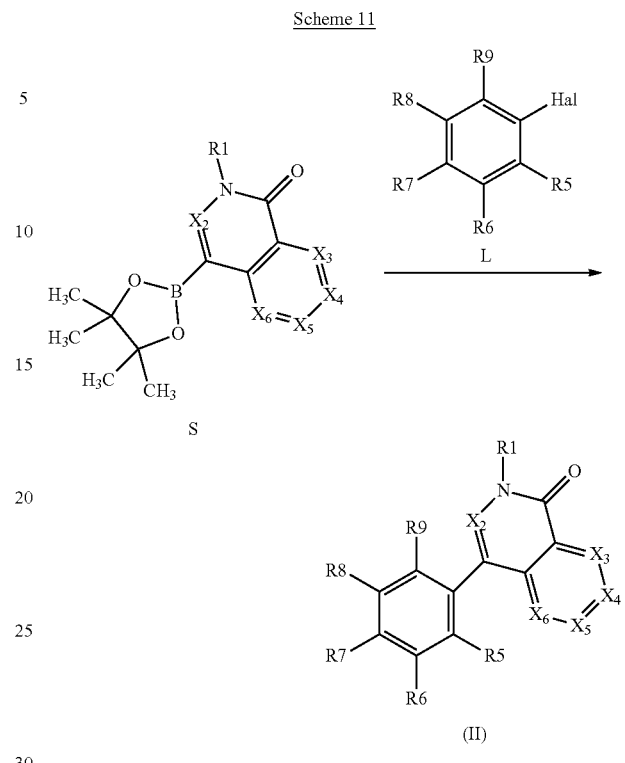
Compound (II) can be synthesized by metal catalyzed Suzuki cross-coupling of the corresponding halogenated starting material Q and L with the boronic acid or ester K and S, respectively.
General Synthesis of Compounds of Type III
The synthesis of key intermediate W and X from starting materials T is illustrated in Scheme 12.
Scheme 12
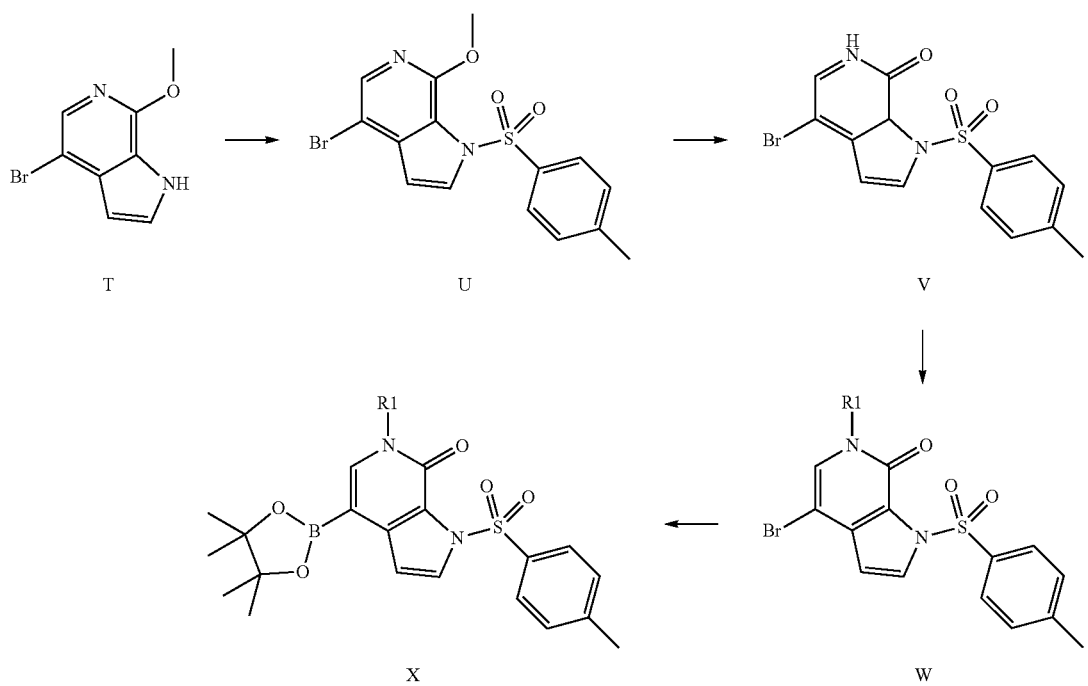

Tosylation of commercially available compound T leads to intermediate U, which is demethylated under acidic conditions. Intermediate W can be synthesized by alkylation of the nitrogen amide of V (eg. introduction of $R_1=CH_3$ by deprotonation of the nitrogen amide with a base and then reaction with $CH_3I$). Finally palladium catalyzed borylation of compound W leads to intermediate X.

The synthesis of compounds of type III from key intermediate W, X, K and L is illustrated in Scheme 13 and Scheme 14.

Scheme 13

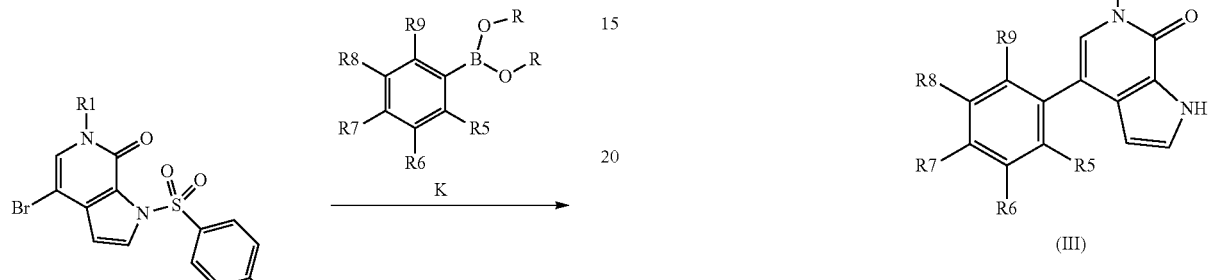

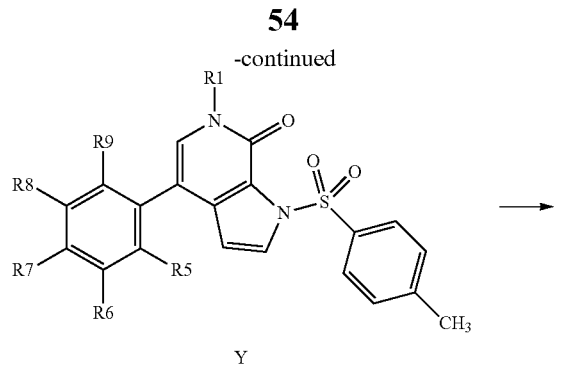

Compound (III) can be synthesized by metal catalyzed Suzuki cross-coupling of the corresponding halogenated starting material W and L with the boronic acid or ester K and X, respectively.

Preparation of Compounds of Type I
Preparation of Intermediate C-1

5-Bromo-1,3-dimethyl-1H-pyridin-2-one

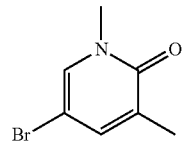

Reaction scheme

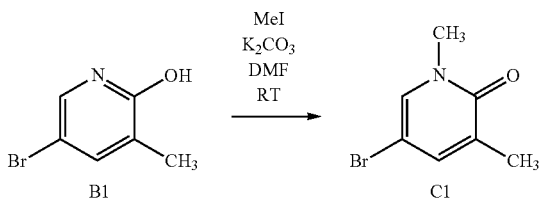

Scheme 14

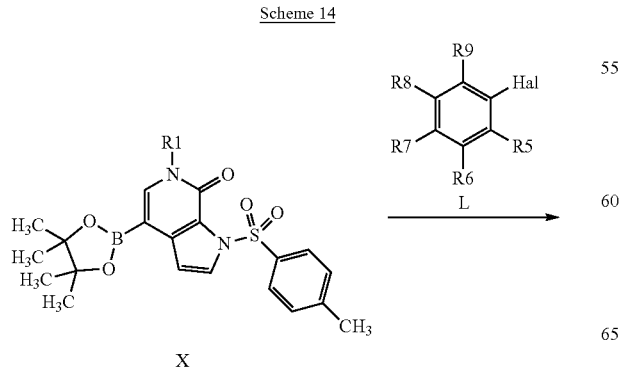

5-Bromo-1,3-dimethyl-1H-pyridin-2-one C-1

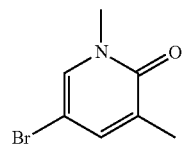

To a suspension of 5-bromo-2-hydroxy-3-methyl pyridine B1 (1.000 g; 5.053 mmol) and potassium carbonate (1.397 g; 10.105 mmol) in DMF (5.0 mL) is carefully added iodomethane (0.346 mL; 5.558 mmol). The reaction mixture is stirred at RT overnight (16 h). The reaction mixture is then quenched with 10% ammonia solution (10.0 mL) and water (30.0 mL) is added. The mixture is extracted with EtOAc (3×50.0 mL). The combined organic layer is dried with $Na_2SO_4$, filtered and concentrated under reduced pressure to afford the product. HPLC-MS: $(M+H)^+=202/204$; $t_{Ret}=0.65$ min; method M1

Preparation of Intermediate C-7

3-Benzyloxy-5-bromo-1-methyl-1H-pyridin-2-one

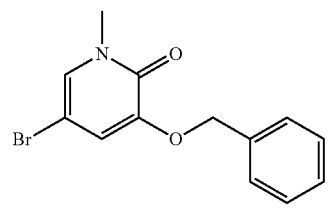

3-Benzyloxy-5-bromo-1,2-dihydro-pyridin-2-ol B-7

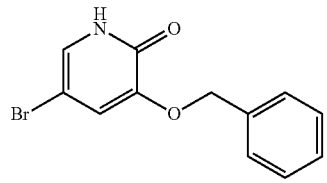 [SMILES: O=c1[nH]cc(Br)cc1OCc1ccccc1]

5-Bromo-3-hydroxy-1H-pyridin-2-one A-7 (500.0 mg; 2.630 mmol) is dissolved in DMF (5.0 mL). NaH (80.0 mg; 3.330 mmol) is added and the reaction mixture is stirred at RT for 2 h. Then bromomethylbenzene (500.0 mg; 2.920 mmol) is added and the solution is stirred at RT overnight. The reaction mixture is quenched with saturated $NH_4Cl$ and extracted with EtOAc. The combined organic layers are dried over $Na_2SO_4$, filtered and concentrated under reduced pressure to afford the desired compound.

HPLC-MS: $(M+H)^+=280/282$; $t_{Ret}=1.23$ min; method M7

3-Benzyloxy-5-bromo-1-methyl-1H-pyridin-2-one C-7

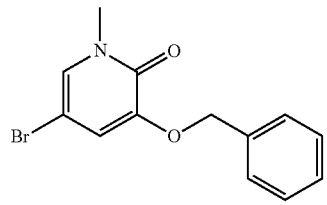 [SMILES: Cn1cc(Br)cc(OCc2ccccc2)c1=O]

Reaction scheme

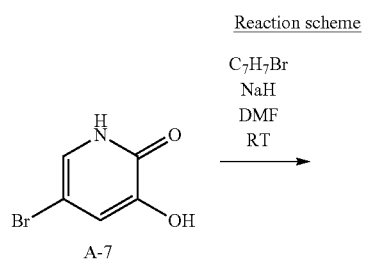

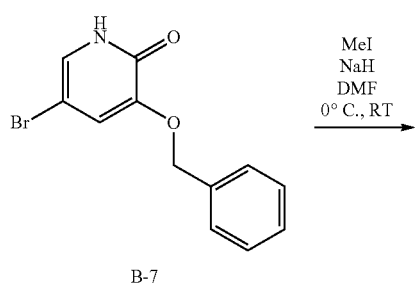

To a solution of 3-benzyloxy-5-bromo-1H-pyridin-2-one B-7 (260.0 mg; 0.930 mmol) in DMF (5.0 mL) is added NaH (75.0 mg; 3.130 mmol) at 0° C. The reaction mixture is stirred at RT for 1 h. MeI (160.0 mg; 1.13 mmol) is then added. The solution is stirred at RT for 2 h. The reaction mixture is poured into ice water and extracted with EtOAc. The combined organic layers are dried over $Na_2SO_4$, filtered and concentrated under reduced pressure to give the desired compound.

HPLC-MS: $(M+H)^+=294/296$

Preparation of Intermediate C-10

5-Bromo-1-cyclopropyl-3-methyl-1H-pyridin-2-one

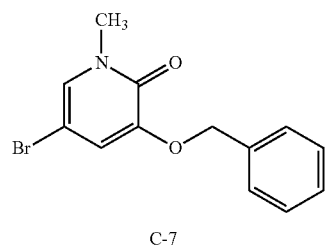

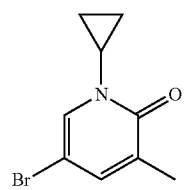

Reaction scheme

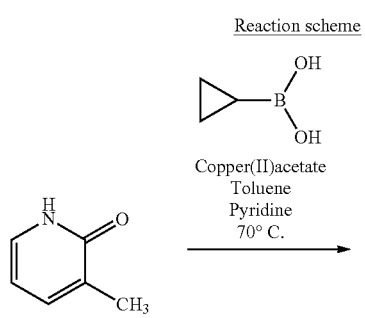

1-Cyclopropyl-3-methyl-1H-pyridin-2-one E10

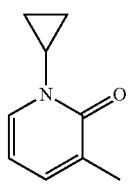

3-Methyl-1H-pyridin-2-one D-10 (100.0 mg; 0.916 mmol), cycloboronic acid (236.1 mg; 2.749 mmol) and copper(II)acetate (166.5 mg; 0.92 mmol) are introduced into a microwave vial. Pyridine (0.250 mL; 3.161 mmol) and toluene (1.0 mL) are added and the vial is heated at 70° C. overnight. The reaction mixture is diluted with 5.0 mL of 2N aqueous HCl. Then EtOAc (10.0 mL) is added and the precipitate is filtered off. The phases are separated and the aqueous layer is extracted with EtOAc (3×10.0 mL). The combined organic layers are dried over $Na_2SO_4$, filtered and concentrated under reduced pressure. The crude material is purified by silica chromatography Combiflash (Column Redisep Rf, 12 g; gradient: DCM/MeOH=100%/0% to 95%/5%; detection wavelength: 214 nm). The product containing fractions are combined and concentrated under reduced pressure to give the desired compound.

HPLC-MS: $(M+H)^+=150$; $t_{Ret}=0.48$ min; method M1

5-Bromo-1-cyclopropyl-3-methyl-1H-pyridin-2-one C-10

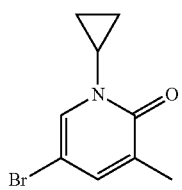

To a solution of 1-cyclopropyl-3-methyl-1H-pyridin-2-one E-10 (100.0 mg; 0.670 mmol) in chloroform (1.0 mL), NBS (119.3 mg; 0.67 mmol) is added and the solution is stirred at RT for 2 h. The crude material is purified by silica chromatography Combiflash (Column Redisep Rf, 12 g; gradient: DCM/MeOH=100%/0% to 95%/5% over 28 column volumes; flow rate=30 mL/min; detection wavelength: 254 nm). The product containing fractions are combined and concentrated under reduced pressure to give the desired compound.

HPLC-MS: $(M+H)^+=228/230$; $t_{Ret}=0.88$ min; method M1

Preparation of Intermediate C-11

3,5-Diiodo-1,6-dimethyl-1H-pyridin-2-one

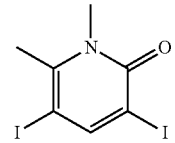

Reaction scheme

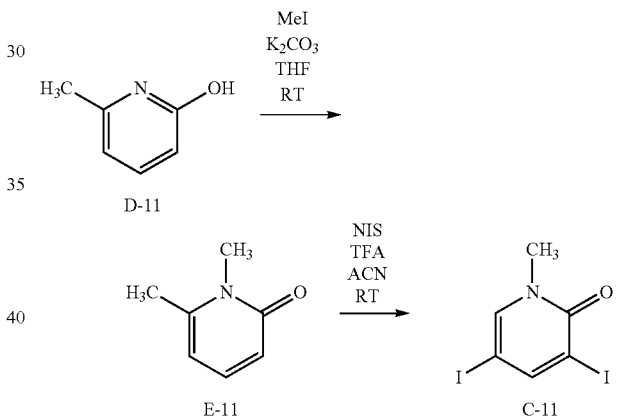

1,6-Dimethyl-1H-pyridin-2-one E-11

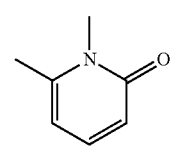

Iodomethane (0.430 mL; 6.780 mmol) is added carefully to a suspension of 6-methyl-pyridin-2-ol D-11 (500.0 mg; 4.44 mmol) and potassium carbonate (1.228 g; 8.889 mmol) in THF (40.0 mL). The reaction mixture is stirred at RT overnight (16 h). The resulting mixture is quenched with 10% ammonia solution (30.0 mL) and extracted twice with DCM. The combined organic layers are dried over $Na_2SO_4$, filtered and concentrated under reduced pressure to afford the product.

HPLC-MS: $(M+H)^+=124$; $t_{Ret}=0.114$ min; method M3

3,5-Diiodo-1,6-dimethyl-1H-pyridin-2-one C-11

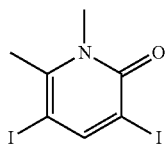

A solution of 1,6-dimethyl-1H-pyridin-2-one E-11 (250.0 mg; 2.030 mmol) and NIS (1004.8 mg; 4.47 mmol) in ACN (5.0 mL) is treated with TFA (48 µL; 0.620 mmol). The reaction mixture is stirred in a closed vessel, impervious to light, at RT for 15 h. The crude material is concentrated under reduced pressure, dissolved in DCM (10.0 mL), washed with aqueous $Na_2S_2O_3$ (10.0 mL) and 1N NaOH (10.0 mL). The organic layer is dried over $Na_2SO_4$, filtered and concentrated under reduced pressure to afford the desired compound.

HPLC-MS: $(M+H)^+=375$; $t_{Ret}=1.01$ min; method M1

Preparation of Intermediate C-12

3-Amino-5-bromo-1-methyl-1H-pyridin-2-one

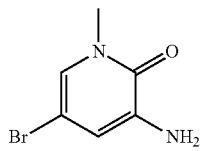

Reaction scheme

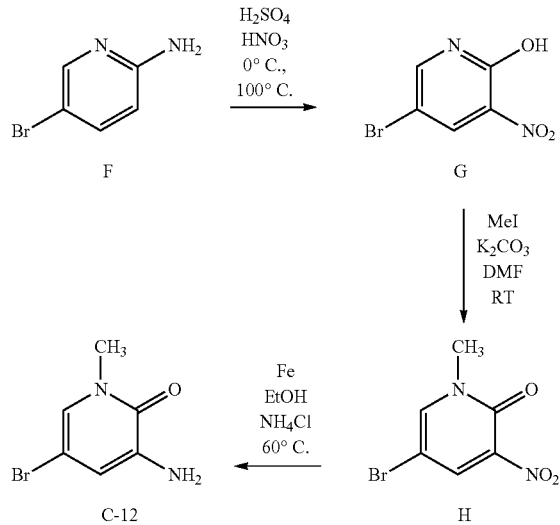

5-Bromo-3-nitro-pyridin-2-ol G

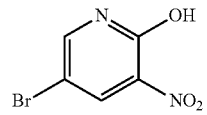

To a solution of concentrated $H_2SO_4$ (150 mL; 0.12 mol) and fuming concentrated $HNO_3$ (100 mL; 0.10 mol) at 0° C. is added 5-bromo-pyridin-2-ylamine F (40.0 g; 0.23 mol) over a period of 1 h. The resulting mixture is heated to 100° C. for 1 day. The reaction mixture is then allowed to cool to RT and poured on crushed ice. The crude material is extracted with DCM (5×200 mL), the combined organic layers are dried over $Na_2SO_4$, filtered and the solvent is removed under reduced pressure to afford the desired compound as a solid.

5-Bromo-1-methyl-3-nitro-1H-pyridin-2-one H

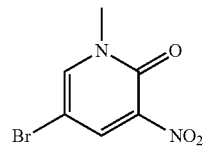

A 1-L round-bottomed flask equipped with a magnetic stirrer is purged with nitrogen, then charged with 5-bromo-3-nitro-pyridin-2-ol G (20.0 g; 0.09 mol), DMF (200 mL) and $K_2CO_3$ (25.2 g; 0.18 mol). The suspension is stirred for 15 min at RT, MeI (14.3 g; 0.10 mol) is added and the mixture is stirred at RT for 18 h. The reaction mixture is diluted with water and extracted with EtOAc (3×200.0 mL). The combined extracts are washed with brine, dried with $Na_2SO_4$, filtered, and concentrated under reduced pressure. The residue is purified by silica gel chromatography.

HPLC-MS: $(M+H)^+=233/235$; $t_{Ret}=0.828$ min; method M7

3-Amino-5-bromo-1-methyl-1H-pyridin-2-one C-12

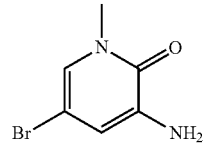

Iron powder (21.6 g; 0.39 mol) is added to a suspension of 5-bromo-1-methyl-3-nitro-1H-pyridin-2-one H (18.0 g; 0.08 mol) in EtOH (120.0 mL) and saturated aqueous $NH_4Cl$ (60.0 mL) at 60° C. The reaction is stirred at 60° C. for 2 h. The reaction mixture is then filtered and the solid residue on the filter is washed with EtOAc. The filtrate is concentrated under reduced pressure and extracted with EtOAc (3×100.0 mL). The combined extracts are washed with brine, dried with $Na_2SO_4$, filtered and concentrated. The residue is purified by column chromatography to afford the desired compound.

HPLC-MS: (M+H)⁺=203/205; t_Ret=1.248 min; method M11

Preparation of Intermediate C-13

(5-Bromo-1-methyl-2-oxo-1,2-dihydro-pyridin-3-yl)-methyl-carbamic acid tert-butyl ester

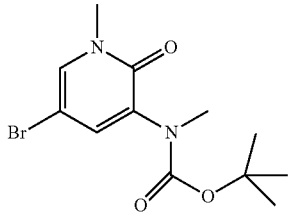 [SMILES: CN(C(=O)OC(C)(C)C)c1cc(Br)cn(C)c1=O]

Reaction scheme

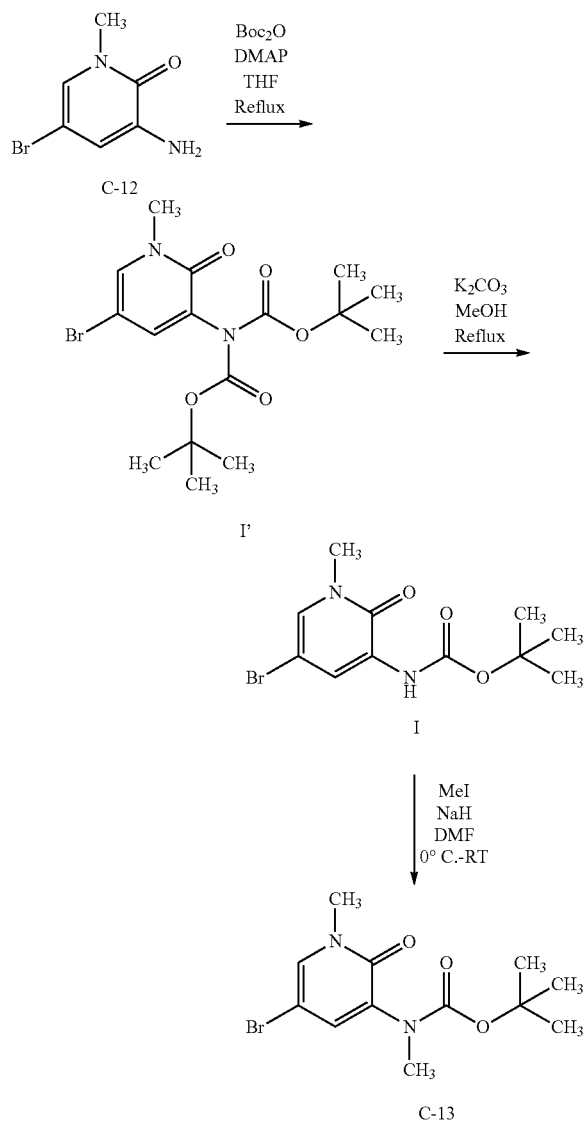

(5-Bromo-1-methyl-2-oxo-1,2-dihydro-pyridin-3-yl)-dicarbamic acid tert-butyl ester I'

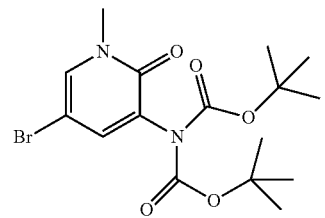 [SMILES: Cn1cc(Br)cc(N(C(=O)OC(C)(C)C)C(=O)OC(C)(C)C)c1=O]

To a solution of 3-amino-5-bromo-1-methyl-1H-pyridin-2-one C-12 (1000 mg; 4.93 mmol) in THF (50.0 mL) is added Boc₂O (1.074 g; 4.93 mmol) and DMAP (1.803 g; 14.78 mmol). The resulting mixture is refluxed overnight. The crude material is poured onto ice water and extracted with EtOAc, the combined organic layers are washed with brine, dried with Na₂SO₄, filtered and concentrated under reduced pressure to afford the residue.

(5-Bromo-1-methyl-2-oxo-1,2-dihydro-pyridin-3-yl)-carbamic acid tert-butyl ester I

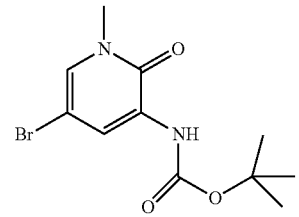 [SMILES: Cn1cc(Br)cc(NC(=O)OC(C)(C)C)c1=O]

K₂CO₃ (1026.613 mg; 7.44 mmol) is added to a solution of (5-bromo-1-methyl-2-oxo-1,2-dihydro-pyridin-3-yl)-dicarbamic acid tert-butyl ester I' (1000.0 mg; 2.48 mmol) in MeOH (50.0 mL). The reaction mixture is refluxed for 5 h and the solution is poured into ice water and extracted with EtOAc. The combined organic layers are washed with brine, dried with Na₂SO₄, filtered and concentrated under reduced pressure to afford the residue which is purified by prep-HPLC to yield the product.

HPLC-MS: (M+H)⁺=247/249

(5-Bromo-1-methyl-2-oxo-1,2-dihydro-pyridin-3-yl)-methyl-carbamic acid tert-butyl ester C-13

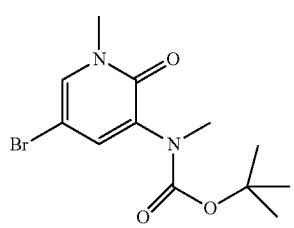 [SMILES: CN(C(=O)OC(C)(C)C)c1cc(Br)cn(C)c1=O]

To a solution of (5-bromo-1-methyl-2-oxo-1,2-dihydro-pyridin-3-yl)-carbamic acid tert-butyl ester (110 mg; 0.36 mmol) in DMF is added 60% NaH at 0° C. The mixture is stirred for 1 h, then MeI (61.4 mg; 0.44 mmol) is added and the solution is stirred at RT for 3 h. The resulting mixture is poured into ice water and extracted with EtOAc. The combined organic layers are washed with brine, dried with Na$_2$SO$_4$, filtered and concentrated under reduced pressure to afford the residue which is purified by prep-TLC to yield the desired compound.

HPLC-MS: (M+H)$^+$=261/263; t$_{Ret}$=1.304 min; method M7 According to the procedure of C-1 the intermediates C-2-C-6 are synthesized. According to the procedure of C-7 the intermediates C-8 and C-9 are synthesized with the exception of omitting the alkylation step A→B (intermediates B-8 and B-9 are commercially available). Intermediates C-14 and C-15 are commercially available.

| # | Structure | MS (M + H)+ | tRet. HPLC [min] | HPLC-Method |
|---|---|---|---|---|
| C-1 | | 202/204 | 0.650 | M1 |
| C-2 | | 216/218 | 0.422 | M4 |
| C-3 | | 216/218 | 0.409 | M1 |
| C-4 | | 216/218 | 0.840 | M1 |
| C-5 | | 203/205 | 0.203 | M4 |
| C-6 | | 159/161 | 0.520 | M1 |
| C-7 | | 294/296 | | |
| C-8 | 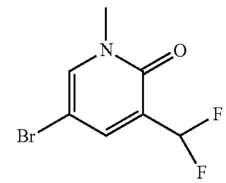 | 238/240 | 1.042 | M7 |
| C-9 | 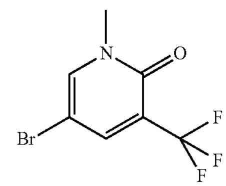 | 256/258 | 0.856 | M7 |
| C-10 | 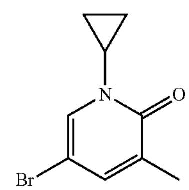 | 228/230 | 0.880 | M1 |
| C-11 | 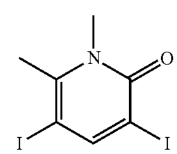 | 375 | 1.010 | M1 |
| C-12 | 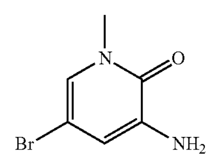 | 203/205 | 1.248 | M11 |
| C-13 | 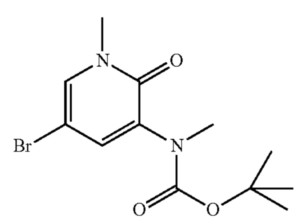 [SMILES: CN(C(=O)OC(C)(C)C)c1cc(Br)cn(C)c1=O] | 261/263 | 1.304 | M7 |
| C-14 | 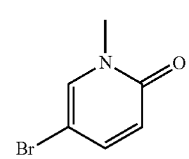 | commercially available | | |
| C-15 | 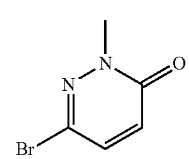 | commercially available | | |

Preparation of intermediate J-1

1,3-Dimethyl-5-(4,4,5,5-tetramethyl-[1,3,2]dioxaborolan-2-yl)-1H-pyridin-2-one

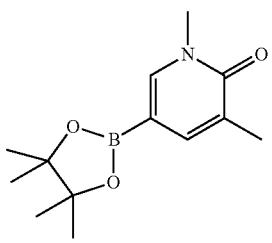

Reaction scheme

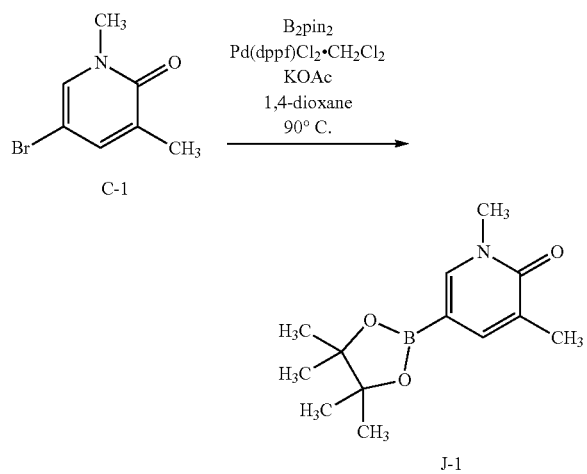

1,3-Dimethyl-5-(4,4,5,5-tetramethyl-[1,3,2]dioxaborolan-2-yl)-1H-pyridin-2-one J-1

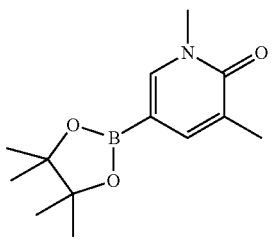

5-Bromo-1,3-dimethyl-1H-pyridin-2-one C-1 (10.0 g; 48.0 mmol), bis(pinacolato)diboron (16.0 g; 63.0 mmol), 1,1'-bis(diphenylphosphino)ferrocene-palladium(II) dichloride, dichlormethane (2.00 g; 2.376 mmol) and potassium acetate (9.423 g; 96.016 mmol) are introduced into a flask. 1,4-Dioxane (100.0 mL) is added and the flask is flushed with argon. The reaction is heated to 90° C. for 3 h. A second portion of bis(pinacolato)diboron (1.200 g; 4.726 mmol) is added and the solution is stirred for an additional 30 min. The reaction mixture is then cooled to RT and filtered through a plug of celite, washed with dioxane (2×100.0 mL).

The filtrate is concentrated under reduced pressure. The residue is then dissolved in DCM (200.0 mL) and washed with water (1×100.0 mL). The water layer is extracted DCM (1×100.0 mL). The combined organic layer is dried with Na$_2$SO$_4$, filtered and concentrated under reduced pressure. The crude material is purified by silica gel chromatography Combiflash (Column Redisep Rf, 330 g; gradient: cyclohexane/EtOAc=100%/0% to 0%/100% over 16 column volumes; flow rate=200 mL/min; detection wavelength: 254 nm). The product containing fractions are combined and concentrated under reduced pressure. The remaining catalyst is filtered off and washed with ethyl acetate. The filtrate is concentrated under reduced pressure to give the desired product as an oil, which crystallizes upon standing.

HPLC-MS: (M+H)$^+$=250; t$_{Ret}$=0.96 min; method M1

According to the procedure of J-1 the intermediates J-2-J-6 are synthesized.

| # | Structure | MS (M + H)+ | tRet. HPLC [min] | HPLC-Method |
|---|---|---|---|---|
| J-1 | 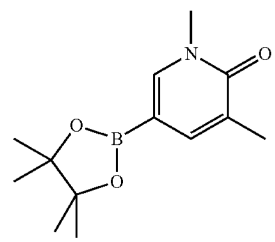 | 250 | 0.960 | M1 |
| J-2 | 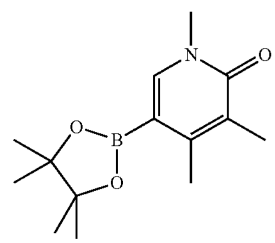 | 264 | 0.638 | M4 |
| J-3 | 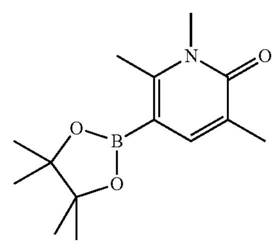 | 264 | 0.628 | M1 |
| J-4 | 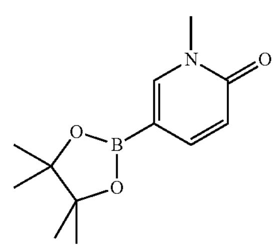 [SMILES: Cn1cc(B2OC(C)(C)C(C)(C)O2)ccc1=O] | 236 | 0.194 | M1 |

-continued
| # | Structure | MS (M + H)+ | tRet. HPLC [min] | HPLC-Method |
|---|---|---|---|---|
| J-5 | 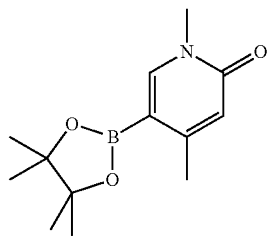 [SMILES: Cc1cc(=O)n(C)cc1B1OC(C)(C)C(C)(C)O1] | 250 | 0.528 | M1 |
| J-6 | 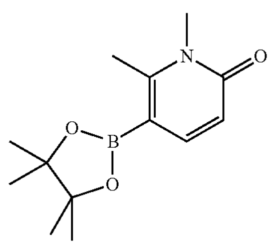 [SMILES: Cc1c(B2OC(C)(C)C(C)(C)O2)ccc(=O)n1C] | 250 | 0.552 | M1 |
General Method for Preparation of Compounds of Type (I)
Method 1:
Preparation of Compound I-1
1,3-Dimethyl-5-[4-((R)-1-pyrrolidin-1-yl-ethyl)-phenyl]-1H-pyridin-2-one
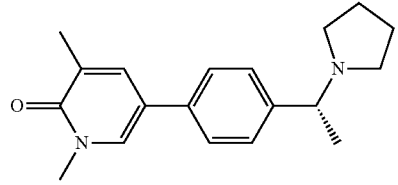 [SMILES: Cc1cc(-c2ccc([C@@H](C)N3CCCC3)cc2)cn(C)c1=O]
And Preparation of Compound I-2
1,3-Dimethyl-5-[4-((S)-1-pyrrolidin-1-yl-ethyl)-phenyl]-1H-pyridin-2-one
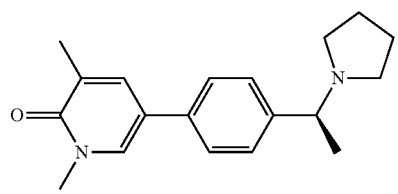 [SMILES: Cc1cc(-c2ccc([C@H](C)N3CCCC3)cc2)cn(C)c1=O]
Reaction scheme
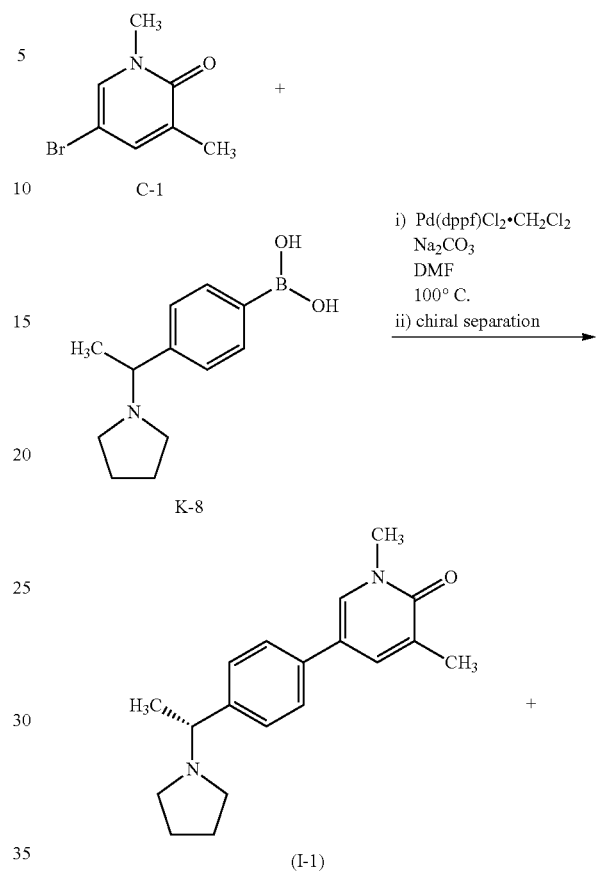
1,3-Dimethyl-5-[4-((R)-1-pyrrolidin-1-yl-ethyl)-phenyl]-1H-pyridin-2-one (I-1)
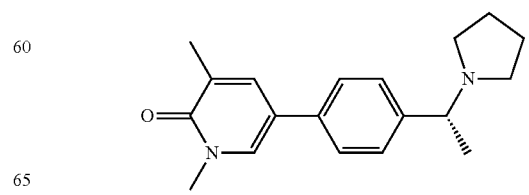

and 1,3-dimethyl-5-[4-((S)-1-pyrrolidin-1-yl-ethyl)-phenyl]-1H-pyridin-2-one (I-2)

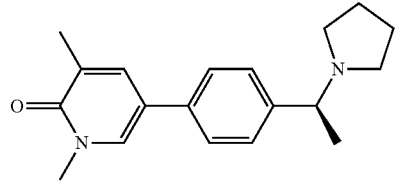 [SMILES: Cc1cc(-c2ccc([C@H](C)N3CCCC3)cc2)cn(C)c1=O]

In a vial 5-bromo-1,3-dimethyl-1H-pyridin-2-one C-1 (138.3 mg; 0.685 mmol), [4-(1-pyrrolidin-1-ylethyl)phenyl] boronic acid K-8 (150.0 mg; 0.685 mmol) and 1,1'-bis(diphenylphosphino)ferrocenepalladium(II) dichloride, dichloromethane (57.6 mg; 0.068 mmol) are weight in. N,N-Dimethylformamide (0.8 mL) and 2N sodium bicarbonate solution (0.856 mL; 1.711 mmol) are added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are concentrated under reduced pressure. A chiral separation is performed (JASCO SFC, column: Chiralpak AD 200×10 mm; 5 µm, mobile phase: MeOH/$CO_2$=40/60). The product containing fractions are pooled and evaporated, then re-dissolved in acetonitrile/water 1:1 and freeze dried.

(Note: The absolute configuration of the enatiomerically pure products I-1 and I-2 is randomly assigned)

1,3-Dimethyl-5-[4-((S)-1-pyrrolidin-1-yl-ethyl)-phenyl]-1H-pyridin-2-one I-1

HPLC-MS: $(M+H)^+$=297; $t_{Ret}$=1.05 min; method M1 LC Chiral LC AD MeOH/$CO_2$ F1 40/60 ee>99%

1,3-Dimethyl-5-[4-((R)-1-pyrrolidin-1-yl-ethyl)-phenyl]-1H-pyridin-2-one I-2

HPLC-MS: $(M+H)^+$=297; $t_{Ret}$=1.05 min; method M1 LC Chiral LC AD MeOH/$CO_2$ F2 40/60 ee>99%

Method 2:
Preparation of Compound I-23

N-[5-(1,5-Dimethyl-6-oxo-1,6-dihydro-pyridin-3-yl)-2-methyl-phenyl]-methanesulfonamide

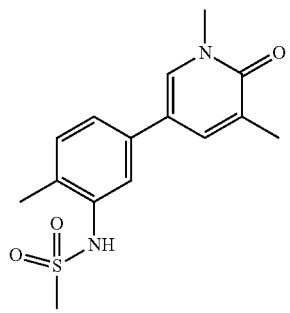 [SMILES: Cc1ccc(-c2cc(C)c(=O)n(C)c2)cc1NS(C)(=O)=O]

Reaction scheme

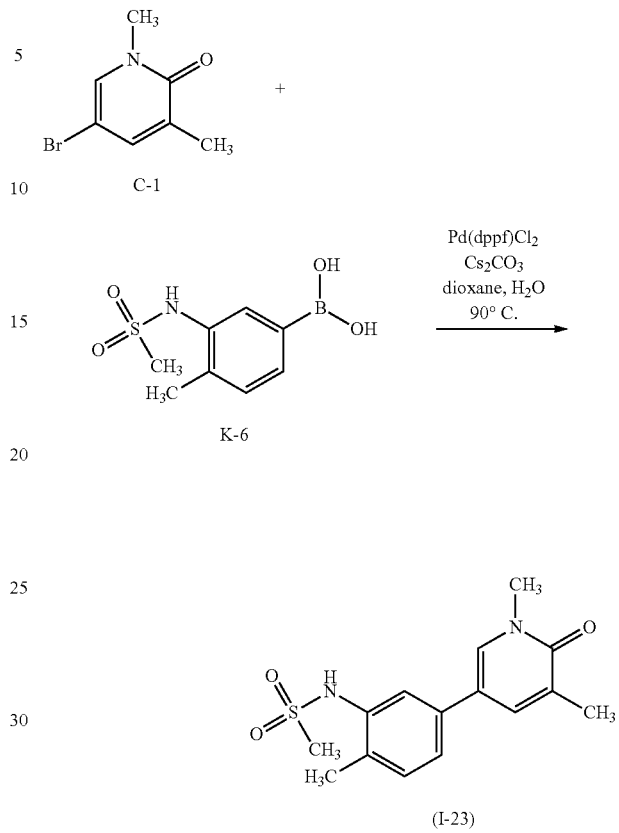

N-[5-(1,5-Dimethyl-6-oxo-1,6-dihydro-pyridin-3-yl)-2-methyl-phenyl]-methanesulfonamide (I-23)

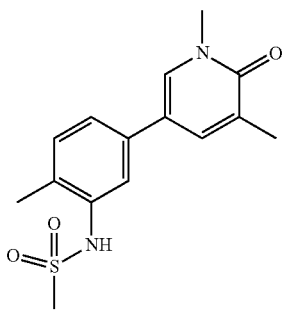 [SMILES: Cc1ccc(-c2cc(C)c(=O)n(C)c2)cc1NS(C)(=O)=O]

To a solution of 5-bromo-1,3-dimethyl-1H-pyridin-2-one C-1 (100.0 mg; 0.495 mmol) in dioxane (4.0 mL) and $H_2O$ (1.0 mL) is added successively [3-(methanesulfonamido)-4-methyl-phenyl]boronic acid K-6 (113.4 mg; 0.495 mmol), $Cs_2CO_3$ (322.5 mg; 0.990 mmol) and Pd(dppf)$Cl_2$ (80.8 mg; 0.099 mmol), the reaction mixture is stirred at 90° C. under $N_2$ for 2 h. The mixture is poured onto ice water, extracted with EtOAc, washed with water and brine, dried over $Na_2SO_4$, filtered and concentrated to give the crude product which is purified by Prep-HPLC to yield the title product.

HPLC-MS: $(M+H)^+$=307.0; $t_{Ret}$=2.181 min; method M11

Method 3:
Preparation of Compound I-30

4-(1,5-Dimethyl-6-oxo-1,6-dihydro-pyridin-3-yl)-N-(1-methyl-piperidin-4-yl)-benzamide

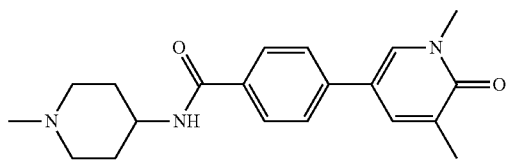 [SMILES: Cc1cc(-c2ccc(C(=O)NC3CCN(C)CC3)cc2)cn(C)c1=O]

Reaction scheme

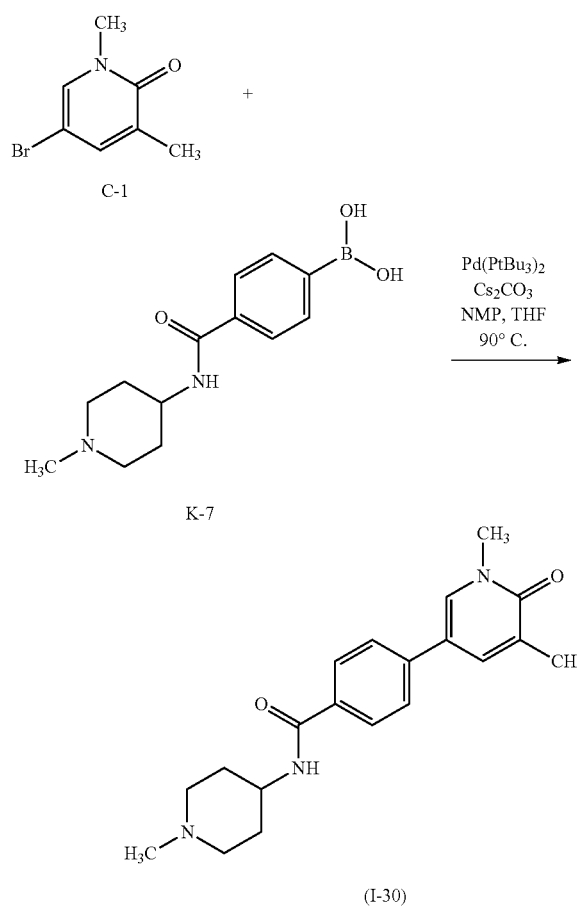

(I-30)

4-(1,5-Dimethyl-6-oxo-1,6-dihydro-pyridin-3-yl)-N-(1-methyl-piperidin-4-yl)-benzamide (I-30)

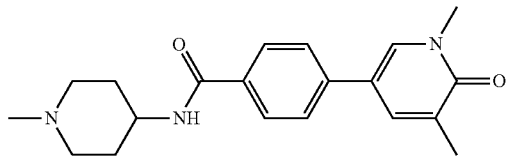 [SMILES: Cc1cc(-c2ccc(C(=O)NC3CCN(C)CC3)cc2)cn(C)c1=O]

[4-[(1-methyl-4-piperidyl)carbamoyl]phenyl]boronic acid K-7 (104.8 mg; 0.400 mmol), 5-bromo-1,3-dimethyl-pyridin-2-one C-1 (83.3 mg; 0.400 mmol), cesium carbonate (260.6 mg; 0.800 mmol) and bis(tri-tert-butylphosphine)palladium(0) (40.9 mg; 0.080 mmol) are suspended in THF/NMP (0.6 mL/0.3 mL). The reaction mixture is flushed with argon, sealed and stirred at 90° C. for 1 h. The reaction mixture is then filtered and purified with the basic (ammonia buffer) RP HPLC system (column: YMC TriaRT C-18 20×50 mm). The product containing fractions are concentrated under reduced pressure. The product is dissolved in acetonitrile/water 1:1 and freeze dried.

HPLC-MS: (M+H)$^+$=340; $t_{Ret}$=0.81 min; method M1

Method 4:
Preparation of Compound I-31

N-[3-(1,5-Dimethyl-6-oxo-1,6-dihydro-pyridin-3-yl)-phenyl]-methanesulfonamide

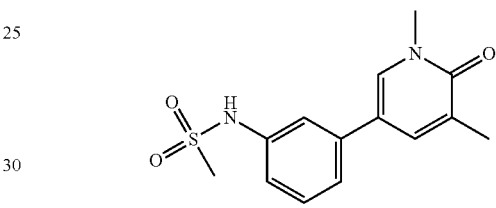

Reaction scheme

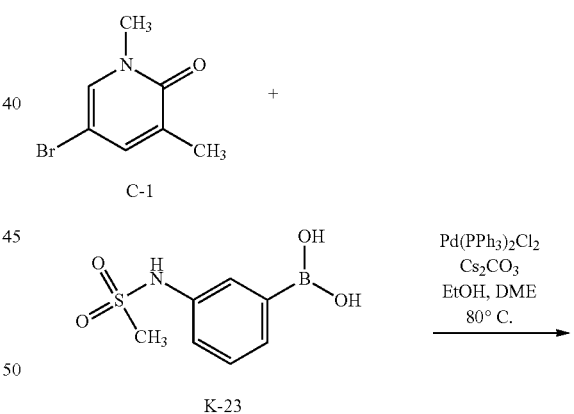

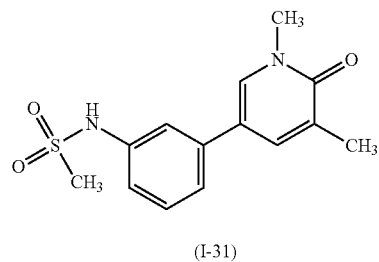

(I-31)

73

N-[3-(1,5-Dimethyl-6-oxo-1,6-dihydro-pyridin-3-yl)-phenyl]-methanesulfonamide (I-31)

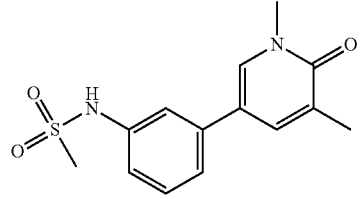 [SMILES: Cc1cc(-c2cccc(NS(C)(=O)=O)c2)cn(C)c1=O]

5-bromo-1,3-dimethyl-pyridin-2-one C-1 (100.0 mg; 0.495 mmol), [3-(methanesulfonamido)phenyl]boronic acid K-23 (127.7 mg; 0.594 mmol), bis(triphenylphosphine)palladium dichloride (17.4 mg; 0.025 mmol) and CsCO₃ solution 2M (0.495 mL; 0.990 mmol) are dissolved in DME/MeOH (2.0 mL/0.5 mL) flushed with argon and stirred at 80° C. for 18 h. Solvent is removed and the residue is dissolved in DMSO, filtered and purified by RP HPLC (Waters Sunfire 19×50 mm, HCOOH).

HPLC-MS: (M+H)$^+$=293; $t_{Ret}$=0.68 min; method M1

Method 5:

Preparation of Compound I-32

N-[2-Methyl-5-(1-methyl-5-methylamino-6-oxo-1,6-dihydro-pyridin-3-yl)-phenyl]-methanesulfonamide

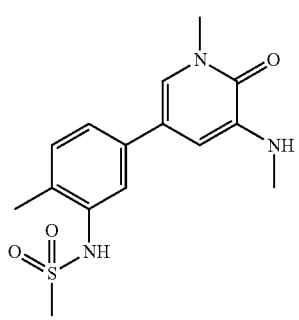

Reaction scheme

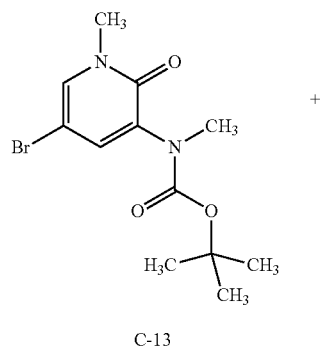

C-13

+

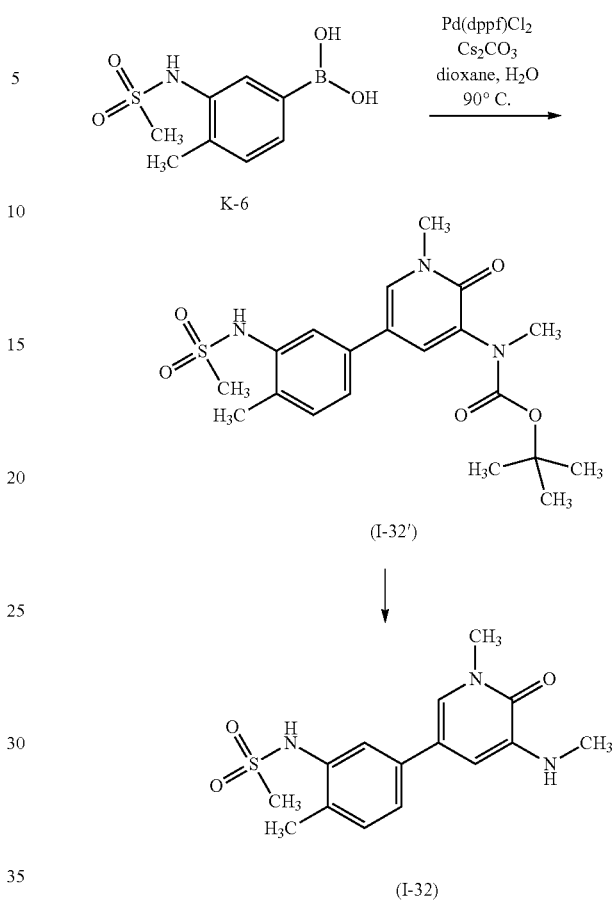

(I-32')

↓

(I-32)

[5-(3-Methanesulfonylamino-4-methyl-phenyl)-1-methyl-2-oxo-1,2-dihydro-pyridin-3-yl]-methyl-carbamic acid tert-butyl ester (I-32')

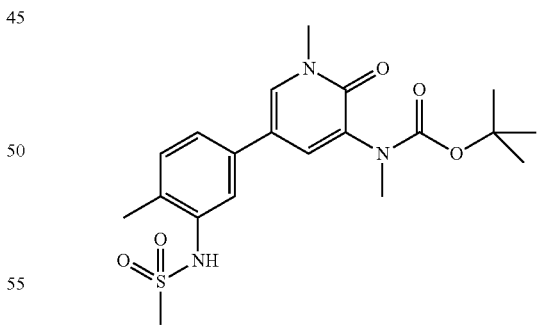

To a solution of tert-butyl N-(5-bromo-1-methyl-2-oxo-3-pyridyl)-N-methyl-carbamate (78.0 mg; 0.246 mmol) in dioxane (4.0 mL) and H₂O (1.0 mL) is added successively [3-(methanesulfonamido)-4-methyl-phenyl]boronic acid (56.3 mg; 0.246 mmol), cesium carbonate (160.2 mg; 0.492 mmol) and [1,1'-bis(diphenylphosphino)ferrocene]dichloropalladium(II) (40.2 mg; 0.049 mmol). The reaction mixture is stirred at 90° C. under N2 for 2 h. The mixture is poured onto ice water, extracted with EtOAc, washed with water and brine dried over Na$_2$SO$_4$, filtered and concentrated to give the crude product which is purified by Prep-HPLC to yield the title product.

Structure confirmed by $^1$H NMR

N-[2-Methyl-5-(1-methyl-5-methylamino-6-oxo-1,6-dihydro-pyridin-3-yl)-phenyl]-methanesulfonamide (I-32)

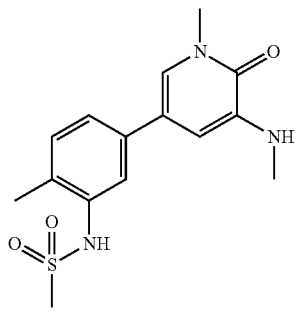

tert-Butyl N-[5-[3-(methanesulfonamido)-4-methyl-phenyl]-1-methyl-2-oxo-3-pyridyl]-N-methyl-carbamate I-32' (210.0 mg; 0.498 mmol) is stirred at reflux for 6 h in a solution of 4N HCl in dioxane (20.323 mL; 81.292 mmol). The precipitated is collected by filtration, washed with dioxane to give the title product.

HPLC-MS: (M+H)$^+$=322.0; t$_{Ret}$=2.546 min; method M10

Method 6:

Preparation of Compound I-33

1,3-Dimethyl-5-(3-methyl-4-piperazin-1-ylmethyl-phenyl)-1H-pyridin-2-one

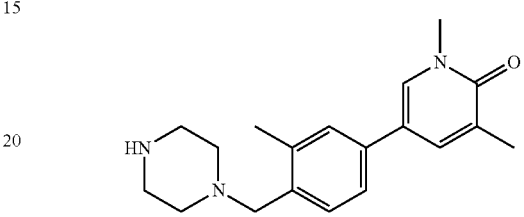

Reaction scheme

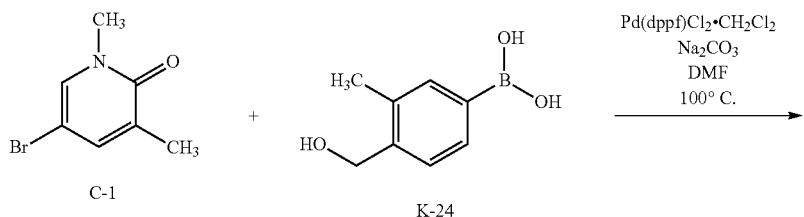

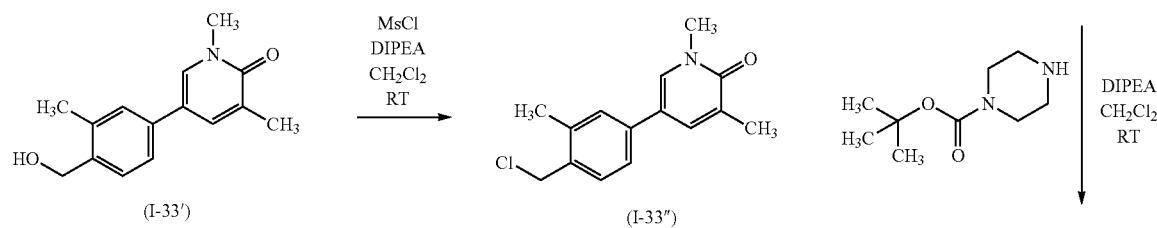

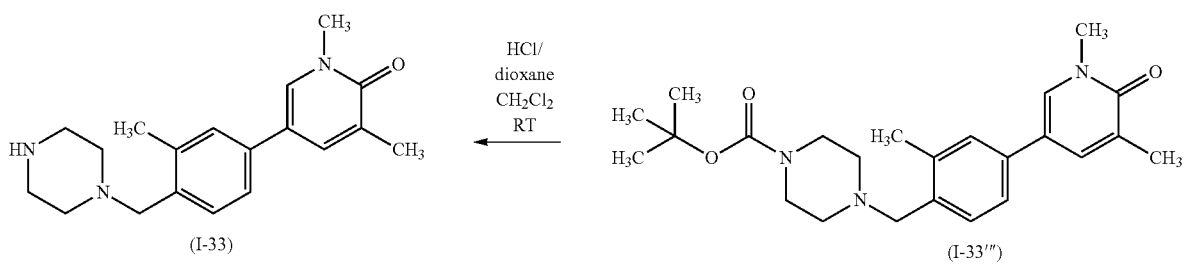

5-(4-Hydroxymethyl-3-methyl-phenyl)-1,3-dimethyl-1H-pyridin-2-one (I-33')

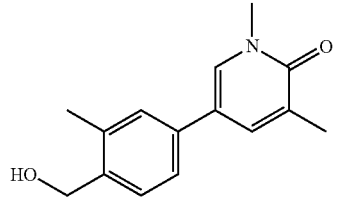 [SMILES: Cc1cc(-c2cc(C)c(=O)n(C)c2)ccc1CO]

In a vial 5-bromo-1,3-dimethyl-1H-pyridin-2-one C-1 (1.00 g; 5.78 mmol) [4-(1-pyrrolidin-1-ylethyl)phenyl]boronic acid K-24 (1.17 g; 5.78 mmol) and 1,1'-bis(diphenylphosphino)ferrocenepalladium(II) dichloride, dichloromethane (472.3 mg; 0.578 mmol) are weight in. N,N-dimethylformamide (5.0 mL) and 2N sodium bicarbonate solution (7.23 mL; 14.5 mmol) are added. The vial is flushed with argon and sealed. The reaction mixture is heated at 100° C. for 1 h. The reaction mixture is diluted with water and extracted with DCM (3×30.0 mL). The combined organic layers are dried with Na$_2$SO$_4$, filtered and concentrated under reduced pressure. The crude material is purified by silica gel chromatography Combiflash (Column Redisep Rf, 40 g; gradient: cyclohexane/EtOAc=100%/0% to 0%/100% over 41 column volumes; flow rate=40 mL/min; detection wavelength: 254 nm). The product containing fractions are combined and concentrated under reduced pressure.

HPLC-MS: (M+H)$^+$=244; t$_{Ret}$=0.99 min; method M1

5-(4-Chloromethyl-3-methyl-phenyl)-1,3-dimethyl-1H-pyridin-2-one (I-33")

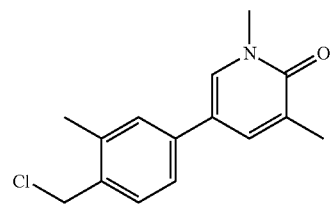 [SMILES: Cc1cc(-c2cc(C)c(=O)n(C)c2)ccc1CCl]

To a solution of 5-(4-hydroxymethyl-3-methyl-phenyl)-1,3-dimethyl-1H-pyridin-2-one I-33' (100.0 mg; 0.411 mmol) in dry dichloromethane (1.0 mL) and DIPEA (0.215 mL; 1.233 mmol), methanesulfonyl chloride (0.048 mL; 0.617 mmol) is added dropwise. The mixture is stirred at RT overnight. The reaction is quenched with water and extracted 3 times with DCM. The combined organic layers are dried with Na$_2$SO$_4$, filtered and concentrated under reduced pressure.

HPLC-MS: (M+H)$^+$=244; t$_{Ret}$=0.98 min; method M1

4-[4-(1,5-Dimethyl-6-oxo-1,6-dihydro-pyridin-3-yl)-2-methyl-benzyl]-piperazine-1-carboxylic acid tert-butyl ester (I-33''')

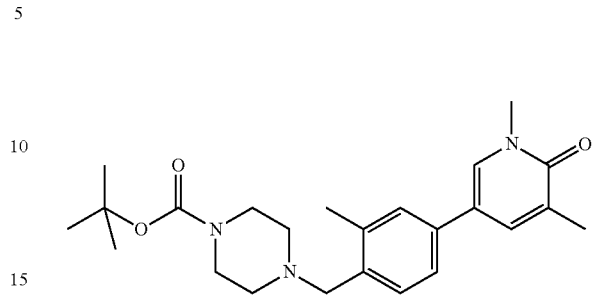

To a solution of 5-(4-chloromethyl-3-methyl-phenyl)-1,3-dimethyl-1H-pyridin-2-one I-33" (105.0 mg; 0.401 mmol) in DIPEA (0.200 mL; 1.146 mmol) and dry dichloromethane (1.0 mL), tert-butyl piperazine-1-carboxylate (213.4; 1.146 mmol) is added. The reaction mixture is stirred overnight at RT. The reaction mixture is extracted 3 times with DCM. The combined organic layers are dried with Na$_2$SO$_4$, filtered and concentrated under reduced pressure.

HPLC-MS: (M+H)$^+$=412.2; t$_{Ret}$=0.75 min; method M1

1,3-Dimethyl-5-(3-methyl-4-piperazin-1-ylmethyl-phenyl)-1H-pyridin-2-one (I-33)

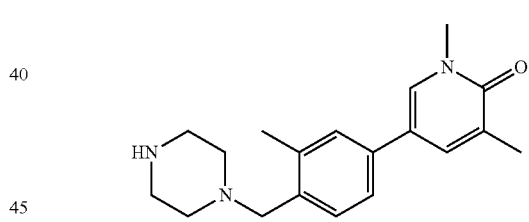

4-[4-(1,5-Dimethyl-6-oxo-1,6-dihydro-pyridin-3-yl)-2-methyl-benzyl]-piperazine-1-carboxylic acid tert-butyl ester I-33''' (150.0 mg; 0.364 mmol) is dissolved in DCM (3.0 mL), and 4N HCl in dioxane (2.0 mL) is added at RT. The reaction mixture is stirred at RT overnight. 1N NaOH is slowly added to the reaction mixture until it is basic. The mixture is extracted with DCM (3×10.0 mL). The combined organic layer is dried with Na$_2$SO$_4$, filtered and concentrated under reduced pressure. The crude product is dissolved in DMSO (1.0 mL) and purified with the basic (ammonia buffer) RP HPLC system (column: X-Bridge C-18 30×50 mm). The product containing fractions are concentrated under reduced pressure, the residue is then dissolved in acetonitrile:water 1:1 and freeze dried.

HPLC-MS: (M+H)$^+$=312; t$_{Ret}$=1.06 min; method M1

Method 7:
Preparation of Compound I-37
1,3-Dimethyl-5-[4-(piperazine-1-carbonyl)-phenyl]-1H-pyridin-2-one
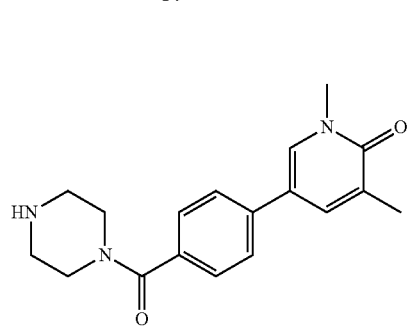
4-(1,5-Dimethyl-6-oxo-1,6-dihydro-pyridin-3-yl)-benzoic acid methyl ester I-37'
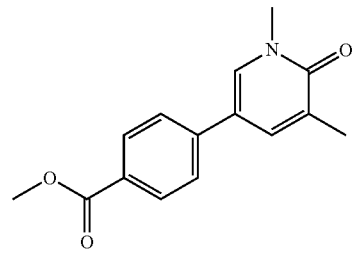 [SMILES: COC(=O)c1ccc(-c2cc(C)c(=O)n(C)c2)cc1]
To a solution of 5-bromo-1,3-dimethyl-1H-pyridin-2-one C-1 (10.0 g; 49.493 mmol) in dioxane/H₂O (50.0 mL/50.0 mL) are added (4-methoxycarbonylphenyl) boronic acid
Reaction scheme
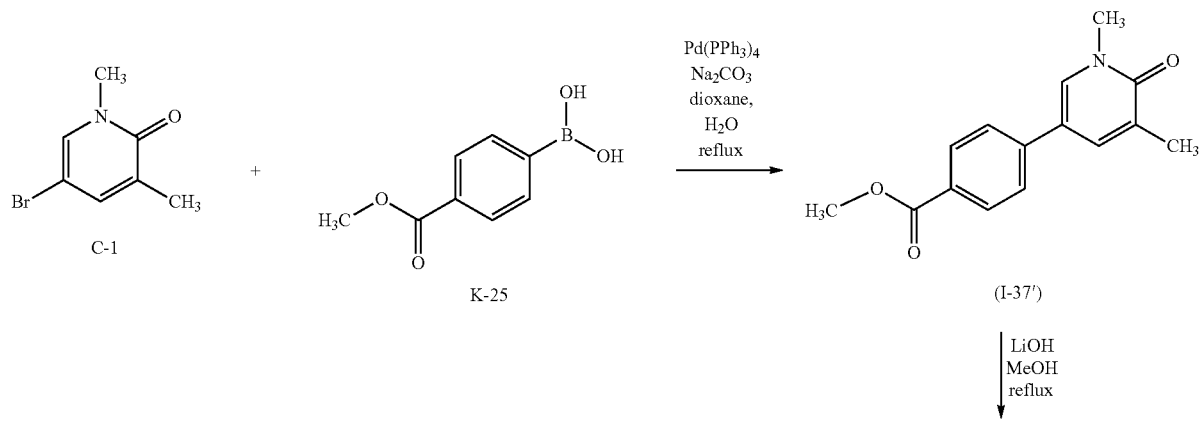
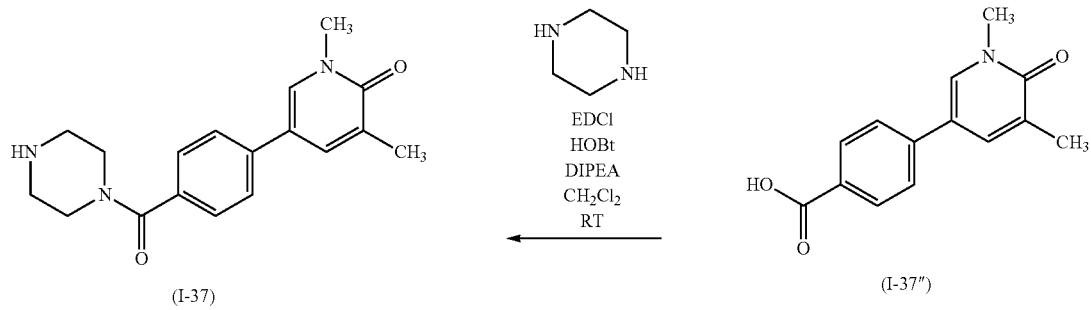

K-25 (10.7 g, 59.456 mmol), Pd(PPh$_3$)$_4$ (0.500 g, 0.433 mmol) and Na$_2$CO$_3$ (17.1 g, 161.321 mmol). The reaction mixture is stirred at reflux overnight. The mixture is filtered over celite and concentrated in vacuo. The residue is purified by NP silica gel chromatography with PE/EA (1:1) to give desired compound.

HPLC-MS: (M+H)$^+$=258; t$_{Ret}$=0.745 min; method M6

4-(1,5-Dimethyl-6-oxo-1,6-dihydro-pyridin-3-yl)-benzoic acid I-37"

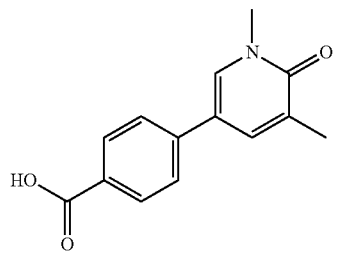 [SMILES: Cc1cc(-c2ccc(C(=O)O)cc2)cn(C)c1=O]

To a solution of 4-(1,5-dimethyl-6-oxo-1,6-dihydro-pyridin-3-yl)-benzoic acid methyl ester I-37' (5.200 g, 20.211 mmol) in MeOH (50.0 mL) is added LiOH (1.200 g, 50.000 mmol). The reaction mixture is stirred at reflux for 2 h. The reaction mixture is then concentrated under reduced pressure and water (50.0 mL) is added to the residue. The aqueous layer is extracted with EA (2×30.0 mL). The pH of the aqueous layer is adjusted to 3 and the formed precipitate is filtered off and dried for 45 h to give desired compound.

TLC Information (Silica, Eluent: DCM:MeOH=20:1); Rf (material)=0.7; Rf (product)=0.0

1,3-Dimethyl-5-[4-(piperazine-1-carbonyl)-phenyl]-1H-pyridin-2-one (I-37)

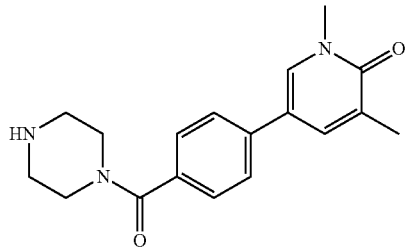 [SMILES: Cc1cc(-c2ccc(C(=O)N3CCNCC3)cc2)cn(C)c1=O]

To a solution of 4-(1,5-dimethyl-6-oxo-3-pyridyl)benzoic acid I-37" (200.0 mg, 0.822 mol) in DCM (5.0 mL) is added EDCI (211.0 mg, 1.227 mmol), HOBt (166.0 mg, 1.23 mmol), DIPEA (0.715 mL, 4.204 mmol) and the reaction mixture is stirred at RT for 0.5 h. Piperazine (85.0 mg, 0.987 mmol) is added and the reaction mixture is stirred at RT overnight. An aqueous solution of NH$_4$Cl (5.0 mL) is added. Phases are separated and the organic layer is washed with aqueous NaHCO$_3$ (10.0 mL) and brine (10.0 mL). The organic layer is dried over Na$_2$SO$_4$, filtered and concentrated in vacuo. The residue is then purified by NP silica gel chromatography with DCM/MeOH (10:1) to give the title product as a solid.

TLC Information (Silica, Eluent: DCM:MeOH=10:1); Rf (material)=0.1; Rf (product)=0.15

Method 8:

Preparation of Compound I-41

5-(4-Dimethylaminomethyl-3-ethyl-5-methoxy-phenyl)-1,3-dimethyl-1H-pyridin-2-one

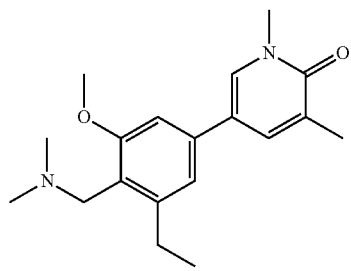

Reaction scheme

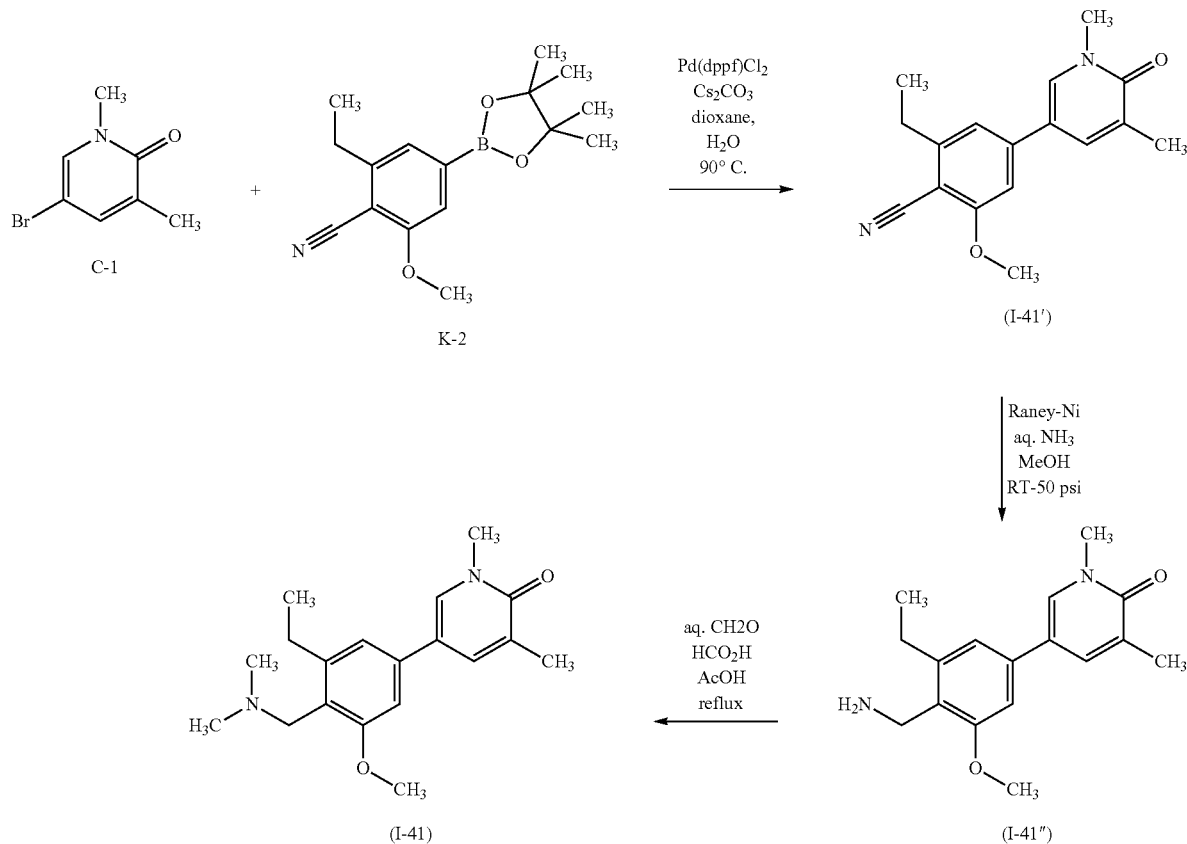

4-(1,5-Dimethyl-6-oxo-1,6-dihydro-pyridin-3-yl)-2-ethyl-6-methoxy-benzonitrile (I-41')

5-(4-Aminomethyl-3-ethyl-5-methoxy-phenyl)-1,3-dimethyl-1H-pyridin-2-one (I-41")

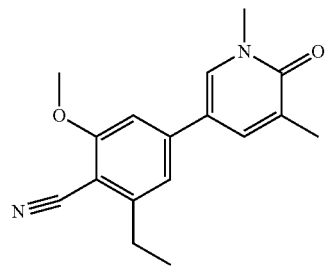 [SMILES: CCc1cc(-c2cc(C)c(=O)n(C)c2)cc(OC)c1C#N]

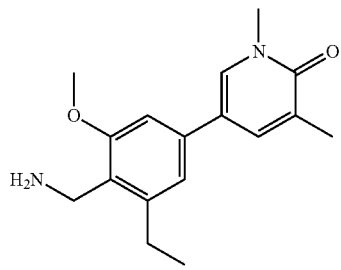 [SMILES: CCc1cc(-c2cc(C)c(=O)n(C)c2)cc(OC)c1CN]

To the solution of 2-ethyl-6-methoxy-4-(4,4,5,5-tetramethyl-1,3,2-dioxaborolan-2-yl)benzonitrile K-2 (570.0 mg; 1.985 mmol) and 5-bromo-1,3-dimethyl-pyridin-2-one C-1 (440.0 mg; 2.178 mmol) in dioxane (20.0 mL) and water (1.0 mL) is added Cs$_2$CO$_3$ (2.000 g; 6.154 mmol), then Pd(dppf)Cl2 (100.0 mg; 0.137 mmol). The mixture is heated to 90° C. for 2 h. The reaction is filtered over a pad of celite and the filtrate is concentrated. The residue is dissolved in EA, washed with brine.

The combined organic layers are dried with Na$_2$SO$_4$, filtered and concentrated under reduced pressure to give the crude product, which is purified with prep-HPLC.

HPLC-MS: (M+H)$^+$=283; $t_{Ret}$=1.363 min; method M7

To the solution of 4-(1,5-dimethyl-6-oxo-1,6-dihydro-pyridin-3-yl)-2-ethyl-6-methoxy-benzonitrile I-41' (350.0 mg; 1.240 mmol) in MeOH (20.0 mL) is added aq. NH$_3$ (1.0 mL) and Raney nickel catalyst (300.0 mg). The mixture is degassed and refilled with H$_2$ twice and stirred under 50 Psi at RT overnight. The reaction mixture is filter, washed with THF/MeOH and concentrated to give the desired compound. The crude material is used in the next step without purification.

HPLC-MS: (M+H)$^+$=283; $t_{Ret}$=1.363 min; method M7

5-(4-Dimethylaminomethyl-3-ethyl-5-methoxy-phenyl)-1,3-dimethyl-1H-pyridin-2-one (I-41)

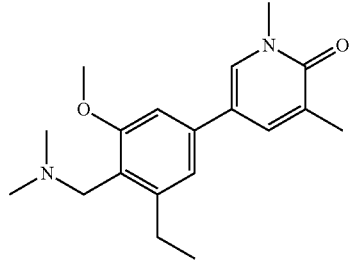

A mixture of 5-(4-aminomethyl-3-ethyl-5-methoxy-phenyl)-1,3-dimethyl-1H-pyridin-2-one I-41" (110.0 mg; 0.384 mmol), aq. CH$_2$O (0.100 mL) and formic acid (0.100 mL) in AcOH (2.0 mL) is heated to reflux overnight. The reaction mixture is concentrated and dissolved in MeOH for purification by prep-HPLC to give the desired compound.

Structure confirmed by $^1$H NMR

Method 9:

Preparation of Compound I-42

1,3-Dimethyl-5-{4-methyl-3-[(pyridin-3-ylmethyl)-amino]-phenyl}-1H-pyridin-2-one

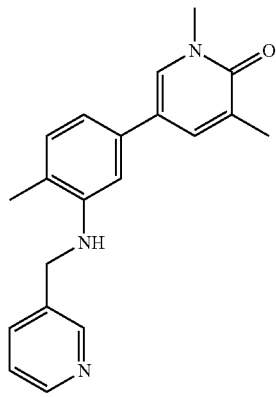

Reaction scheme

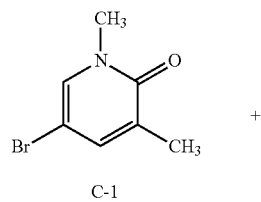

+

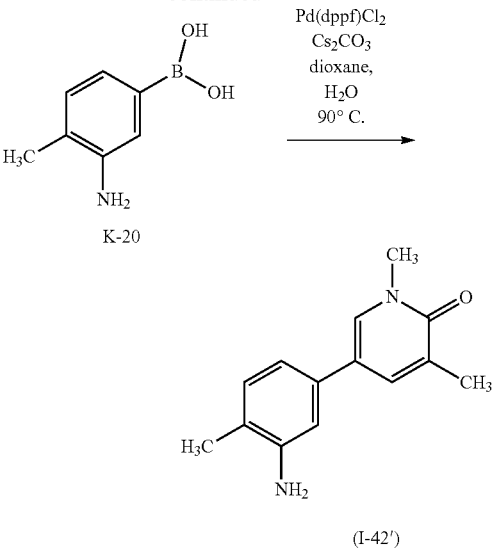

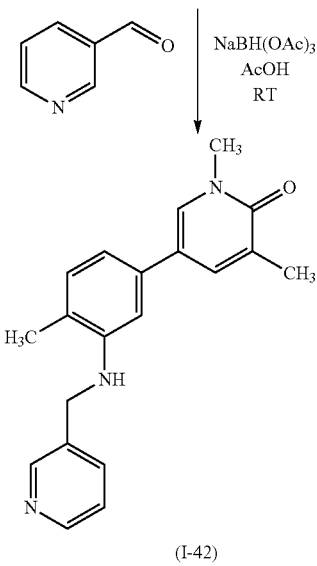

(I-42)

5-(3-Amino-4-methyl-phenyl)-1,3-dimethyl-1H-pyridin-2-one (I-42')

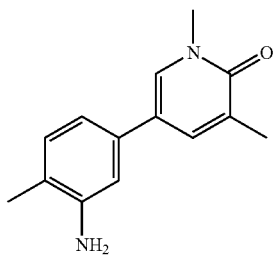

5-bromo-1,3-dimethyl-pyridin-2-one C-1 (7.000 g; 0.035 mol), (3-amino-4-methyl-phenyl)boronic acid K-20 (7.846 g; 0.052 mol), Cs$_2$CO$_3$ (33.883 g; 0.104 mol), Pd(dppf)$_2$Cl$_2$ (1.472 g; 0.002 mol) are dissolved in dioxane/H$_2$O=3:1 (50.0 mL) under N$_2$. The reaction mixture is heated to 90°

C. for 12 h. After the reaction is completed, the solvent is removed and water is added to the mixture. The mixture is extracted with DCM and the organic layer is washed with water and brine. The combined organic layers are dried with Na2SO4, filtered and concentrated under reduced pressure. The product is then purified by HPLC.

TLC Information (Silica, Eluent: PE:EA=1:2); Rf (product)=0.5

1,3-Dimethyl-5-{4-methyl-3-[(pyridin-3-ylmethyl)-amino]-phenyl}-1H-pyridin-2-one (I-42)

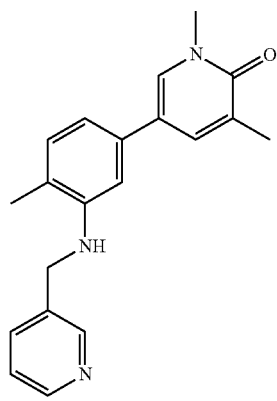

5-(3-Amino-4-methyl-phenyl)-1,3-dimethyl-1H-pyridin-2-one I-42' (0.200 g; 0.876 mmol) and pyridine-3-carbaldehyde (0.103 g; 0.964 mmol) are dissolved in AcOH (20.0 mL) and the mixture is stirred at RT for 12 h. Then NaBH(OAc)3 (0.375 g; 1.752 mmol) is added and it is stirred at RT for 5 h. The solvent is removed and the product is purified by prep-HPLC.

TLC Information (Silica, Eluent: PE:EA=1:1); Rf (product)=0.5

Method 10:

Preparation of Compound I-43

3-Iodo-1-methyl-5-[4-(4-methyl-piperazine-1-carbonyl)-phenyl]-1H-pyridin-2-one

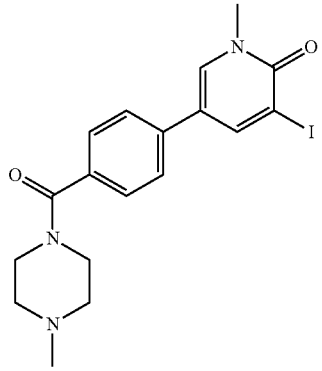 [SMILES: CN1CCN(C(=O)c2ccc(-c3cc(I)c(=O)n(C)c3)cc2)CC1]

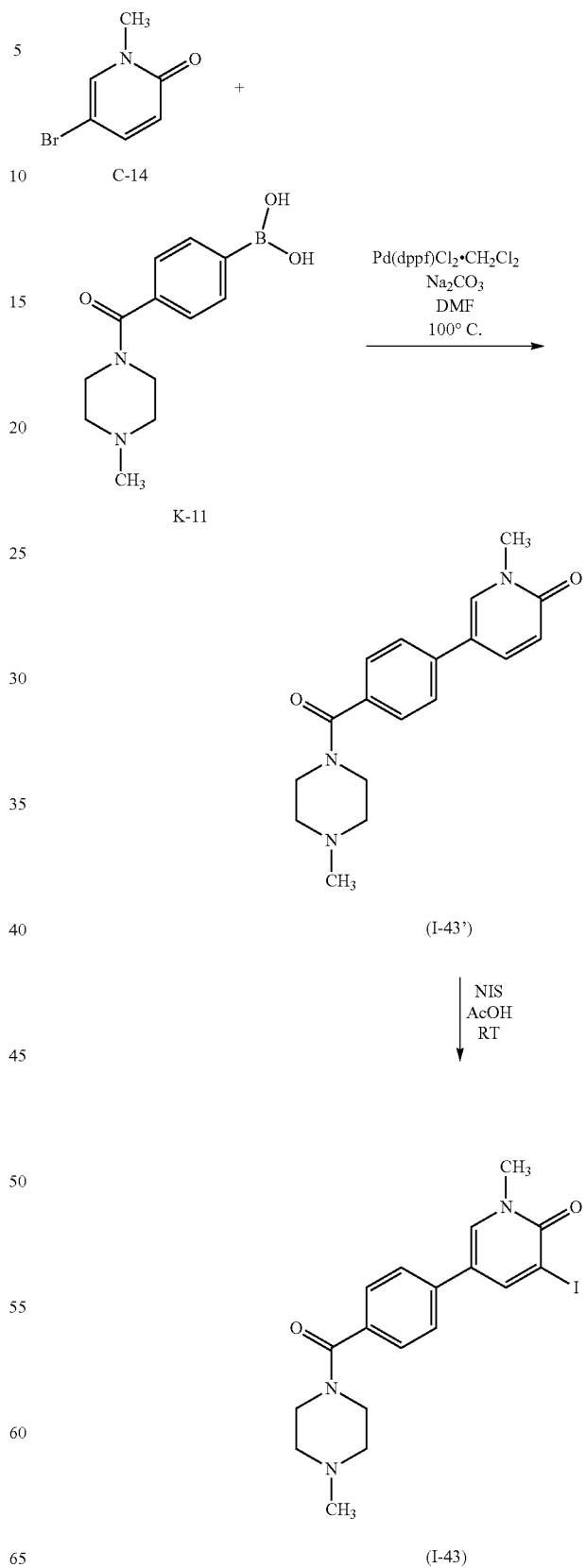

1-Methyl-5-[4-(4-methyl-piperazine-1-carbonyl)-phenyl]-1H-pyridin-2-one (I-43')

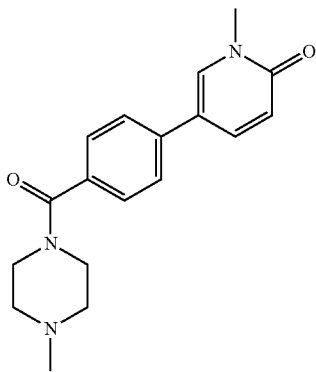 [SMILES: CN1CCN(C(=O)c2ccc(-c3ccc(=O)n(C)c3)cc2)CC1]

In a vial 5-bromo-1-methyl-pyridin-2-one C-14 (97.1 mg; 0.517 mmol), [4-(4-methylpiperazine-1-carbonyl)phenyl] boronic acid hydrochloride K-11 (150.0 mg; 0.517 mmol) and 1,1'-bis(diphenylphosphino)ferrocenepalladium(II) dichloride, dichloromethane (42.2 mg; 0.052 mmol) are weight in. N,N-dimethylformamide (0.800 mL) and an 2N aqueous sodium bicarbonate solution (0.646 mL; 1.291 mmol) are added. The vial is flushed with argon and sealed. The reaction mixture is heated for 1 h at 100° C. To the reaction mixture one drop of water is added and the mixture is filtered and purified with the basic (ammonia buffer) RP HPLC system (column: X-Bridge C-18 30×50 mm). The product containing fractions are concentrated under reduced pressure. Once more freeze dried with acetonitrile: water.

HPLC-MS: (M+H)$^+$=312.2; $t_{Ret}$=0.25 min; method M2

3-Iodo-1-methyl-5-[4-(4-methyl-piperazine-1-carbonyl)-phenyl]-1H-pyridin-2-one (I-43)

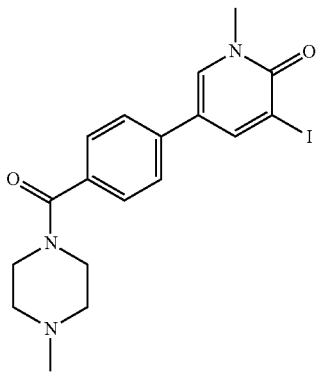 [SMILES: CN1CCN(C(=O)c2ccc(-c3cc(I)c(=O)n(C)c3)cc2)CC1]

1-Methyl-5-[4-(4-methyl-piperazine-1-carbonyl)-phenyl]-1H-pyridin-2-one I-43' (52.0 mg; 0.167 mmol) is dissolved in acetic acid 99-100% (1.0 mL) and N-iodosuccinimide (56.4 mg; 0.250 mmol) is added at RT. The reaction is stirred in a closed vessel with light protection. The reaction mixture is concentrated under reduced pressure. The crude product is dissolved in DCM (10.0 mL) and extracted with aqueous saturated Na$_2$HCO$_3$ (10.0 mL) solution. Aqueous layer is with DCM (2×10 mL). The combined organic layer is dried over Na$_2$SO$_4$, filtered and concentrated under reduced pressure. The crude material is dissolved in DMSO (1.0 mL), filtered and purified with the basic (ammonia buffer) RP HPLC system (column: X-Bridge C-18 30×50 mm). The product containing fractions are concentrated under reduced pressure. The product is dissolved in acetonitrile/water 1:1 and freeze dried.

HPLC-MS: (M+H)$^+$=438; $t_{Ret}$=0.85 min; method M1

Method 11:

Preparation of compound I-45

3-Hydroxy-1-methyl-5-[4-(4-methyl-piperazine-1-carbonyl)-phenyl]-1H-pyridin-2-one

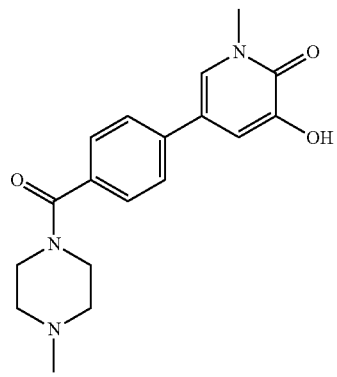 [SMILES: CN1CCN(C(=O)c2ccc(-c3cc(O)c(=O)n(C)c3)cc2)CC1]

Reaction scheme

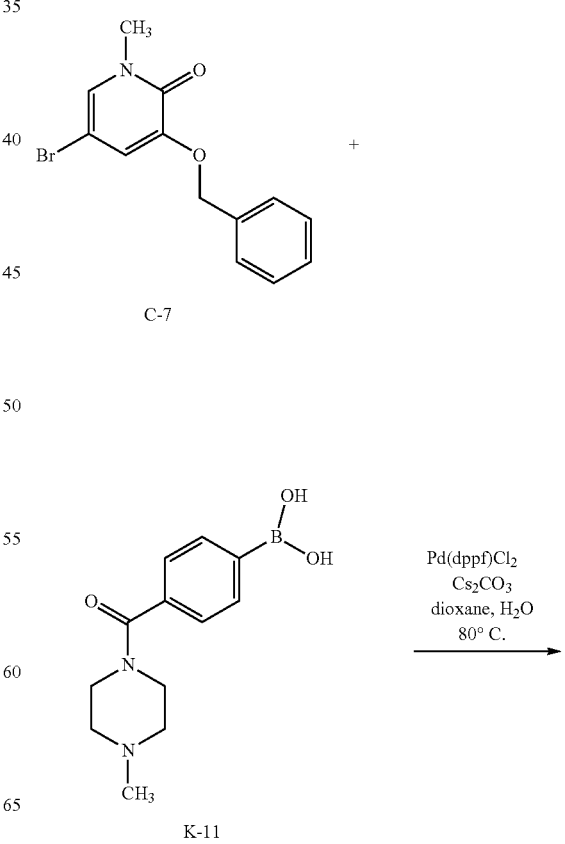

-continued

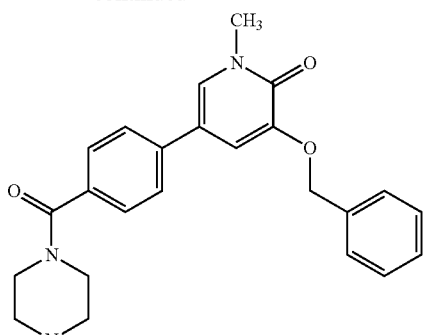

(I-45')

Pd/C
MeOH
RT, 50 Psi

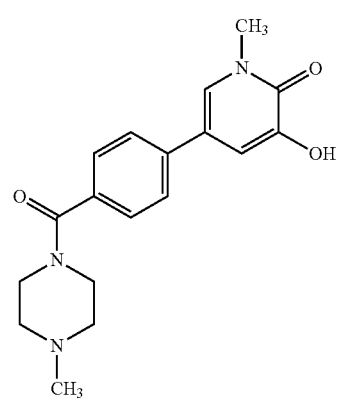

(I-45)

3-Benzyloxy-1-methyl-5-[4-(4-methyl-piperazine-1-carbonyl)-phenyl]-1H-pyridin-2-one (I-45')

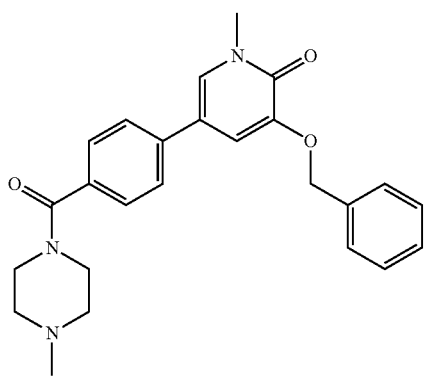 [SMILES: CN1CCN(C(=O)c2ccc(-c3cc(OCc4ccccc4)c(=O)n(C)c3)cc2)CC1]

To the solution of 3-benzyloxy-5-bromo-1-methyl-pyridin-2-one C-7 (135.0 mg; 0.459 mmol) in dioxane (5.0 mL) and water (1.0 mL) is added [4-(4-methylpiperazine-1-carbonyl)phenyl]boronic acid K-11 (120.0 mg; 0.484 mmol), $Cs_2CO_3$ (450 mg; 1.381 mmol), $Pd(dppf)Cl_2$ (25.0 mg; 0.034 mmol). The mixture is stirred at 80° C. for 2 h. The mixture is concentrated under reduced pressure. Water is added to the residue and the mixture is extracted with EA. The combined organic layer is dried over $Na_2SO_4$, filtered and concentrated under reduced pressure.

HPLC-MS: $(M+H)^+=418$; $t_{Ret}=1.42$ min; method M5

3-Hydroxy-1-methyl-5-[4-(4-methyl-piperazine-1-carbonyl)-phenyl]-1H-pyridin-2-one (I-45)

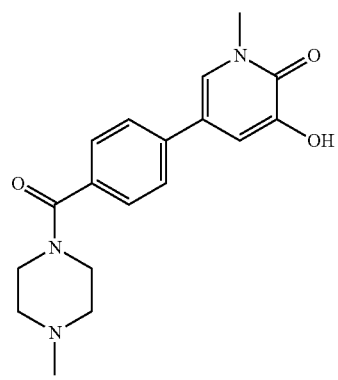 [SMILES: CN1CCN(C(=O)c2ccc(-c3cc(O)c(=O)n(C)c3)cc2)CC1]

To a solution of 3-benzyloxy-1-methyl-5-[4-(4-methyl-piperazine-1-carbonyl)-phenyl]-1H-pyridin-2-one I-45' (120.0 mg; 0.287 mmol) in MeOH (10.0 mL), Pd/C (50.0 mg) is added and stirred at RT and 50 psi $H_2$ pressure overnight. The catalyst is filters off and the filtrate is concentrated under reduced pressure. The compound is purified with prep-HPLC.

Structure confirmed by $^1$H NMR

According to the procedure of I-1 the examples I-2 to I-4 and I-5 to I-22 and I-213 (with the exception of the chiral separation) are synthesized. According to the procedure of I-23 the examples I-24 to I-29 are synthesized. According to the procedure of I-33 (with the exception of the acidic N-Boc deprotection step), the examples I-34 to I-36 are synthesized. According to the procedure of I-37, the examples I-38 to I-40 are synthesized. According to the procedure of I-43 (with the exception of replacing NIS by NBS in the last step), the examples I-44 is synthesized.

| # | Structure | MS (M + H)+ | 'Ret. HPLC [min] | HPLC-Method |
|---|---|---|---|---|
| I-1 | 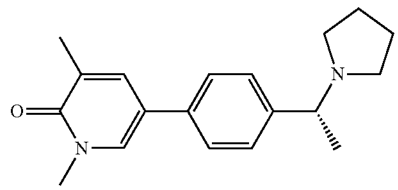 [SMILES: Cc1cc(-c2ccc([C@@H](C)N3CCCC3)cc2)cn(C)c1=O] | 297 | 1.050 | M1 |
| I-2 | 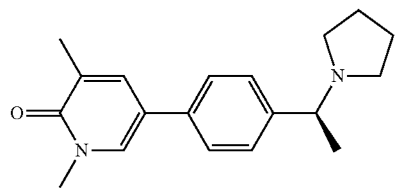 [SMILES: Cc1cc(-c2ccc([C@H](C)N3CCCC3)cc2)cn(C)c1=O] | 297 | 1.050 | M1 |
| I-3 | 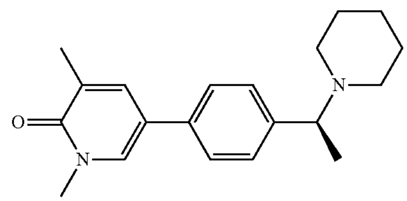 [SMILES: Cc1cc(-c2ccc([C@H](C)N3CCCCC3)cc2)cn(C)c1=O] | 311 | 1.170 | M1 |
| I-4 | 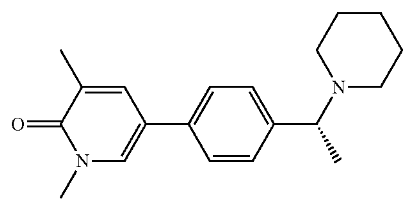 | 311 | 1.170 | M1 |
| I-5 | 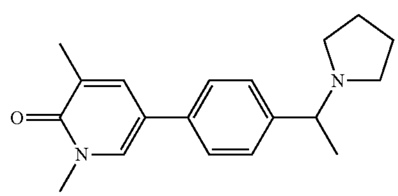 | 297 | 1.150 | M1 |
| I-6 | 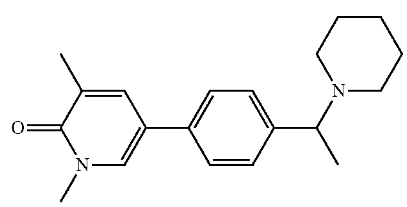 [SMILES: Cc1cc(-c2ccc([C@@H](C)N3CCCCC3)cc2)cn(C)c1=O] | 311 | 1.270 | M1 |
| I-7 | 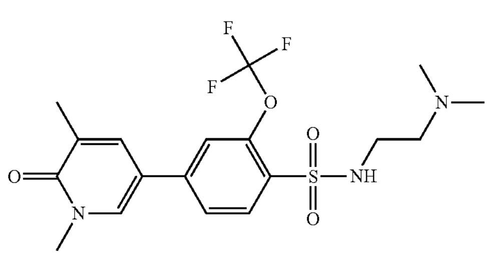 [SMILES: Cc1cc(-c2ccc(S(=O)(=O)NCCN(C)C)c(OC(F)(F)F)c2)cn(C)c1=O] | 434 | 1.030 | M1 |

-continued

| # | Structure | MS (M + H)+ | 'Ret. HPLC [min] | HPLC-Method |
|---|---|---|---|---|
| I-8 | 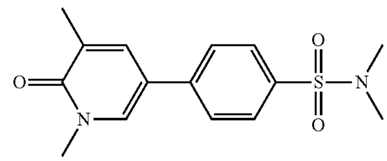 [SMILES: Cc1cc(-c2ccc(S(=O)(=O)N(C)C)cc2)cn(C)c1=O] | 307 | 0.910 | M1 |
| I-9 | 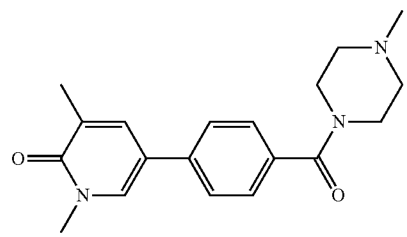 [SMILES: Cc1cc(-c2ccc(C(=O)N3CCN(C)CC3)cc2)cn(C)c1=O] | 326 | 0.780 | M1 |
| I-10 | 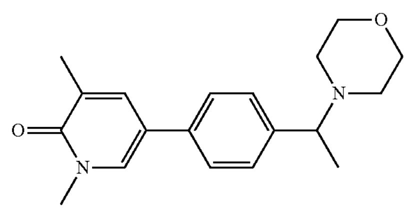 [SMILES: Cc1cc(-c2ccc(C(C)N3CCOCC3)cc2)cn(C)c1=O] | 313 | 0.990 | M1 |
| I-11 | 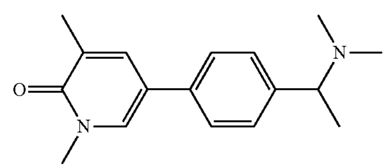 [SMILES: Cc1cc(-c2ccc(C(C)N(C)C)cc2)cn(C)c1=O] | 271 | 1.020 | M1 |
| I-12 | 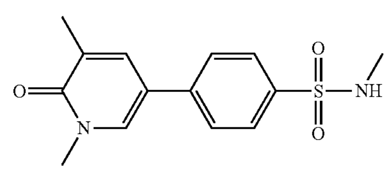 [SMILES: CNS(=O)(=O)c1ccc(-c2cc(C)c(=O)n(C)c2)cc1] | 293 | 0.760 | M1 |
| I-13 | 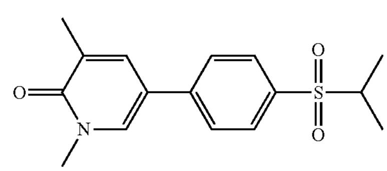 [SMILES: Cc1cc(-c2ccc(S(=O)(=O)C(C)C)cc2)cn(C)c1=O] | 306 | 0.910 | M1 |
| I-14 | 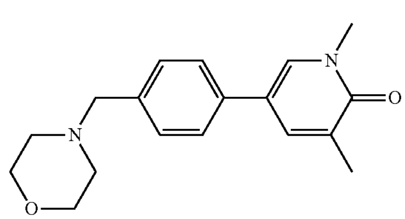 [SMILES: Cc1cc(-c2ccc(CN3CCOCC3)cc2)cn(C)c1=O] | 299 | 1.090 | M1 |

-continued

| # | Structure | MS (M + H)+ | 'Ret. HPLC [min] | HPLC-Method |
|---|---|---|---|---|
| I-15 | 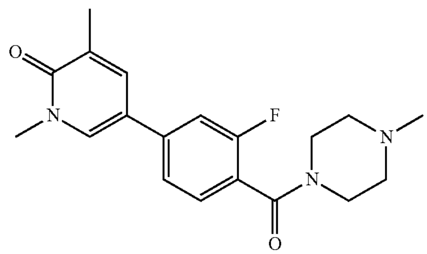 [SMILES: Cc1cc(-c2ccc(C(=O)N3CCN(C)CC3)c(F)c2)cn(C)c1=O] | 344 | 0.830 | M1 |
| I-16 | 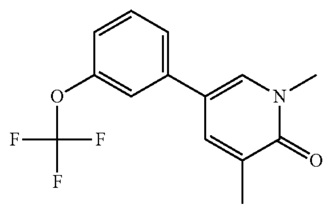 [SMILES: Cc1cc(-c2cccc(OC(F)(F)F)c2)cn(C)c1=O] | 284 | 1.220 | M1 |
| I-17 | 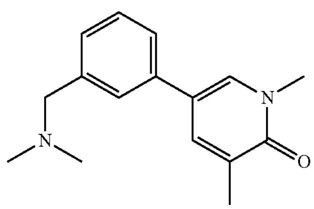 | 257 | 0.970 | M1 |
| I-18 | 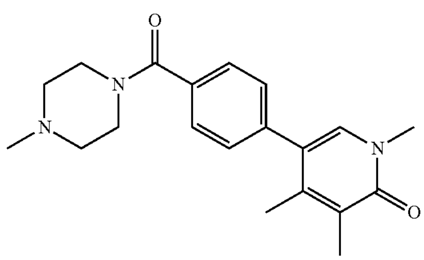 | 340 | 0.830 | M1 |
| I-19 | 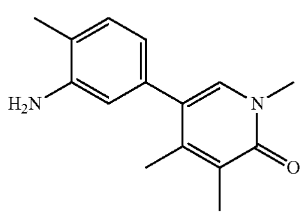 [SMILES: Cc1ccc(-c2cn(C)c(=O)c(C)c2C)cc1N] | 243 | 0.930 | M1 |
| I-20 | 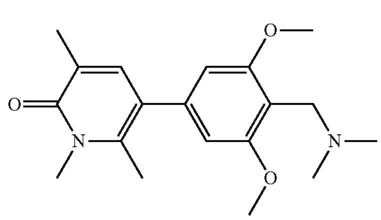 [SMILES: COc1cc(-c2cc(C)c(=O)n(C)c2C)cc(OC)c1CN(C)C] | 331 | 0.920 | M1 |

-continued
| # | Structure | MS (M + H)+ | 'Ret. HPLC [min] | HPLC-Method |
|---|---|---|---|---|
| I-21 | 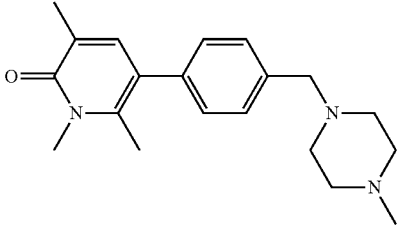 [SMILES: Cc1cc(-c2ccc(CN3CCN(C)CC3)cc2)c(C)n(C)c1=O] | 326 | 0.940 | M1 |
| I-22 | 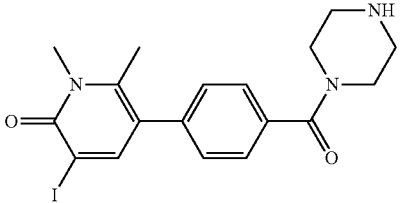 [SMILES: Cc1c(-c2ccc(C(=O)N3CCNCC3)cc2)cc(I)c(=O)n1C] | 438 | 0.790 | M1 |
| I-23 | 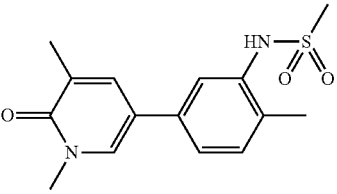 | 307 | 2.181 | M11 |
| I-24 | 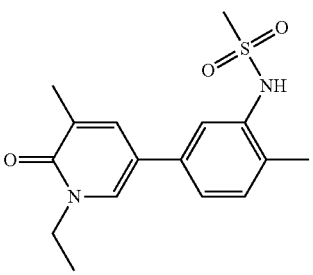 [SMILES: CCn1cc(-c2ccc(C)c(NS(C)(=O)=O)c2)cc(C)c1=O] | 321 | NMR | |
| I-25 | 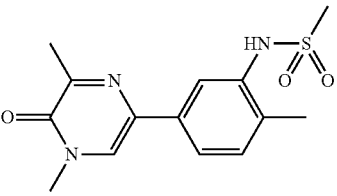 [SMILES: Cc1ccc(-c2cn(C)c(=O)c(C)n2)cc1NS(C)(=O)=O] | 308 | 2.452 | |
| I-26 | 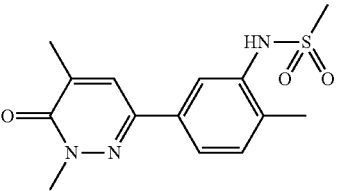 [SMILES: Cc1ccc(-c2cc(C)c(=O)n(C)n2)cc1NS(C)(=O)=O] | 308 | 3.092 | M10 |

-continued
| # | Structure | MS (M + H)+ | Ret. HPLC [min] | HPLC-Method |
|---|---|---|---|---|
| I-27 | 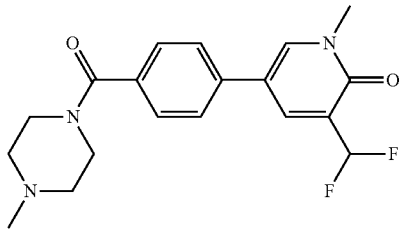 | 362 | NMR | |
| I-28 | 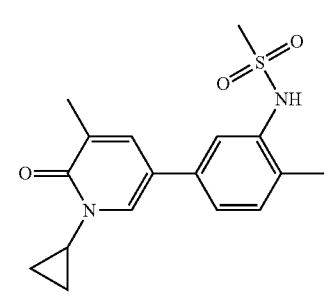 [SMILES: Cc1ccc(-c2cc(C)c(=O)n(C3CC3)c2)cc1NS(C)(=O)=O] | 333 | NMR | |
| I-29 | 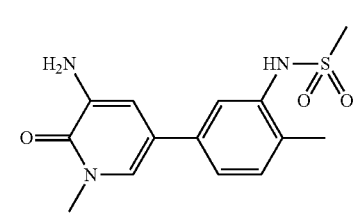 [SMILES: Cc1ccc(-c2cc(N)c(=O)n(C)c2)cc1NS(C)(=O)=O] | 308 | 2.299 | M10 |
| I-30 | 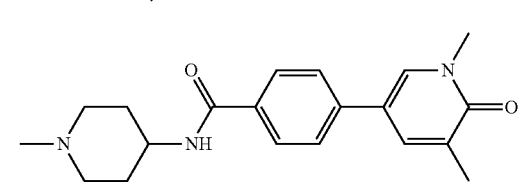 | 340 | 0.810 | M1 |
| I-31 | 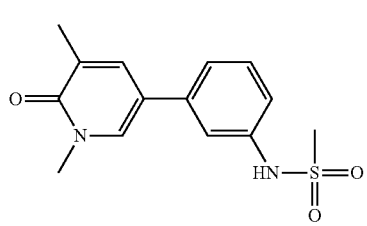 [SMILES: Cc1cc(-c2cccc(NS(C)(=O)=O)c2)cn(C)c1=O] | 293 | 0.680 | M1 |
| I-32 | 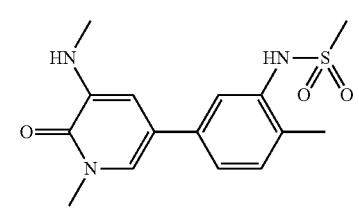 [SMILES: CNc1cc(-c2ccc(C)c(NS(C)(=O)=O)c2)cn(C)c1=O] | 322 | 2.546 | M10 |
| I-33 | 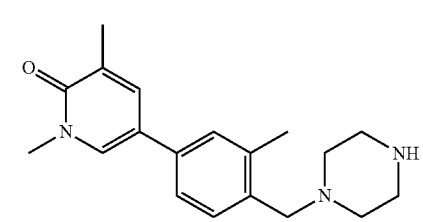 [SMILES: Cc1cc(-c2cc(C)c(=O)n(C)c2)ccc1CN1CCNCC1] | 312 | 1.060 | M1 |

| # | Structure | MS (M + H)+ | Ret. HPLC [min] | HPLC-Method |
|---|---|---|---|---|
| I-34 | 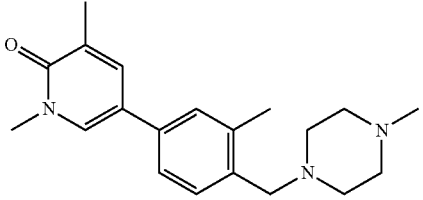 [SMILES: Cc1cc(-c2cc(C)c(=O)n(C)c2)ccc1CN1CCN(C)CC1] | 326 | 1.190 | M1 |
| I-35 | 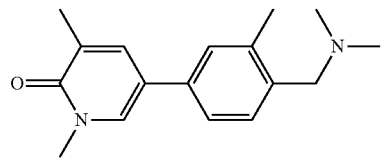 [SMILES: Cc1cc(-c2cc(C)c(=O)n(C)c2)ccc1CN(C)C] | 271 | 1.220 | M1 |
| I-36 | 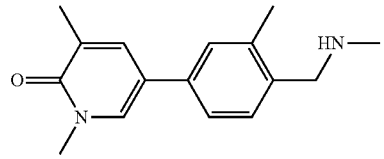 [SMILES: CNCc1ccc(-c2cc(C)c(=O)n(C)c2)cc1C] | 257 | 1.030 | M1 |
| I-37 | 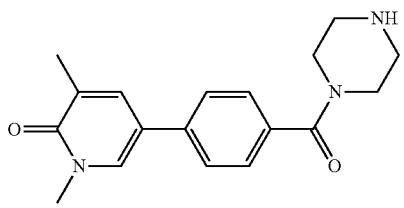 [SMILES: Cc1cc(-c2ccc(C(=O)N3CCNCC3)cc2)cn(C)c1=O] | 312 | NMR Observed by TLC Rf = 0.15 (MeOH/DCM 1:10) | |
| I-38 | 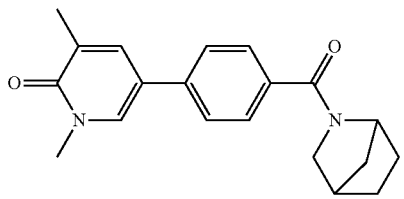 [SMILES: Cc1cc(-c2ccc(C(=O)N3CC4CCC3C4)cc2)cn(C)c1=O] | 323 | NMR Observed by TLC Rf = 0.40 (MeOH/DCM 1:20) | |
| I-39 | 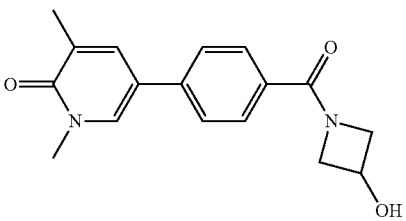 [SMILES: Cc1cc(-c2ccc(C(=O)N3CC(O)C3)cc2)cn(C)c1=O] | 299 | NMR Observed by TLC Rf = 0.40 (MeOH/DCM 1:20) | |
| I-40 | 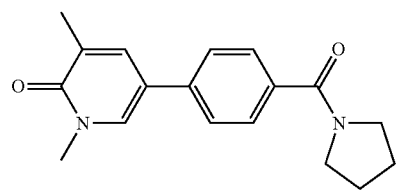 [SMILES: Cc1cc(-c2ccc(C(=O)N3CCCC3)cc2)cn(C)c1=O] | 297 | NMR Observed by TLC Rf = 0.30 (MeOH/DCM 1:20) | |

-continued

| # | Structure | MS (M + H)+ | 'Ret. HPLC [min] | HPLC-Method |
|---|---|---|---|---|
| I-41 | 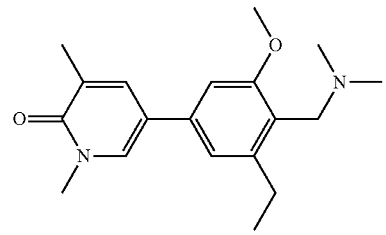 [SMILES: CCc1cc(-c2cc(C)c(=O)n(C)c2)cc(OC)c1CN(C)C] | 315 | NMR | |
| I-42 | 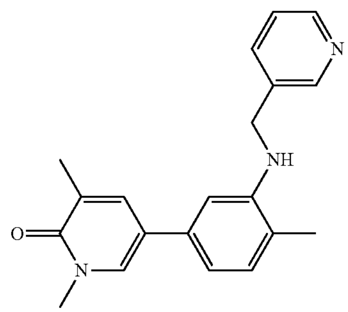 [SMILES: Cc1ccc(-c2cc(C)c(=O)n(C)c2)cc1NCc1cccnc1] | 320 | 2.336 | M10 |
| I-43 | 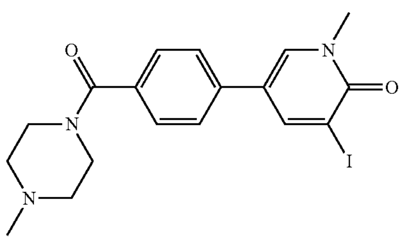 [SMILES: CN1CCN(C(=O)c2ccc(-c3cc(I)c(=O)n(C)c3)cc2)CC1] | 438 | 0.85 | M1 |
| I-44 | 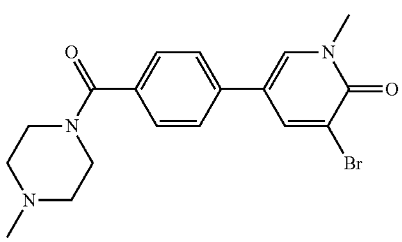 | 391 | NMR | M1 |
| I-45 | 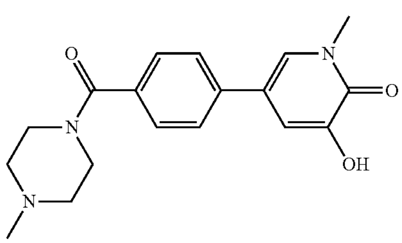 [SMILES: CN1CCN(C(=O)c2ccc(-c3cc(O)c(=O)n(C)c3)cc2)CC1] | 328 | NMR | |
| I-213 | 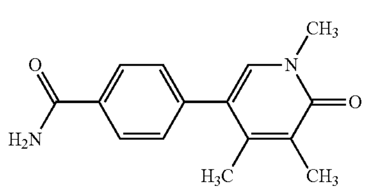 [SMILES: Cc1c(-c2ccc(C(N)=O)cc2)cn(C)c(=O)c1C] | 257 | 0.62 | M1 |

Method 12:
Preparation of Compound I-47

5-[4-(3-Hydroxy-azetidin-1-ylmethyl)-3-methoxy-phenyl]-1,3-dimethyl-1H-pyridin-2-one (I-47)

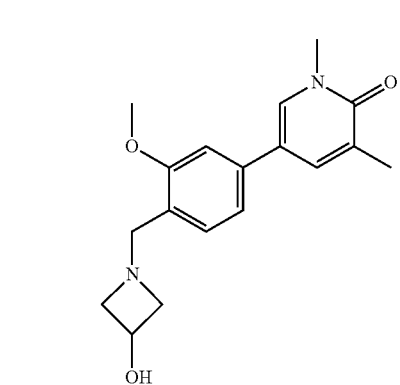 [SMILES: COc1cc(-c2cc(C)c(=O)n(C)c2)ccc1CN1CC(O)C1]

Reaction scheme

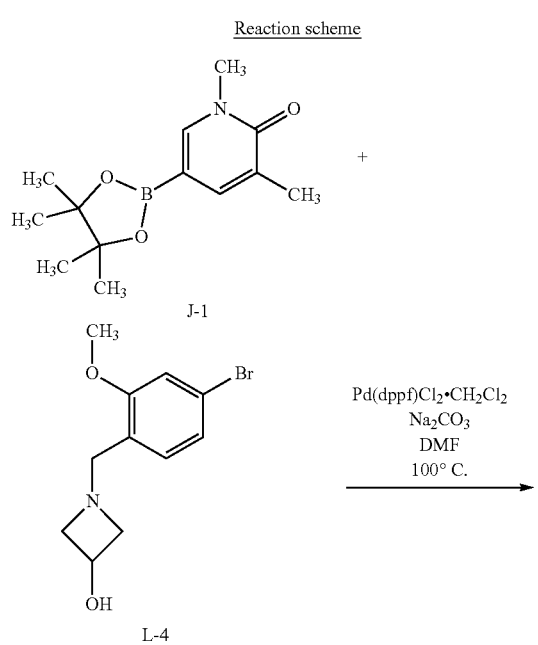

5-[4-(3-Hydroxy-azetidin-1-ylmethyl)-3-methoxy-phenyl]-1,3-dimethyl-1H-pyridin-2-one (I-47)

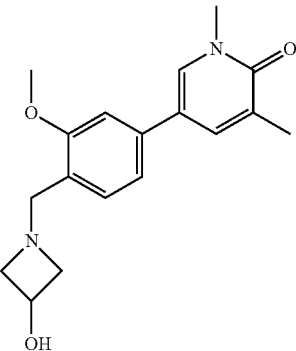 [SMILES: COc1cc(-c2cc(C)c(=O)n(C)c2)ccc1CN1CC(O)C1]

In a vial 1-[(4-bromo-2-methoxy-phenyl)methyl]azetidin-3-ol L-4 (76.5 mg; 0.281 mmol), 1,3-dimethyl-5-(4,4,5,5-tetramethyl-[1,3,2]dioxaborolan-2-yl)-1H-pyridin-2-one J-1 (70.0 mg; 0.281 mmol) and 1,1'-bis(diphenylphosphino)ferrocene-palladium(II) dichloride, dichloromethane (22.9 mg; 0.028 mmol) are weight in. N,N-dimethylformamide (0.800 mL) and sodium carbonate solution (2N; 0.351 mL; 0.702 mmol) are added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are concentrated under reduced pressure. Once more freeze dried with acetonitrile/water 1:1.

HPLC-MS: $(M+H)^+=315$; $t_{Ret}=0.79$ min; method M1

Method 13:
Preparation of Compound I-137

5-(4-Aminomethyl-phenyl)-1,3,4-trimethyl-1H-pyridin-2-one

Reaction scheme

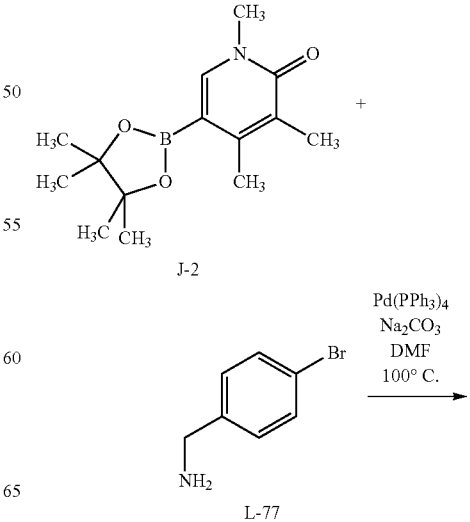

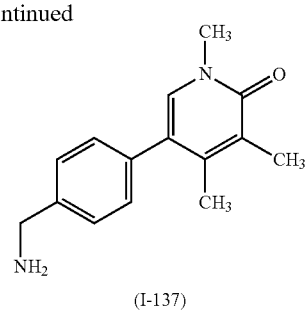

(I-137)

5-(4-Aminomethyl-phenyl)-1,3,4-trimethyl-1H-pyridin-2-one (I-137)

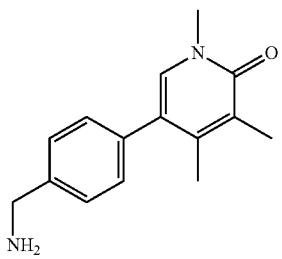 [SMILES: Cc1c(-c2ccc(CN)cc2)cn(C)c(=O)c1C]

1,3,4-Trimethyl-5-(4,4,5,5-tetramethyl-[1,3,2]dioxaborolan-2-yl)-1H-pyridin-2-one J-2 (75.0 mg; 0.219 mmol), (4-bromophenyl)methanamine hydrochloride L-77 (58.5 mg; 0.263 mmol), tetrakis(triphenylphosphine)palladium(0) (50.6 mg; 0.044 mmol) and an 2N aqueous solution of sodium bicarbonate (0.274 mL; 0.547 mmol) are suspended in DMF (1.0 mL). The vial is purged for 5 min with argon, sealed and then heated to 100° C. for 1 h. The mixture is then concentrated under reduced pressure and the product purified by NP silica gel chromatography (DCM/MeOH/NH3 0 to 5%).

HPLC-MS: (M+H)$^+$=243; $t_{Ret}$=0.75 min; method M1

Method 14:

Preparation of Compound I-143

5-[4-(3-Amino-azetidin-1-ylmethyl)-3,5-dimethoxyphenyl]-1,3-dimethyl-1H-pyridin-2-one

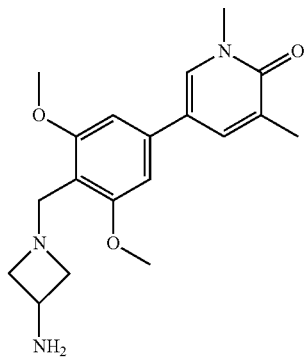 [SMILES: COc1cc(-c2cc(C)c(=O)n(C)c2)cc(OC)c1CN1CC(N)C1]

Reaction scheme

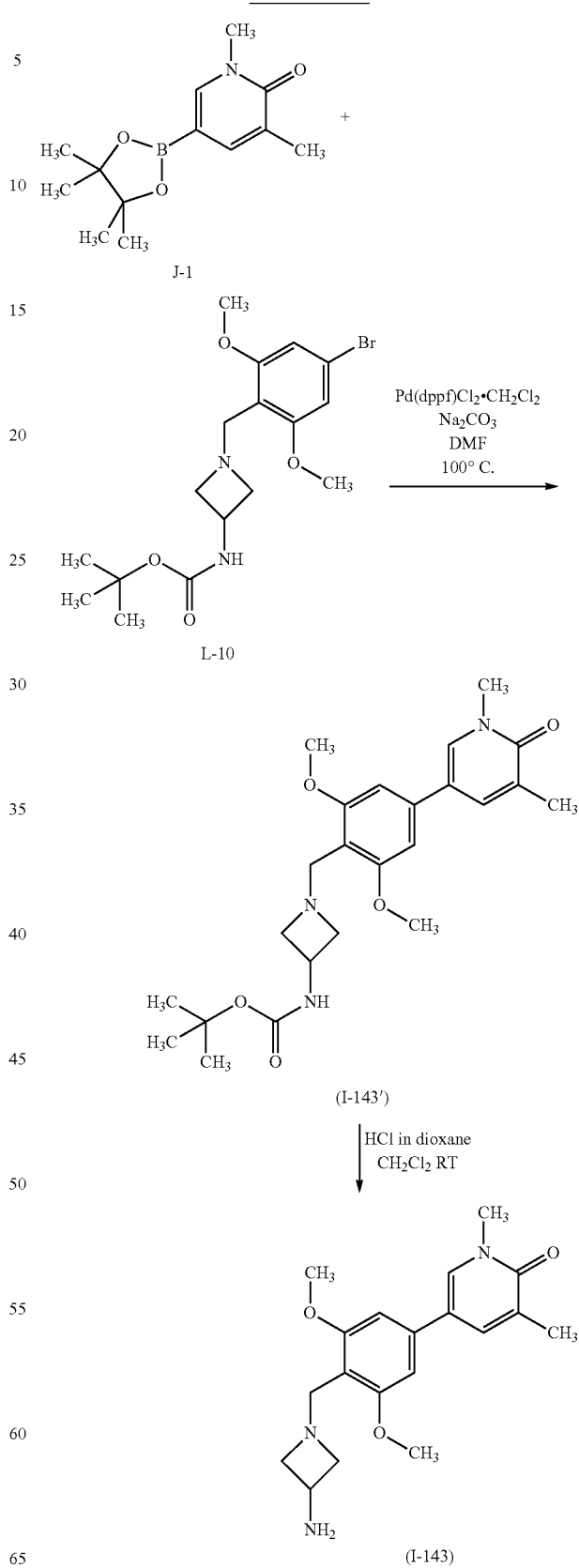

{1-[4-(1,5-Dimethyl-6-oxo-1,6-dihydro-pyridin-3-yl)-2,6-dimethoxy-benzyl]-azetidin-3-yl}-carbamic acid tert-butyl ester (I-143')

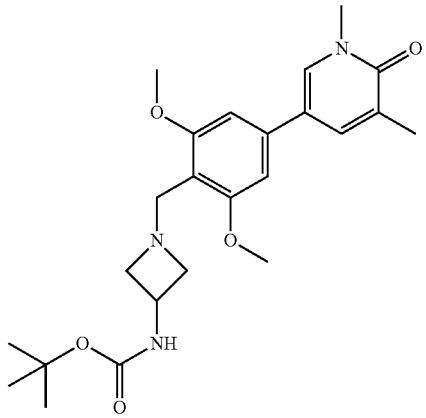 [SMILES: COc1cc(-c2cc(C)c(=O)n(C)c2)cc(OC)c1CN1CC(NC(=O)OC(C)(C)C)C1]

[1-(4-Bromo-2,6-dimethoxy-benzyl)-azetidin-3-yl]-carbamic acid tert-butyl ester L-10 (120.0 mg; 0.299 mmol), 1,3-dimethyl-5-(4,4,5,5-tetramethyl-[1,3,2]dioxaborolan-2-yl)-1H-pyridin-2-one J-1 (81.9 mg; 0.329 mmol) and 1,1'-bis(diphenylphosphino)ferrocenepalladium(II) dichloride, dichloromethane (50.4 mg; 0.060 mmol) are dissolved in DMF (1.5 mL). An aqueous solution of sodium carbonate (2M; 0.299 mL; 0.598 mmol) is added. The flask is purged for 5 min with argon, sealed and then heated to 80° C. for 1 h. The reaction mixture is filtered and purified on RP chromatographed (Basic HPLC) to afford the product after lyophilization.

HPLC-MS: (M+H)$^+$=260.2; $t_{Ret}$=0.53 min; method M1

5-[4-(3-Amino-azetidin-1-ylmethyl)-3,5-dimethoxy-phenyl]-1,3-dimethyl-1H-pyridin-2-one (I-143)

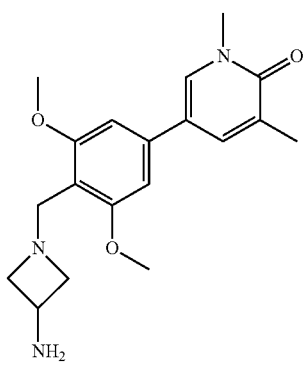 [SMILES: COc1cc(-c2cc(C)c(=O)n(C)c2)cc(OC)c1CN1CC(N)C1]

{1-[4-(1,5-Dimethyl-6-oxo-1,6-dihydro-pyridin-3-yl)-2,6-dimethoxy-benzyl]-azetidin-3-yl}-carbamic acid tert-butyl ester I-143' (90.0 mg; 0.203 mmol) is dissolved in DCM dry (10.0 mL). 4M Hydrogen chloride in dioxane (0.507 mL; 2.029 mmol) is added and the reaction mixture is stirred at RT overnight. The mixture is then concentrated under reduced pressure. The residue is dissolved in MeOH and the free base is generated using a SPX 2 cartridge.

HPLC-MS: (M+H)$^+$=344; $t_{Ret}$=0.80 min; method M1

Method 15:

Preparation of Compound I-157

5-[3-Ethyl-5-methoxy-4-(piperazine-1-carbonyl)-phenyl]-1,3-dimethyl-1H-pyridin-2-one

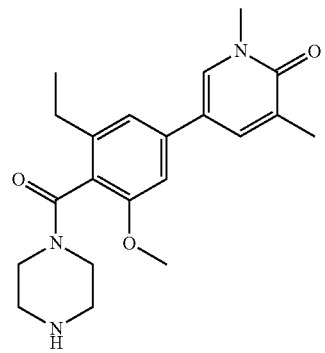 [SMILES: CCc1cc(-c2cc(C)c(=O)n(C)c2)cc(OC)c1C(=O)N1CCNCC1]

Reaction scheme

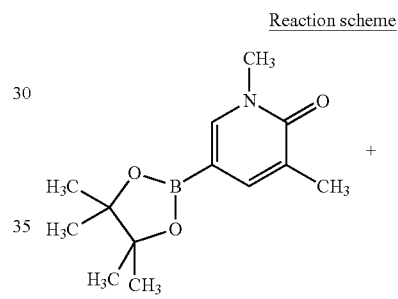

J-1

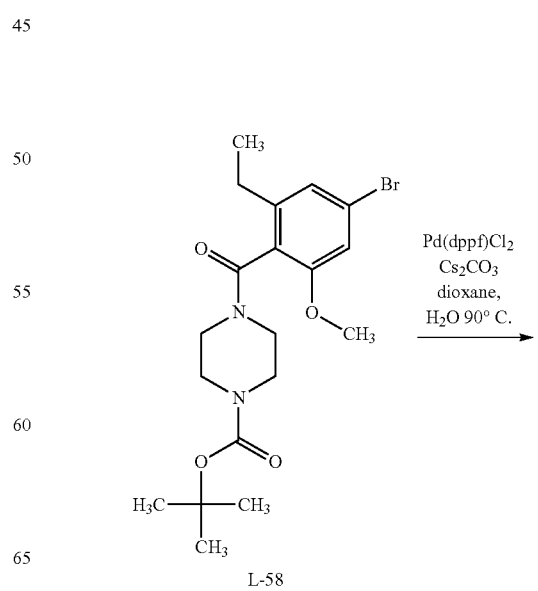

L-58

113
-continued

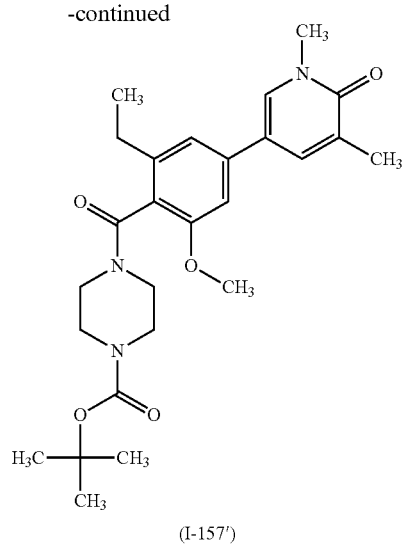

(I-157')

↓ HCl MeOH
RT

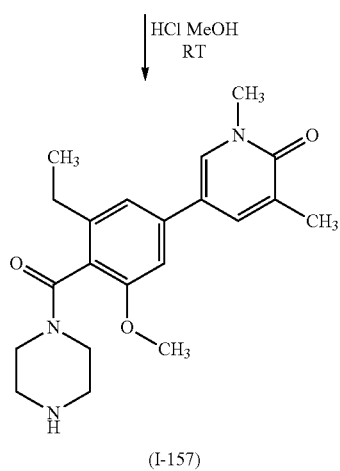

(I-157)

4-[4-(1,5-Dimethyl-6-oxo-1,6-dihydro-pyridin-3-yl)-2-ethyl-6-methoxy-benzoyl]-piperazine-1-carboxylic acid tert-butyl ester (I-157')

To a solution of tert-butyl 4-(4-bromo-2-ethyl-6-methoxybenzoyl) piperazine-1-carboxylate L-58 (100.0 mg; 0.211 mmol) and 1,3-dimethyl-5-(4,4,5,5-tetramethyl-[1,3,2]dioxaborolan-2-yl)-1H-pyridin-2-one J-1 (120.0 mg; 0.482 mmol) in dioxane (3.0 mL) and water (0.5 mL) are added $Cs_2CO_3$ (250.0 mg; 0.769 mmol) and $Pd(dppf)Cl_2$ (50.0 mg; 0.068 mmol). The mixture is heated to 90° C. and stirred for 2 h. The reaction is filtered over a pad of celite and the filtrate is concentrated under reduced pressure. Water is added to the mixture and the residue is extracted with EA. The organic layer is and washed once with brine, dried with $Na_2SO_4$, filtered and concentrated under reduced pressure to give the crude product, which is purified with prep-HPLC.

HPLC-MS: $(M+H)^+=370$; $t_{Ret}=1.00$ min; method M8

5-[3-Ethyl-5-methoxy-4-(piperazine-1-carbonyl)-phenyl]-1,3-dimethyl-1H-pyridin-2-one (I-157)

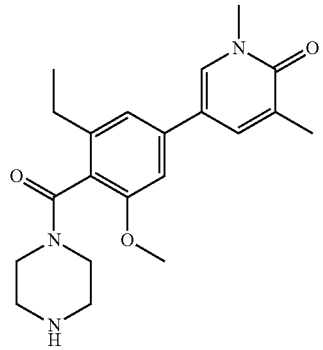 [SMILES: CCc1cc(-c2cc(C)c(=O)n(C)c2)cc(OC)c1C(=O)N1CCNCC1]

4N HCl in MeOH (4.0 mL) is added to 4-[4-(1,5-dimethyl-6-oxo-1,6-dihydro-pyridin-3-yl)-2-ethyl-6-methoxy-benzoyl]-piperazine-1-carboxylic acid tert-butyl ester I-157' (35.0 mg; 0.075 mmol) and the mixture is stirred at RT for 2 h. The reaction mixture is concentrated under reduced pressure. The crude material is purified by basic prep-HPLC to obtain the free base.

Method 16:
Preparation of Compound I-164

3-Iodo-5-[3-methoxy-4-(piperazine-1-carbonyl)-phenyl]-1-methyl-1H-pyridin-2-one

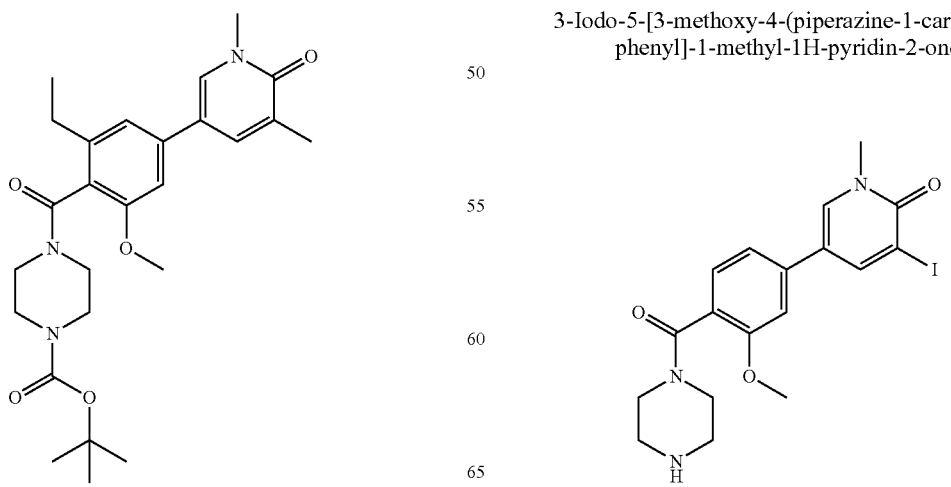

Reaction scheme
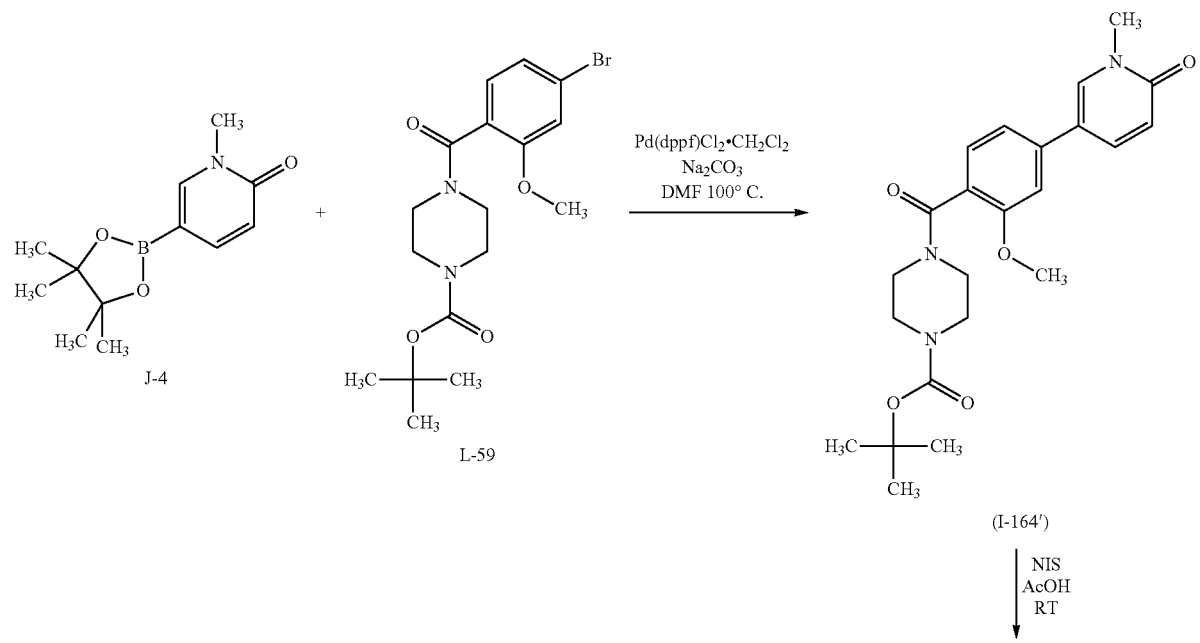
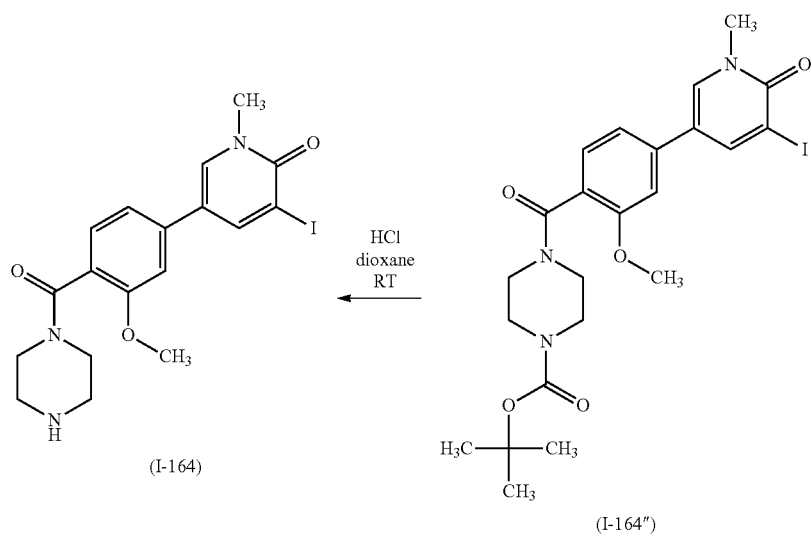

4-[2-Methoxy-4-(1-methyl-6-oxo-1,6-dihydro-pyridin-3-yl)-benzoyl]-piperazine-1-carboxylic acid tert-butyl ester (I-164')

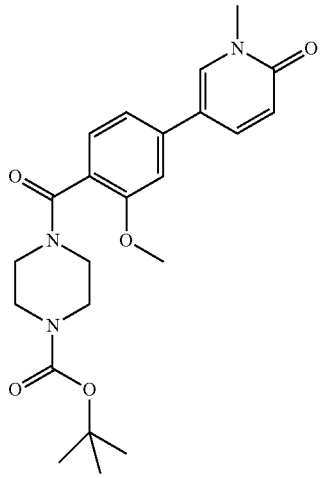 [SMILES: COc1cc(-c2ccc(=O)n(C)c2)ccc1C(=O)N1CCN(C(=O)OC(C)(C)C)CC1]

In a vial 4-(4-iodo-2-methoxy-benzoyl)-piperazine-1-carboxylic acid tert-butyl ester L-59 (189.7 mg; 0.425 mmol), 1-methyl-5-(4,4,5,5-tetramethyl-[1,3,2]dioxaborolan-2-yl)-1H-pyridin-2-one J-4 (100.0 mg; 0.425 mmol) and [1,1'-bis(diphenylphosphino)ferrocene]dichloropalladium(II), dichloromethane (34.7 mg; 0.043 mmol) are introduced. N,N-dimethylformamide (800 µL) and an aqueous solution of sodium carbonate solution (2N, 0.530 mL) are added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are concentrated under reduced pressure.

HPLC-MS: (M+H)$^+$=428; $t_{Ret}$=1.03 min; method M1

4-[4-(5-Iodo-1-methyl-6-oxo-1,6-dihydro-pyridin-3-yl)-2-methoxy-benzoyl]-piperazine-1-carboxylic acid tert-butyl ester (164")

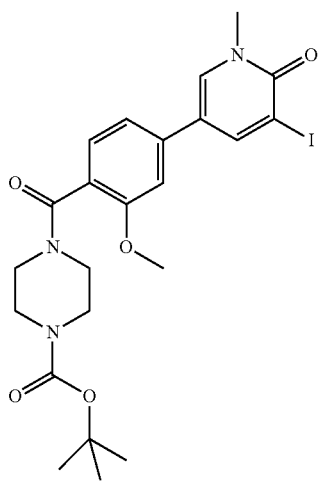 [SMILES: COc1cc(-c2cc(I)c(=O)n(C)c2)ccc1C(=O)N1CCN(C(=O)OC(C)(C)C)CC1]

4-[2-Methoxy-4-(1-methyl-6-oxo-1,6-dihydro-pyridin-3-yl)-benzoyl]-piperazine-1-carboxylic acid tert-butyl ester I-164' (75.6 mg; 0.177 mmol) is dissolved in acetic acid (1.0 mL) and N-iodosuccinimide (59.7 mg; 0.265 mmol) is added at RT. The reaction is stirred in a closed vessel with light protection at RT for 2 h. The reaction mixture is concentrated under reduced pressure. The crude product is dissolved in DCM (10.0 mL) and extracted with aqueous saturated Na$_2$HCO$_3$ (10.0 mL) solution. The aqueous layer is extracted with DCM (2×10.0 mL). The combined organic layer is dried over Na$_2$SO$_4$, filtered and concentrated under reduced pressure. The crude product is dissolved in DMSO (1.0 mL), filtered and purified with the basic (ammonia buffer) RP HPLC system (column: X-Bridge C-18 30×50 mm). The product containing fractions are concentrated under reduced pressure.

HPLC-MS: (M+H)$^+$=554; $t_{Ret}$=0.61 min; method M2

3-Iodo-5-[3-methoxy-4-(piperazine-1-carbonyl)-phenyl]-1-methyl-1H-pyridin-2-one (I-164)

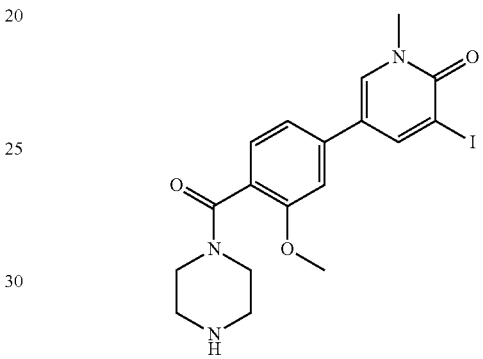

4N HCl in dioxane (2.0 mL; 8.000 mmol) is added to 4-[4-(5-iodo-1-methyl-6-oxo-1,6-dihydro-pyridin-3-yl)-2-methoxy-benzoyl]-piperazine-1-carboxylic acid tert-butyl ester I-164" (50.0 mg; 0.090 mmol) at RT. The reaction mixture is stirred at RT overnight. The reaction mixture is concentrated under reduced pressure. The crude material is partitioned between DCM and saturated NaHCO$_3$-solution and extracted 3 times with DCM. The combined organic layers are dried over Na$_2$SO$_4$, filtered and concentrated under reduced pressure. The product is dissolved in acetonitrile/water 1:1 and freeze dried.

HPLC-MS: (M+H)$^+$=454; $t_{Ret}$=0.73 min; method M1

Method 17:
Preparation of Compound I-169

5-[3-Ethanesulfonylmethyl-4-(piperazine-1-carbonyl)-phenyl]-1,3-dimethyl-1H-pyridin-2-one

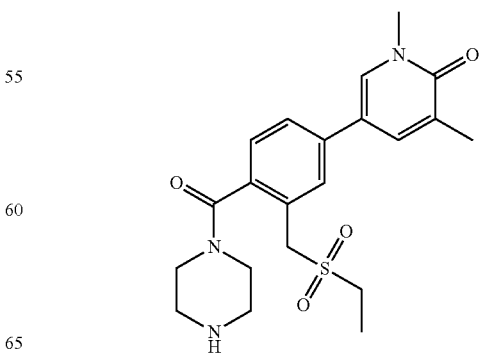

Reaction scheme
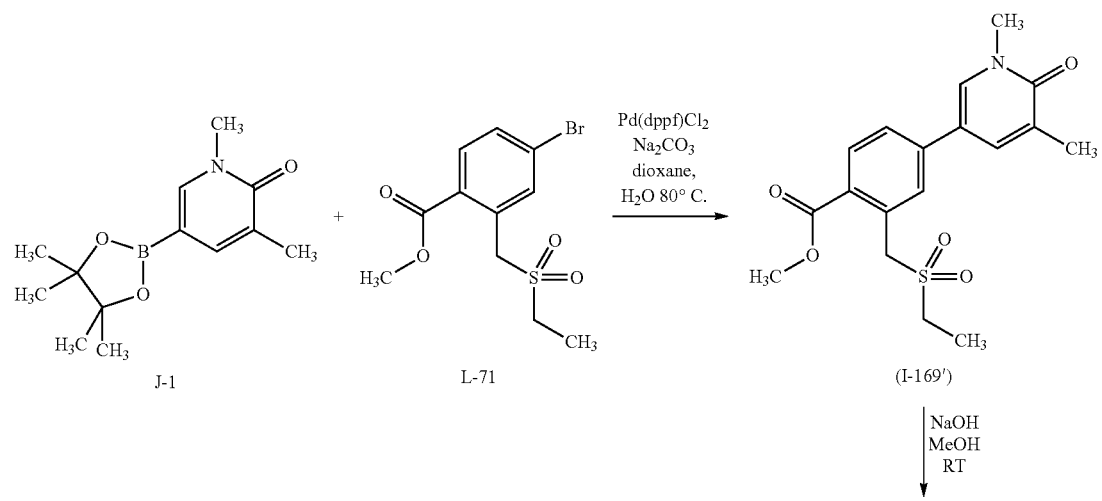
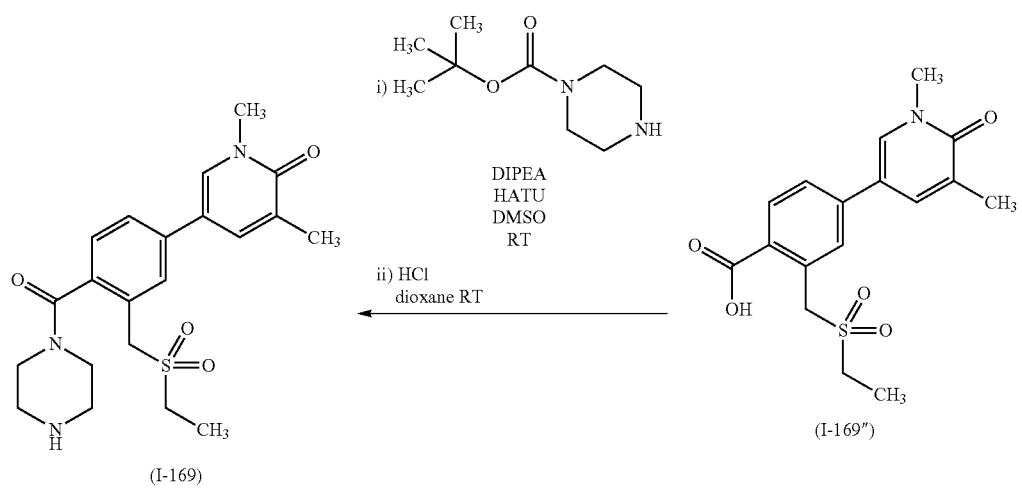

121

4-(1,5-Dimethyl-6-oxo-1,6-dihydro-pyridin-3-yl)-2-ethanesulfonylmethyl-benzoic acid methyl ester (I-169')

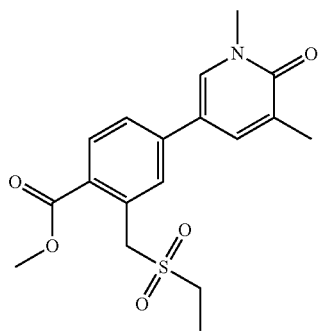

To a solution of methyl 4-bromo-2-[(ethanesulfonyl)methyl]benzoate L-71 (4.000 g; 12.454 mmol) in dioxane (30.0 mL) and water (10.0 mL) are added 1,3-dimethyl-5-(4,4,5,5-tetramethyl-[1,3,2]dioxaborolan-2-yl)-1H-pyridin-2-one J-1 (4.000 g; 16.057 mmol), Pd(dppf)Cl$_2$ (0.274 g; 0.374 mmol) and Na$_2$CO$_3$ (3.960 g; 37.361 mmol). The mixture is stirred at 80° C. for 12 h. The solution is then concentrated in vacuo and dissolved in ethyl acetate and water. The aqueous layer is extracted twice with ethyl acetate. The combined organic layer is dried over Na$_2$SO$_4$, filtered and concentrated under reduced pressure. The crude material is purified by HPLC to give the expected product.

Structure confirmed by $^1$H NMR

4-(1,5-Dimethyl-6-oxo-1,6-dihydro-pyridin-3-yl)-2-ethanesulfonylmethyl-benzoic acid (I-169")

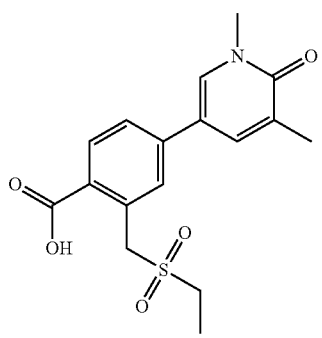 [SMILES: CCS(=O)(=O)Cc1cc(-c2cc(C)c(=O)n(C)c2)ccc1C(=O)O]

To a solution of 4-(1,5-dimethyl-6-oxo-1,6-dihydro-pyridin-3-yl)-2-ethanesulfonylmethyl-benzoic acid methyl ester I-169' (1.5 g; 4.127 mmol) in methanol (15.0 mL), an aqueous solution of sodium hydroxide (2M; 0.495 g; 12.382 mmol) is added and stirred at RT for 4 h. The pH is then adjusted to acidic by adding a 2M aqueous solution of HCl, until precipitation occurs and the precipitate is filtered off. The solid is washed with water and methanol to give the desired product.

HPLC-MS: (M+H)$^+$=350; t$_{Ret}$=1.98 min; method M11

122

5-[3-Ethanesulfonylmethyl-4-(piperazine-1-carbonyl)-phenyl]-1,3-dimethyl-1H-pyridin-2-one (I-169)

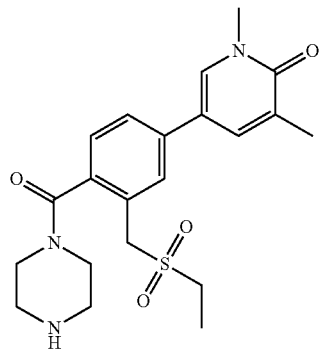 [SMILES: CCS(=O)(=O)Cc1cc(-c2cc(C)c(=O)n(C)c2)ccc1C(=O)N1CCNCC1]

4-(1,5-Dimethyl-6-oxo-1,6-dihydro-pyridin-3-yl)-2-ethanesulfonylmethyl-benzoic acid I-169" (100.0 mg; 0.286 mmol), HATU (130.6 mg; 0.343 mmol), N-ethyldiisopropylamine (0.14 mL; 0.859 mmol) and DMSO (800 µL) are introduced in a flask, the mixture is stirred for 15 min at RT. Piperazine-1-carboxylic acid tert-butyl ester (80.0 mg; 0.429 mmol) is then added and the mixture is stirred overnight at RT. A 4N HCl solution in dioxane (1.0 mL; 4.000 mmol) is added to the reaction mixture, and the mixture is stirred at RT for 2 h. Then the reaction is made basic by addition of a 1N aqueous solution of NaOH and extracted 3 times with DCM. The combined organic layer is dried over Na$_2$SO$_4$, filtered and concentrated under reduced pressure. The crude product is dissolved in DMSO (1.0 mL), filtered and purified with the basic (ammonia buffer) RP HPLC system (column: X-Bridge C-18 30×50 mm). The product containing fractions are concentrated under reduced pressure. The product is dissolved in acetonitrile/water 1:1 and freeze dried.

HPLC-MS: (M+H)$^+$=418; t$_{Ret}$=0.63 min; method M1

Method 18:

Preparation of Compound I-173

5-[2-Methoxy-4-(4-methyl-piperazine-1-carbonyl)-phenyl]-1,3-dimethyl-1H-pyridin-2-one

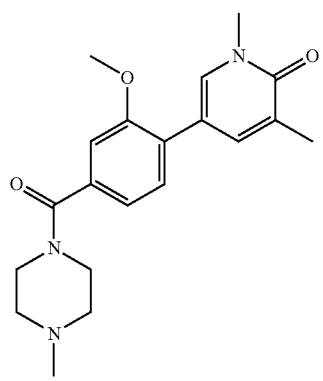 [SMILES: COc1cc(C(=O)N2CCN(C)CC2)ccc1-c1cc(C)c(=O)n(C)c1]

123

Reaction scheme

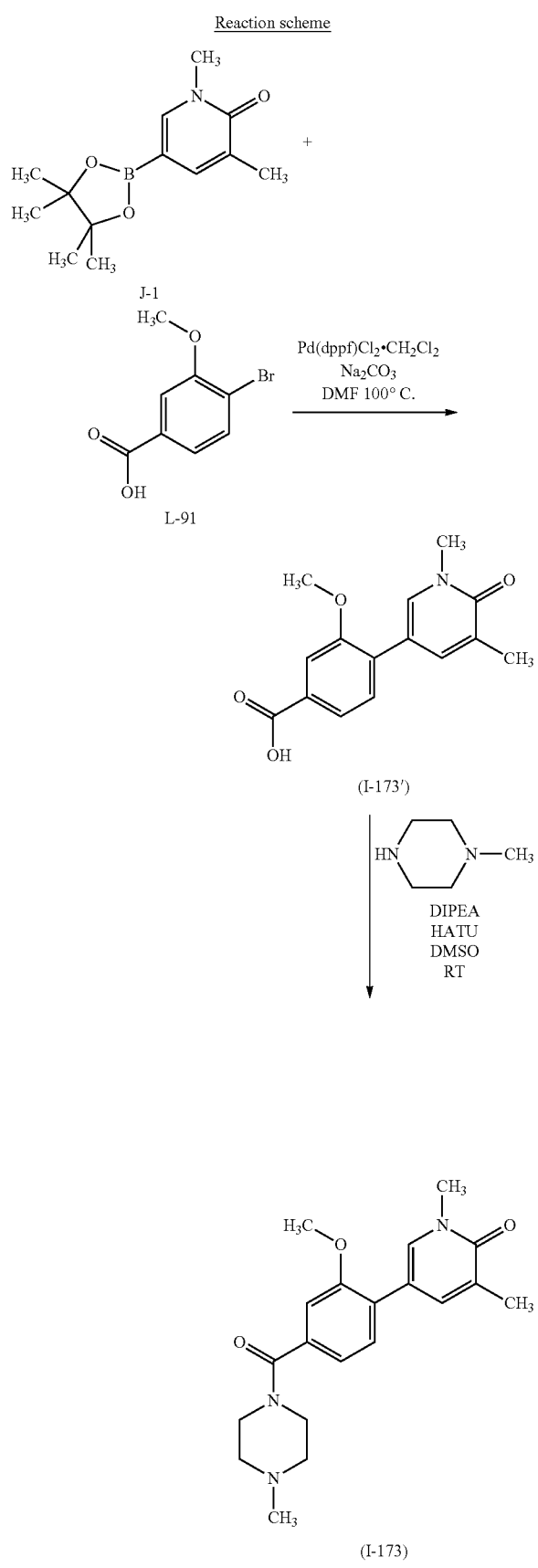

(I-173′)

(I-173)

124

4-(1,5-Dimethyl-6-oxo-1,6-dihydro-pyridin-3-yl)-3-methoxy-benzoic acid (I-173′)

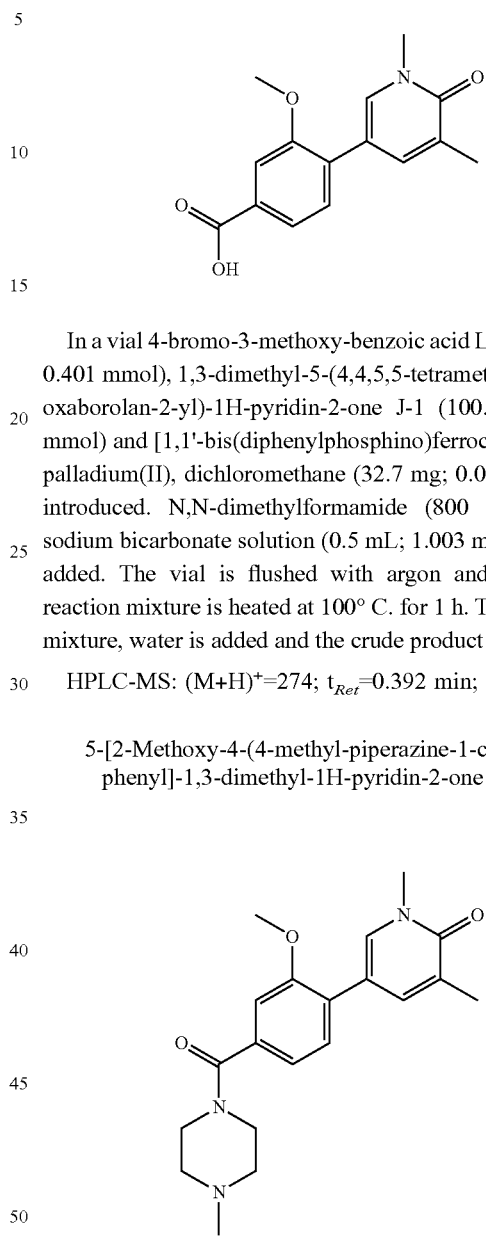

In a vial 4-bromo-3-methoxy-benzoic acid L-91 (92.6 mg; 0.401 mmol), 1,3-dimethyl-5-(4,4,5,5-tetramethyl-[1,3,2]dioxaborolan-2-yl)-1H-pyridin-2-one J-1 (100.0 mg; 0.401 mmol) and [1,1′-bis(diphenylphosphino)ferrocene]dichloropalladium(II), dichloromethane (32.7 mg; 0.040 mmol) are introduced. N,N-dimethylformamide (800 µL) and 2N sodium bicarbonate solution (0.5 mL; 1.003 mmol) are then added. The vial is flushed with argon and sealed. The reaction mixture is heated at 100° C. for 1 h. To the reaction mixture, water is added and the crude product is filtered off.

HPLC-MS: $(M+H)^+=274$; $t_{Ret}=0.392$ min; method M4

5-[2-Methoxy-4-(4-methyl-piperazine-1-carbonyl)-phenyl]-1,3-dimethyl-1H-pyridin-2-one (I-173)

4-(1,5-Dimethyl-6-oxo-1,6-dihydro-pyridin-3-yl)-3-methoxy-benzoic acid I-173′ (110.0 mg; 0.201 mmol), HATU (91.8 mg; 0.242 mmol), N-ethyldiisopropylamine (0.098 mL; 0.604 mmol) and DMSO (800 µL) are introduced in a flask and the mixture is stirred at RT for 15 min. 1-Methyl-piperazine (0.034 mL; 0.302 mmol) is then added and the reaction is stirred overnight at RT. The reaction mixture is then filtered and purified with the acidic RP HPLC system (column: X-Bridge C-18, 30×50 mm). The product containing fractions are concentrated under reduced pressure and freeze dried.

HPLC-MS: $(M+H)^+=356$; $t_{Ret}=0.82$ min; method M1

Method 19:
Preparation of Compound I-177

1,3-Dimethyl-5-[4-(4-methyl-piperazine-1-carbonyl)-3-trifluoromethoxy-phenyl]-1H-pyridin-2-one

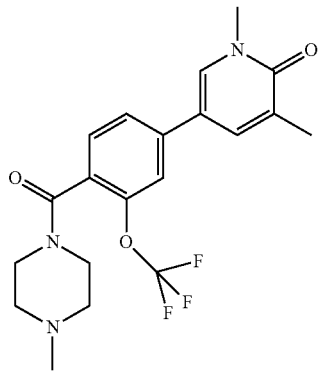 [SMILES: Cc1cc(-c2ccc(C(=O)N3CCN(C)CC3)c(OC(F)(F)F)c2)cn(C)c1=O]

Reaction scheme

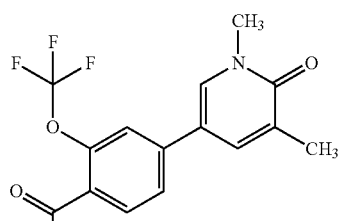

(I-177')

4-(1,5-Dimethyl-6-oxo-1,6-dihydro-pyridin-3-yl)-2-trifluoromethoxy-benzoic acid (I-177')

1,3-Dimethyl-5-(4,4,5,5-tetramethyl-[1,3,2]dioxaborolan-2-yl)-1H-pyridin-2-one J-1 (150.0 mg; 0.457 mmol), 4-bromo-2-trifluoromethoxy-benzoic acid L-95 (159.6 mg; 0.549 mmol), tetrakis(triphenylphosphine)palladium(0) (105.7 mg; 0.091 mmol) and an 2N aqueous solution of sodium bicarbonate (0.572 mL; 1.143 mmol) are suspended in DMF (1.0 mL), the flask is purged for 5 min with argon. The reaction is heated to 100° C. for 1 h. The reaction is then concentrated under reduced pressure and the residue is purified on SP chromatography (DCM/MeOH 0 to 15%) to afford the product.

HPLC-MS: $(M+H)^+=328$; $t_{Ret}=0.48$ min; method M4

1,3-Dimethyl-5-[4-(4-methyl-piperazine-1-carbonyl)-3-trifluoromethoxy-phenyl]-1H-pyridin-2-one (I-177)

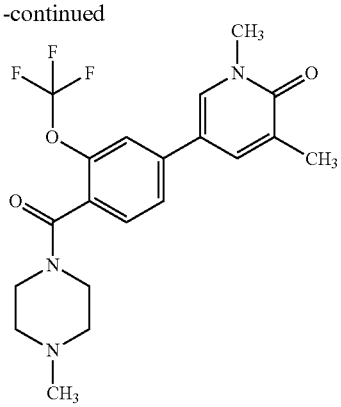

(I-177)

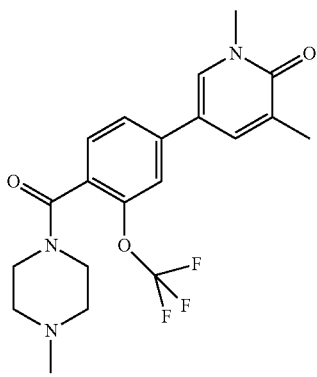 [SMILES: Cc1cc(-c2ccc(C(=O)N3CCN(C)CC3)c(OC(F)(F)F)c2)cn(C)c1=O]

4-(1,5-Dimethyl-6-oxo-1,6-dihydro-pyridin-3-yl)-2-trifluoromethoxy-benzoic acid I-177 (150.0 mg; 0.445 mmol) is suspended in thionyl chloride (25.0 mL) and the reaction is stirred at RT overnight. The suspension slowly dissolves. SOCl$_2$ is evaporated and the residue is dissolved in DCM (25.0 mL). Triethylamine (66.9 µl; 0.489 mmol) and 1-Methyl-piperazine (54.2 µl; 0.489 mmol) are added subsequently and the resulting reaction mixture is stirred at RT for 3 h. The reaction mixture is filtered and purified by NP silica gel chromatography (MeOH/DCM 0 to 10%) to afford the product.

HPLC-MS: (M+H)$^+$=410; $t_{Ret}$=0.95 min; method M1

Method 20:

Preparation of Compound I-178

5-[4-(3-Chloro-azetidin-1-ylmethyl)-3-methoxy-phenyl]-1,3-dimethyl-1H-pyridin-2-one

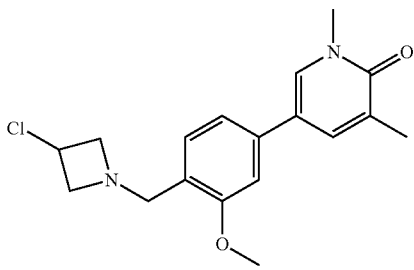 [SMILES: COc1cc(-c2cc(C)c(=O)n(C)c2)ccc1CN1CC(Cl)C1]

Reaction scheme

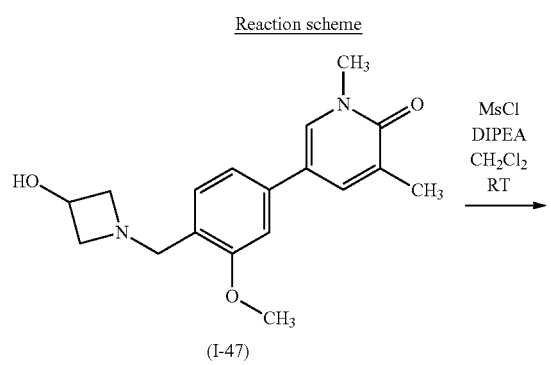

5-[4-(3-Chloro-azetidin-1-ylmethyl)-3-methoxy-phenyl]-1,3-dimethyl-1H-pyridin-2-one (I-178)

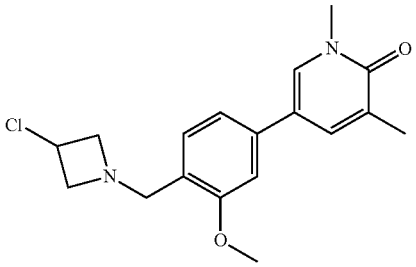 [SMILES: COc1cc(-c2cc(C)c(=O)n(C)c2)ccc1CN1CC(Cl)C1]

Methanesulfonyl chloride (0.037 mL; 0.477 mmol) is added dropwise to a solution of 5-[4-(3-hydroxy-azetidin-1-ylmethyl)-3-methoxy-phenyl]-1,3-dimethyl-1H-pyridin-2-one I-47 (100.0 mg; 0.318 mmol) in dry DCM (1.0 mL) and DIPEA (0.167 mL; 0.954 mmol). The reaction is stirred at RT overnight. The reaction mixture is quenched with water and extracted 3 times with DCM. The combined organic layer is dried and concentrated under reduced pressure. The crude material is dissolved in DMSO (1.0 mL), filtered and purified first with the basic (ammonia buffer) RP HPLC system (column: X-Bridge C-18 30×50 mm). The product containing fractions are concentrated under reduced pressure, the purity is not satisfactory therefore the residue is purified a second time. The residue is dissolved in DMSO (1.0 mL), filtered and purified with the acidic (formic acid) RP HPLC system (column: Sunfire C-18 20×50 mm). The product containing fractions are concentrated under reduced pressure. The product is dissolved in acetonitrile/water 1:1 and freeze dried.

HPLC-MS: (M+H)$^+$=333; $t_{Ret}$=1.08 min; method M1

Method 21:

Preparation of Compound I-179

5-[4-(3-Hydroxy-azetidin-1-ylmethyl)-phenyl]-1,3-dimethyl-1H-pyridin-2-one

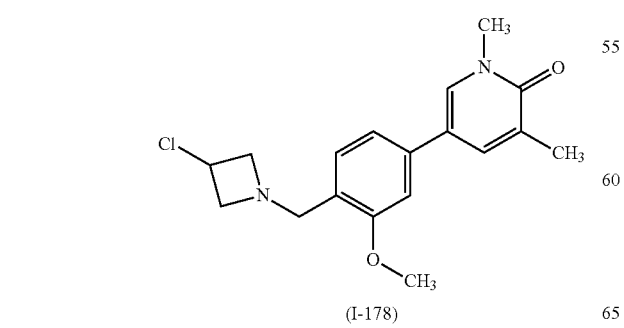
(I-178)

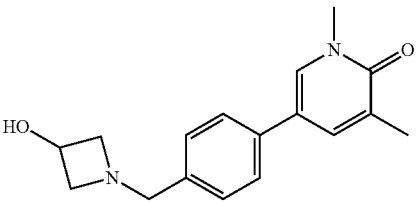 [SMILES: Cc1cc(-c2ccc(CN3CC(O)C3)cc2)cn(C)c1=O]

Reaction scheme

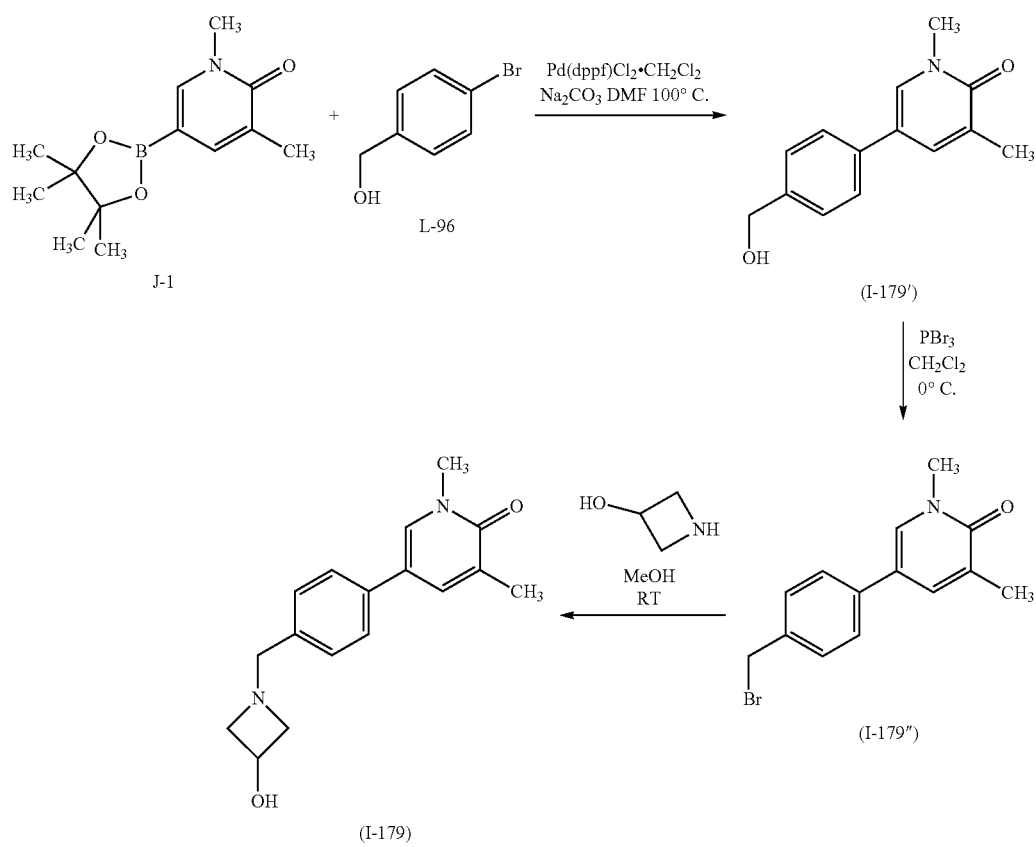

5-(4-Hydroxymethyl-phenyl)-1,3-dimethyl-1H-pyridin-2-one (I-179')

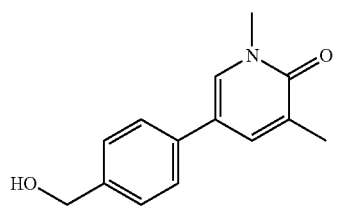 [SMILES: Cc1cc(-c2ccc(CO)cc2)cn(C)c1=O]

5-(4-Bromomethyl-phenyl)-1,3-dimethyl-1H-pyridin-2-one (I-179")

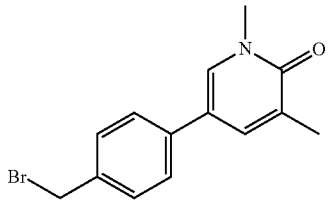 [SMILES: Cc1cc(-c2ccc(CBr)cc2)cn(C)c1=O]

In a vial (4-bromo-phenyl)-methanol L-96 (150.2 mg; 0.803 mmol), 1,3-dimethyl-5-(4,4,5,5-tetramethyl-[1,3,2]dioxaborolan-2-yl)-1H-pyridin-2-one J-1 (200.0 mg; 0.803 mmol) and [1,1'-bis(diphenylphosphino)ferrocene]dichloropalladium(II), dichloromethane (32.7 mg; 0.040 mmol) are introduced. DMF (800 µL) and an 2N aqueous solution of sodium bicarbonate (0.5 mL) are then added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are combined and concentrated under reduced pressure.

HPLC-MS: $(M+H)^+$=230; $t_{Ret}$=0.69 min; method M1

5-(4-Hydroxymethyl-phenyl)-1,3-dimethyl-1H-pyridin-2-one I-179' (500.0 mg; 2.181 mmol) is dissolved in DCM (10.0 mL) and cooled to 0° C. Phosphorus tribromide (295.2 mg; 1.090 mmol) is added dropwise to the stirred reaction mixture. The mixture is then stirred at 0° C. for 30 min. After the reaction is completed, it is quenched by adding water dropwise. The product is extracted with DCM. The organic layer is washed with water and brine. The reaction is dried with $Na_2SO_4$, filtered and the solvent is removed under reduced pressure to give product.

TLC Information (Silica, Eluent: PE:EA=2:1); Rf (product)=0.5

131

5-[4-(3-Hydroxy-azetidin-1-ylmethyl)-phenyl]-1,3-dimethyl-1H-pyridin-2-one (I-179)

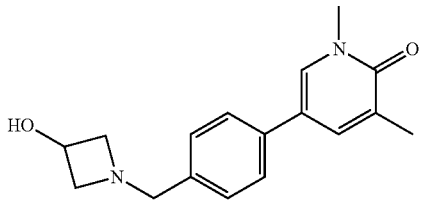 [SMILES: Cc1cc(-c2ccc(CN3CC(O)C3)cc2)cn(C)c1=O]

5-(4-Bromomethyl-phenyl)-1,3-dimethyl-1H-pyridin-2-one I-179" (5.000 g; 0.017 mol) is dissolved in DCM (10.0 mL), azetidin-3-ol (6.254 g; 0.086 mol) is added to the mixture and the reaction is stirred at RT for 12 h. Solvent is removed and the crude material is purified by prep-HPLC to give the desired product.

132

TLC Information (Silica, Eluent: DCM:MeOH=15:1); Rf (product)=0.5
Method 22:
Preparation of Compound I-186

5-(2,5-Dimethyl-4-piperazin-1-ylmethyl-phenyl)-1,3-dimethyl-1H-pyridin-2-one

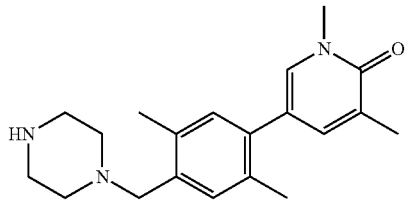

Reaction scheme

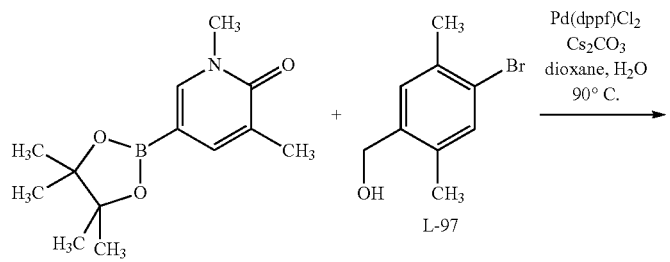

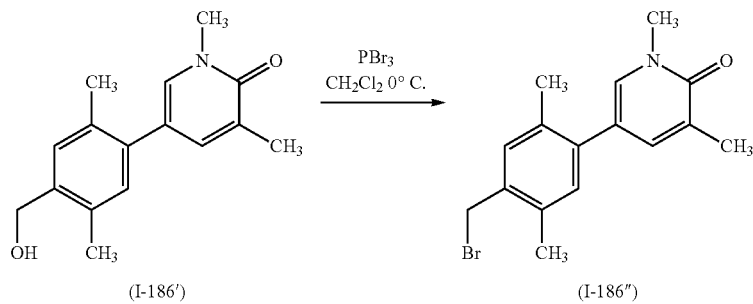

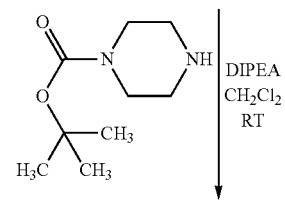

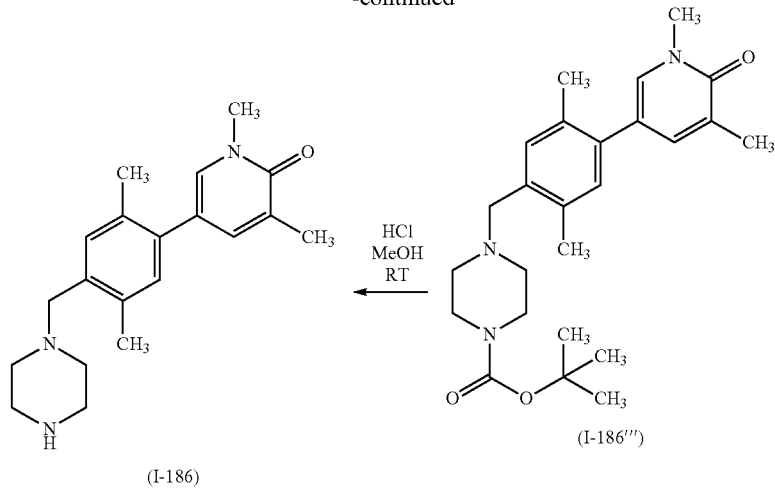

5-(4-Hydroxymethyl-2,5-dimethyl-phenyl)-1,3-dimethyl-1H-pyridin-2-one (I-186')

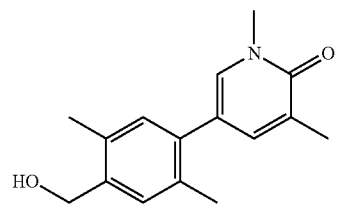 [SMILES: Cc1cc(-c2cc(C)c(=O)n(C)c2)c(C)cc1CO]

To the solution of (4-bromo-2,5-dimethyl-phenyl)-methanol L-97 (2.000 g; 9.299 mmol) and 1,3-dimethyl-5-(4,4,5,5-tetramethyl-[1,3,2]dioxaborolan-2-yl)-1H-pyridin-2-one J-1 (2.500 g; 10.036 mmol) in dioxane (50.0 mL) and water (2.0 mL) are added Cs$_2$CO$_3$ (8.200 g; 25.231 mmol), followed by Pd(dppf)Cl2 (0.500 g; 0.683 mmol). The mixture is heated to 90° C. and stirred for 2 h. The reaction is filtered over a pad of celite. The filtrate is concentrated under reduced pressure. The crude material is dissolved with EA and washed with brine and dried with Na$_2$SO$_4$. It is concentrated under reduced pressure and the crude material is purified by normal phase chromatography (PE:EA=5:1).

HPLC-MS: (M+H)$^+$=258; t$_{Ret}$=1.07 min; method M7

5-(4-Bromomethyl-2,5-dimethyl-phenyl)-1,3-dimethyl-1H-pyridin-2-one (I-186")

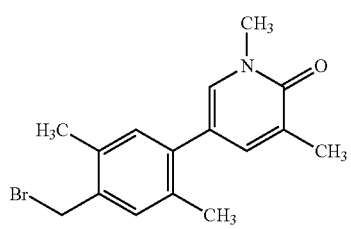 [SMILES: Cc1cc(-c2cc(C)c(=O)n(C)c2)c(C)cc1CBr]

To a solution of 5-(4-hydroxymethyl-2,5-dimethyl-phenyl)-1,3-dimethyl-1H-pyridin-2-one I-186' (500.0 mg; 1.943 mmol) in DCM (5.0 mL) is added phosphorus tribromide (1.800 g; 6.742 mmol) at 0° C. The reaction is left to warm to RT and stirred at RT overnight. The reaction is then poured onto aqueous NaHCO$_3$ and extracted with EA. The combined organic layer is washed with brine, dried and concentrated under reduced pressure to give the crude product. The compound is used in the next step without further purification.

TLC Information (Silica, Eluent: DCM:MeOH=10:1); Rf (product)=0.6

4-[4-(1,5-Dimethyl-6-oxo-1,6-dihydro-pyridin-3-yl)-2,5-dimethyl-benzyl]-piperazine-1-carboxylic acid tert-butyl ester (I-186''')

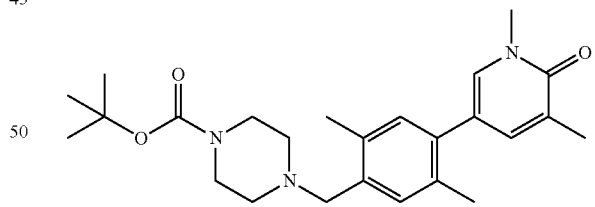

To the solution of 5-(4-bromomethyl-2,5-dimethyl-phenyl)-1,3-dimethyl-1H-pyridin-2-one I-186" (150.0 mg; 0.468 mmol) in DCM (5.0 mL) is added DIPEA (0.100 mL; 0.556 mmol) and piperazine-1-carboxylic acid tert-butyl ester (90.0 mg; 0.483 mmol). The mixture is stirred at RT for 2 h. The reaction mixture is concentrated under reduced pressure. The compound is used in the next step without further purification.

TLC Information (Silica, Eluent: DCM:MeOH=20:1); Rf (product)=0.6

5-(2,5-Dimethyl-4-piperazin-1-ylmethyl-phenyl)-1,3-dimethyl-1H-pyridin-2-one (I-186)

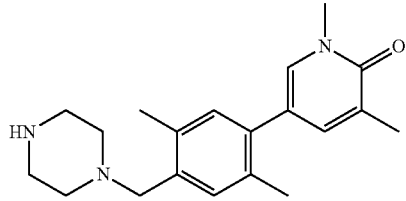 [SMILES: Cc1cc(-c2cc(C)c(=O)n(C)c2)c(C)cc1CN1CCNCC1]

To 4-[4-(1,5-dimethyl-6-oxo-1,6-dihydro-pyridin-3-yl)-2,5-dimethyl-benzyl]-piperazine-1-carboxylic acid tert-butyl ester I-186''' (120.0 mg; 0.282 mmol) is added 4M HCl in MeOH (4.0 mL). The reaction is stirred at RT for 2 h. The reaction is then concentrated under reduced pressure and the residue is dissolved in MeOH and purified by prep-HPLC to give the desired compound.

Structure confirmed by 1H NMR

Method 23:

Preparation of Compound I-188

5-[3-Hydroxy-4-(4-methyl-piperazine-1-carbonyl)-phenyl]-1,3-dimethyl-1H-pyridin-2-one

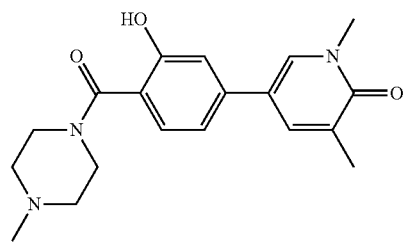 [SMILES: Cc1cc(-c2ccc(C(=O)N3CCN(C)CC3)c(O)c2)cn(C)c1=O]

Reaction scheme

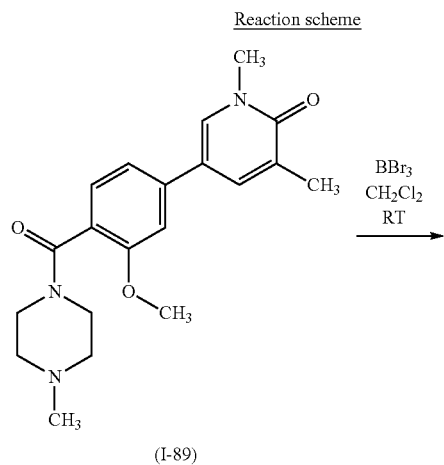

5-[3-Hydroxy-4-(4-methyl-piperazine-1-carbonyl)-phenyl]-1,3-dimethyl-1H-pyridin-2-one (I-188)

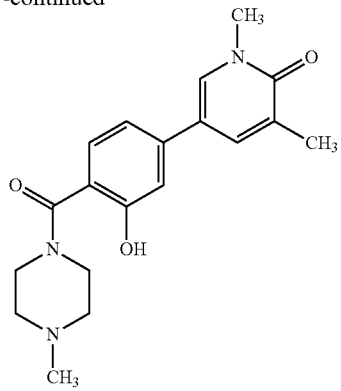

Boron tribromide (50.0 µl; 0.519 mmol) is carefully added to a solution of 5-[3-methoxy-4-(4-methyl-piperazine-1-carbonyl)-phenyl]-1,3-dimethyl-1H-pyridin-2-one I-89 (50.0 mg; 0.141 mmol) in dry dichloromethane (1.0 mL). The mixture is stirred at RT for 1 h. Then the reaction mixture is added dropwise to MeOH (1.0 mL) and then diluted with water (10.0 mL). The mixture is extracted 3 times with DCM (10.0 mL). The combined organic layer is dried with Na$_2$SO$_4$, filtered and concentrated under reduced pressure. The crude material is purified by silica chromatography Combiflash (Column Redisep Rf, 12 g; gradient: DCM/MeOH=100%/0% to 80%/20% over 28 column volumes; flow rate=30 mL/min; detection wavelength: 254 nm). The product containing fractions are combined and concentrated under reduced pressure.

HPLC-MS: (M+H)$^+$=342; t$_{Ret}$=0.89 min; method M1

Method 24:

Preparation of Compound I-189

5-{4-[(S)-1-(2,5-Diaza-bicyclo[2.2.1]hept-2-yl)methyl]-phenyl}-1,3-dimethyl-1H-pyridin-2-one

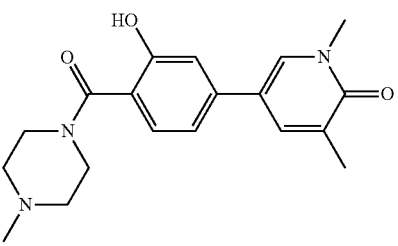 [SMILES: Cc1cc(-c2ccc(C(=O)N3CCN(C)CC3)c(O)c2)cn(C)c1=O]

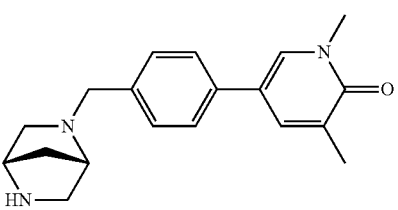 [SMILES: Cc1cc(-c2ccc(CN3C[C@@H]4C[C@H]3CN4)cc2)cn(C)c1=O]

Reaction scheme
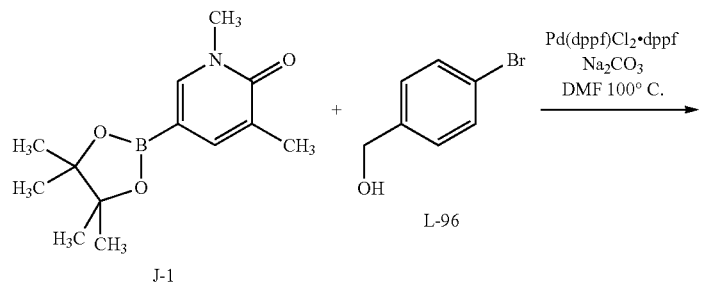
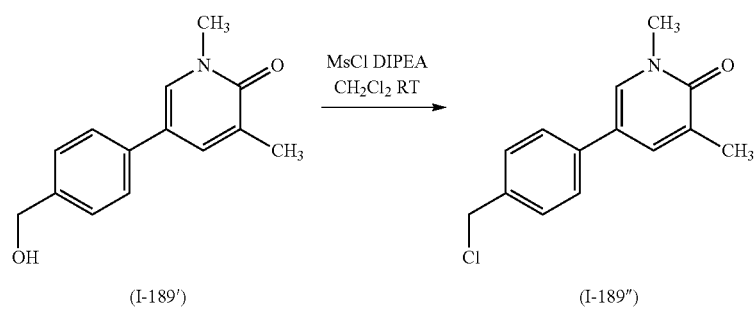
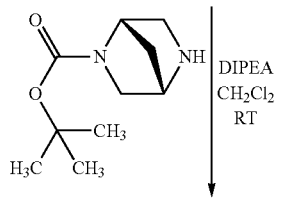
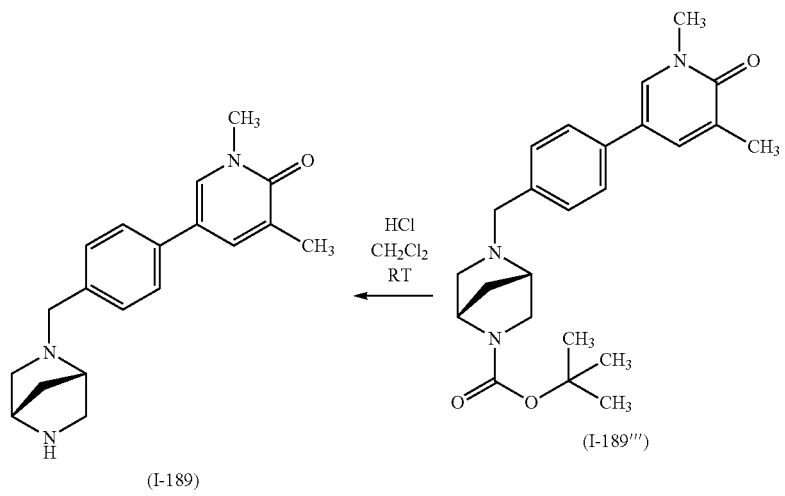

5-(4-Hydroxymethyl-phenyl)-1,3-dimethyl-1H-pyridin-2-one (I-189')

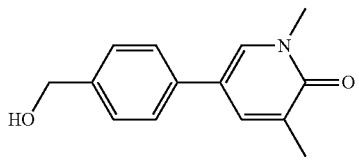 [SMILES: Cc1cc(-c2ccc(CO)cc2)cn(C)c1=O]

In a vial 4-bromobenzyl alcohol L-96 (150.0 mg; 0.802 mmol), boronic acid pinacol ester 1,3-dimethyl-5-(4,4,5,5-tetramethyl-[1,3,2]dioxaborolan-2-yl)-1H-pyridin-2-one J-1 (200.0 mg; 0.803 mmol) and [1,1'-bis(diphenylphosphino)ferrocene]dichloropalladium(II), dichloromethane (33 mg; 40.1 µmol) are weight in. DMF (800 µL) and a 2N solution of sodium bicarbonate (501 µL; 1.003 mmol) are added. The vial is flushed with argon and sealed. The reaction mixture is heated at 100° C. for 1 h. Water is then added to the reaction mixture. The mixture is filtered and purified with the basic (ammonia buffer) RP HPLC system (column: X-Bridge C-18 30×50 mm). The product containing fractions are combined and concentrated under reduced pressure.

HPLC/MS: (M+H)$^+$=230; $t_{Ret}$=0.69 min; method M1

5-{4-[(S)-1-(2,5-Diaza-bicyclo[2.2.1]hept-2-yl)methyl]-phenyl}-1,3-dimethyl-1H-pyridin-2-one (I-189'')

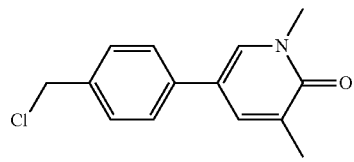 [SMILES: Cc1cc(-c2ccc(CCl)cc2)cn(C)c1=O]

To a solution of 5-(4-hydroxymethyl-phenyl)-1,3-dimethyl-1H-pyridin-2-one I-189' (46.0 mg; 0.201 mmol) in dry DCM (1.0 mL) and DIPEA (0.100 mL; 0.573 mmol), methanesulfonyl chloride (0.023 mL; 0.301 mmol) is added dropwise. The mixture is stirred at RT overnight. A second portion of DIPEA (0.070 mL; 0.401 mmol) and methanesulfonyl chloride (0.016 mL; 0.201 mmol) are added and the mixture is stirred at RT for additional 24 h. The reaction is then quenched with water and extracted 3 times with DCM. The combined organic layers are dried with Na$_2$SO$_4$, filtered and concentrated under reduced pressure.

HPLC/MS: (M+H)$^+$=248; $t_{Ret}$=1.24 min; method M1

(S)-5-[4-(1,5-Dimethyl-6-oxo-1,6-dihydro-pyridin-3-yl)-benzyl]-2,5-diaza-bicyclo[2.2.1]heptane-2-carboxylic acid tert-butyl ester (I-189''')

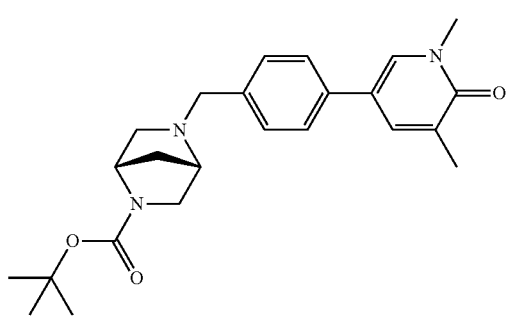 [SMILES: Cc1cc(-c2ccc(CN3C[C@@H]4C[C@H]3CN4C(=O)OC(C)(C)C)cc2)cn(C)c1=O]

To a solution of 5-(4-chloromethyl-phenyl)-1,3-dimethyl-1H-pyridin-2-one I-189'' (95.0 mg; 0.192 mmol) in DIPEA (0.100 mL; 0.573 mmol) and dry DCM (1.0 mL), tert-butyl (1S,4S)-(−)-2,5-diazabicyclo[2.2.1]heptane-2-carboxylate (57.025 mg; 0.288 mmol) is added. The mixture is stirred overnight at RT. The reaction mixture is then extracted 3 times with DCM. The combined organic layers are dried and concentrated under reduced pressure.

HPLC/MS: (M+H)$^{30}$=410; $t_{Ret}$=0.63 min; method M2

5-{4-[(S)-1-(2,5-Diaza-bicyclo[2.2.1]hept-2-yl)methyl]-phenyl}-1,3-dimethyl-1H-pyridin-2-one (I-189)

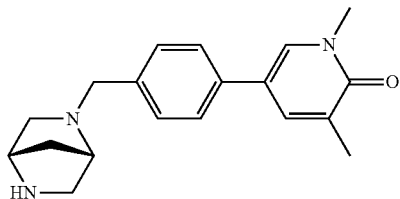 [SMILES: Cc1cc(-c2ccc(CN3C[C@@H]4C[C@H]3CN4)cc2)cn(C)c1=O]

4M HCl in dioxane (2.0 mL) is added to a solution of (S)-5-[4-(1,5-dimethyl-6-oxo-1,6-dihydro-pyridin-3-yl)-benzyl]-2,5-diaza-bicyclo[2.2.1]heptane-2-carboxylic acid tert-butyl ester I-189''' (91.0 mg; 0.111 mmol) in DCM (3.0 mL). The reaction mixture is stirred at RT for 4 h. The reaction mixture is then concentrated under reduced pressure. The crude material is purified by silica chromatography Combiflash (Column Redisep Rf, 12 g; gradient: DCM/MeOH=100%/0% to 85%/15% over 40 column volumes; flow rate=30 mL/min; detection wavelength: 214 nm). The product containing fractions are combined and concentrated under reduced pressure to give the desired compound.

HPLC/MS: (M+H)$^+$=310; $t_{Ret}$=0.98 min; method M1

Method 25:

Preparation of Compound I-194

5-[3-Hydroxy-4-(4-methyl-piperazin-1-ylmethyl)-phenyl]-1,3-dimethyl-1H-pyridin-2-one

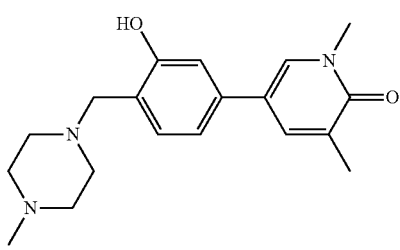 [SMILES: Cc1cc(-c2ccc(CN3CCN(C)CC3)c(O)c2)cn(C)c1=O]

And Preparation of Compound I-195

5-[3-(2-Methoxy-ethoxy)-4-(4-methyl-piperazin-1-ylmethyl)-phenyl]-1,3-dimethyl-1H-pyridin-2-one

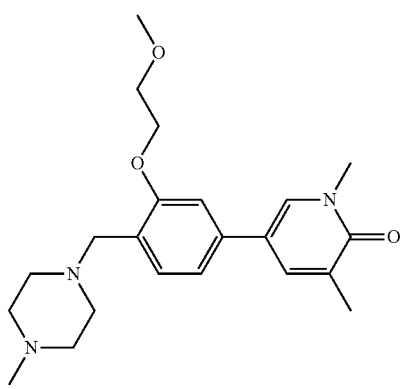 [SMILES: COCCOc1cc(-c2cc(C)c(=O)n(C)c2)ccc1CN1CCN(C)CC1]

Reaction scheme

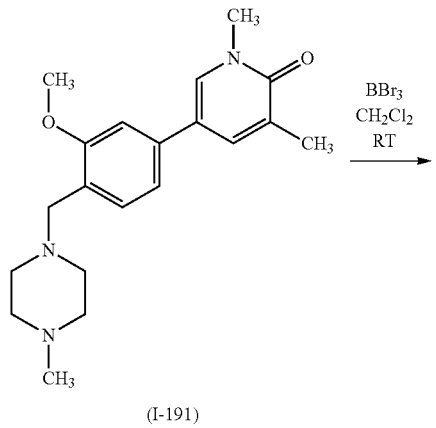

(I-191)

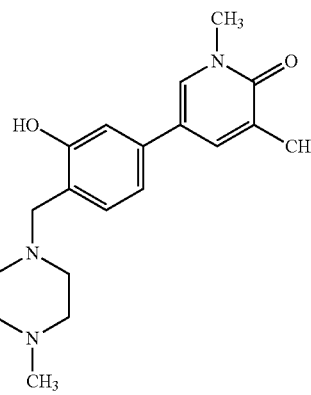

(I-194)

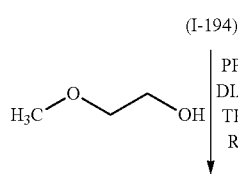

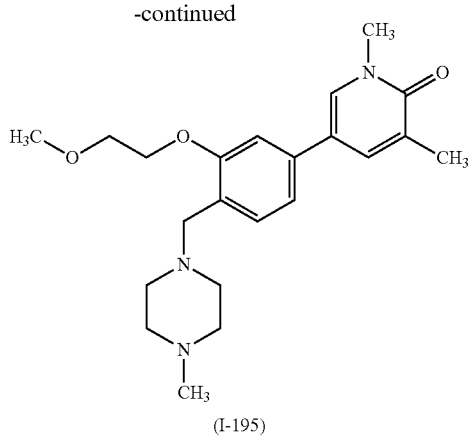

(I-195)

5-[3-Hydroxy-4-(4-methyl-piperazin-1-ylmethyl)-phenyl]-1,3-dimethyl-1H-pyridin-2-one (I-194)

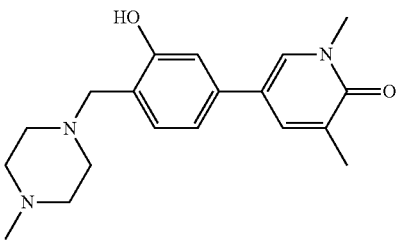

Boron tribromide (395.074 µl; 4.100 mmol) is carefully added to a solution of 5-[3-methoxy-4-(4-methyl-piperazin-1-ylmethyl)-phenyl]-1,3-dimethyl-1H-pyridin-2-one I-191 (400.0 mg; 1.171 mmol) in dry DCM (4.0 mL). The mixture is stirred at RT for 1 h. A second portion of boron tribromide (100.0 µl; 1.038 mmol) is added and the mixture is stirred for an additional 1 h. The reaction mixture is then added dropwise to 1.0 mL of MeOH. The mixture is diluted with water (5.0 mL) and an aqueous solution of NaOH (1M, 10.0 mL), and extracted with DCM (3×10.0 mL). The combined organic layers are dried with $Na_2SO_4$, filtered and concentrated under reduced pressure. The crude product is dissolved in DMSO (1.5 mL), filtered and purified with the basic (ammonia buffer) RP HPLC system (column: X-Bridge C-18 30×50 mm). The product containing fractions are concentrated under reduced pressure.

HPLC/MS: $(M+H)^+=328$; $t_{Ret}=0.95$ min; method M1

5-[3-(2-Methoxy-ethoxy)-4-(4-methyl-piperazin-1-ylmethyl)-phenyl]-1,3-dimethyl-1H-pyridin-2-one (I-195)

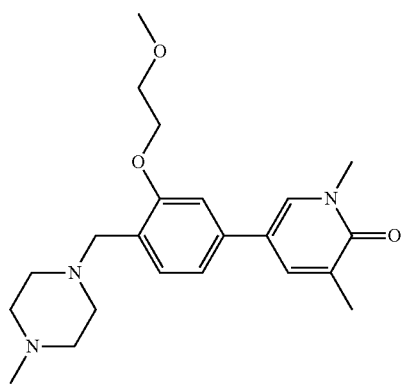 [SMILES: COCCOc1cc(-c2cc(C)c(=O)n(C)c2)ccc1CN1CCN(C)CC1]

5-[3-Hydroxy-4-(4-methyl-piperazin-1-ylmethyl)-phenyl]-1,3-dimethyl-1H-pyridin-2-one I-194 (30.0 mg; 0.092 mmol), 2-methoxyethanol (8.733 µl; 0.110 mmol) and triphenylphosphine (33.6 mg; 0.128 mmol) are dissolved in dry THF (1.0 mL). The mixture is stirred at RT and a solution of diisopropylazodicarboxylate (25 µl; 0.128 mmol) in dry THF (0.500 mL) is added dropwise. The reaction mixture is stirred at RT overnight. The reaction is then quenched with water and extracted 3 times with DCM. The combined organic layers are dried and concentrated under reduced pressure. The crude material is dissolved in 1 mL DMSO, filtered and purified with the acidic (formic acid) RP HPLC system (column: Sunfire C-18 20×50 mm). The product containing fractions are concentrated under reduced pressure.

HPLC/MS: (M+H)$^+$=386; $t_{Ret}$=0.93 min; method M1

Method 26:

Preparation of Compound I-197

5-[3-Ethoxy-4-(4-methyl-piperazin-1-ylmethyl)-phenyl]-1,3-dimethyl-1H-pyridin-2-one

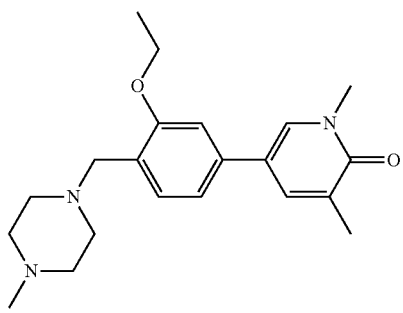 [SMILES: CCOc1cc(-c2cc(C)c(=O)n(C)c2)ccc1CN1CCN(C)CC1]

Reaction scheme

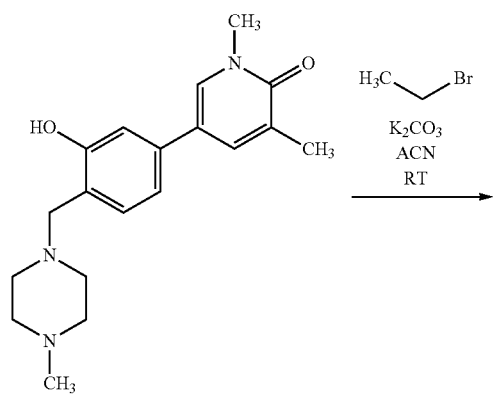

(I-194)

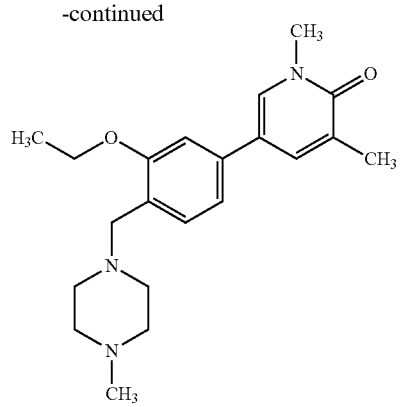

(I-197)

5-[3-Ethoxy-4-(4-methyl-piperazin-1-ylmethyl)-phenyl]-1,3-dimethyl-1H-pyridin-2-one (I-197)

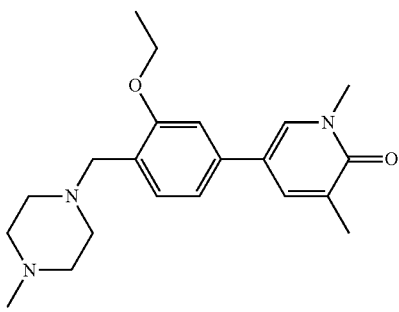 [SMILES: CCOc1cc(-c2cc(C)c(=O)n(C)c2)ccc1CN1CCN(C)CC1]

To a suspension of 5-[3-hydroxy-4-(4-methyl-piperazin-1-ylmethyl)-phenyl]-1,3-dimethyl-1H-pyridin-2-one I-194 (55.0 mg; 0.168 mmol) and potassium carbonate (69.6 mg; 0.504 mmol) in acetonitrile (1.5 mL), bromoethane (0.019 mL; 0.252 mmol) is added dropwise. The reaction mixture is stirred at RT overnight. The reaction mixture is then diluted with water and extracted 3 times with DCM. The combined organic layers are dried with Na$_2$SO$_4$, filtered and concentrated under reduced pressure. The crude mixture is dissolved in DMSO, filtered and purified with the basic (ammonia buffer) RP HPLC system (column: X-Bridge C-18 30×50 mm).

HPLC/MS: (M+H)$^+$=356; $t_{Ret}$=1.05 min; method M1

Method 27:

Preparation of Compound I-198

5-{4-[4-(3-Amino-benzyl)-piperazin-1-ylmethyl]-3-methoxy-phenyl}-1,3-dimethyl-1H-pyridin-2-one

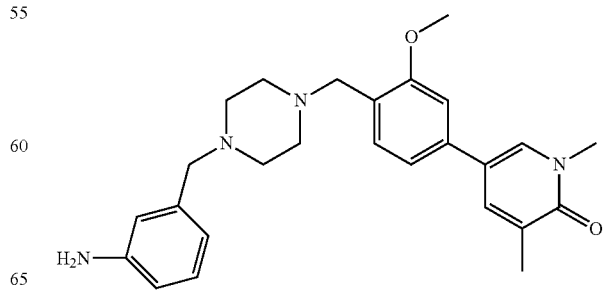

Reaction scheme

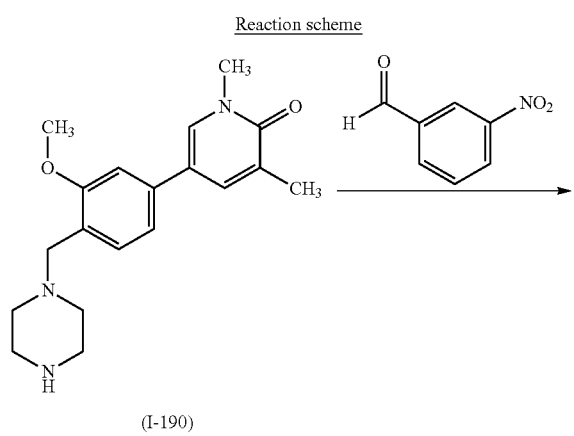

(I-190)

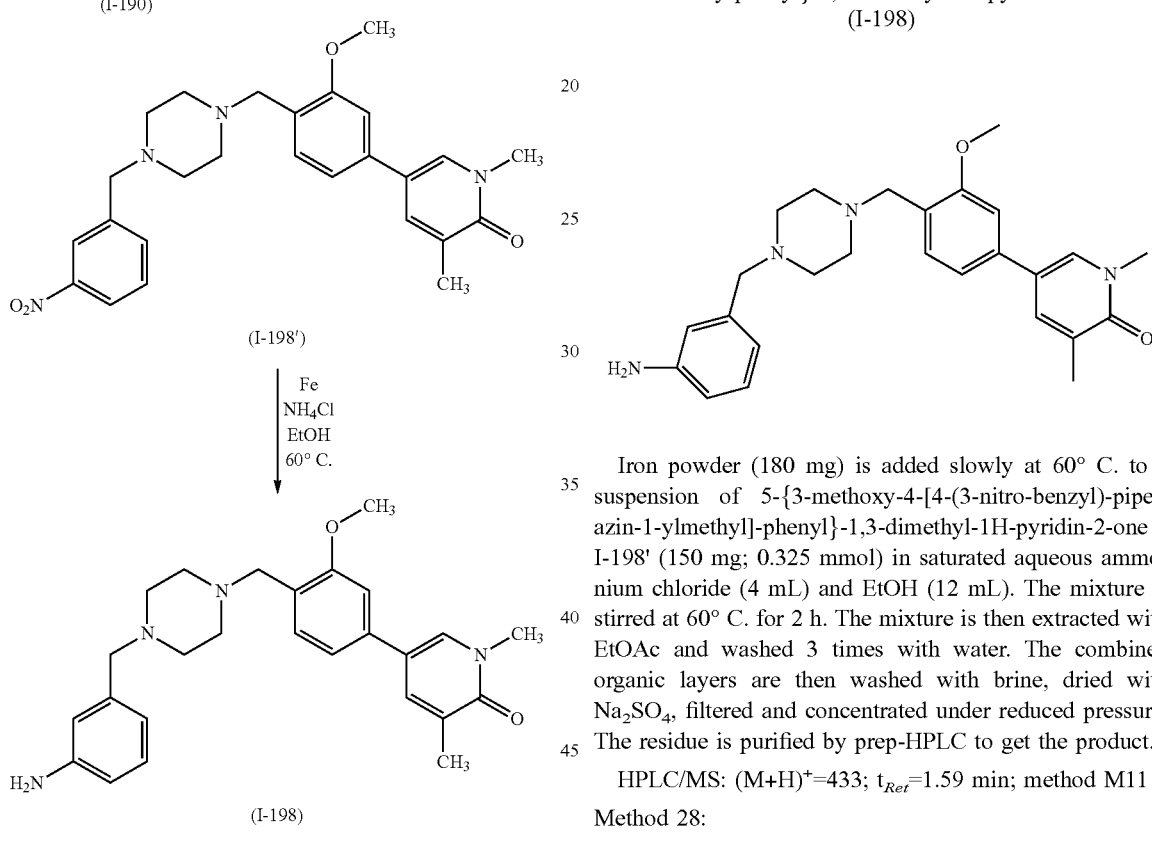

5-{3-Methoxy-4-[4-(3-nitro-benzyl)-piperazin-1-ylmethyl]-phenyl}-1,3-dimethyl-1H-pyridin-2-one
(I-198')

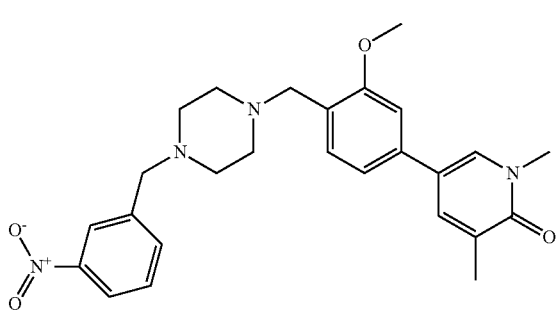 [SMILES: COc1cc(-c2cc(C)c(=O)n(C)c2)ccc1CN1CCN(Cc2cccc([N+](=O)[O-])c2)CC1]

A mixture of 5-(3-methoxy-4-piperazin-1-ylmethyl-phenyl)-1,3-dimethyl-1H-pyridin-2-one I-190 (225.0 mg; 0.0602 mmol) and 3-nitrobenzaldehyde (125.0 mg; 1.208 mmol) in DCM (20 mL) is stirred at RT for 30 min. Sodium triacetoxyborohydride (750 mg) is then added slowly. The mixture is stirred at RT overnight. Water is then added slowly to the mixture and extracted with DCM. The combined organic layers are dried with $Na_2SO_4$, filtered and concentrated under reduced pressure. The residue is used in the next step without further purification.

HPLC/MS: $(M+H)^+=433$; $t_{Ret}=1.15$ min; method M8

5-{4-[4-(3-Amino-benzyl)-piperazin-1-ylmethyl]-3-methoxy-phenyl}-1,3-dimethyl-1H-pyridin-2-one
(I-198)

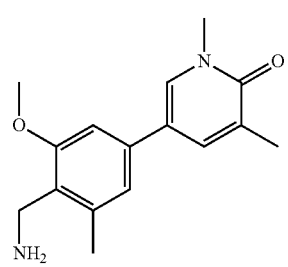 [SMILES: COc1cc(-c2cc(C)c(=O)n(C)c2)cc(C)c1CN]

Iron powder (180 mg) is added slowly at 60° C. to a suspension of 5-{3-methoxy-4-[4-(3-nitro-benzyl)-piperazin-1-ylmethyl]-phenyl}-1,3-dimethyl-1H-pyridin-2-one I-198' (150 mg; 0.325 mmol) in saturated aqueous ammonium chloride (4 mL) and EtOH (12 mL). The mixture is stirred at 60° C. for 2 h. The mixture is then extracted with EtOAc and washed 3 times with water. The combined organic layers are then washed with brine, dried with $Na_2SO_4$, filtered and concentrated under reduced pressure. The residue is purified by prep-HPLC to get the product.

HPLC/MS: $(M+H)^+=433$; $t_{Ret}=1.59$ min; method M11

Method 28:
Preparation of Compound I-202

5-(4-Aminomethyl-3-methoxy-5-methyl-phenyl)-1,3-dimethyl-1H-pyridin-2-one

And Preparation of Compound I-203
5-(4-Dimethylaminomethyl-3-methoxy-5-methyl-phenyl)-1,3-dimethyl-1H-pyridin-2-one
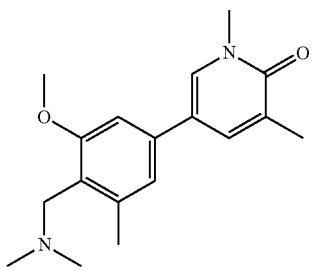
Reaction scheme
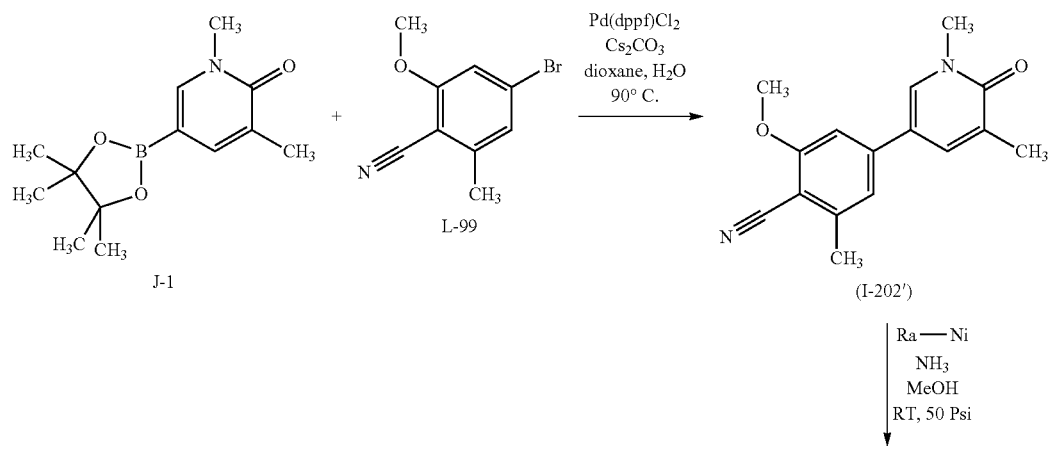
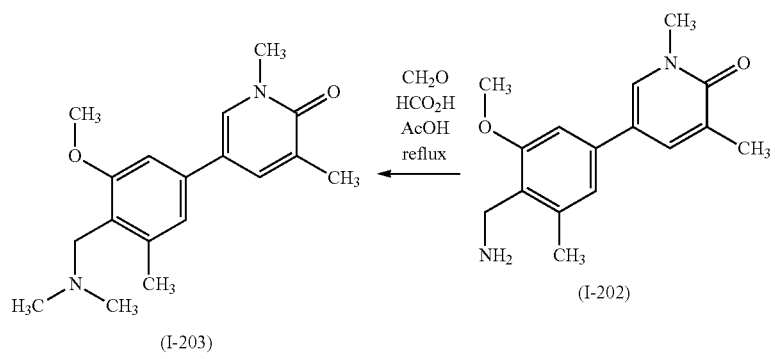

149

4-(1,5-Dimethyl-6-oxo-1,6-dihydro-pyridin-3-yl)-2-methoxy-6-methyl-benzonitrile (I-202')

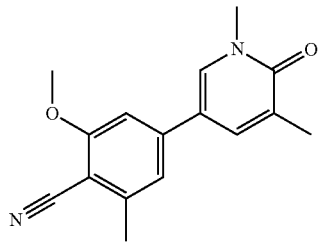 [SMILES: COc1cc(-c2cc(C)c(=O)n(C)c2)cc(C)c1C#N]

To a solution of 4-bromo-2-methoxy-6-methyl-benzonitrile L-99 (1.000 g; 4.423 mmol) and 1,3-dimethyl-5-(4,4,5,5-tetramethyl-[1,3,2]dioxaborolan-2-yl)-1H-pyridin-2-one J-1 (1.100 g; 4.416 mmol) in dixoane (50 mL) and water (2 mL) is added cesium carbonate (4.500 g; 13.846 mmol) and then [1,1'-bis(diphenylphosphino)ferrocene]dichloropalladium(II) (200.0 mg, 0.273 mmol). The reaction mixture is stirred at 90° C. for 2 h. The reaction mixture is then filtered through a pad of celite. The filtrate is concentrated, dissolved in ethylacetate and washed with brine. The combined organic layers are then dried with $Na_2SO_4$, filtered and concentrated under reduced pressure. The residue is purified by prep-HPLC.

HPLC/MS: $(M+H)^+=269$; $t_{Ret}=1.16$ min; method M8

5-(4-Aminomethyl-3-methoxy-5-methyl-phenyl)-1,3-dimethyl-1H-pyridin-2-one (I-202)

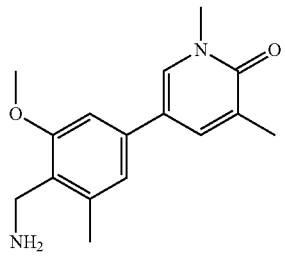 [SMILES: COc1cc(-c2cc(C)c(=O)n(C)c2)cc(C)c1CN]

To the solution of 4-(1,5-dimethyl-6-oxo-1,6-dihydro-pyridin-3-yl)-2-methoxy-6-methyl-benzonitrile I-202' (200.0 mg; 0.745 mmol) in MeOH (15 mL) is added aqueous ammonia (500 µL) and Raney-Ni (200.0 mg). The mixture is degassed and refilled with $H_2$ twice and stirred at RT under 50 Psi overnight. The reaction mixture is then filtered and the residue is washed with THF/MeOH. The filtrated is then concentrated to give the desired compound, which is used in the next step without purification HPLC/MS: $(M+H)^+=273$; $t_{Ret}=0.8$ min; method M7

150

5-(4-Dimethylaminomethyl-3-methoxy-5-methyl-phenyl)-1,3-dimethyl-1H-pyridin-2-one (I-203)

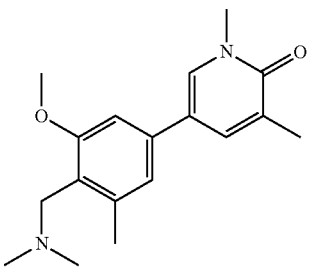

5-(4-Aminomethyl-3-methoxy-5-methyl-phenyl)-1,3-dimethyl-1H-pyridin-2-one I-202 (50.0 mg; 0.184 mmol) is mixed with aqueous formaldehyde (50 µL), formic acid (50 µL) and acetic acid (1 mL). The mixture is heated at reflux overnight. The reaction mixture is then concentrated under reduced pressure. The residue is dissolved in methanol and purified by prep-HPLC.

The structure is confirmed by $^1$H NMR

Method 29:
Preparation of Compound I-204

5-[3-Dimethylamino-4-(4-methyl-piperazin-1-ylmethyl)-phenyl]-1,3-dimethyl-1H-pyridin-2-one

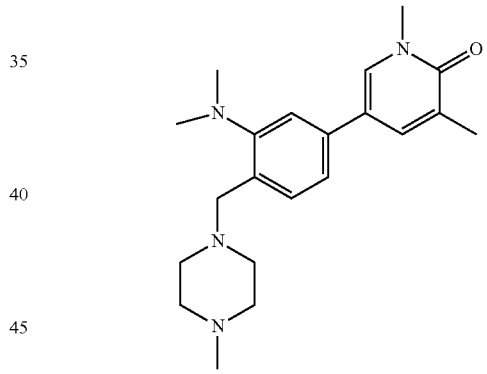

Reaction scheme

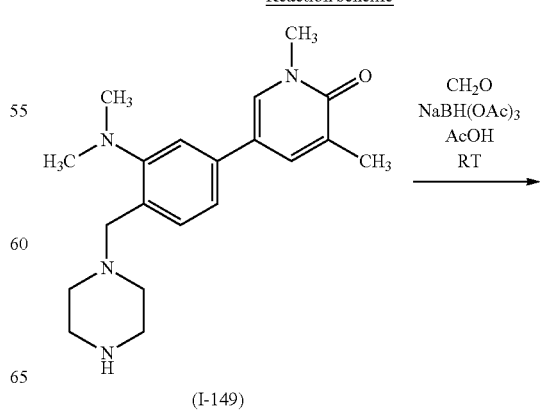

-continued

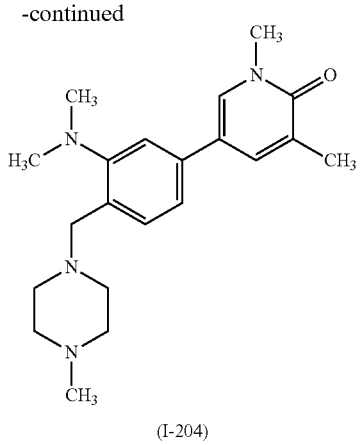

(I-204)

5-[3-Dimethylamino-4-(4-methyl-piperazin-1-ylmethyl)-phenyl]-1,3-dimethyl-1H-pyridin-2-one (I-204)

5-(3-Dimethylamino-4-piperazin-1-ylmethyl-phenyl)-1,3-dimethyl-1H-pyridin-2-one I-149 (80.0 mg; 0,235 mmol) is dissolved in THF (3.0 mL). Acetic acid (42 µl 0,705 mmol) and formaldehyde (35 µL; 0.470 mmol) are added. The reaction mixture is stirred at RT for 30 min. Sodium triacetoxyborohydride (132.5 mg; 0.705 mmol) is added. The reaction mixture is stirred at RT for an additional 2 h. MeOH (20 mL) is added and the reaction mixture is concentrated under reduced pressure. The residue is dissolved in DCM (100 mL) extracted with saturated NaHCO₃ solution (50 mL) with Na₂SO₄, filtered and concentrated under reduced pressure.

The crude material is purified by silica gel chromatography Combiflash (gradient: DCM/MeOH 2N NH₃=100%/0% to 90%/10%). The product containing fractions are combined and concentrated under reduced pressure to give the desired compound.

HPLC/MS: (M+H)⁺=355; $t_{Ret}$=1.03 min; method M1

Method 30:
Preparation of Compound I-205

5-{3,5-Dimethoxy-4-[(1-methyl-azetidin-3-ylamino)-methyl]-phenyl}-1,3-dimethyl-1H-pyridin-2-one

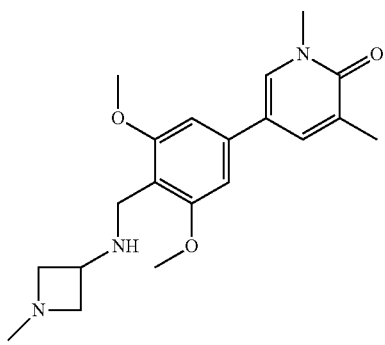

Reaction scheme

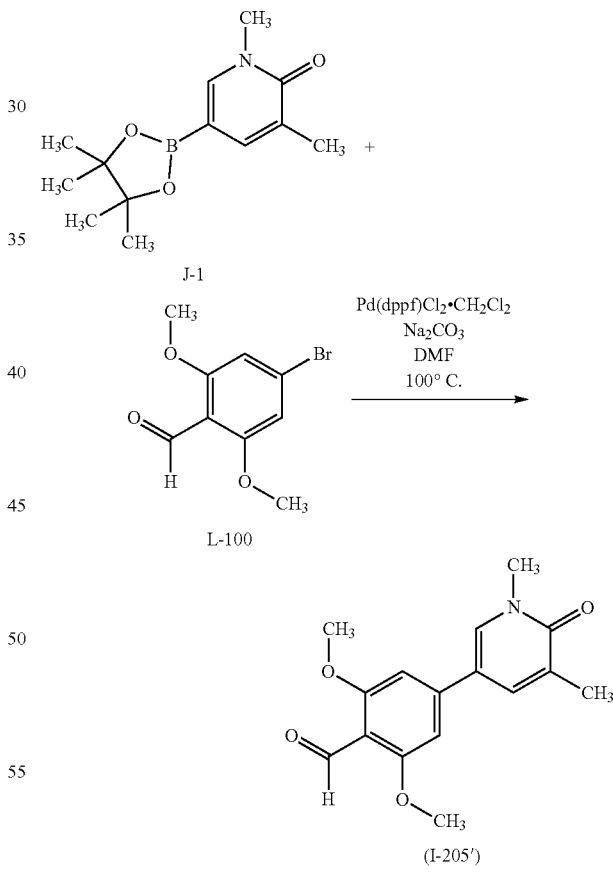

153

-continued

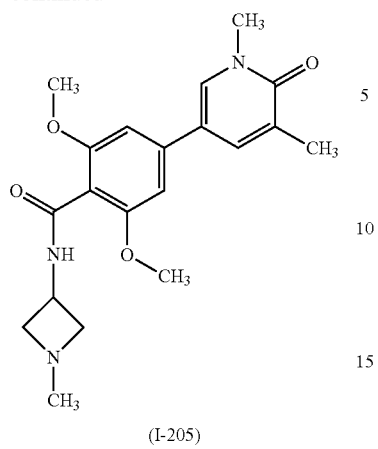

(I-205)

4-(1,5-Dimethyl-6-oxo-1,6-dihydro-pyridin-3-yl)-2,6-dimethoxy-benzaldehyde (I-205')

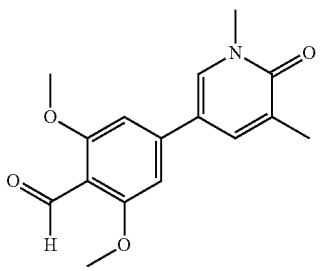 [SMILES: COc1cc(-c2cc(C)c(=O)n(C)c2)cc(OC)c1C=O]

In a vial 4-bromo-2,6-dimethoxybenzaldehyde L-100 (517.8 mg; 2.007 mmol), 1,3-dimethyl-5-(4,4,5,5-tetramethyl-[1,3,2]dioxaborolan-2-yl)-1H-pyridin-2-one J-1 (500.0 mg; 2.007 mmol) and [1,1'-bis(diphenylphosphino) ferrocene]dichloropalladium(II), dichloromethane (169.0 mg; 0.201 mmol) are introduced. DMF (4 mL) and a 2N aqueous solution of sodium bicarbonate (2.5 mL) are added. The vial is flushed with argon and sealed. The reaction mixture is heated at 100° C. for 1 h. Water (a drop) is added to the reaction mixture and the mixture is filtered. The filtrate is purified with the basic (ammonia buffer) RP HPLC system (column: X-Bridge C-18 30×50 mm). The product containing fractions are concentrated under reduced pressure.

HPLC/MS: (M+H)$^+$=288; t$_{Ret}$=0.84 min; method M1

154

5-{3,5-Dimethoxy-4-[(1-methyl-azetidin-3-ylamino)-methyl]-phenyl}-1,3-dimethyl-1H-pyridin-2-one (I-205)

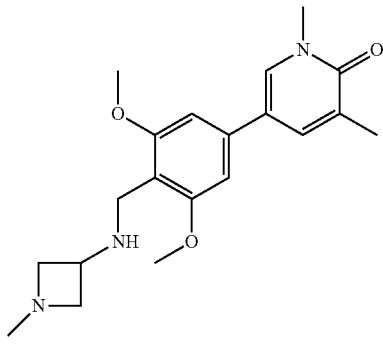

2-Amino-1-N-methyl-azetidine dihydrochloride (63.1 mg; 0.397 mmol), sodium acetate (32.6 mg; 0.397 mmol), acetic acid (15 µL; 0.265 mmol) and DCM (1 mL) are introduced in a flask. The mixture is stirred at RT for 10 min, then 4-(1,5-dimethyl-6-oxo-1,6-dihydro-pyridin-3-yl)-2,6-dimethoxy-benzaldehyde I-205' (80.0 mg; 0.265 mmol) is added, the mixture is stirred at RT for 30 min. Finally sodium triacetoxyborohydride (115.6 mg; 0.529 mmol) is added to the reaction mixture. The reaction mixture is stirred at RT overnight. The reaction mixture is then partitioned between dichloromethane and saturated aqueous sodium bicarbonate. The solution is dried over Na$_2$SO$_4$, filtered and concentrated under reduced pressure. The crude product is dissolved in DMSO (1 mL), filtered and purified with the basic (ammonia buffer) RP HPLC system (column: X-Bridge C-18 30×50 mm). The product containing fractions are combined and concentrated under reduced pressure.

HPLC/MS: (M+H)$^+$=358; t$_{Ret}$=0.84 min; method M1

Method 31:

Preparation of Compound I-206

5-[4-(3-Dimethylamino-azetidin-1-ylmethyl)-3-methoxy-phenyl]-1,3-dimethyl-1H-pyridin-2-one

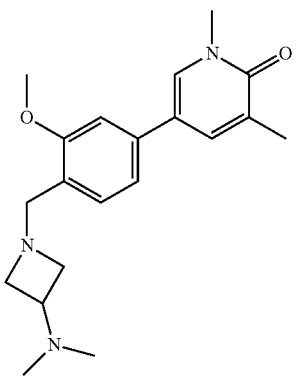 [SMILES: COc1cc(-c2cc(C)c(=O)n(C)c2)ccc1CN1CC(N(C)C)C1]

Reaction scheme
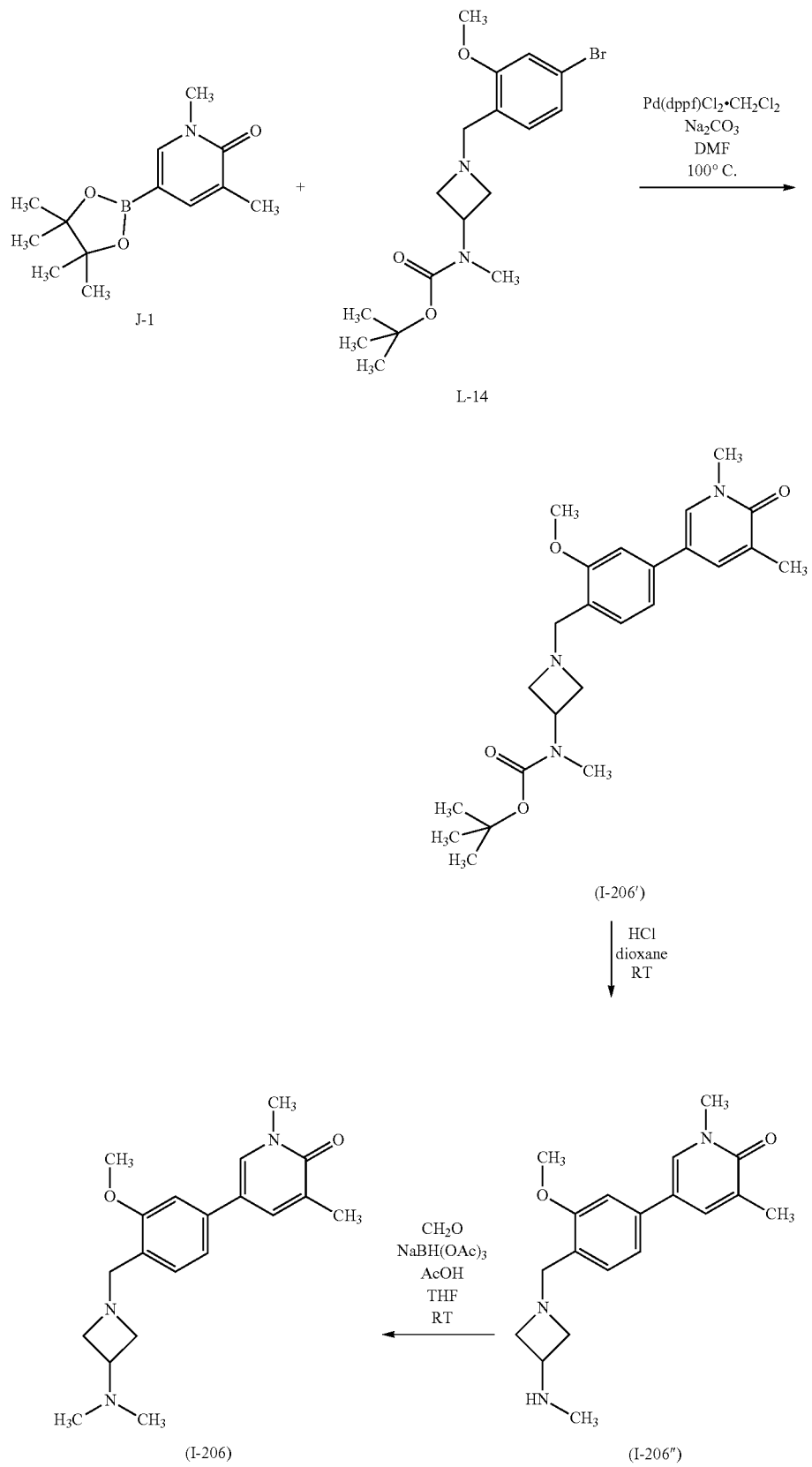

{1-[4-(1,5-Dimethyl-6-oxo-1,6-dihydro-pyridin-3-yl)-2-methoxy-benzyl]-azetidin-3-yl}-methyl-carbamic acid tert-butyl ester (I-206')

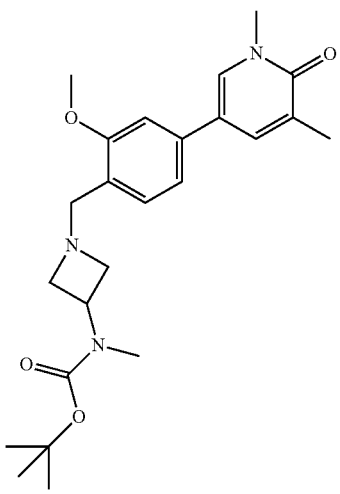 [SMILES: COc1cc(-c2cc(C)c(=O)n(C)c2)ccc1CN1CC(N(C)C(=O)OC(C)(C)C)C1]

[1-(4-Bromo-2-methoxy-benzyl)-azetidin-3-yl]-methyl-carbamic acid tert-butyl ester L-14 (127.4 mg; 0.281 mmol), 1,3-dimethyl-5-(4,4,5,5-tetramethyl-[1,3,2]dioxaborolan-2-yl)-1H-pyridin-2-one J-1 (70.0 mg; 0.281 mmol) and [1,1'-bis(diphenylphosphino)ferrocene]dichloropalladium(II), dichloromethane (23.0 mg; 0.028 mmol) are introduced in a vial. DMF (800 µL) and a 2N aqueous solution of sodium bicarbonate (351 µM) are added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are concentrated under reduced pressure.

HPLC/MS: (M+H)$^+$=428; $t_{Ret}$=0.63 min; method M2

5-[3-Methoxy-4-(3-methylamino-azetidin-1-ylmethyl)-phenyl]-1,3-dimethyl-1H-pyridin-2-one (I-206")

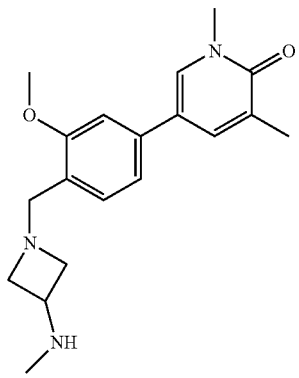 [SMILES: CNC1CN(Cc2ccc(-c3cc(C)c(=O)n(C)c3)cc2OC)C1]

{1-[4-(1,5-Dimethyl-6-oxo-1,6-dihydro-pyridin-3-yl)-2-methoxy-benzyl]-azetidin-3-yl}-methyl-carbamic acid tert-butyl ester I-206' (50.0 mg; 0.117 mmol) is treated with 4M HCl in dioxane (1.0 mL; 4.000 mmol). The reaction mixture is stirred at RT overnight. The reaction mixture is then made basic by addition of 1N NaOH solution and extracted with 3×10.0 mL DCM. The combined organic layers are dried with Na$_2$SO$_4$, filtered and concentrated under reduced pressure. The crude product is dissolved in of DMSO (1 mL), filtered and purified twice with the basic (ammonia buffer) RP HPLC system (column: X-Bridge C-18 30×50 mm). The product containing fractions are combined and concentrated under reduced pressure.

HPLC/MS: (M+H)$^+$=328; $t_{Ret}$=0.83 min; method M1

5-[4-(3-Dimethylamino-azetidin-1-ylmethyl)-3-methoxy-phenyl]-1,3-dimethyl-1H-pyridin-2-one (I-206)

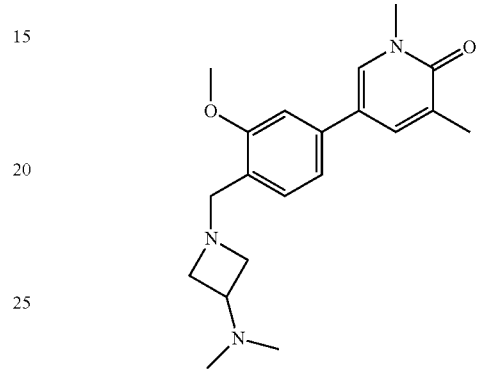

5-[3-Methoxy-4-(3-methylamino-azetidin-1-ylmethyl)-phenyl]-1,3-dimethyl-1H-pyridin-2-one I-206" (72.0 mg; 0.220 mmol) and formaldehyde (0.020 mL; 0.264 mmol) are dissolved in dry THF (1 mL) and treated with sodium triacetoxyborohydride (0.140 g; 0.660 mmol) and acetic acid (500 µl; 8.743 mmol). The reaction is stirred at RT overnight. The reaction mixture is then partitioned between DCM and saturated aqueous sodium bicarbonate. It is extracted twice with DCM. The combined organic layers are dried over Na$_2$SO$_4$, filtered and concentrated under reduced pressure. The residue is dissolved in DMSO (1 mL), filtered and purified with the basic (ammonia buffer) RP HPLC system (column: X-Bridge C-18 30×50 mm). The product containing fractions are combined and concentrated under reduced pressure.

HPLC/MS: (M+H)$^+$=342; $t_{Ret}$=0.89 min; method M1

Method 32:

Preparation of Compound I-207

5-{4-[(Azetidin-3-yl-methyl-amino)-methyl]-3,5-dimethoxy-phenyl}-1,3-dimethyl-1H-pyridin-2-one

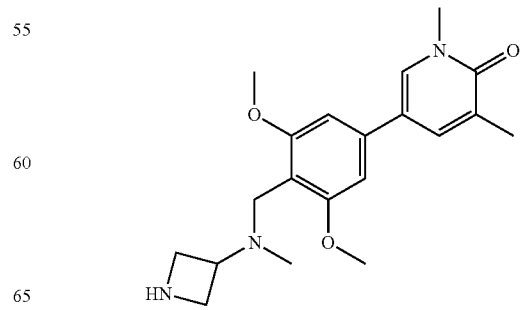

And Preparation of Compound I-208
5-(3,5-Dimethoxy-4-{[methyl-(1-methyl-azetidin-3-yl)-amino]-methyl}-phenyl)-1,3-dimethyl-1H-pyridin-2-one
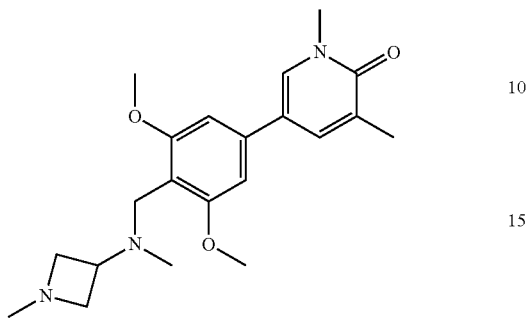
Reaction scheme
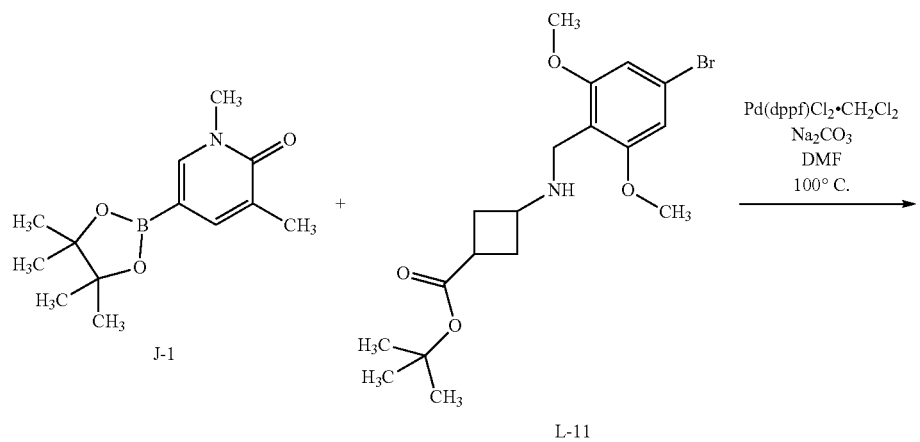
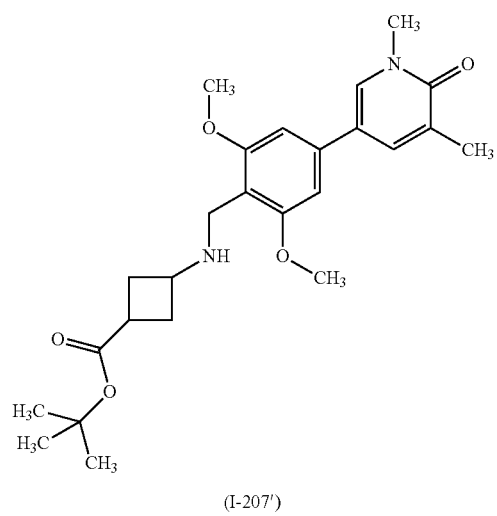

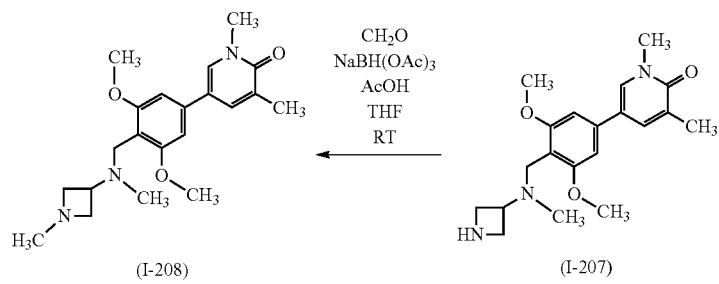 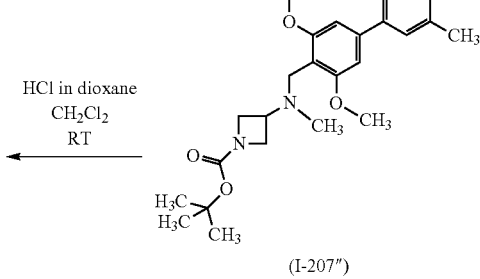

3-[4-(1,5-Dimethyl-6-oxo-1,6-dihydro-pyridin-3-yl)-2,6-dimethoxy-benzylamino]-azetidine-1-carboxylic acid tert-butyl ester (I-207')

3-{[4-(1,5-Dimethyl-6-oxo-1,6-dihydro-pyridin-3-yl)-2,6-dimethoxy-benzyl]-methyl-amino}-azetidine-1-carboxylic acid tert-butyl ester (I-207")

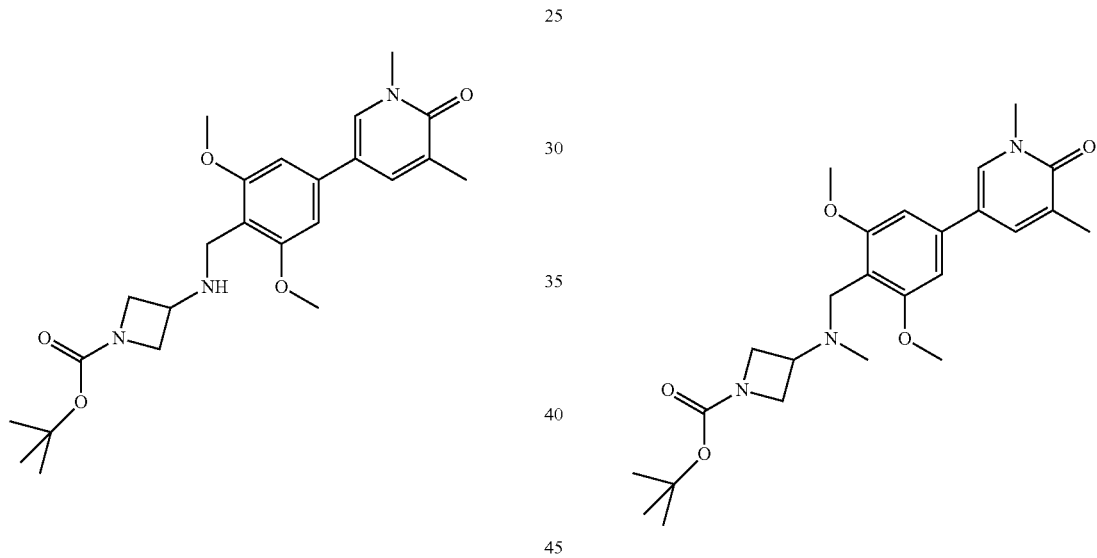

3-(4-Bromo-2,6-dimethoxy-benzylamino)-azetidine-1-carboxylic acid tert-butyl ester L-11 (508.7 mg; 1.204 mmol), 1,3-dimethyl-5-(4,4,5,5-tetramethyl-[1,3,2]dioxaborolan-2-yl)-1H-pyridin-2-one J-1 (300.0 mg; 1.204 mmol) and [1,1'-bis(diphenylphosphino)ferrocene]dichloropalladium(II), dichloromethane (101.4 mg; 0.120 mmol) are introduced in a vial. DMF (2 mL) and a 2N solution of sodium bicarbonate (1.5 mL) are added. The vial is flushed with argon and sealed. The reaction mixture is heated at 100° C. for 1 h. To the reaction mixture one drop of water is added and the mixture is filtered and purified with the basic (ammonia buffer) RP HPLC system (column: X-Bridge C-18 30×50 mm). The product containing fractions are combined and concentrated under reduced pressure HPLC/MS: $(M+H)^+$=272; $t_{Ret}$=0.43 min; method M4

3-[4-(1,5-Dimethyl-6-oxo-1,6-dihydro-pyridin-3-yl)-2,6-dimethoxy-benzylamino]-azetidine-1-carboxylic acid tert-butyl ester I-207' (200.0 mg; 0.451 mmol) and formaldehyde (0.041 mL; 0.541 mmol) are dissolved in dry THF (2.0 mL) and treated with sodium triacetoxyborohydride (0.287 g; 1.353 mmol) and acetic acid (0.100 mL; 1.749 mmol). The reaction is stirred at RT overnight. The reaction mixture is partitioned between DCM and saturated aqueous sodium bicarbonate. It is extracted twice with DCM. The combined organic layers are dried over $Na_2SO_4$, filtered and concentrated under reduced pressure.

HPLC/MS: $(M+H)^+$=458; 272; $t_{Ret}$=0.69 min; method M2

5-{4-[(Azetidin-3-yl-methyl-amino)-methyl]-3,5-dimethoxy-phenyl}-1,3-dimethyl-1H-pyridin-2-one (I-207)

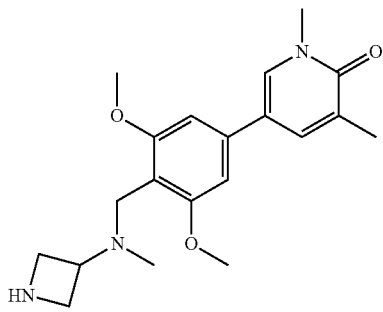 [SMILES: COc1cc(-c2cc(C)c(=O)n(C)c2)cc(OC)c1CN(C)C1CNC1]

3-{[4-(1,5-Dimethyl-6-oxo-1,6-dihydro-pyridin-3-yl)-2,6-dimethoxy-benzyl]-methyl-amino}-azetidine-1-carboxylic acid tert-butyl ester I-207" (200.0 mg; 0.437 mmol) is dissolved in dichloromethane (1.0 mL) and treated with 4M HCl in dioxane (1.0 mL; 4.000 mmol). The reaction mixture is stirred at RT for 3 h. The reaction mixture is then neutralised with 1M NaOH and extracted with DCM (3×10.0 mL). The combined organic layers are dried and concentrated under reduced pressure. The crude product is dissolved in DMSO (1 mL), filtered and purified with the basic (ammonia buffer) RP HPLC system (column: X-Bridge C-18 30×50 mm). The product containing fractions are combined and concentrated under reduced pressure.

HPLC/MS: $(M+H)^+=358$; $t_{Ret}=0.82$ min; method M1

5-(3,5-Dimethoxy-4-{[methyl-(1-methyl-azetidin-3-yl)-amino]-methyl}-phenyl)-1,3-dimethyl-1H-pyridin-2-one (I-208)

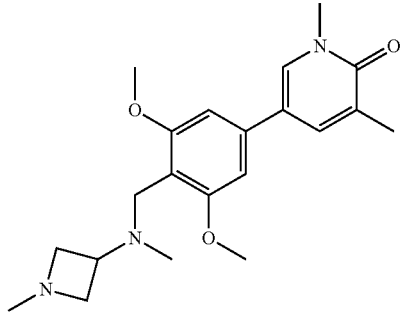

5-{4-[(Azetidin-3-yl-methyl-amino)-methyl]-3,5-dimethoxy-phenyl}-1,3-dimethyl-1H-pyridin-2-one I-207 (60.0 mg; 0.168 mmol) and formaldehyde (0.015 mL; 0.201 mmol) are dissolved in tetrahydrofurane, extra dry (1.0 mL) and treated with sodium triacetoxyborohydride (0.107 g; 0.504 mmol) and acetic acid (0.050 mL; 0.874 mmol). The reaction is stirred at RT overnight. The reaction mixture is partitioned between DCM and saturated aqueous sodium bicarbonate. It is extracted twice with DCM. The combined organic layers are dried over $Na_2SO_4$, filtered and concentrated under reduced pressure. The crude product is dissolved in DMSO (1 mL), filtered and purified with the basic (ammonia buffer) RP HPLC system (column: X-Bridge C-18 30×50 mm). The product containing fractions are concentrated under reduced pressure.

HPLC/MS: $(M+H)^+=372$; $t_{Ret}=0.94$ min; method M1

Method 33:

Preparation of Compound I-209

1,3-Dimethyl-5-(2-methyl-2,3-dihydro-1H-isoindol-5-yl)-1H-pyridin-2-one

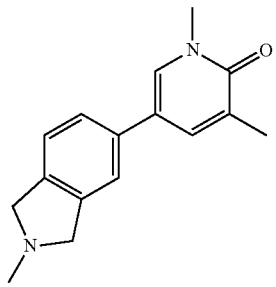

Reaction scheme

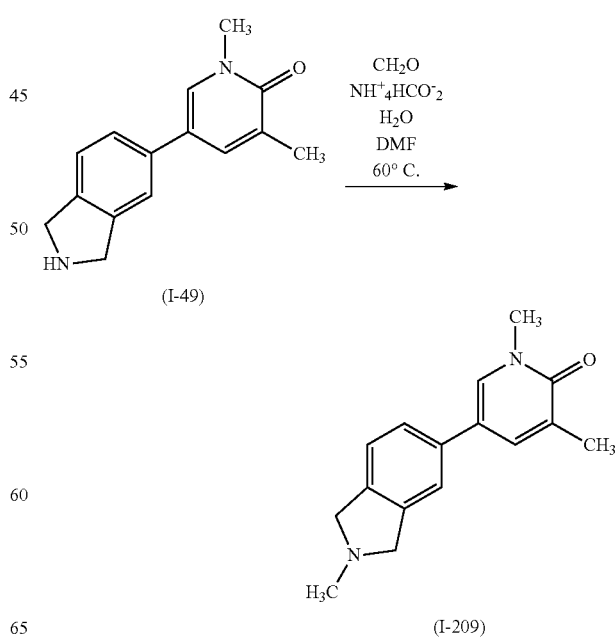

1,3-Dimethyl-5-(2-methyl-2,3-dihydro-1H-isoindol-5-yl)-1H-pyridin-2-one (I-209)

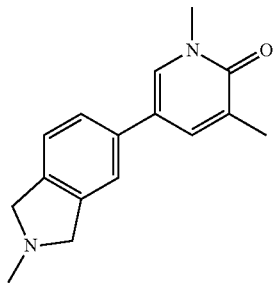

Formaldehyde (11.5 μL; 0.156 mmol) is added to a solution of 5-(2,3-dihydro-1H-isoindol-5-yl)-1,3-dimethyl-1H-pyridin-2-one I-49 (15.0 mg; 0.062 mmol) in DMF (750 μL). The mixture is stirred at 60° C. for 20 min. A solution of ammonium formate (78.7 mg; 1.248 mmol in 750 μL water) is then added. The mixture is stirred at 60° C. for 20 min. Formic acid is then added and the solution is stirred at 60° C. overnight. The crude product is then cooled down and purified directly on basic RP HPLC system (Gilson; column 5-70; 10 min; 200 nm; flow rate 50.0 mL). The product containing fractions are concentrated under reduced pressure.

HPLC/MS: $(M+H)^+$=255; $t_{Ret}$=0.89 min; method M1

According to the procedure of I-47 the examples I-46, I-48 to I-136 and I-214 are synthesized. According to the procedure of I-137 the examples I-138-I-142 are synthesized. According to the procedure of I-143 the examples I-144 to I-156 are synthesized. According to the procedure of I-157 the examples I-158 to I-163 are synthesized. According to the procedure of I-164 (with the exception of the acidic N-Boc deprotection step), the examples I-165 to I-168 are synthesized. According to the procedure of I-169, the example I-170 is synthesized. According to the procedure of I-169 (with the exception of the acidic N-Boc deprotection step), the examples I-171 to I-172 are synthesized. According to the procedure of I-173, the examples I-174 to I-176 are synthesized. According to the procedure of I-179, the examples I-180 to I-185 are synthesized. According to the procedure of I-186 (with the exception of the acidic N-Boc deprotection step), the example I-187 is synthesized. According to the procedure of I-189, the example I-190 is synthesized. According to the procedure of I-189 (with the exception of the acidic N-Boc deprotection step), the examples I-191 to I-193 are synthesized. According to the procedure of I-195, the example I-196 is synthesized. According to the procedure of I-198 (with the exception of the last nitro group reduction step), the examples I-199 to I-201 are synthesized. According to the procedure of I-209, the examples I-210 to I-212 are synthesized.

| # | Structure | MS $(M+H)^+$ | $t_{Ret.}$ HPLC [min] | HPLC-Method |
|---|---|---|---|---|
| I-46 | 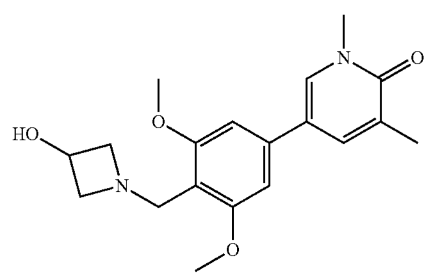 [SMILES: COc1cc(-c2cc(C)c(=O)n(C)c2)cc(OC)c1CN1CC(O)C1] | 345 | 0.830 | M1 |
| I-47 | 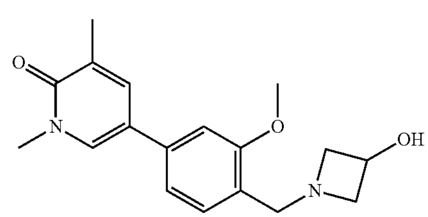 [SMILES: COc1cc(-c2cc(C)c(=O)n(C)c2)ccc1CN1CC(O)C1] | 315 | 0.790 | M1 |
| I-48 | 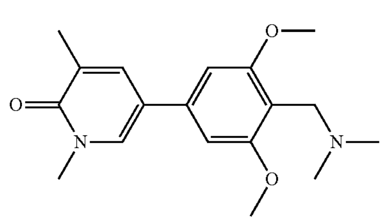 [SMILES: COc1cc(-c2cc(C)c(=O)n(C)c2)cc(OC)c1CN(C)C] | 317 | 0.900 | M1 |

| # | Structure | MS (M + H)+ | t_Ret. HPLC [min] | HPLC-Method |
|---|---|---|---|---|
| I-49 | 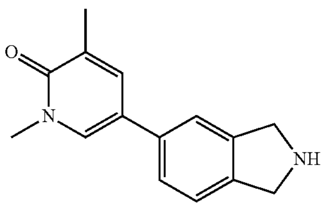 [SMILES: Cc1cc(-c2ccc3c(c2)CNC3)cn(C)c1=O] | 285/241 | 0.69/0.60 | M1 |
| I-50 | 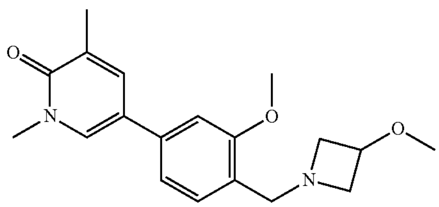 [SMILES: COc1cc(-c2cc(C)c(=O)n(C)c2)ccc1CN1CC(OC)C1] | 329 | 0.960 | M1 |
| I-51 | 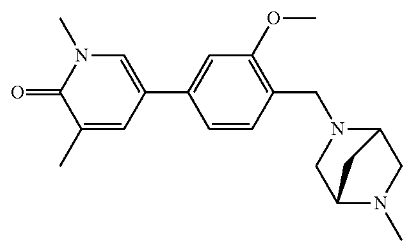 [SMILES: COc1cc(-c2cc(C)c(=O)n(C)c2)ccc1CN1C[C@@H]2CC1CN2C] | 354 | 0.910 | M1 |
| I-52 | 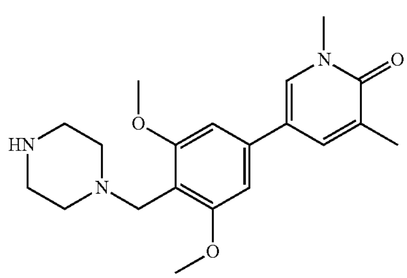 [SMILES: COc1cc(-c2cc(C)c(=O)n(C)c2)cc(OC)c1CN1CCNCC1] | 358 | 0.880 | M1 |
| I-53 | 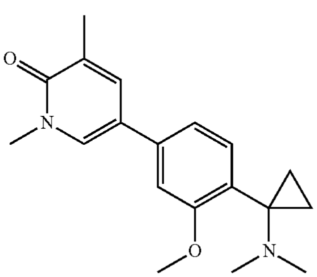 [SMILES: COc1cc(-c2cc(C)c(=O)n(C)c2)ccc1C1(N(C)C)CC1] | 313 | 1.060 | M1 |
| I-54 | 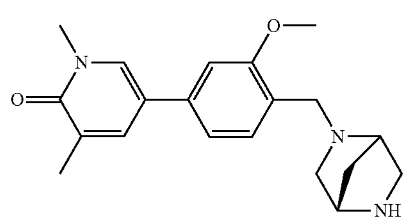 | 340 | 0.850 | M1 |

-continued

| # | Structure | MS (M + H)⁺ | t$_{Ret.}$ HPLC [min] | HPLC-Method |
|---|---|---|---|---|
| I-55 | 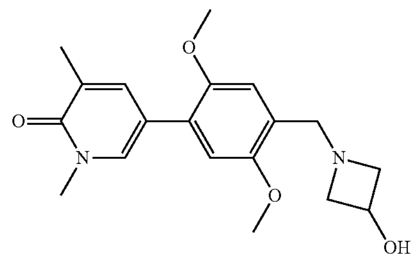 [SMILES: COc1cc(-c2cc(C)c(=O)n(C)c2)c(OC)cc1CN1CC(O)C1] | 345 | 0.820 | M1 |
| I-56 | 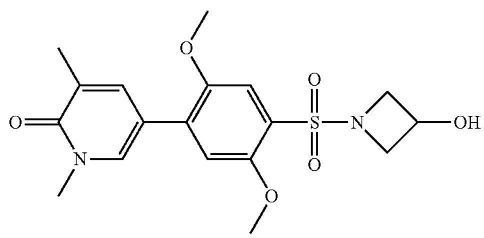 [SMILES: COc1cc(S(=O)(=O)N2CC(O)C2)c(OC)cc1-c1cc(C)c(=O)n(C)c1] | 395 | 0.810 | M1 |
| I-57 | 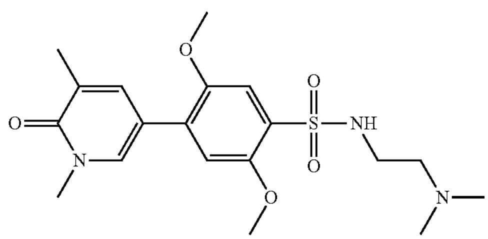 [SMILES: COc1cc(S(=O)(=O)NCCN(C)C)c(OC)cc1-c1cc(C)c(=O)n(C)c1] | 410 | 0.940 | M1 |
| I-58 | 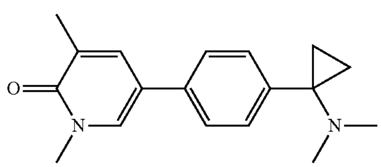 [SMILES: Cc1cc(-c2ccc(C3(N(C)C)CC3)cc2)cn(C)c1=O] | 283 | 1.060 | M1 |
| I-59 | 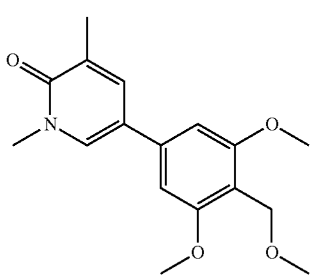 [SMILES: COCc1c(OC)cc(-c2cc(C)c(=O)n(C)c2)cc1OC] | 304 | 0.980 | M1 |
| I-60 | 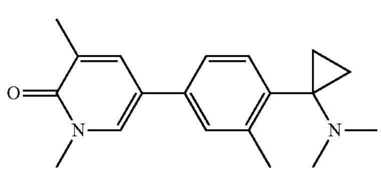 [SMILES: Cc1cc(-c2cc(C)c(=O)n(C)c2)ccc1C1(N(C)C)CC1] | 297 | 1.100 | M1 |

-continued

| # | Structure | MS (M + H)⁺ | $t_{Ret.}$ HPLC [min] | HPLC-Method |
|---|---|---|---|---|
| I-61 | 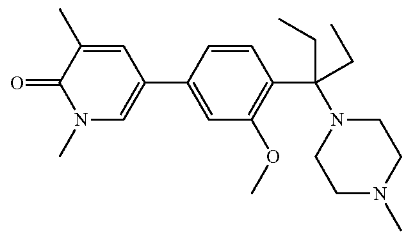 [SMILES: CCC(CC)(c1ccc(-c2cc(C)c(=O)n(C)c2)cc1OC)N1CCN(C)CC1] | 298 | 1.35 | M1 |
| I-62 | 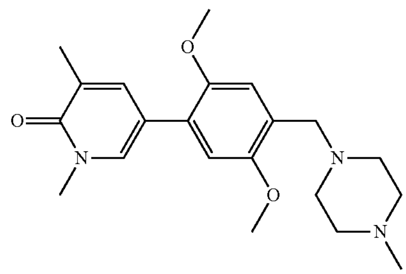 [SMILES: COc1cc(-c2cc(C)c(=O)n(C)c2)c(OC)cc1CN1CCN(C)CC1] | 372 | 0.95 | M1 |
| I-63 | 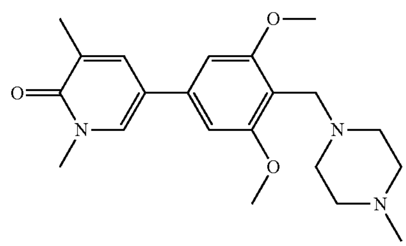 [SMILES: COc1cc(-c2cc(C)c(=O)n(C)c2)cc(OC)c1CN1CCN(C)CC1] | 372 | 0.93 | M1 |
| I-64 | 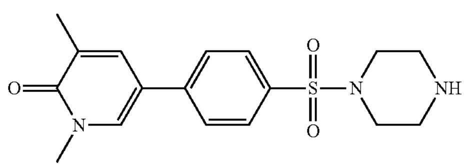 [SMILES: Cc1cc(-c2ccc(S(=O)(=O)N3CCNCC3)cc2)cn(C)c1=O] | 348 | 0.79 | M1 |
| I-65 | 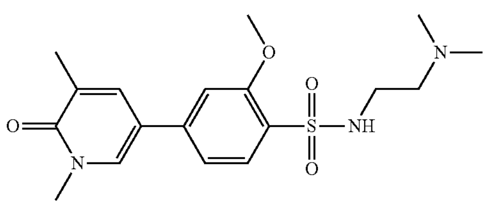 [SMILES: COc1cc(-c2cc(C)c(=O)n(C)c2)ccc1S(=O)(=O)NCCN(C)C] | 380 | 0.91 | M1 |
| I-66 | 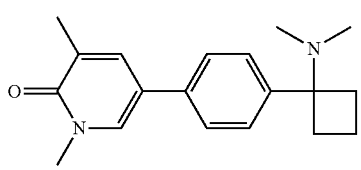 [SMILES: Cc1cc(-c2ccc(C3(N(C)C)CCC3)cc2)cn(C)c1=O] | 252 | 1.07 | M1 |
| I-67 | 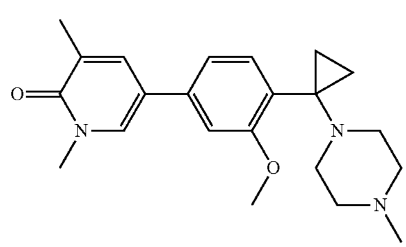 [SMILES: COc1cc(-c2cc(C)c(=O)n(C)c2)ccc1C1(N2CCN(C)CC2)CC1] | 368 | 1.11 | M1 |

-continued

| # | Structure | MS (M + H)+ | t_Ref. HPLC [min] | HPLC-Method |
|---|---|---|---|---|
| I-68 | 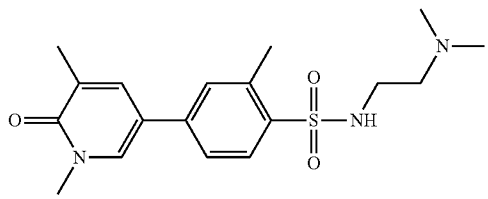 [SMILES: Cc1cc(-c2cc(C)c(=O)n(C)c2)ccc1S(=O)(=O)NCCN(C)C] | 364 | 0.94 | M1 |
| I-69 | 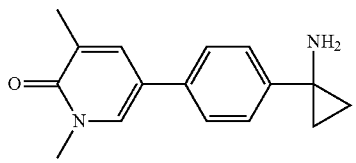 [SMILES: Cc1cc(-c2ccc(C3(N)CC3)cc2)cn(C)c1=O] | 255 | 1.01 | M1 |
| I-70 | 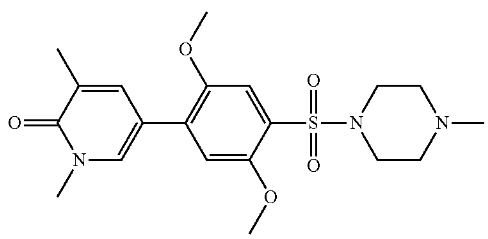 [SMILES: COc1cc(S(=O)(=O)N2CCN(C)CC2)c(OC)cc1-c1cc(C)c(=O)n(C)c1] | 422 | 0.94 | M1 |
| I-71 | 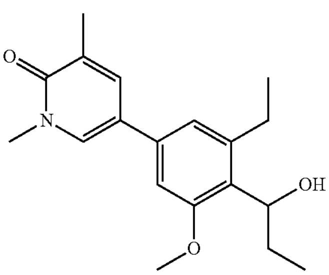 [SMILES: CCc1cc(-c2cc(C)c(=O)n(C)c2)cc(OC)c1C(O)CC] | 316 | 1.09 | M1 |
| I-72 | 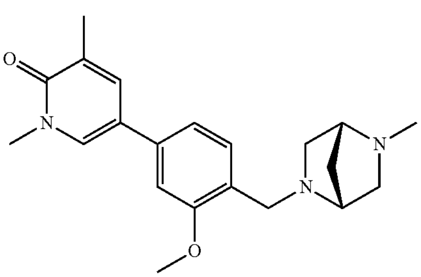 | 354 | 0.87 | M1 |
| I-73 | 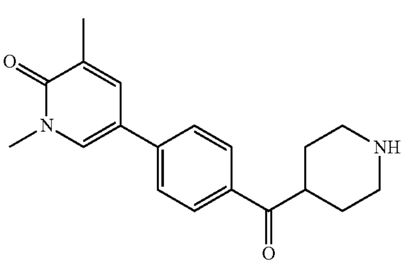 [SMILES: Cc1cc(-c2ccc(C(=O)C3CCNCC3)cc2)cn(C)c1=O] | 311 | 0.74 | M1 |

-continued

| # | Structure | MS (M + H)+ | t_Ret. HPLC [min] | HPLC-Method |
|---|---|---|---|---|
| I-74 | 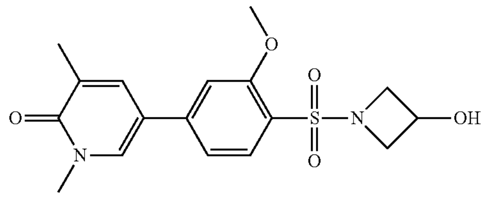 [SMILES: COc1cc(-c2cc(C)c(=O)n(C)c2)ccc1S(=O)(=O)N1CC(O)C1] | 365 | 0.77 | M1 |
| I-75 | 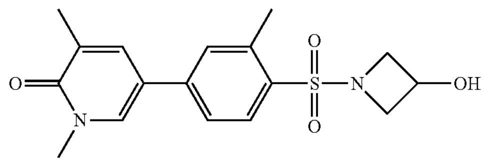 [SMILES: Cc1cc(-c2cc(C)c(=O)n(C)c2)ccc1S(=O)(=O)N1CC(O)C1] | 349 | 0.85 | M1 |
| I-76 | 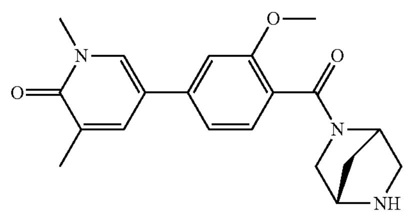 [SMILES: COc1cc(-c2cc(C)c(=O)n(C)c2)ccc1C(=O)N1C[C@@H]2CC1CN2] | 354 | 0.66 | M1 |
| I-77 | 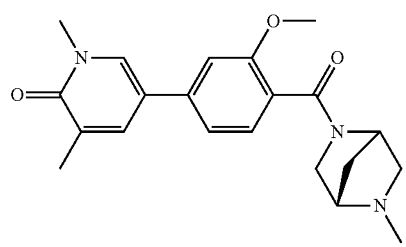 [SMILES: COc1cc(-c2cc(C)c(=O)n(C)c2)ccc1C(=O)N1C[C@@H]2CC1CN2C] | 368 | 0.76 | M1 |
| I-78 | 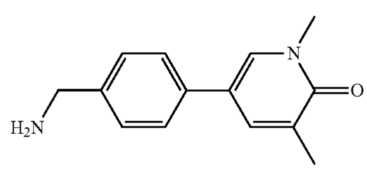 [SMILES: Cc1cc(-c2ccc(CN)cc2)cn(C)c1=O] | 229 | 0.65 | M1 |
| I-79 | 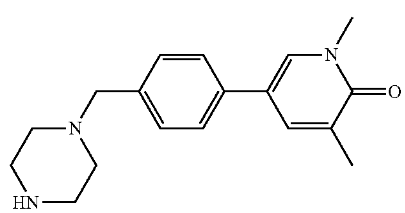 [SMILES: Cc1cc(-c2ccc(CN3CCNCC3)cc2)cn(C)c1=O] | 298 | 0.81 | M1 |
| I-80 | 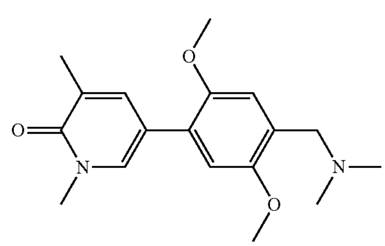 | 317 | 0.97 | M1 |

-continued

| # | Structure | MS (M + H)⁺ | t$_{Ret.}$ HPLC [min] | HPLC-Method |
|---|---|---|---|---|
| I-81 | 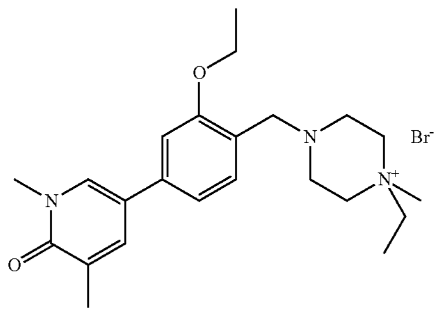 | 384 | 1.12 | M1 |
| I-82 | 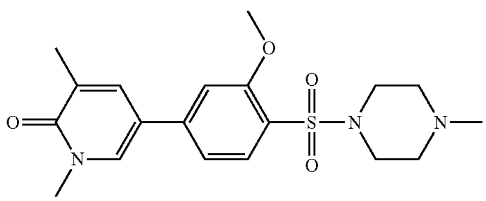 [SMILES: COc1cc(-c2cc(C)c(=O)n(C)c2)ccc1S(=O)(=O)N1CCN(C)CC1] | 392 | 0.91 | M1 |
| I-83 | 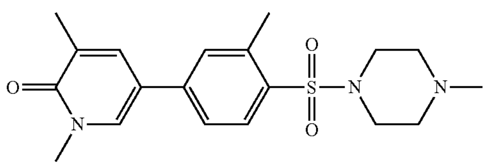 [SMILES: Cc1cc(-c2cc(C)c(=O)n(C)c2)ccc1S(=O)(=O)N1CCN(C)CC1] | 376 | 0.98 | M1 |
| I-84 | 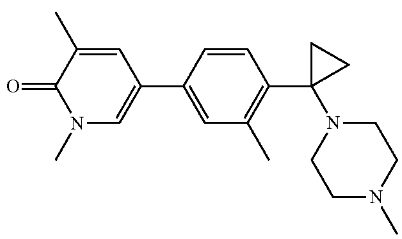 [SMILES: Cc1cc(-c2cc(C)c(=O)n(C)c2)ccc1C1(N2CCN(C)CC2)CC1] | 352 | 1.13 | M1 |
| I-85 | 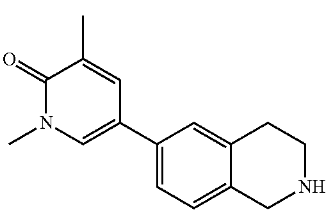 [SMILES: Cc1cc(-c2ccc3c(c2)CCNC3)cn(C)c1=O] | 255 | 0.78 | M1 |
| I-86 | 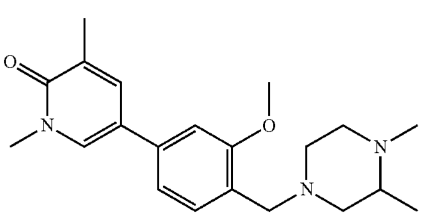 | 356 | 0.98 | M1 |
| I-87 | 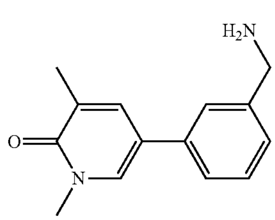 [SMILES: Cc1cc(-c2cccc(CN)c2)cn(C)c1=O] | 229 | 0.73 | M1 |

-continued

| # | Structure | MS (M + H)+ | t_Ret. HPLC [min] | HPLC-Method |
|---|---|---|---|---|
| I-88 | 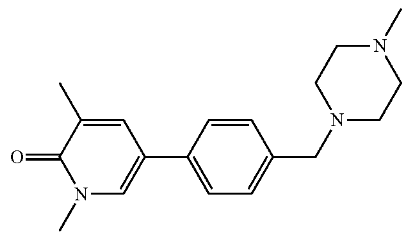 [SMILES: Cc1cc(-c2ccc(CN3CCN(C)CC3)cc2)cn(C)c1=O] | 312 | 1.05 | M1 |
| I-89 | 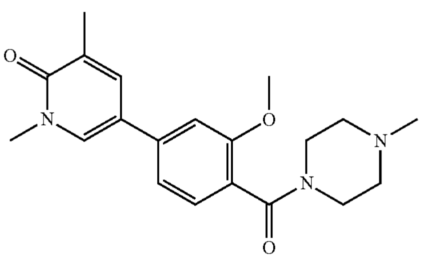 | 356 | 0.84 | M1 |
| I-90 | 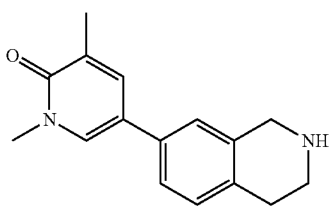 [SMILES: Cc1cc(-c2ccc3c(c2)CNCC3)cn(C)c1=O] | 255 | 0.79 | M1 |
| I-91 | 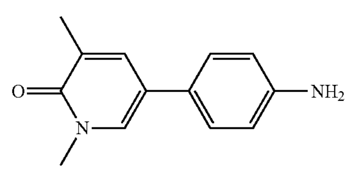 [SMILES: Cc1cc(-c2ccc(N)cc2)cn(C)c1=O] | 215 | 1.817 | M11 |
| I-92 | 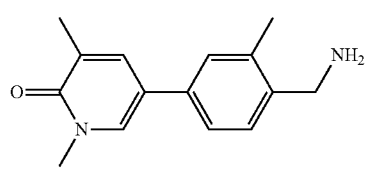 [SMILES: Cc1cc(-c2cc(C)c(=O)n(C)c2)ccc1CN] | 243 | 0.76 | M1 |
| I-93 | 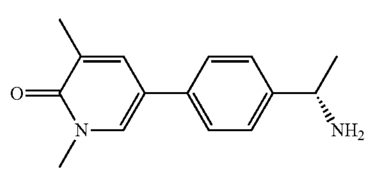 [SMILES: Cc1cc(-c2ccc([C@H](C)N)cc2)cn(C)c1=O] | 243 | 0.77 | M1 |
| I-94 | 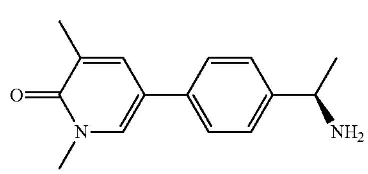 [SMILES: Cc1cc(-c2ccc([C@@H](C)N)cc2)cn(C)c1=O] | 243 | 0.77 | M1 |

-continued

| # | Structure | MS (M + H)+ | t_Ret. HPLC [min] | HPLC-Method |
|---|---|---|---|---|
| I-95 | 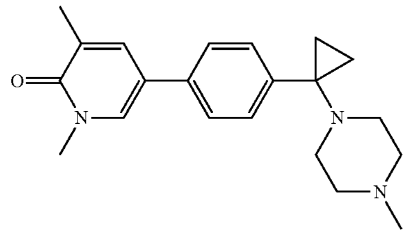 [SMILES: Cc1cc(-c2ccc(C3(N4CCN(C)CC4)CC3)cc2)cn(C)c1=O] | 338 | 1.08 | M1 |
| I-96 | 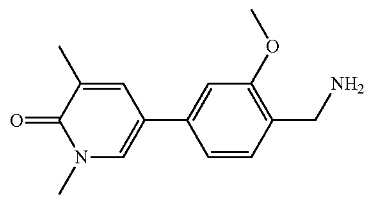 [SMILES: COc1cc(-c2cc(C)c(=O)n(C)c2)ccc1CN] | 242/259 | 0.73 | M1 |
| I-97 | 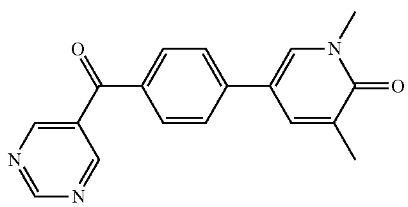 [SMILES: Cc1cc(-c2ccc(C(=O)c3cncnc3)cc2)cn(C)c1=O] | 306 | 1.02 | M1 |
| I-98 | 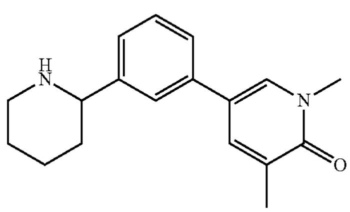 [SMILES: Cc1cc(-c2cccc(C3CCCCN3)c2)cn(C)c1=O] | 283 | 0.97 | M1 |
| I-99 | 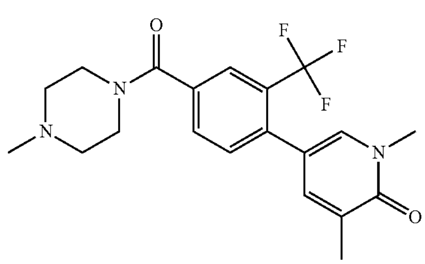 [SMILES: Cc1cc(-c2ccc(C(=O)N3CCN(C)CC3)cc2C(F)(F)F)cn(C)c1=O] | 250 | 1.1 | M1 |
| I-100 | 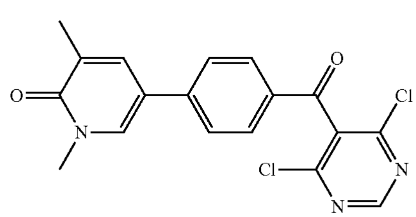 [SMILES: Cc1cc(-c2ccc(C(=O)c3c(Cl)ncnc3Cl)cc2)cn(C)c1=O] | 374 | 1.14 | M1 |

-continued

| # | Structure | MS (M + H)⁺ | t_Ret. HPLC [min] | HPLC-Method |
|---|---|---|---|---|
| I-101 | 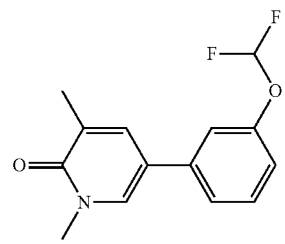 [SMILES: Cc1cc(-c2cccc(OC(F)F)c2)cn(C)c1=O] | 266 | 1.08 | M1 |
| I-102 | 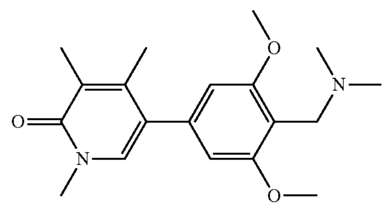 [SMILES: COc1cc(-c2cn(C)c(=O)c(C)c2C)cc(OC)c1CN(C)C] | 331 | 0.95 | M1 |
| I-103 | 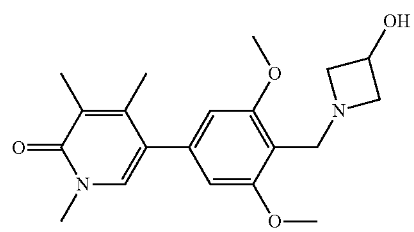 [SMILES: COc1cc(-c2cn(C)c(=O)c(C)c2C)cc(OC)c1CN1CC(O)C1] | 359 | 0.85 | M1 |
| I-104 | 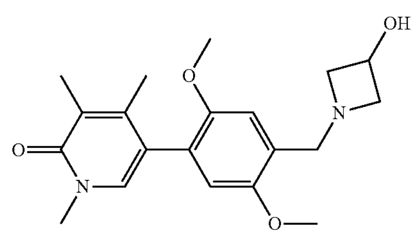 [SMILES: COc1cc(-c2cn(C)c(=O)c(C)c2C)c(OC)cc1CN1CC(O)C1] | 359 | 0.82 | M1 |
| I-105 | 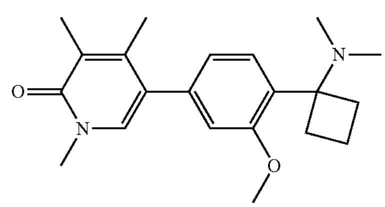 [SMILES: COc1cc(-c2cn(C)c(=O)c(C)c2C)ccc1C1(N(C)C)CCC1] | 296 | 1.17 | M1 |
| I-106 | 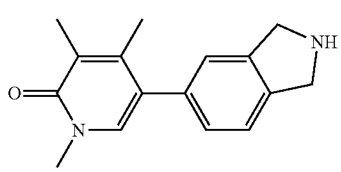 [SMILES: Cc1c(-c2ccc3c(c2)CNC3)cn(C)c(=O)c1C] | 255 | 0.69 | M1 |
| I-107 | 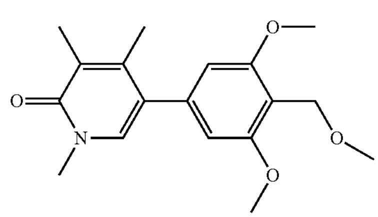 [SMILES: COCc1c(OC)cc(-c2cn(C)c(=O)c(C)c2C)cc1OC] | 318 | 1.03 | M1 |

-continued

| # | Structure | MS (M + H)+ | t_Ret. HPLC [min] | HPLC-Method |
|---|---|---|---|---|
| I-108 | 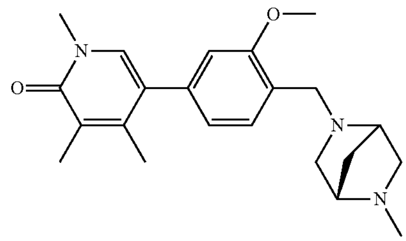 [SMILES: COc1cc(-c2cn(C)c(=O)c(C)c2C)ccc1CN1C[C@@H]2CC1CN2C] | 368 | 0.97 | M1 |
| I-109 | 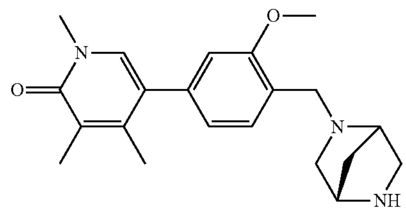 [SMILES: COc1cc(-c2cn(C)c(=O)c(C)c2C)ccc1CN1C[C@@H]2CC1CN2] | 354 | 0.93 | M1 |
| I-110 | 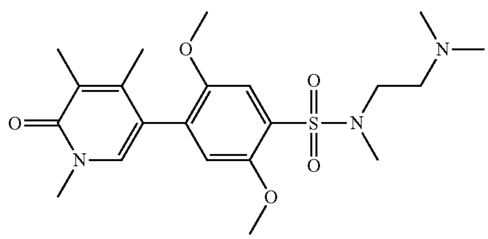 [SMILES: COc1cc(S(=O)(=O)N(C)CCN(C)C)c(OC)cc1-c1cn(C)c(=O)c(C)c1C] | 438 | 0.95 | M1 |
| I-111 | 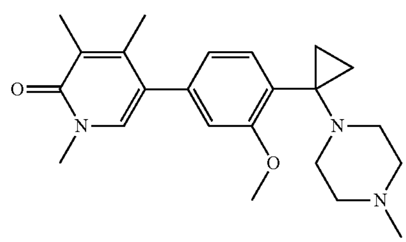 [SMILES: COc1cc(-c2cn(C)c(=O)c(C)c2C)ccc1C1(N2CCN(C)CC2)CC1] | 382 | 1.15 | M1 |
| I-112 | 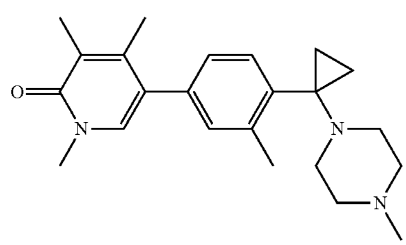 [SMILES: Cc1cc(-c2cn(C)c(=O)c(C)c2C)ccc1C1(N2CCN(C)CC2)CC1] | 366 | 1.18 | M1 |
| I-113 | 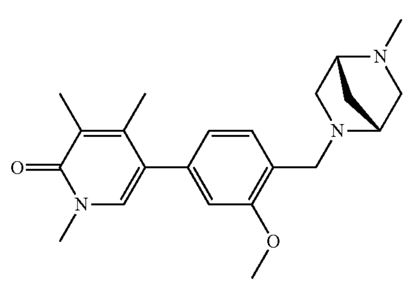 [SMILES: COc1cc(-c2cn(C)c(=O)c(C)c2C)ccc1CN1C[C@H]2C[C@@H]1CN2C] | 368 | 0.91 | M1 |

-continued

| # | Structure | MS (M + H)+ | t_Ret. HPLC [min] | HPLC-Method |
|---|---|---|---|---|
| I-114 | 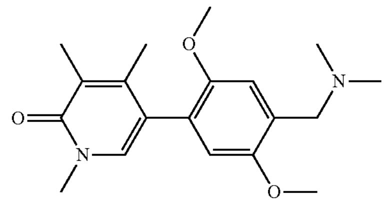 [SMILES: COc1cc(-c2cn(C)c(=O)c(C)c2C)c(OC)cc1CN(C)C] | 331 | 0.960 | M1 |
| I-115 | 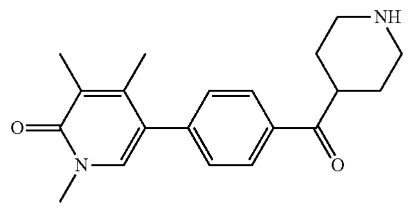 [SMILES: Cc1c(-c2ccc(C(=O)C3CCNCC3)cc2)cn(C)c(=O)c1C] | 325 | 0.79 | M1 |
| I-116 | 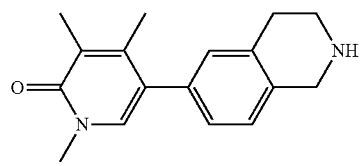 [SMILES: Cc1c(-c2ccc3c(c2)CCNC3)cn(C)c(=O)c1C] | 269 | 0.8 | M1 |
| I-117 | 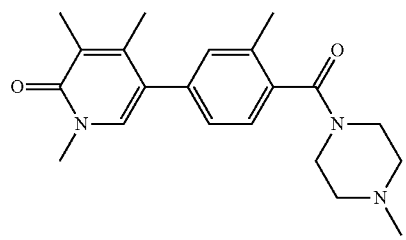 [SMILES: Cc1cc(-c2cn(C)c(=O)c(C)c2C)ccc1C(=O)N1CCN(C)CC1] | 354 | 0.85 | M1 |
| I-118 | 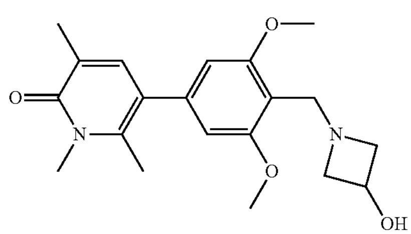 [SMILES: COc1cc(-c2cc(C)c(=O)n(C)c2C)cc(OC)c1CN1CC(O)C1] | 359 | 0.83 | M1 |
| I-119 | 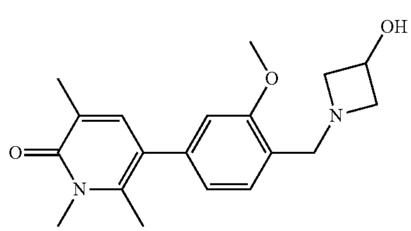 [SMILES: COc1cc(-c2cc(C)c(=O)n(C)c2C)ccc1CN1CC(O)C1] | 329 | 0.830 | M1 |
| I-120 | 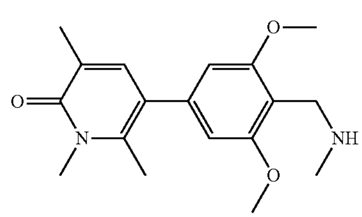 [SMILES: CNCc1c(OC)cc(-c2cc(C)c(=O)n(C)c2C)cc1OC] | 331 | 0.930 | M1 |

-continued

| # | Structure | MS (M + H)⁺ | t_Ret. HPLC [min] | HPLC-Method |
|---|---|---|---|---|
| I-121 | 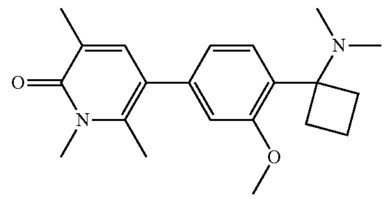 [SMILES: COc1cc(-c2cc(C)c(=O)n(C)c2C)ccc1C1(N(C)C)CCC1] | 296 | 1.100 | M1 |
| I-122 | 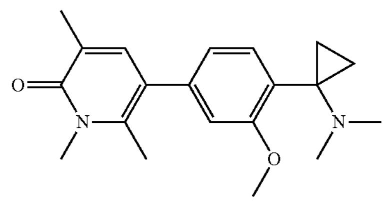 [SMILES: COc1cc(-c2cc(C)c(=O)n(C)c2C)ccc1C1(N(C)C)CC1] | 327 | 1.110 | M1 |
| I-123 | 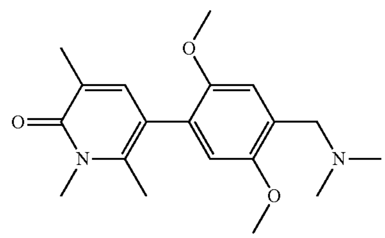 [SMILES: COc1cc(-c2cc(C)c(=O)n(C)c2C)c(OC)cc1CN(C)C] | 331 | 1.000 | M1 |
| I-124 | 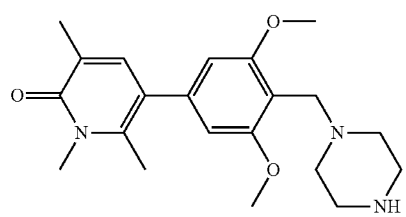 [SMILES: COc1cc(-c2cc(C)c(=O)n(C)c2C)cc(OC)c1CN1CCNCC1] | 372 | 0.920 | M1 |
| I-125 | 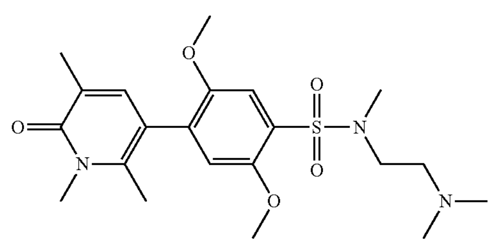 [SMILES: COc1cc(S(=O)(=O)N(C)CCN(C)C)c(OC)cc1-c1cc(C)c(=O)n(C)c1C] | 438 | 0.950 | M1 |
| I-126 | 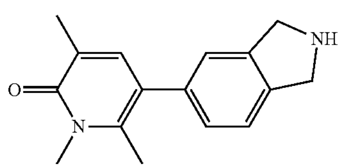 [SMILES: Cc1cc(-c2ccc3c(c2)CNC3)c(C)n(C)c1=O] | 255 | 0.770 | M1 |
| I-127 | 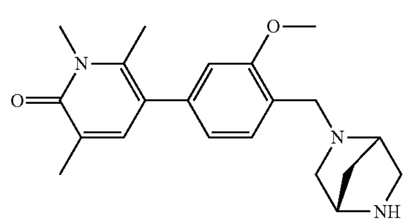 [SMILES: COc1cc(-c2cc(C)c(=O)n(C)c2C)ccc1CN1C[C@@H]2CC1CN2] | 354 | 0.900 | M1 |

-continued
| # | Structure | MS (M + H)+ | t_Ret. HPLC [min] | HPLC-Method |
|---|---|---|---|---|
| I-128 | 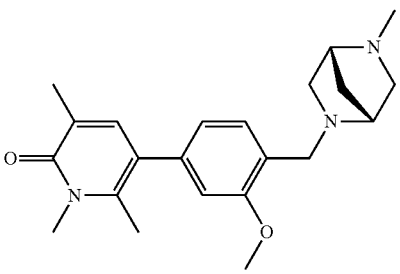 [SMILES: COc1cc(-c2cc(C)c(=O)n(C)c2C)ccc1CN1C[C@H]2C[C@@H]1CN2C] | 368 | 0.910 | M1 |
| I-129 | 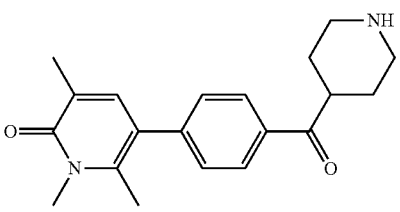 [SMILES: Cc1cc(-c2ccc(C(=O)C3CCNCC3)cc2)c(C)n(C)c1=O] | 325 | 0.790 | M1 |
| I-130 | 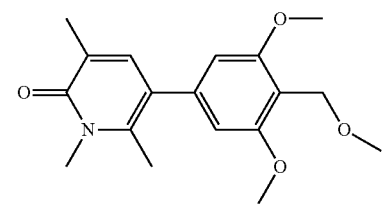 [SMILES: COCc1c(OC)cc(-c2cc(C)c(=O)n(C)c2C)cc1OC] | 318 | 1.030 | M1 |
| I-131 | 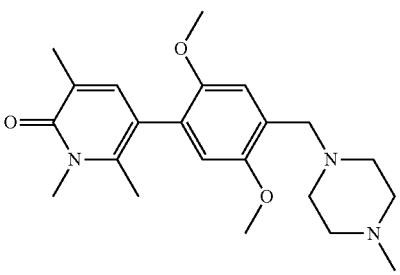 [SMILES: COc1cc(-c2cc(C)c(=O)n(C)c2C)c(OC)cc1CN1CCN(C)CC1] | 386 | 0.970 | M1 |
| I-132 | 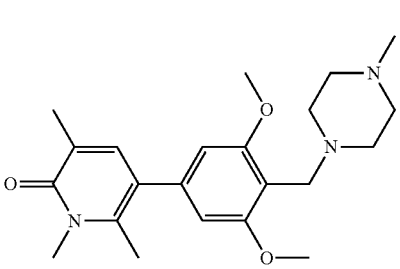 [SMILES: COc1cc(-c2cc(C)c(=O)n(C)c2C)cc(OC)c1CN1CCN(C)CC1] | 386 | 0.970 | M1 |
| I-133 | 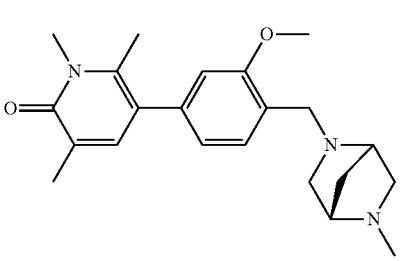 [SMILES: COc1cc(-c2cc(C)c(=O)n(C)c2C)ccc1CN1C[C@@H]2CC1CN2C] | 368 | 0.970 | M1 |

-continued
| # | Structure | MS (M + H)+ | t_Ret. HPLC [min] | HPLC-Method |
|---|---|---|---|---|
| I-134 | 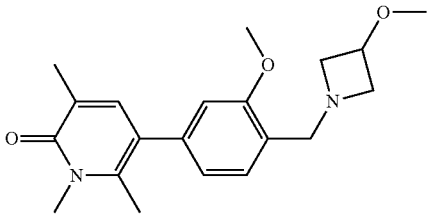 [SMILES: COc1cc(-c2cc(C)c(=O)n(C)c2C)ccc1CN1CC(OC)C1] | 343 | 1.000 | M1 |
| I-135 | 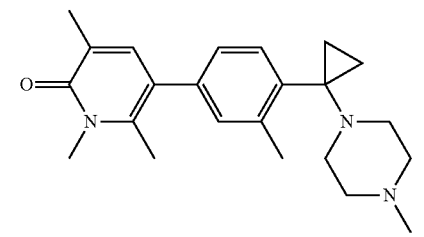 [SMILES: Cc1cc(-c2cc(C)c(=O)n(C)c2C)ccc1C1(N2CCN(C)CC2)CC1] | 366 | 1.190 | M1 |
| I-136 | 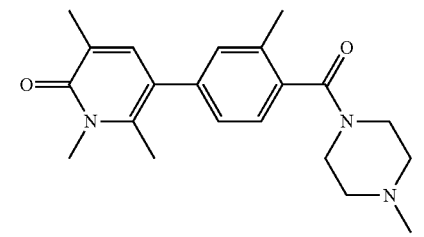 | 354 | 0.870 | M1 |
| I-137 | 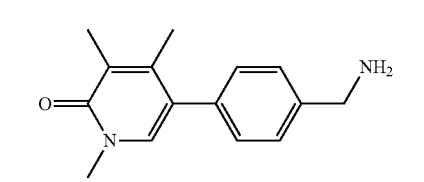 | 243 | 0.750 | M1 |
| I-138 | 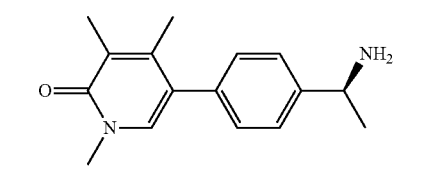 [SMILES: Cc1c(-c2ccc([C@H](C)N)cc2)cn(C)c(=O)c1C] | 257 | 0.830 | M1 |
| I-139 | 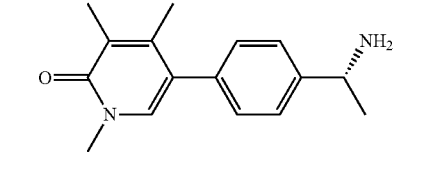 | 257 | 0.830 | M1 |
| I-140 | 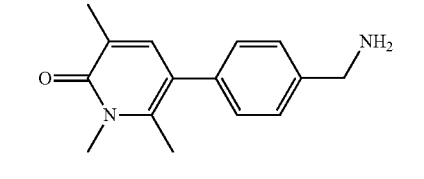 [SMILES: Cc1cc(-c2ccc(CN)cc2)c(C)n(C)c1=O] | 243 | 0.770 | M1 |
| I-141 | 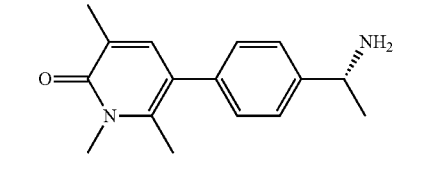 [SMILES: Cc1cc(-c2ccc([C@@H](C)N)cc2)c(C)n(C)c1=O] | 257 | 0.850 | M1 |

| # | Structure | MS (M + H)+ | t_Ret. HPLC [min] | HPLC-Method |
|---|---|---|---|---|
| I-142 | 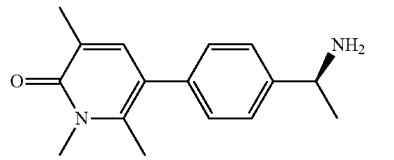 [SMILES: Cc1cc(-c2ccc([C@H](C)N)cc2)c(C)n(C)c1=O] | 257 | 0.850 | M1 |
| I-143 | 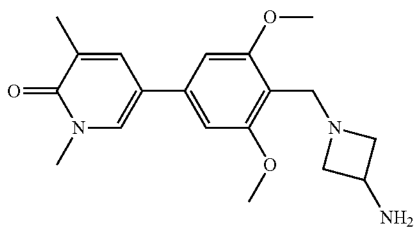 [SMILES: COc1cc(-c2cc(C)c(=O)n(C)c2)cc(OC)c1CN1CC(N)C1] | 344 | 0.800 | M1 |
| I-144 | 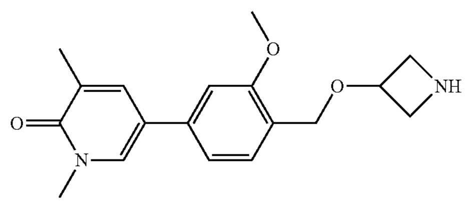 [SMILES: COc1cc(-c2cc(C)c(=O)n(C)c2)ccc1COC1CNC1] | 315 | 0.790 | M1 |
| I-145 | 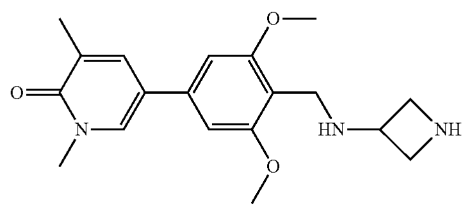 [SMILES: COc1cc(-c2cc(C)c(=O)n(C)c2)cc(OC)c1CNC1CNC1] | 344 | 0.850 | M1 |
| I-146 | 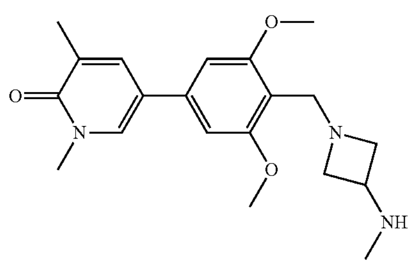 [SMILES: CNC1CN(Cc2c(OC)cc(-c3cc(C)c(=O)n(C)c3)cc2OC)C1] | 358 | 0.830 | M1 |
| I-147 | 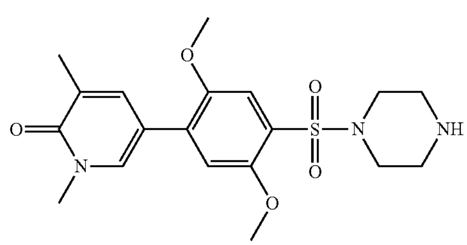 [SMILES: COc1cc(S(=O)(=O)N2CCNCC2)c(OC)cc1-c1cc(C)c(=O)n(C)c1] | 408 | 0.840 | M1 |
| I-148 | 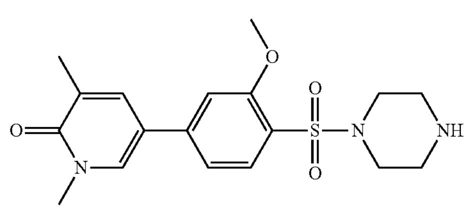 [SMILES: COc1cc(-c2cc(C)c(=O)n(C)c2)ccc1S(=O)(=O)N1CCNCC1] | 378 | 0.800 | M1 |

-continued

| # | Structure | MS (M + H)+ | t_Ret. HPLC [min] | HPLC-Method |
|---|---|---|---|---|
| I-149 | 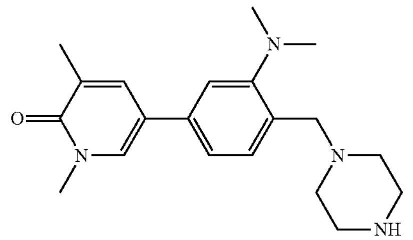 [SMILES: Cc1cc(-c2ccc(CN3CCNCC3)c(N(C)C)c2)cn(C)c1=O] | 341 | 0.910 | M1 |
| I-150 | 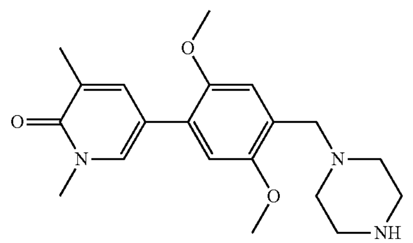 [SMILES: COc1cc(-c2cc(C)c(=O)n(C)c2)c(OC)cc1CN1CCNCC1] | 358 | 0.890 | M1 |
| I-151 | 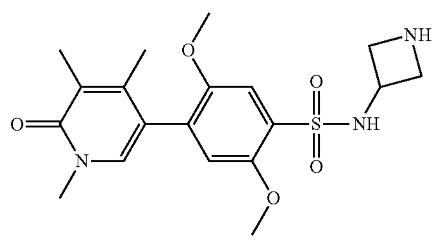 [SMILES: COc1cc(S(=O)(=O)NC2CNC2)c(OC)cc1-c1cn(C)c(=O)c(C)c1C] | 408 | 0.690 | M1 |
| I-152 | 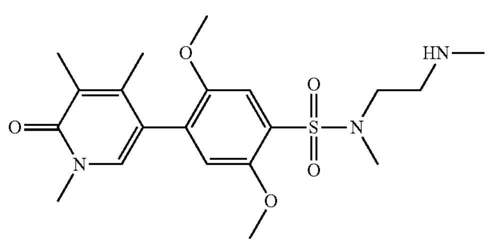 [SMILES: CNCCN(C)S(=O)(=O)c1cc(OC)c(-c2cn(C)c(=O)c(C)c2C)cc1OC] | 424 | 0.840 | M1 |
| I-153 | 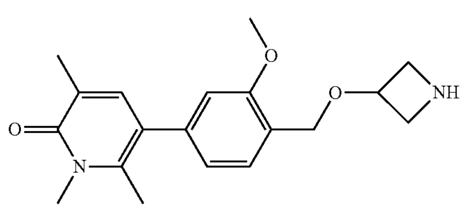 [SMILES: COc1cc(-c2cc(C)c(=O)n(C)c2C)ccc1COC1CNC1] | 329 | 0.860 | M1 |
| I-154 | 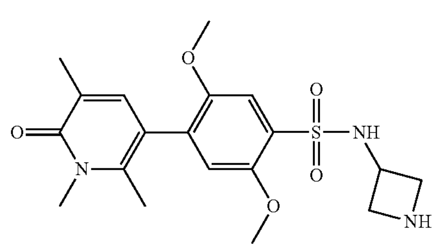 [SMILES: COc1cc(S(=O)(=O)NC2CNC2)c(OC)cc1-c1cc(C)c(=O)n(C)c1C] | 408 | 0.660 | M1 |

-continued

| # | Structure | MS (M + H)⁺ | t_Ret. HPLC [min] | HPLC-Method |
|---|---|---|---|---|
| I-155 | 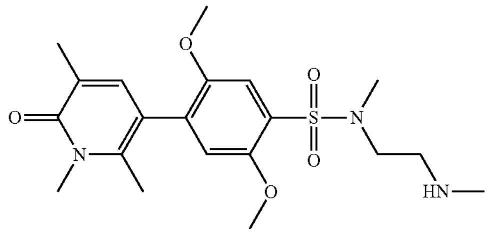 [SMILES: CNCCN(C)S(=O)(=O)c1cc(OC)c(-c2cc(C)c(=O)n(C)c2C)cc1OC] | 424 | 0.830 | M1 |
| I-156 | 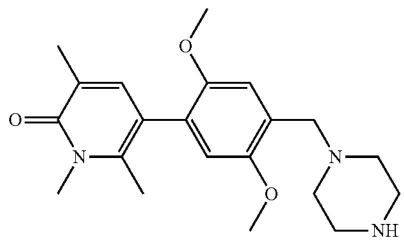 [SMILES: COc1cc(-c2cc(C)c(=O)n(C)c2C)c(OC)cc1CN1CCNCC1] | 372 | 0.940 | M1 |
| I-157 | 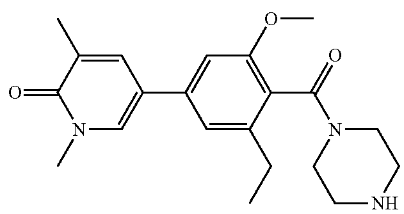 [SMILES: CCc1cc(-c2cc(C)c(=O)n(C)c2)cc(OC)c1C(=O)N1CCNCC1] | 370 | NMR | |
| I-158 | 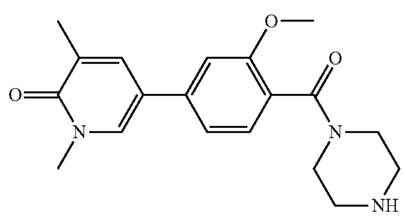 [SMILES: COc1cc(-c2cc(C)c(=O)n(C)c2)ccc1C(=O)N1CCNCC1] | 342 | 1.463 | M11 |
| I-159 | 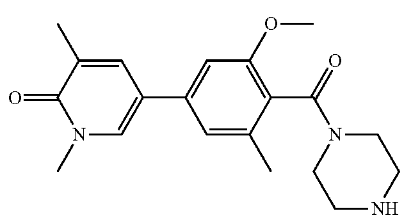 [SMILES: COc1cc(-c2cc(C)c(=O)n(C)c2)cc(C)c1C(=O)N1CCNCC1] | 356 | NMR | |
| I-160 | 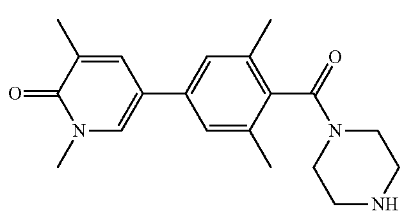 [SMILES: Cc1cc(-c2cc(C)c(=O)n(C)c2)cc(C)c1C(=O)N1CCNCC1] | 340 | NMR | |
| I-161 | 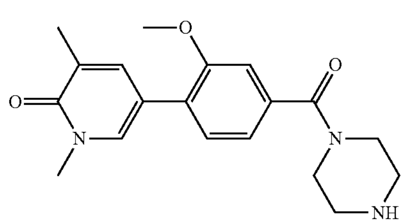 [SMILES: COc1cc(C(=O)N2CCNCC2)ccc1-c1cc(C)c(=O)n(C)c1] | 342 | 1.506 | M11 |

-continued

| # | Structure | MS (M + H)⁺ | t_Ret. HPLC [min] | HPLC-Method |
|---|---|---|---|---|
| I-162 | 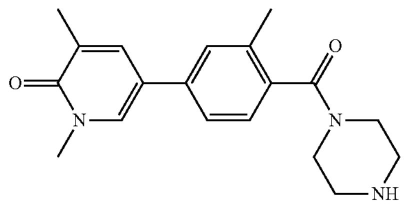 [SMILES: Cc1cc(-c2cc(C)c(=O)n(C)c2)ccc1C(=O)N1CCNCC1] | 326 | 1.506 | M11 |
| I-163 | 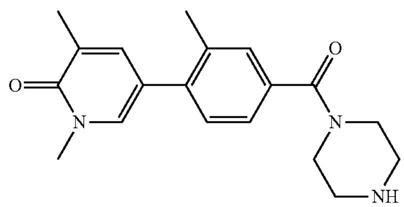 [SMILES: Cc1cc(C(=O)N2CCNCC2)ccc1-c1cc(C)c(=O)n(C)c1] | 326 | 1.540 | M11 |
| I-164 | 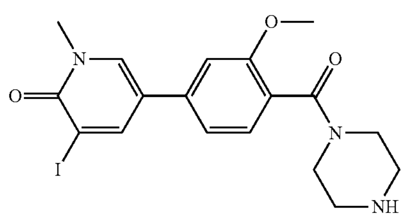 [SMILES: COc1cc(-c2cc(I)c(=O)n(C)c2)ccc1C(=O)N1CCNCC1] | 454 | 0.730 | M1 |
| I-165 | 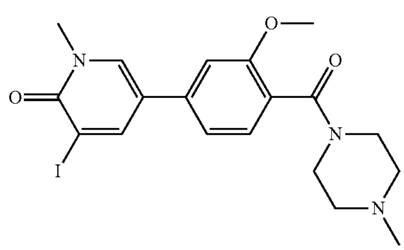 [SMILES: COc1cc(-c2cc(I)c(=O)n(C)c2)ccc1C(=O)N1CCN(C)CC1] | 454 | 0.990 | M1 |
| I-166 | 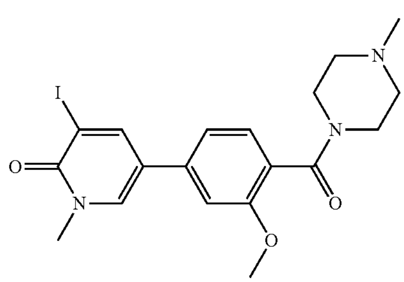 [SMILES: COc1cc(-c2cc(I)c(=O)n(C)c2)ccc1C(=O)N1CCN(C)CC1] | 468 | 0.860 | M1 |
| I-167 | 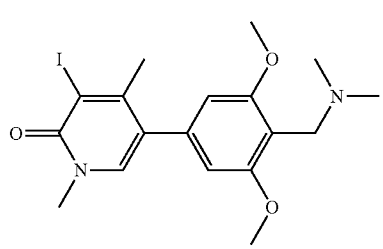 [SMILES: COc1cc(-c2cn(C)c(=O)c(I)c2C)cc(OC)c1CN(C)C] | 443 | 1.000 | M1 |

| # | Structure | MS (M + H)+ | t_Ret. HPLC [min] | HPLC-Method |
|---|---|---|---|---|
| I-168 | 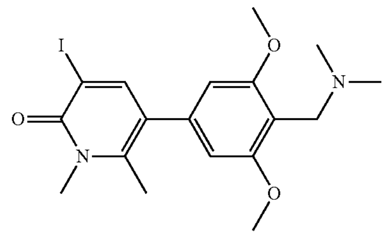 [SMILES: COc1cc(-c2cc(I)c(=O)n(C)c2C)cc(OC)c1CN(C)C] | 443 | 0.980 | M1 |
| I-169 | 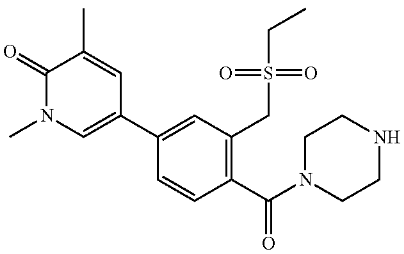 [SMILES: CCS(=O)(=O)Cc1cc(-c2cc(C)c(=O)n(C)c2)ccc1C(=O)N1CCNCC1] | 418 | 0.630 | M1 |
| I-170 | 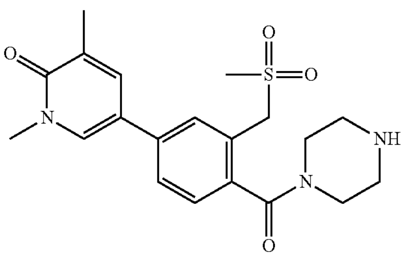 [SMILES: Cc1cc(-c2ccc(C(=O)N3CCNCC3)c(CS(C)(=O)=O)c2)cn(C)c1=O] | 404 | 0.500 | M1 |
| I-171 | 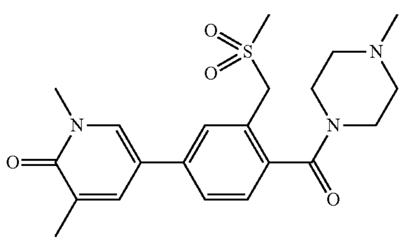 [SMILES: Cc1cc(-c2ccc(C(=O)N3CCN(C)CC3)c(CS(C)(=O)=O)c2)cn(C)c1=O] | 418 | 1.910 | M11 |
| I-172 | 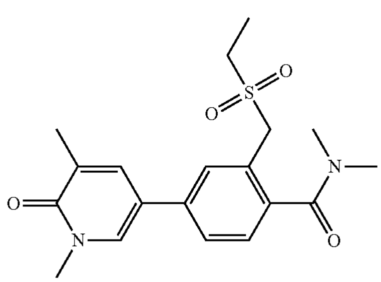 [SMILES: CCS(=O)(=O)Cc1cc(-c2cc(C)c(=O)n(C)c2)ccc1C(=O)N(C)C] | 377 | 0.770 | M1 |
| I-173 | 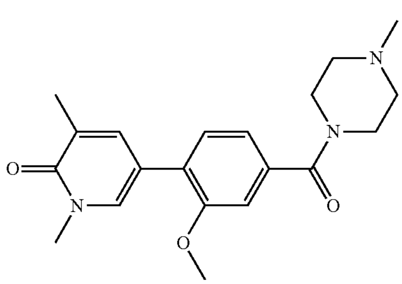 [SMILES: COc1cc(C(=O)N2CCN(C)CC2)ccc1-c1cc(C)c(=O)n(C)c1] | 356 | 0.820 | M1 |

-continued

| # | Structure | MS (M + H)+ | t_Ret. HPLC [min] | HPLC-Method |
|---|---|---|---|---|
| I-174 | 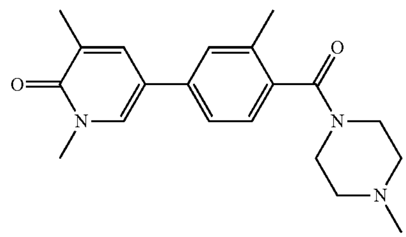 [SMILES: Cc1cc(-c2cc(C)c(=O)n(C)c2)ccc1C(=O)N1CCN(C)CC1] | 340 | 0.800 | M1 |
| I-175 | 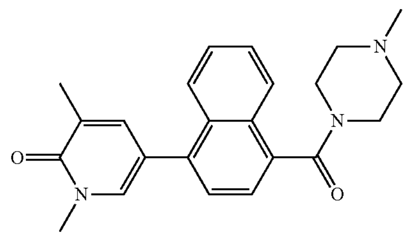 [SMILES: Cc1cc(-c2ccc(C(=O)N3CCN(C)CC3)c3ccccc23)cn(C)c1=O] | 376 | 0.910 | M1 |
| I-176 | 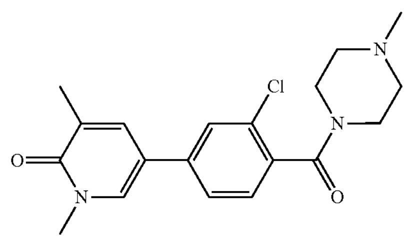 [SMILES: Cc1cc(-c2ccc(C(=O)N3CCN(C)CC3)c(Cl)c2)cn(C)c1=O] | 360 | 0.860 | M1 |
| I-177 | 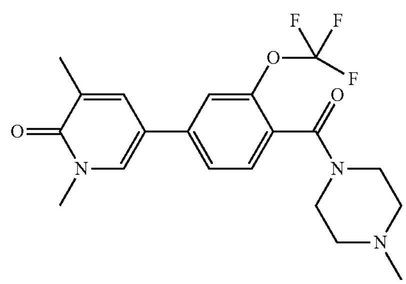 [SMILES: Cc1cc(-c2ccc(C(=O)N3CCN(C)CC3)c(OC(F)(F)F)c2)cn(C)c1=O] | 410 | 0.950 | M1 |
| I-178 | 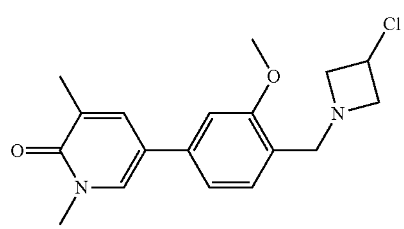 [SMILES: COc1cc(-c2cc(C)c(=O)n(C)c2)ccc1CN1CC(Cl)C1] | 333 | 1.080 | M1 |
| I-179 | 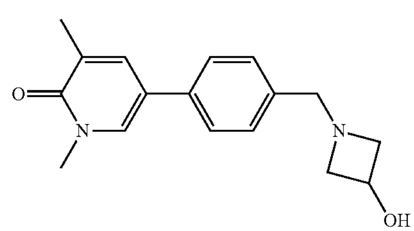 [SMILES: Cc1cc(-c2ccc(CN3CC(O)C3)cc2)cn(C)c1=O] | 285 | | |

| # | Structure | MS (M + H)+ | t_Ret. HPLC [min] | HPLC-Method |
|---|---|---|---|---|
| I-180 | 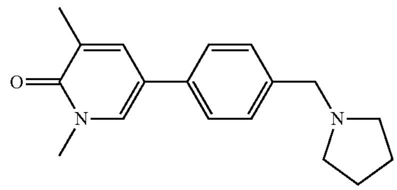 [SMILES: Cc1cc(-c2ccc(CN3CCCC3)cc2)cn(C)c1=O] | | observed by TLC Rf = 0.5 (Eluent DCM:MeOH) = 15:1 | |
| I-181 | 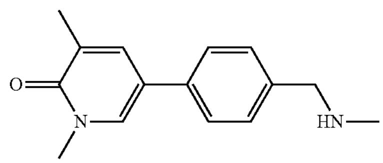 [SMILES: CNCc1ccc(-c2cc(C)c(=O)n(C)c2)cc1] | | observed by TLC Rf = 0.5 (Eluent DCM:MeOH) = 15:1 | |
| I-182 | 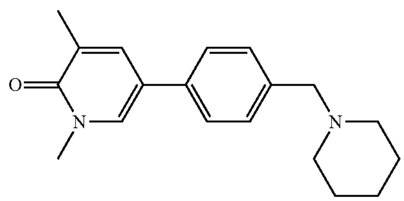 [SMILES: Cc1cc(-c2ccc(CN3CCCCC3)cc2)cn(C)c1=O] | | observed by TLC Rf = 0.5 (Eluent DCM:MeOH) = 15:1 | |
| I-183 | 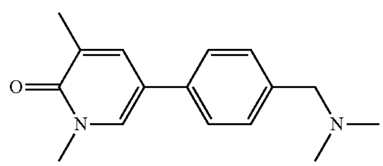 [SMILES: Cc1cc(-c2ccc(CN(C)C)cc2)cn(C)c1=O] | | observed by TLC Rf = 0.5 (Eluent DCM:MeOH) = 15:1 | |
| I-184 | 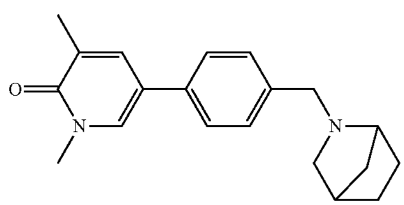 [SMILES: Cc1cc(-c2ccc(CN3CC4CCC3C4)cc2)cn(C)c1=O] | | observed by TLC Rf = 0.5 (Eluent DCM:MeOH) = 15:1 | |
| I-185 | 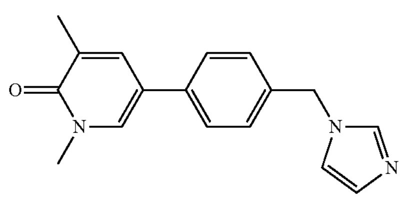 [SMILES: Cc1cc(-c2ccc(Cn3ccnc3)cc2)cn(C)c1=O] | | observed by TLC Rf = 0.5 (Eluent DCM:MeOH) = 15:1 | |
| I-186 | 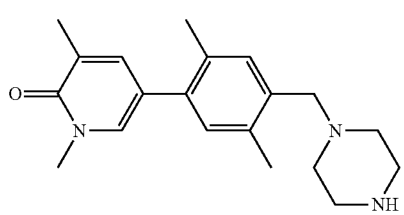 [SMILES: Cc1cc(-c2cc(C)c(=O)n(C)c2)c(C)cc1CN1CCNCC1] | 326 | NMR | |

| # | Structure | MS (M + H)+ | t_{Ret.} HPLC [min] | HPLC-Method |
|---|---|---|---|---|
| I-187 | 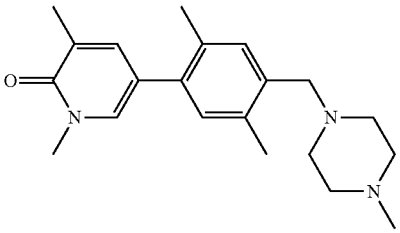 [SMILES: Cc1cc(-c2cc(C)c(=O)n(C)c2)c(C)cc1CN1CCN(C)CC1] | 340 | NMR | |
| I-188 | 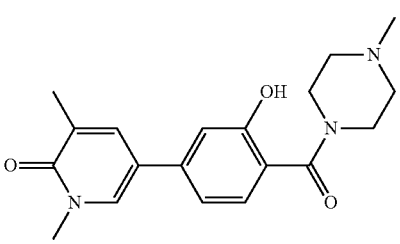 [SMILES: Cc1cc(-c2ccc(C(=O)N3CCN(C)CC3)c(O)c2)cn(C)c1=O] | 342 | 0.890 | |
| I-189 | 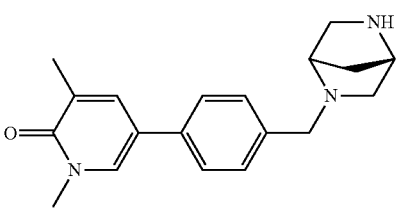 [SMILES: Cc1cc(-c2ccc(CN3C[C@@H]4CC3CN4)cc2)cn(C)c1=O] | 310 | 0.980 | M1 |
| I-190 | 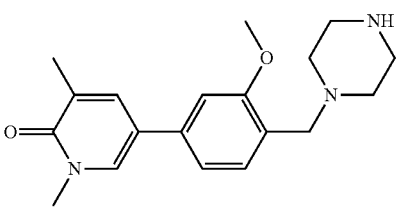 [SMILES: COc1cc(-c2cc(C)c(=O)n(C)c2)ccc1CN1CCNCC1] | 328 | 0.860 | M1 |
| I-191 | 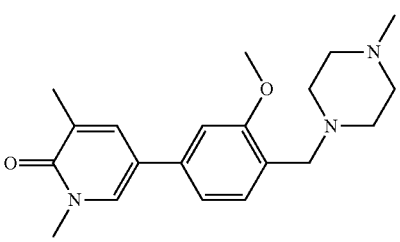 [SMILES: COc1cc(-c2cc(C)c(=O)n(C)c2)ccc1CN1CCN(C)CC1] | 342 | 0.920 | M1 |
| I-192 | 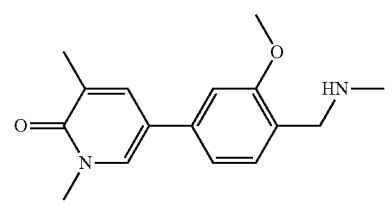 [SMILES: CNCc1ccc(-c2cc(C)c(=O)n(C)c2)cc1OC] | 273 | 0.800 | M1 |
| I-193 | 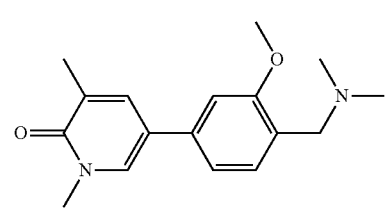 [SMILES: COc1cc(-c2cc(C)c(=O)n(C)c2)ccc1CN(C)C] | 287 | 0.940 | M1 |

| # | Structure | MS (M + H)⁺ | t_Ret. HPLC [min] | HPLC-Method |
|---|---|---|---|---|
| I-194 | 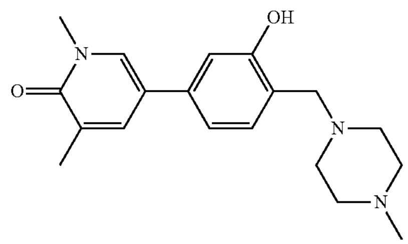 [SMILES: Cc1cc(-c2ccc(CN3CCN(C)CC3)c(O)c2)cn(C)c1=O] | 386 | 0.930 | M1 |
| I-195 | 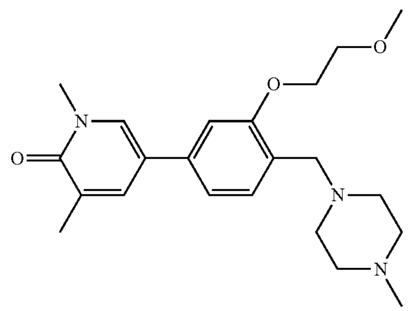 [SMILES: COCCOc1cc(-c2cc(C)c(=O)n(C)c2)ccc1CN1CCN(C)CC1] | 386 | 0.930 | M1 |
| I-196 | 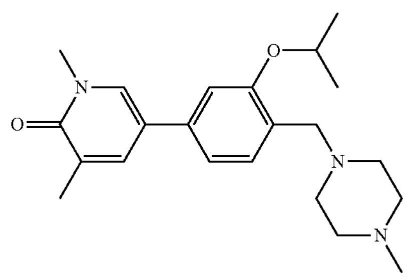 [SMILES: Cc1cc(-c2ccc(CN3CCN(C)CC3)c(OC(C)C)c2)cn(C)c1=O] | 370 | 1.080 | M1 |
| I-197 | 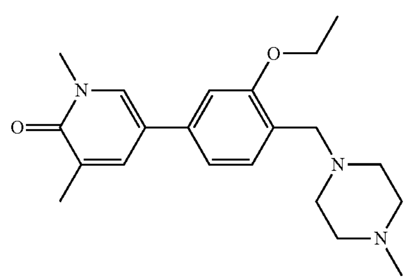 [SMILES: CCOc1cc(-c2cc(C)c(=O)n(C)c2)ccc1CN1CCN(C)CC1] | 356 | 1.430 | M1 |
| I-198 | 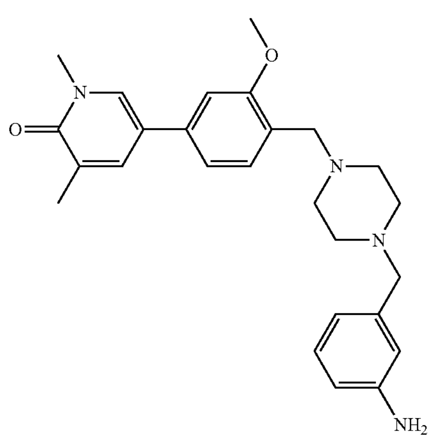 [SMILES: COc1cc(-c2cc(C)c(=O)n(C)c2)ccc1CN1CCN(Cc2cccc(N)c2)CC1] | 433 | 1.593 | M11 |

-continued

| # | Structure | MS (M + H)+ | t_Ref. HPLC [min] | HPLC-Method |
|---|---|---|---|---|
| I-199 | 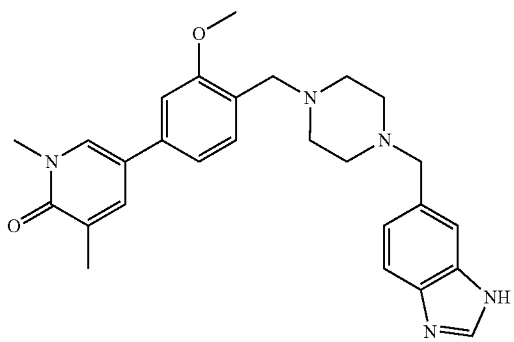 [SMILES: COc1cc(-c2cc(C)c(=O)n(C)c2)ccc1CN1CCN(Cc2ccc3nc[nH]c3c2)CC1] | 458 | 1.644 | M11 |
| I-200 | 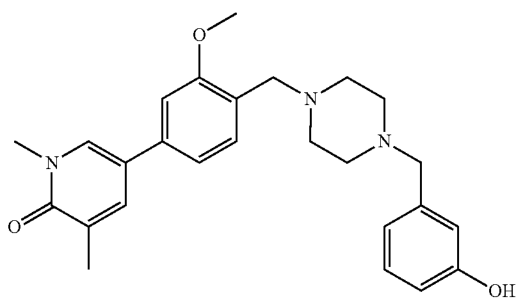 [SMILES: COc1cc(-c2cc(C)c(=O)n(C)c2)ccc1CN1CCN(Cc2cccc(O)c2)CC1] | 434 | 1.791 | M11 |
| I-201 | 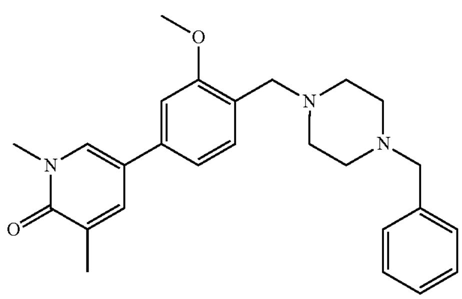 [SMILES: COc1cc(-c2cc(C)c(=O)n(C)c2)ccc1CN1CCN(Cc2ccccc2)CC1] | 452 | 2.224 | M11 |
| I-202 | 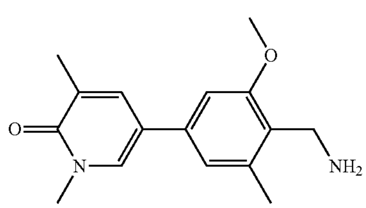 [SMILES: COc1cc(-c2cc(C)c(=O)n(C)c2)cc(C)c1CN] | 256 | 0.890 | M7 |
| I-203 | 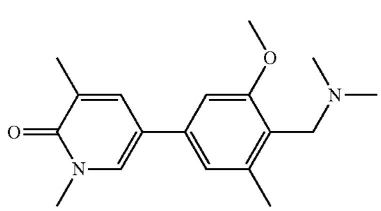 [SMILES: COc1cc(-c2cc(C)c(=O)n(C)c2)cc(C)c1CN(C)C] | 301 | NMR | |

-continued
| # | Structure | MS (M + H)⁺ | t_Ret. HPLC [min] | HPLC-Method |
|---|---|---|---|---|
| I-204 | 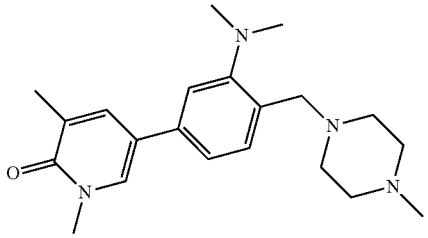 [SMILES: Cc1cc(-c2ccc(CN3CCN(C)CC3)c(N(C)C)c2)cn(C)c1=O] | 355 | 1.030 | M1 |
| I-205 | 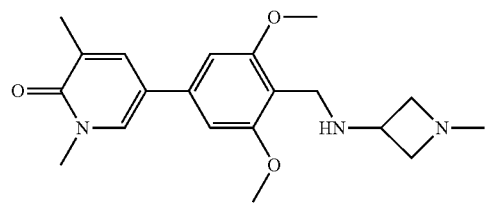 [SMILES: COc1cc(-c2cc(C)c(=O)n(C)c2)cc(OC)c1CNC1CN(C)C1] | 358 | 0.840 | M1 |
| I-206 | 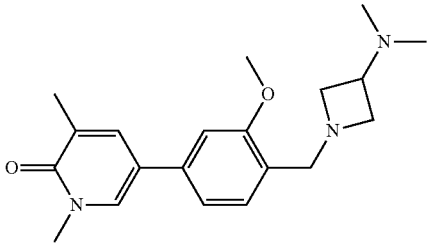 [SMILES: COc1cc(-c2cc(C)c(=O)n(C)c2)ccc1CN1CC(N(C)C)C1] | 342 | 0.890 | M1 |
| I-207 | 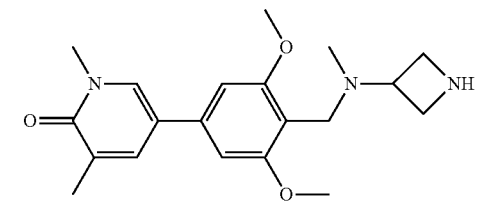 [SMILES: COc1cc(-c2cc(C)c(=O)n(C)c2)cc(OC)c1CN(C)C1CNC1] | 358 | 0.820 | M1 |
| I-208 | 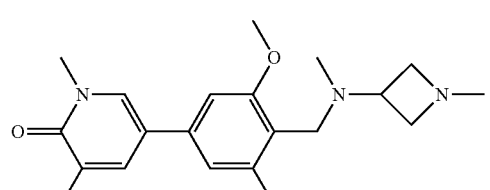 | 372 | 0.940 | M1 |
| I-209 | 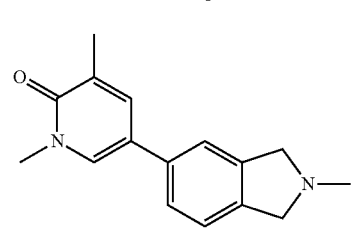 | 255 | 0.890 | M1 |
| I-210 | 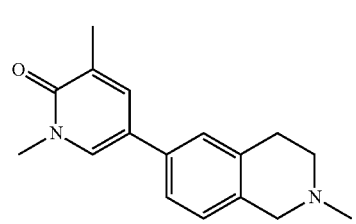 [SMILES: Cc1cc(-c2ccc3c(c2)CCN(C)C3)cn(C)c1=O] | 269 | 0.960 | M1 |

-continued
| # | Structure | MS (M + H)+ | t_Ref. HPLC [min] | HPLC-Method |
|---|---|---|---|---|
| I-211 | 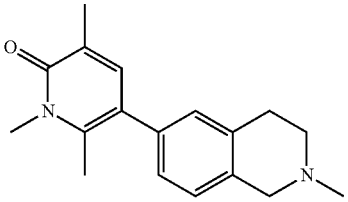 [SMILES: Cc1cc(-c2ccc3c(c2)CCN(C)C3)c(C)n(C)c1=O] | 283 | 1.010 | M1 |
| I-212 | 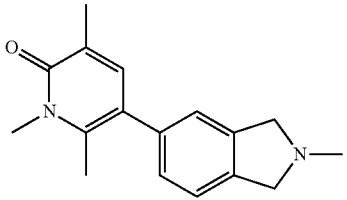 [SMILES: Cc1cc(-c2ccc3c(c2)CN(C)C3)c(C)n(C)c1=O] | 269 | 0.950 | M1 |
| I-214 | 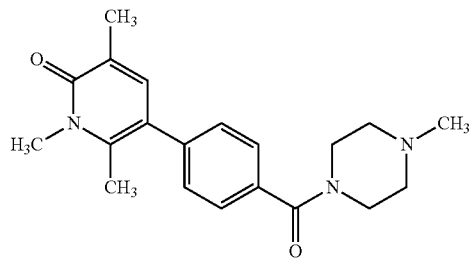 [SMILES: Cc1cc(-c2ccc(C(=O)N3CCN(C)CC3)cc2)c(C)n(C)c1=O] | 340 | 0.82 | M1 |
| I-215 | 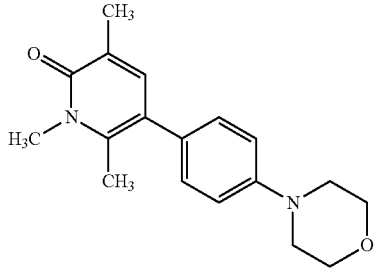 [SMILES: Cc1cc(-c2ccc(N3CCOCC3)cc2)c(C)n(C)c1=O] | 299 | 2.35 | M11 |

Preparation of Compounds of Type II
Preparation of Intermediate Q-1

4-Bromo-2-methyl-2H-isoquinolin-1-one

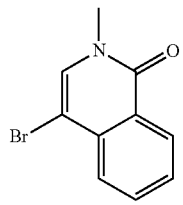

Reaction scheme

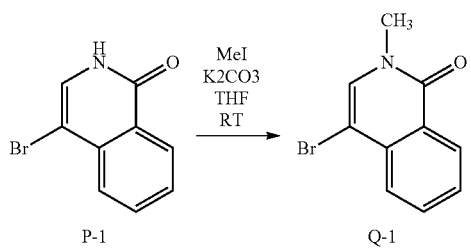

4-Bromo-2-methyl-2H-isoquinolin-1-one Q-1

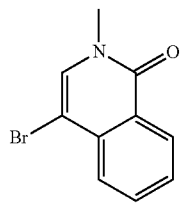

To a suspension of 4-bromo-1(2H)-isoquinolinone P-1 (1.000 g; 4.240 mmol) and potassium carbonate (1.172 g; 8.480 mmol) in tetrahydrofuran (10.0 mL), iodomethane (0.423 mL; 6.664 mmol) are added. The reaction mixture is stirred overnight at RT. The reaction mixture is quenched with 10% ammonia solution (30 mL) and water (50 mL) is added. THF is removed under reduced pressure. The precipitated product is filtered off and dried under reduced pressure.

HPLC-MS: (M+H)$^+$=238; t$_{Ret}$=1.02 min; method M1

Preparation of Intermediate Q-7

4-Iodo-2-methyl-2H-[2,6]naphthyridin-1-one

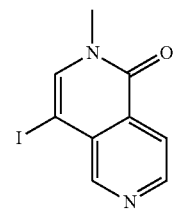

Reaction scheme

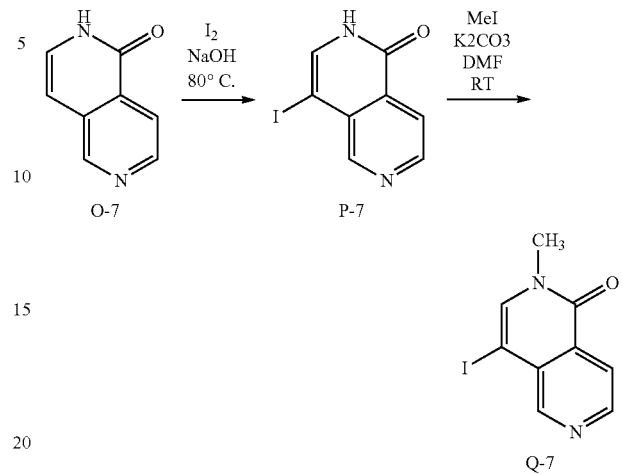

4-Iodo-2H-[2,6]naphthyridin-1-one (P-7)

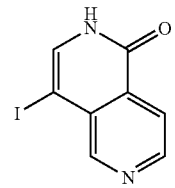

To a solution of 2,6-naphthyridin-1(2H)-one O-7 (2.000 g; 13.685 mmol) in 1 N NaOH (50 mL), iodine (6.947 g, 27.370 mmol) is added. The mixture is stirred at 80° C. for 16 h. The mixture is diluted with water and filtered. The filter cake is dried to give crude product as solid.

HPLC-MS: (M+H)$^+$=273; t$_{Ret}$=0.889 min; method M8

4-Iodo-2-methyl-2H-[2,6]naphthyridin-1-one (Q-7)

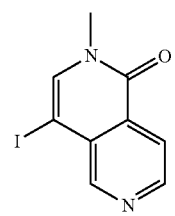

To a solution of 4-iodo-2,6-naphthyridin-1(2H)-one P-7 (1.000 g; 3.676 mmol) in DMF (50 mL), potassium carbonate (1.522 g; 11.028 mmol) and methyliodide (1.044 g; 7.352 mmol) are added. The mixture is stirred at RT for 24 h. Water is added and the aqueous layer is extracted with ethyl acetate. The organic layer is washed with brine, dried and evaporated to dryness to give crude product.

HPLC-MS: (M+H)$^+$=287; t$_{Ret}$=0.573 min; method M6

Preparation of Intermediate Q-9

4-Bromo-2,5-dimethyl-2H-isoquinolin-1-one

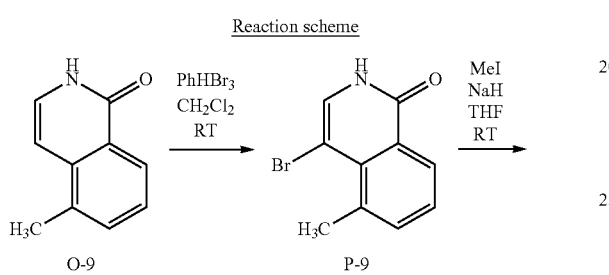

Reaction scheme

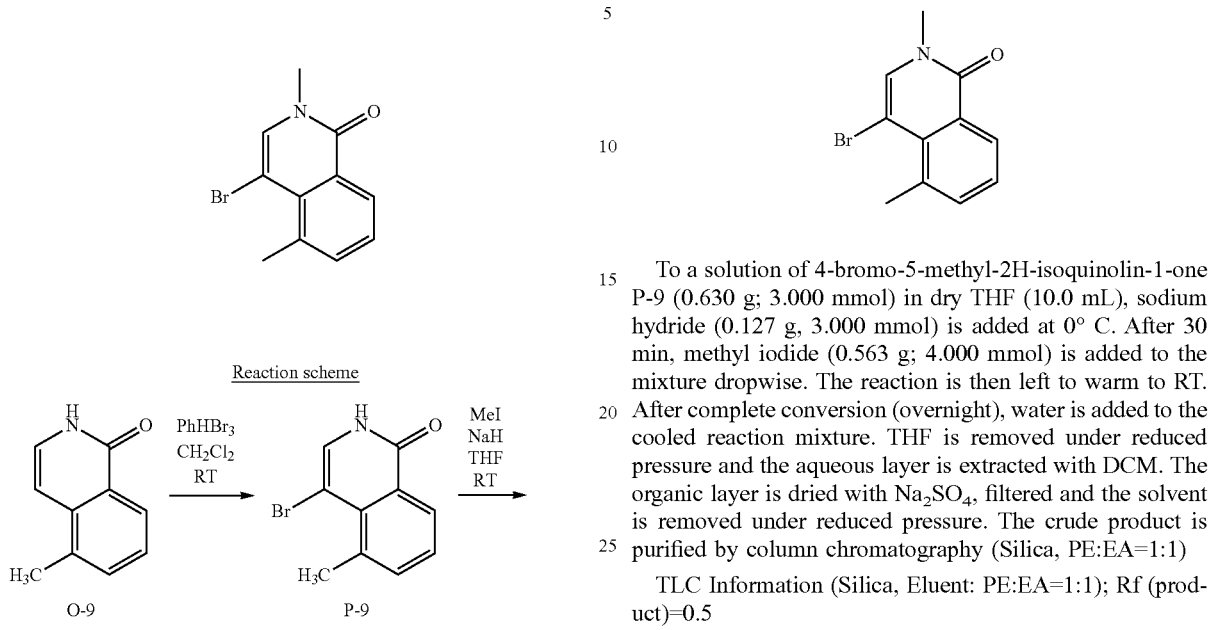

To a solution of 5-methyl-2H-isoquinolin-1-one O-9 (0.800 g; 5.000 mmol) in DCM (5 mL), pyridinium bromide perbromide (4.779 g; 15.000 mmol) is added. The reaction is stirred at RT for 5 h. To the reaction mixture aq. NaHCO₃ is added and the aqueous layer is extracted with DCM. The organic layer is washed with sat. NaS₂O₃ solution, dried with Na₂SO₄, filtered and concentrated under reduced pressure.

TLC Information (Silica, Eluent: PE:EA=2:1); Rf (product)=0.5

4-Bromo-2,5-dimethyl-2H-isoquinolin-1-one Q-9

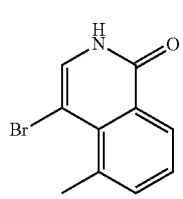

To a solution of 4-bromo-5-methyl-2H-isoquinolin-1-one P-9 (0.630 g; 3.000 mmol) in dry THF (10.0 mL), sodium hydride (0.127 g, 3.000 mmol) is added at 0° C. After 30 min, methyl iodide (0.563 g; 4.000 mmol) is added to the mixture dropwise. The reaction is then left to warm to RT. After complete conversion (overnight), water is added to the cooled reaction mixture. THF is removed under reduced pressure and the aqueous layer is extracted with DCM. The organic layer is dried with Na₂SO₄, filtered and the solvent is removed under reduced pressure. The crude product is purified by column chromatography (Silica, PE:EA=1:1)

TLC Information (Silica, Eluent: PE:EA=1:1); Rf (product)=0.5

Preparation of Intermediate Q-10

4-Bromo-5-fluoro-2-methyl-2H-isoquinolin-1-one

Reaction scheme

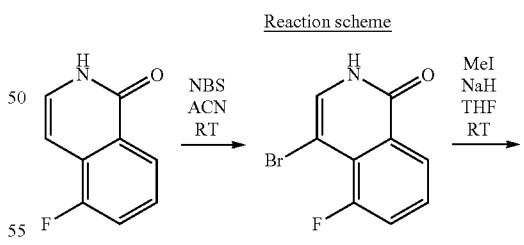

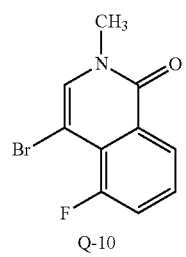

4-Bromo-5-fluoro-2H-isoquinolin-1-one P-10

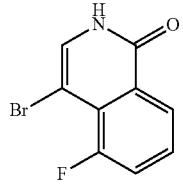

N-Bromosuccinimide (0.432 g; 2.000 mmol) is added to a solution of 5-fluoro-2H-isoquinolin-1-one O-10 (0.360 g; 2.000 mmol) in acetonitrile (25 mL), the mixture is stirred at RT for 12 h. After full conversion the solvent is removed and purified by preparative HPLC.

TLC Information (Silica, Eluent: DCM:MeOH=15:1); Rf (product)=0.5

4-Bromo-5-fluoro-2-methyl-2H-isoquinolin-1-one Q-10

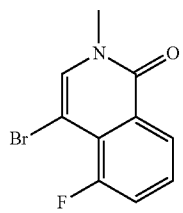

To a solution of 4-bromo-5-fluoro-2H-isoquinolin-1-one P-10 (0.130 g; 0.050 mmol) in dry THF (3 mL), sodium hydride (0.025 g; 0.645 mmol) is added at 0° C. After 30 min methyl iodide (0.112 g; 0.800 mmol) is added to the mixture dropwise. The reaction is then left to warm to RT. After complete conversion water is added to the cooled reaction mixture. THF is removed under reduced pressure and the aqueous layer is extracted with DCM. The organic layer is dried with $Na_2SO_4$, filtered and the solvent is removed under reduced pressure. The crude product is purified by preparative HPLC.

TLC Information (Silica, Eluent: DCM/MeOH=20:1); Rf (product)=0.5

Preparation of Intermediate Q-11

4-Bromo-2-cyclopropyl-2H-isoquinolin-1-one

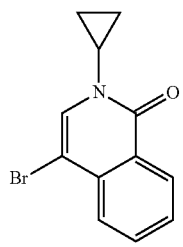

Reaction scheme

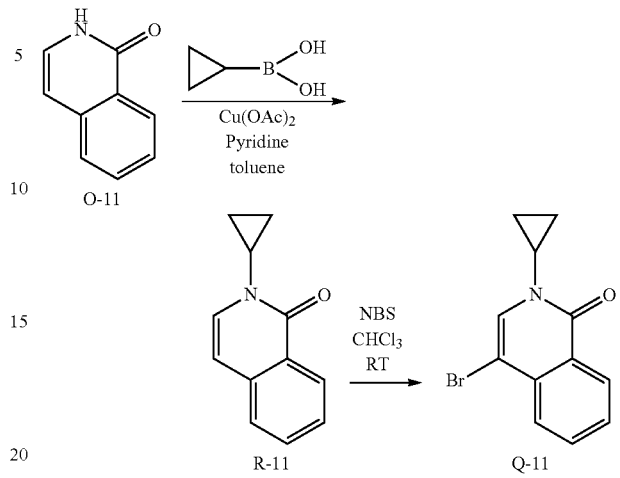

2-Cyclopropyl-2H-isoquinolin-1-one R-11

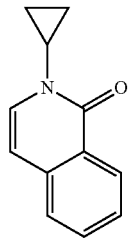 [SMILES: O=c1c2ccccc2ccn1C1CC1]

To a solution of 2H-isoquinolin-1-one O-11 (1.000 g; 6.889 mmol)) in toluene (10 mL), cyclopropylboronic acid (1.775 g; 20.667 mmol), copper (II) acetate (1.251 g; 6.889 mmol) and pyridine (2.500 mL; 31.606 mmol) are added. The mixture is heated overnight at 70° C. A 2N aqueous HCl solution (20 mL) is added, followed by ethyl acetate (50 mL) and the suspension is filtered off. The phases are separated and the aqueous layer is extracted 3 times with ethyl acetate (50 mL). The combined organic layers are dried with $Na_2SO_4$, filtered off and concentrated under reduced pressure. The crude product is purified by Combiflash (Column Redisep Rf, 40 g; gradient: cyclohexane/EtOAc=100%/0% to 50%/50% over 20 column volumes; flow rate=40 mL/min; detection wavelength: 254 nm)

HPLC-MS: $(M+H)^+=186$; $t_{Ret}=0.89$ min; method M1

4-Bromo-2-cyclopropyl-2H-isoquinolin-1-one Q-11

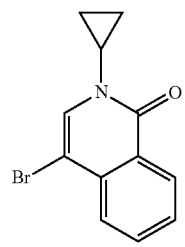 [SMILES: O=c1c2ccccc2c(Br)cn1C1CC1]

To a solution of 2-cyclopropyl-2H-isoquinolin-1-one R-11 (1.500 g; 6.479 mmol) in chloroform (10.0 mL), N-bromosuccinimide (1.200 g; 6.742 mmol) is added at RT. The reaction mixture is stirred for 2 h. The solvent is removed under reduced pressure and the crude product is purified by Combiflash (Column Redisep Rf, 40 g; gradient: DCM/MeOH=100%/0% to 95%/5% over 20 column volumes; flow rate=40 mL/min; detection wavelength: 254 nm). The product containing fractions are concentrated under reduced pressure.

HPLC-MS: $(M+H)^+$=264/266; $t_{Ret}$=1.14 min; method M1

Preparation of Intermediate Q-12

4-Bromo-5-methoxy-2-methyl-2H-isoquinolin-1-one

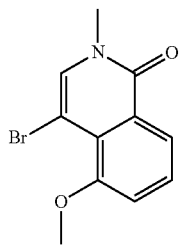

Reaction scheme

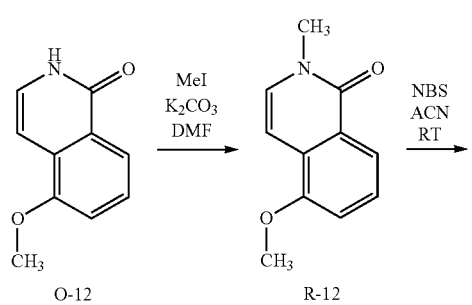

O-12   R-12

5-Methoxy-2-methyl-2H-isoquinolin-1-one R-12

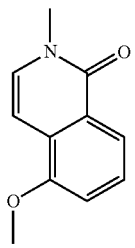

To a solution of 5-methoxy-2H-isoquinoline-1-one O-12 (1.500 g; 8.562 mmol) in DMF (20 mL), potassium carbonate (3.545 g; 25.686 mmol) and methyl iodide (1.207 g; 8.562 mmol) are added at RT. After complete conversion water is added to the cooled reaction mixture. The reaction mixture is poured onto ice water and extracted with EA. The organic layer is dried with $Na_2SO_4$, filtered and the solvent is removed under reduced pressure. The crude product is purified by NP silica gel chromatography.

HPLC-MS: $(M+H)^+$=190; $t_{Ret}$=1.151 min; method M7

4-Bromo-5-methoxy-2-methyl-2H-isoquinolin-1-one Q-12

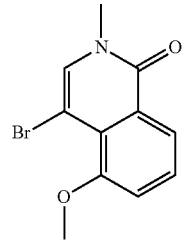

To a solution of 5-methoxy-2-methyl-2H-isoquinolin-1-one R-12 (1.100 g; 5.814 mmol) in acetonitrile (20.0 mL), N-bromosuccinimide (1.242 g; 6.976 mmol) is added at RT. The reaction mixture is stirred for 24 h. After full conversion the reaction mixture is poured into ice water and extracted with EA. The combined organic layers are washed with brine, dried with $Na_2SO_4$, filtered and the solvent is removed under reduced pressure. The crude product is purified by silica gel chromatography.

HPLC-MS: $(M+H)^+$=268/270; $t_{Ret}$=0.721 min; method M6

Preparation of Intermediate Q-13

4-Bromo-2-methyl-7-nitro-2H-isoquinolin-1-one

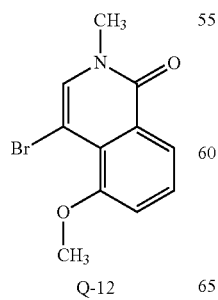

Reaction scheme

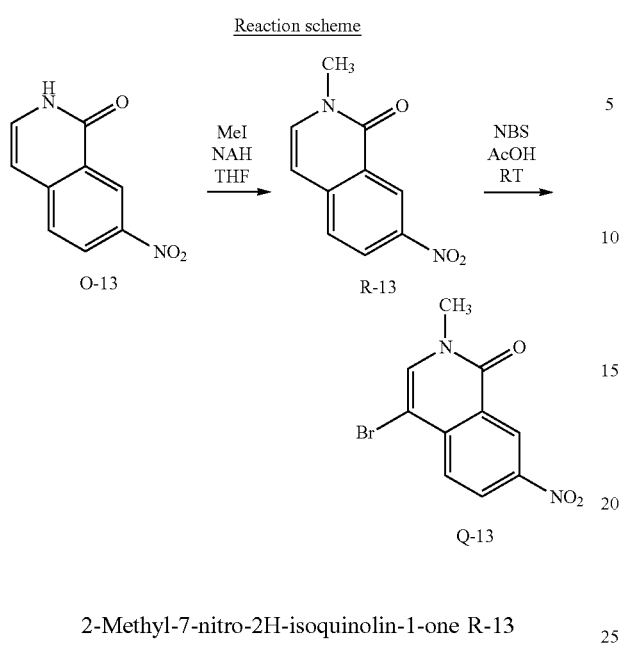

2-Methyl-7-nitro-2H-isoquinolin-1-one R-13

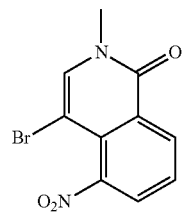

To a solution of 7-nitro-2H-isoquinolin-1-one O-13 (7.800 g; 0.041 mol) in dry THF (15 mL), sodium hydride (1.477 g; 0.062 mol) is added at 0° C. After 3 h methyl iodide (6.987 g; 0.049 mol) is added to the mixture dropwise. After complete conversion (3 h), water is added at 0° C. The reaction mixture is then extracted with EA. The combined organic layers are washed with brine, dried with Na$_2$SO$_4$, filtered and the solvent is removed under reduced pressure. The crude product is purified by silica gel chromatography.

TLC Information (Silica, Eluent: PE:EA=5:1); Rf (product)=0.5

4-Bromo-2-methyl-7-nitro-2H-isoquinolin-1-one Q-13

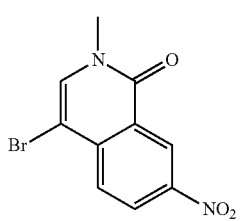 [SMILES: Cn1cc(Br)c2ccc([N+](=O)[O-])cc2c1=O]

To a solution of 2-methyl-7-nitro-2H-isoquinolin-1-one R-13 (2.000 g; 0.010 mol) in acetonitrile (3.0 mL), N-bromosuccinimide (1.918 g; 0.011 mol) is added at RT. The reaction mixture is stirred at RT for 5 h. The reaction mixture is then poured onto ice water and extracted with DCM. The combined organic layers are washed with brine, dried, filtered and the solvent is removed under reduced pressure. The crude product is purified by silica gel chromatography.

TLC Information (Silica, Eluent: PE:EA=2:1); Rf (product)=0.5

Preparation of Intermediate Q-14

4-Bromo-2-methyl-5-nitro-2H-isoquinolin-1-one

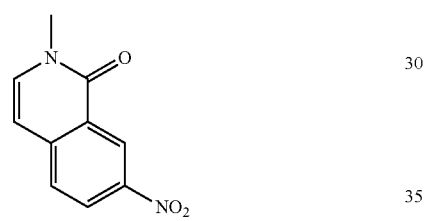

Reaction scheme

4-Bromo-2-methyl-5-nitro-2H-isoquinolin-1-one Q-14

To a solution of 2-methyl-5-nitro-2H-isoquinolin-1-one R-14 (0.070 g; 0.343 mmol) in dichloromethane (3.0 mL), bromine (0.603 g; 3.775 mmol) is added at RT. The reaction mixture is stirred at RT for 5 h. After full conversion the reaction mixture is poured on ice water and extracted with DCM. The combined organic layers are washed with brine, dried with Na$_2$SO$_4$, filtered and the solvent is removed under reduced pressure. The crude product is purified by silica gel chromatography.

HPLC-MS: (M+H)$^+$=283/285; t$_{Ret}$=0.721 min; method M7

229

Preparation of Intermediate Q-15

4-Bromo-2-methyl-6-pyrazol-1-ylmethyl-2H-isoquinolin-1-one

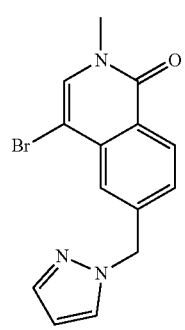

Reaction scheme

Allylpalladium chloride dimer
SPhos
Cs₂CO₃
cyclopentylmethylether
H₂O
100° C.

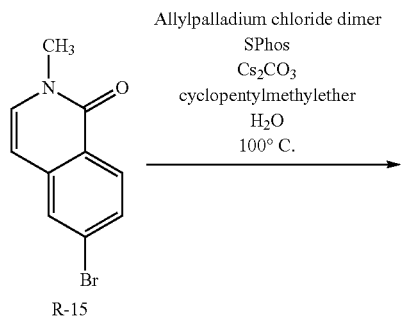

230

2-Methyl-6-pyrazol-1-ylmethyl-2H-isoquinolin-1-one R-15'

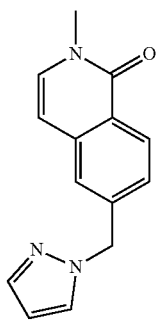

In a vial 6-bromo-2-methyl-2H-isoquinolin-1-one R-15 (0.100 g; 0.420 mmol), potassium trifluoro-1H-(pyrazol-1-ylmethyl) boron (0.079 g; 0.420 mmol), allylpalladium chloride dimer (7.7 mg; 0.021 mmol), sodium 2-dicyclohexylphosphino-2,6-dimethoxy-1,1-biphenyl-3-sulfonathydrate (22.7 mg; 0.042 mmol) and cesium carbonate (0.101 mL; 1.260 mmol) are introduced. Cyclopentyl methyl ether (800 µl) and water (200 µl) are then added. The vial is flushed with argon and sealed. The reaction mixture is heated at 100° C. for 24 h. After complete conversion the reaction mixture is diluted with DCM, MeOH and water. The phases are separated and the mixture is extracted 2 more times with DCM. The combined organic layers are dried with Na₂SO₄, filtered and concentrated under reduced pressure. The crude material is dissolved with DMSO (1 mL), filtered and purified with the basic (ammonia buffer) RP HPLC system (column: X-Bridge C-18 30×50 mm). The product containing fractions are concentrated under reduced pressure.

HPLC-MS: $(M+H)^+=240$; $t_{Ret}=0.73$ min; method M1

4-Bromo-2-methyl-6-pyrazol-1-ylmethyl-2H-isoquinolin-1-one Q-15

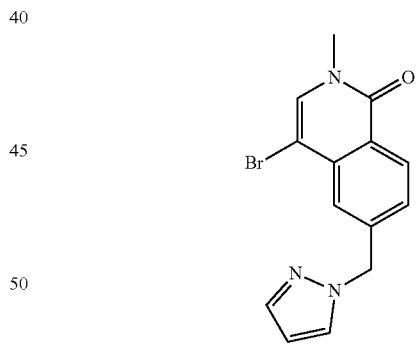

To a solution of 2-methyl-6-pyrazol-1-ylmethyl-2H-isoquinolin-1-one R-15' (0.050 g; 0.209 mmol) in chloroform (1 mL), N-bromosuccinimide (0.039 g; 0.217 mmol) is added at RT. The reaction mixture is stirred at RT for 2 h. After complete conversion the reaction mixture is concentrated under reduced pressure. The crude product is purified by Combiflash (Column Redisep Rf, 12 g; gradient: DCM/MeOH=100%/0% to 90%/10% over 28 column volumes; flow rate=30 mL/min; detection wavelength: 254 nm)

HPLC-MS: $(M+H)^+=318$; $t_{Ret}=0.94$ min; method M1

According to the procedure of Q-1, the intermediates Q-2-Q-6 are synthesized. According to the procedure of Q-7 with the exception of omitting the halogenation step O→P (intermediate P-8 with hal=Br is commercially available), the intermediate Q-8 is synthesized.

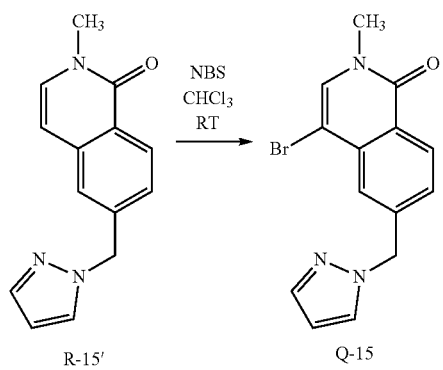

| # | Structure | MS (M + H)+ | tRet. HPLC [min] | HPLC-Method |
|---|---|---|---|---|
| Q-1 | 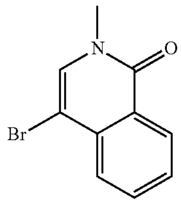 | 238 | 1.02 | M1 |
| Q-2 | 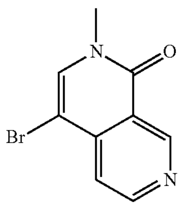 | 239 | 0.92 | M1 |
| Q-3 | 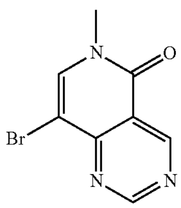 | 240/242 | 0.29 | M1 |
| Q-4 | 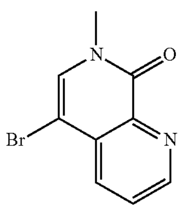 | 239 | 0.87 | M1 |
| Q-5 | 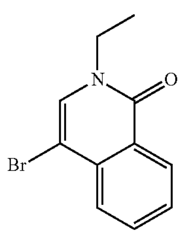 | 252 | 1.12 | M1 |
| Q-6 | 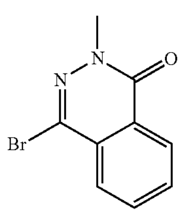 | 239 | 1.16 | M1 |
| Q-7 | 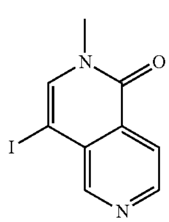 | 287 | 0.57 | M6 |
| Q-8 | | 239/241 | 0.52 | M6 |
| Q-9 | | Observed by TLC Rf = 0.50 (PE:EtOAc 1:1) | | |
| Q-10 | | Observed by TLC Rf = 0.50 (DCM:MeOH 20:1) | | |
| Q-11 | | 264/266 | 1.14 | M1 |
| Q-12 | | 268/270 | 0.721 | M6 |
| Q-13 | | Observed by TLC Rf = 0.50 (PE:EtOAc 2:1) | | |

-continued

| # | Structure | MS (M + H)+ | t_Ret. HPLC [min] | HPLC-Method |
|---|---|---|---|---|
| Q-14 | 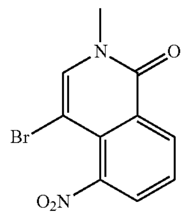 [SMILES: Cn1cc(Br)c2c([N+](=O)[O-])cccc2c1=O] | 283 | 1.33 | M7 |
| Q-15 | 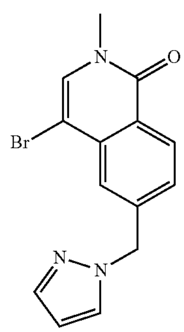 [SMILES: Cn1cc(Br)c2cc(Cn3cccn3)ccc2c1=O] | 318 | 0.94 | M1 |

Preparation of Intermediate S-1

2-Methyl-4-(4,4,5,5-tetramethyl-[1,3,2]dioxaborolan-2-yl)-2H-isoquinolin-1-one

Reaction scheme

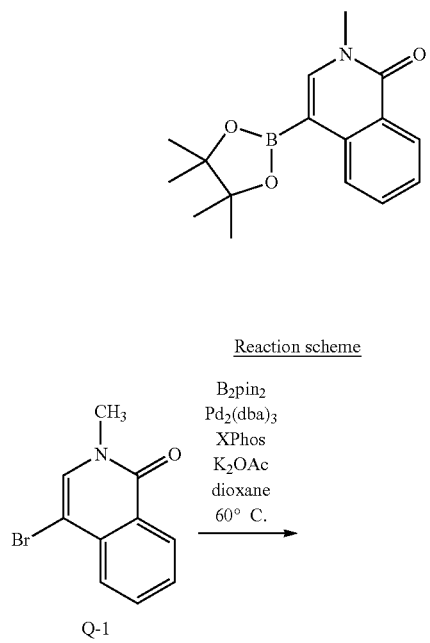

2-Methyl-4-(4,4,5,5-tetramethyl-[1,3,2]dioxaborolan-2-yl)-2H-isoquinolin-1-one S-1

4-Bromo-2-methyl-2H-isoquinolin-1-one Q-1 (0.550 g; 2.241 mmol), bispinacolatodiboron (1.250 g; 4.922 mmol), tris(dibenzylideneacetone)-dipalladium(0) (0.260 g; 0.275 mmol), XPHOS (0.310 g; 0.650 mmol) and potassium acetate (0.600 g; 6.114 mmol) are introduced in a round bottom flask. 1,4-dioxane (12 mL) is added and the flask is flushed with argon. The reaction mixture is stirred at 60° C. (Drysyn) for 8 h. The reaction mixture is then cooled to RT and filtered through a plug of celite. The filtrate is concentrated under reduced pressure. The residue is dissolved in DCM (100 mL) and washed with water (100.0 mL). The combined organic layer is dried with Na$_2$SO$_4$, filtered and concentrated under reduced pressure. The residue is purified by silica gel chromatography Combiflash (Column Redisep Rf, 40 g; gradient: cyclohexane/EtOAc=100%/0% to 70%/30% over 13 column volumes; flow rate=40 mL/min; detection wavelength: 254 nm). The product containing fractions are combined and concentrated under reduced pressure.

HPLC-MS: (M+H)$^+$=286; t$_{Ret}$=1.483 min; method M7

| # | Structure | MS (M + H)+ | t_Ret. HPLC [min] | HPLC-Method |
|---|---|---|---|---|
| S-1 | 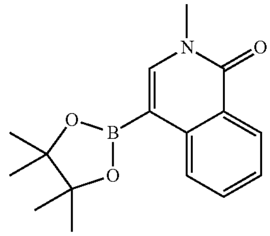 [SMILES: Cn1cc(B2OC(C)(C)C(C)(C)O2)c2ccccc2c1=O] | 286 | 1.483 | M7 |

General Method for Preparation of Compounds of Type II
Method 1:
Preparation of Compound II-1

4-[4-(3-Hydroxy-azetidin-1-ylmethyl)-3,5-dimethoxy-phenyl]-2-methyl-2H-isoquinolin-1-one

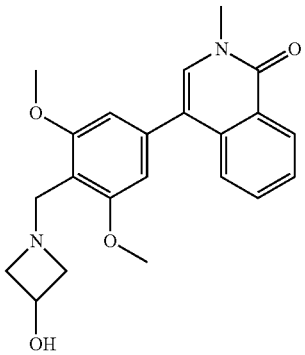 [SMILES: COc1cc(-c2cn(C)c(=O)c3ccccc23)cc(OC)c1CN1CC(O)C1]

Reaction scheme

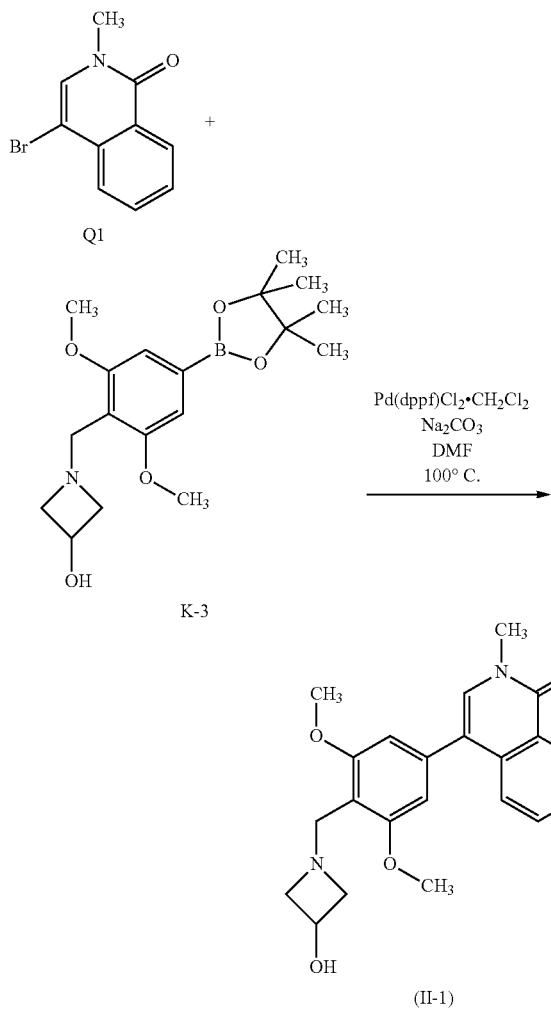

4-[4-(3-Hydroxy-azetidin-1-ylmethyl)-3,5-dimethoxy-phenyl]-2-methyl-2H-isoquinolin-1-one (II-1)

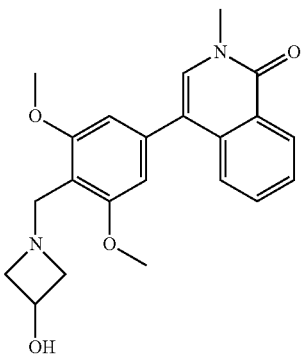 [SMILES: COc1cc(-c2cn(C)c(=O)c3ccccc23)cc(OC)c1CN1CC(O)C1]

4-Bromo-2-methyl-2H-isoquinolin-1-one Q-1 (0.070 g; 0.294 mmol) and 1,1'-bis(diphenylphosphino)ferrocene palladium(II) dichloride (0.025 g; 0.029 mmol) are added to a solution of 1-[2,6-dimethoxy-4-(4,4,5,5-tetramethyl[1,3,2]dioxaborolan-2-yl)-benzyl]-azetidin-3-ol K-3 followed by addition of a 2N sodium bicarbonate solution (0.368 mL; 0.735 mmol). The reaction mixture is stirred at 100° C. for 1 h. The reaction mixture is then cooled to RT, water is added and the mixture is filtered. The filtrate is purified by RP HPLC (column: X-Bridge C-18 30×50 mm). The product containing fractions are combined and concentrated under reduced pressure and further purified by NP silica gel chromatography Combiflash (column Redisep Rf, 12 g; gradient: DCM/MeOH/NH$_3$=100%/0% to 10%/0.1% over 28 column volumes; flow rate=30 mL/min; detection wavelength: 254 nm). The product containing fractions are combined and concentrated under reduced pressure, dissolved in acetonitrile/water=1:1 and freeze dried.

HPLC-MS: (M+H)$^+$=381; t$_{Ret}$=1.02 min; method M1

Method 2:
Preparation of Compound II-21

5-(4-Dimethylaminomethyl-3,5-dimethoxy-phenyl)-7-methyl-7H-[1,7]naphthyridin-8-one

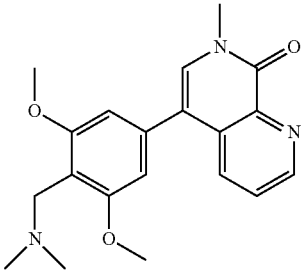 [SMILES: COc1cc(-c2cn(C)c(=O)c3ncccc23)cc(OC)c1CN(C)C]

Reaction scheme

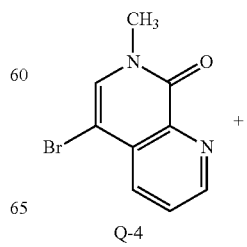

Method 3:
Preparation of Compound II-28

N-[5-(2,5-Dimethyl-1-oxo-1,2-dihydro-isoquinolin-4-yl)-2-methyl-phenyl]-methanesulfonamide

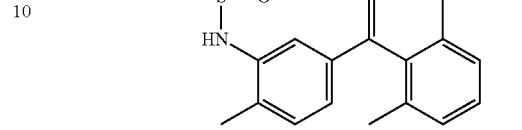

Reaction scheme

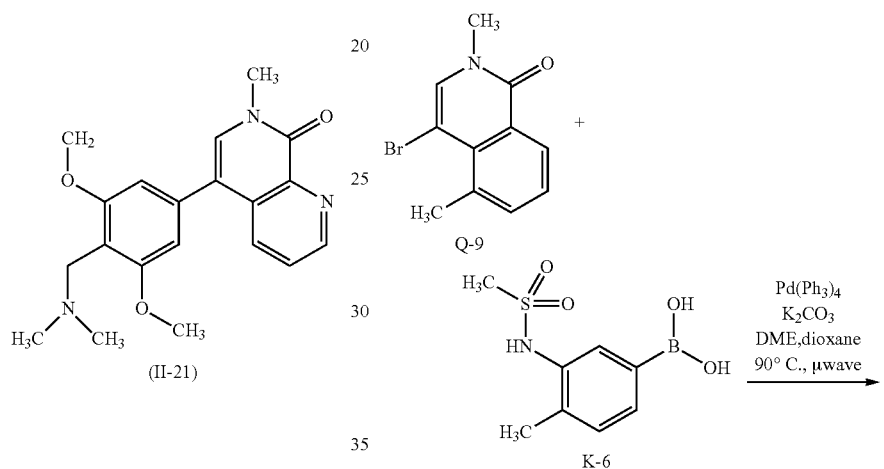

N-[5-(2,5-Dimethyl-1-oxo-1,2-dihydro-isoquinolin-4-yl)-2-methyl-phenyl]-methanesulfonamide (II-28)

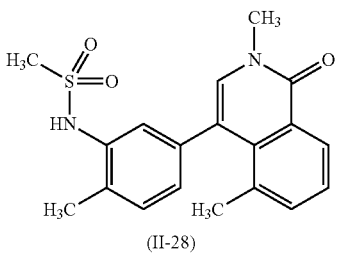

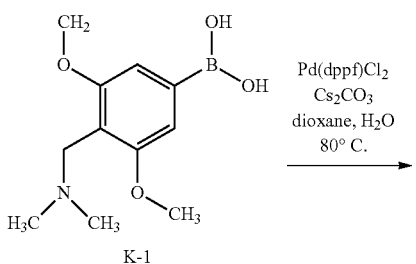

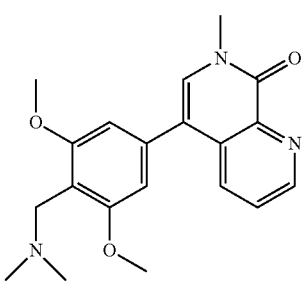 [SMILES: COc1cc(-c2cn(C)c(=O)c3ncccc23)cc(OC)c1CN(C)C]

5-(4-Dimethylaminomethyl-3,5-dimethoxy-phenyl)-7-methyl-7H-[1,7]naphthyridin-8-one (II-21)

A mixture of 5-bromo-7-methyl-1,7-naphthyridin-8(7H)-one Q-4 (0.100 g; 0.418 mmol), (4-((dimethylamino)methyl)-3,5-dimethoxyphenyl)boronic acid K-1 (0.100 g; 0.418 mmol), 1,1'-bis(diphenylphosphino)ferrocenepalladium(II) dichloride (0.061 g; 0.084 mmol) and potassium carbonate (0.173 g, 1.255 mmol) in dioxane/water 10:1 (11 mL) are stirred at 80° C. under $N_2$ for 1 h. The reaction mixture is then cooled to RT and after addition of water extracted with ethyl acetate. The organic layer is washed with brine, dried with $Na_2SO_4$, filtered and evaporated to dryness. The residue is purified by prepTLC.

HPLC-MS: $(M+H)^+$=354; $t_{Ret}$=2.037 min; method M10

4-Bromo-2,5-dimethyl-2H-isoquinolin-1-one Q-9 (0.500 g; 2.000 mmol) and 4-methyl-(3-methylsulfonylamino)phenyl boronic acid K-6 (0.729 g; 3.000 mmol) are dissolved in DME/water 3:1. Potassium carbonate (0.821 g; 6.000 mmol) and tetrakis(triphenylphosphine)palladium(0) (0.023 g; 0.020 mmol) are added under N2 and the mixture is heated in a microwave for 20 min. The reaction mixture is then evaporated and purified by RP HPLC.

TLC Information (Silica, Eluent: PE:EA=1:1); Rf (product)=0.5 Structure confirmed by ¹H NMR
Method 4:
Preparation of Compound II-30
8-[4-(3-Amino-azetidin-1-ylmethyl)-3,5-dimethoxy-phenyl]-6-methyl-6H-pyrido[4,3-d]pyrimidin-5-one
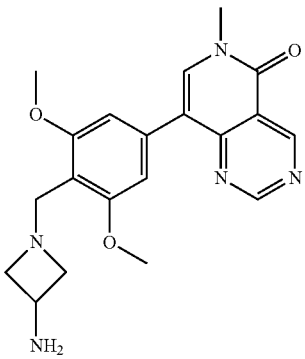 [SMILES: COc1cc(-c2cn(C)c(=O)c3cncnc23)cc(OC)c1CN1CC(N)C1]
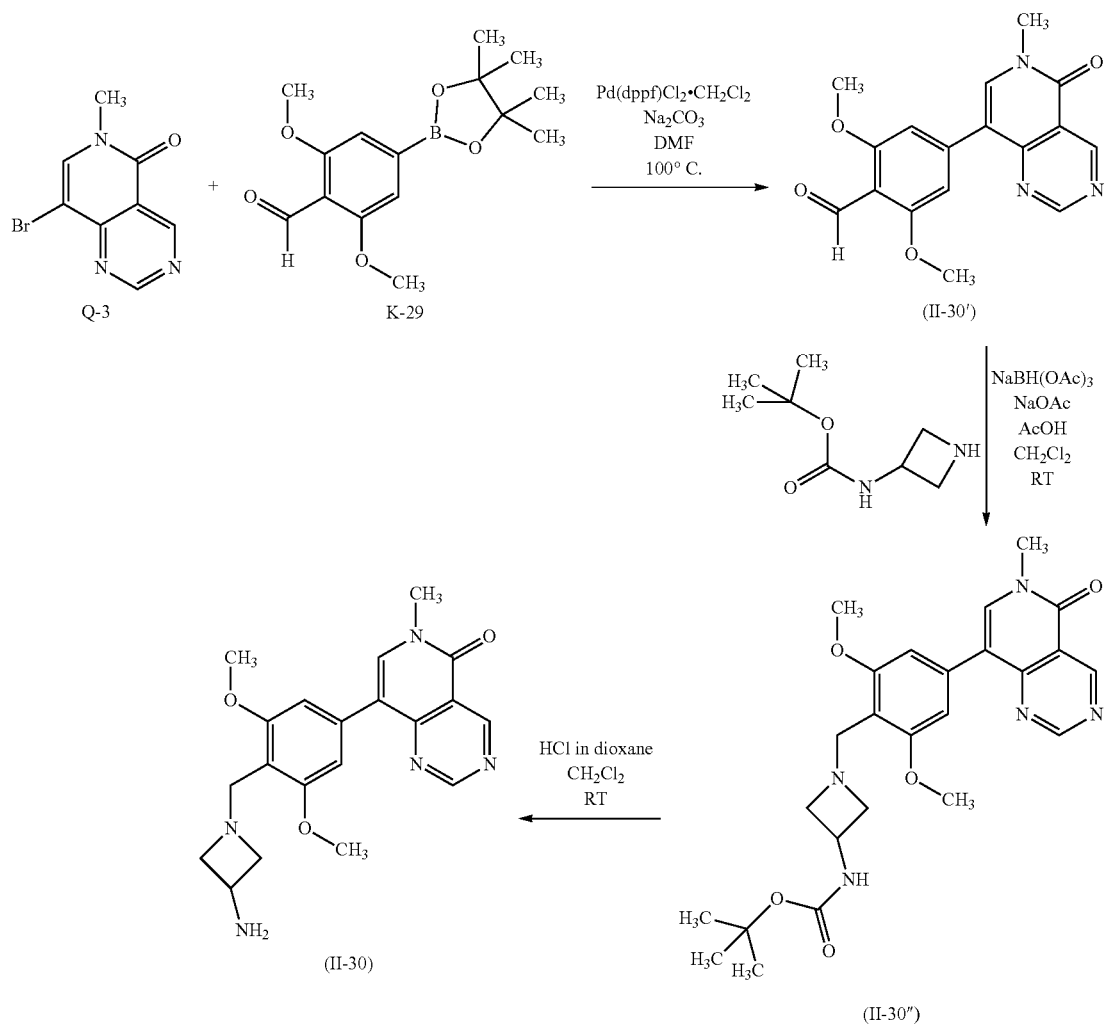

2,6-Dimethoxy-4-(6-methyl-5-oxo-5,6-dihydro-pyrido[4,3-d]pyrimidin-8-yl)-benzaldehyde (II-30')

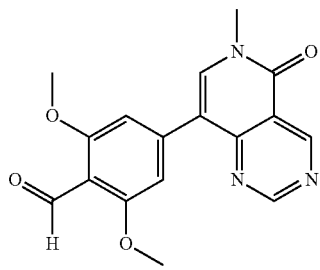 [SMILES: COc1cc(-c2cn(C)c(=O)c3cncnc23)cc(OC)c1C=O]

8-Bromo-6-methyl-6H-pyrido[4,3-d]pyrimidine-5-one Q-3 (0.200 g; 0.833 mmol), 3,5-dimethoxy-4-formyl phenyl boronic acid K-29 (0.175 g; 0.833 mmol), 1,1'-bis(diphenylphosphino)ferrocenepalladium(II) dichloride (0.070 g; 0.083 mmol) and a 2N solution of sodium bicarbonate in water are dissolved in DMF (5 mL). The reaction mixture is purged with Ar for 5 min and then heated at 80° C. for 2 h. The reaction mixture is then concentrated under reduced pressure and purified by NP silica gel chromatography (gradient: DCM/MeOH and 2N $NH_3$ (0.1%)=0% to 10%). The product containing fractions are combined and concentrated under reduced pressure and directly used for the next reaction step.

HPLC-MS: $(M+H)^+$=326; $t_{Ret}$=0.34 min; method M2

{1-[2,6-Dimethoxy-4-(6-methyl-5-oxo-5,6-dihydro-pyrido[4,3-d]pyrimidin-8-yl)-benzyl]-azetidin-3-yl}-carbamic acid tert-butyl ester (II-30")

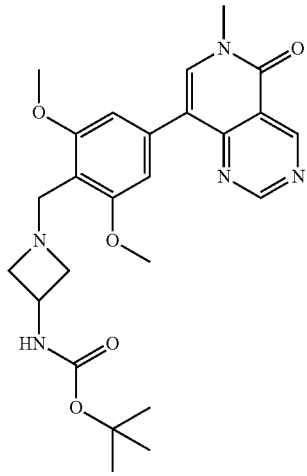 [SMILES: COc1cc(-c2cn(C)c(=O)c3cncnc23)cc(OC)c1CN1CC(NC(=O)OC(C)(C)C)C1]

2,6-Dimethoxy-4-(6-methyl-5-oxo-5,6-dihydro-pyrido[4,3-d]pyrimidin-8-yl)-benzaldehyde II-30' (0.095 g; 0.292 mmol), azetidine-3-yl carbamic acid tert-butyl ester (0.075 g; 0.438 mmol) and sodium acetate (0.036 g; 0.438 mmol) are dissolved in dry DCM (5 mL). After addition of acetic acid (0.018 g; 0.292 mmol) the reaction mixture is stirred for 30 min. Sodium triacetoxyborohydride (0.096 g; 0.438 mmol) and the reaction mixture is stirred at RT overnight. The reaction mixture is diluted with DCM (50 mL) and washed with water (2×20 mL), the organic phase is separated, dried ($Na_2SO_4$), filtrated and the filtrate is concentrated under reduced pressure. The crude product is purified by NP silica gel chromatography (gradient: DCM/MeOH and 2N $NH_3$ (0.1%)=0% to 10%). The product containing fractions are combined and concentrated under reduced pressure and directly used for the next reaction step.

HPLC-MS: $(M+H)^+$=482; $t_{Ret}$=0.54 min; method M2

8-[4-(3-Amino-azetidin-1-ylmethyl)-3,5-dimethoxy-phenyl]-6-methyl-6H-pyrido[4,3-d]pyrimidin-5-one (II-30)

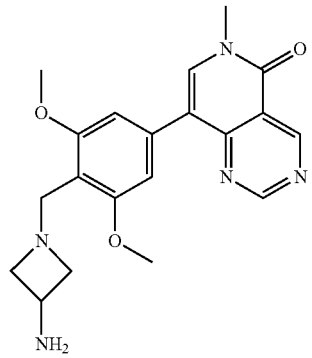 [SMILES: COc1cc(-c2cn(C)c(=O)c3cncnc23)cc(OC)c1CN1CC(N)C1]

{1-(2,6-Dimethoxy-4-(6-methyl-5-oxo-5,6-dihydro-pyrido[4,3-d]pyrimidin-8-yl)-benzyl)-azetidin-3-yl}-carbamic acid tert-butyl ester II-30" (0.058 g; 0.120 mmol) is dissolved in DCM (5 mL) and treated with 4N HCl (0.602 mmol). The reaction mixture is stirred at RT overnight, diluted with DCM (50 mL). The reaction mixture is diluted with DCM (50 mL), washed with water (2×20 mL), the organic phase is separated, dried with $Na_2SO_4$, filtrated and the filtrate is concentrated under reduced pressure. The crude product is purified by NP silica gel chromatography (gradient: DCM/MeOH and 2N $NH_3$ (0.1%)=0% to 10%). The product containing fractions are combined and concentrated under reduced pressure.

HPLC-MS: $(M+H)^+$=382; $t_{Ret}$=0.68 min; method M1

Method 5:

Preparation of Compound II-35

Ethanesulfonic acid [2-methyl-5-(2-methyl-1-oxo-1,2-dihydro-isoquinolin-4-yl)-phenyl]-amide

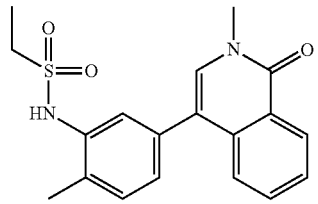 [SMILES: CCS(=O)(=O)Nc1cc(-c2cn(C)c(=O)c3ccccc23)ccc1C]

Reaction scheme

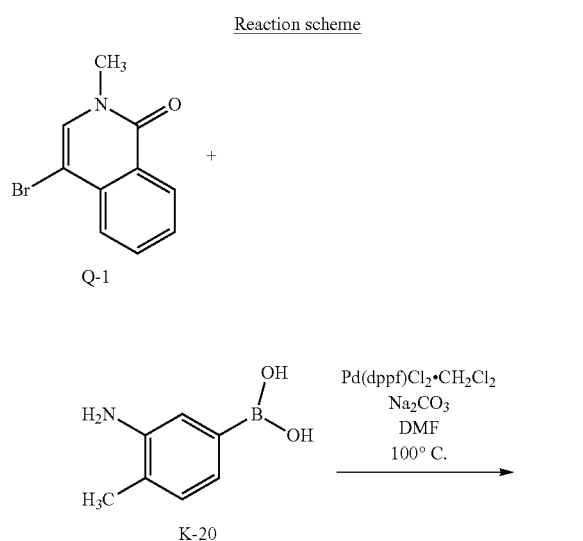

4-(3-Amino-4-methyl-phenyl)-2-methyl-2H-isoquinolin-1-one (II-35')

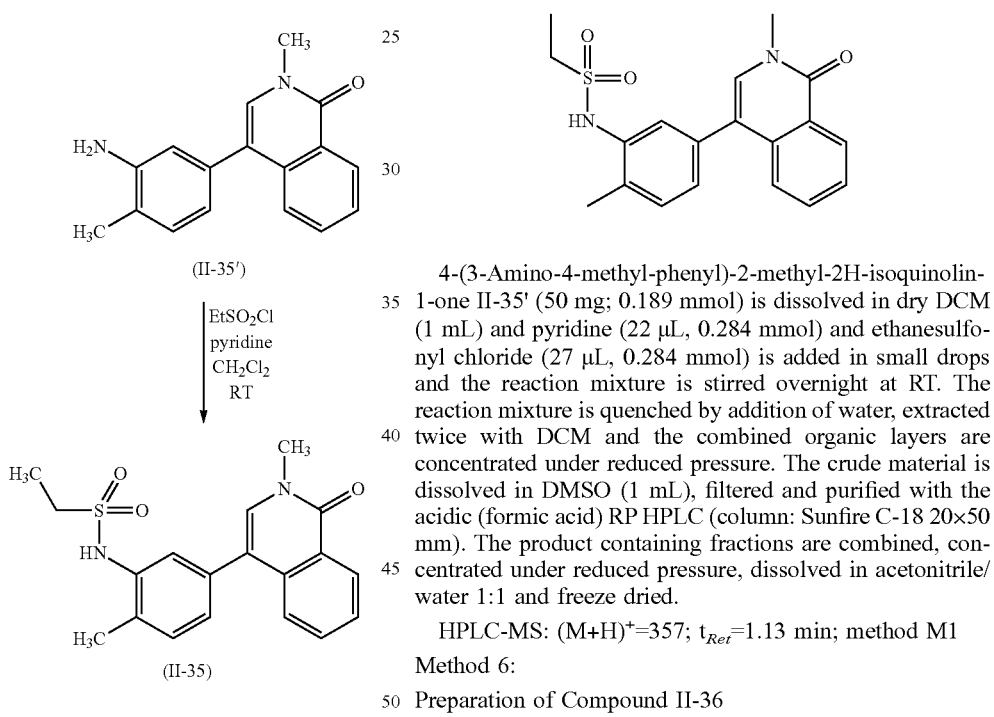

4-Bromo-2-methyl-2H-isoquinolin-1-one Q-1 (0.186 g; 0.779 mmol), 3-amino-4-methylphenyl boronic acid K-20 (0.120 g; 0.779 mmol) and 1,1'-bis(diphenylphosphino)ferrocene palladium(II) dichloride (0.064 g; 0.078 mmol) are dissolved in DMF (0.8 mL). A 2N sodium bicarbonate solution (0.974 mL; 1.947 mmol) is added and the reaction mixture is stirred under argon at 100° C. for 1 h. The reaction mixture is then cooled to RT, water is added and the mixture is filtered. The filtrate is purified by NP silica gel chromatography Combiflash (column Redisep Rf, 12 g; gradient: DCM/MeOH=100%/0% to 95%/5% over 26.5 column volumes; flow rate=30 mL/min; detection wavelength: 254 nm). The product containing fractions are combined and concentrated under reduced pressure, dissolved in acetonitrile/water=1:1 and freeze dried.

HPLC-MS: $(M+H)^+$=265; $t_{Ret}$=1.06 min; method M1

Ethanesulfonic acid [2-methyl-5-(2-methyl-1-oxo-1,2-dihydro-isoquinolin-4-yl)-phenyl]-amide (II-35)

4-(3-Amino-4-methyl-phenyl)-2-methyl-2H-isoquinolin-1-one II-35' (50 mg; 0.189 mmol) is dissolved in dry DCM (1 mL) and pyridine (22 µL, 0.284 mmol) and ethanesulfonyl chloride (27 µL, 0.284 mmol) is added in small drops and the reaction mixture is stirred overnight at RT. The reaction mixture is quenched by addition of water, extracted twice with DCM and the combined organic layers are concentrated under reduced pressure. The crude material is dissolved in DMSO (1 mL), filtered and purified with the acidic (formic acid) RP HPLC (column: Sunfire C-18 20×50 mm). The product containing fractions are combined, concentrated under reduced pressure, dissolved in acetonitrile/water 1:1 and freeze dried.

HPLC-MS: $(M+H)^+$=357; $t_{Ret}$=1.13 min; method M1

Method 6:

Preparation of Compound II-36

N-[5-(5-Hydroxy-2-methyl-1-oxo-1,2-dihydro-isoquinolin-4-yl)-2-methyl-phenyl]-methanesulfonamide

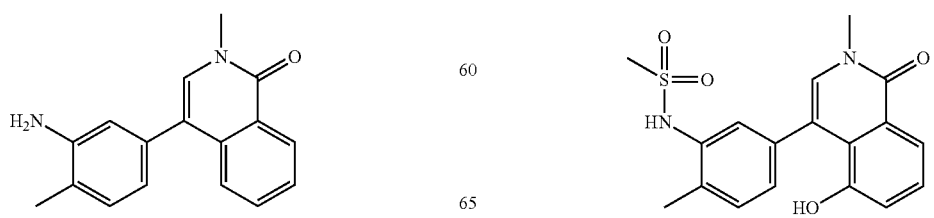

Reaction scheme

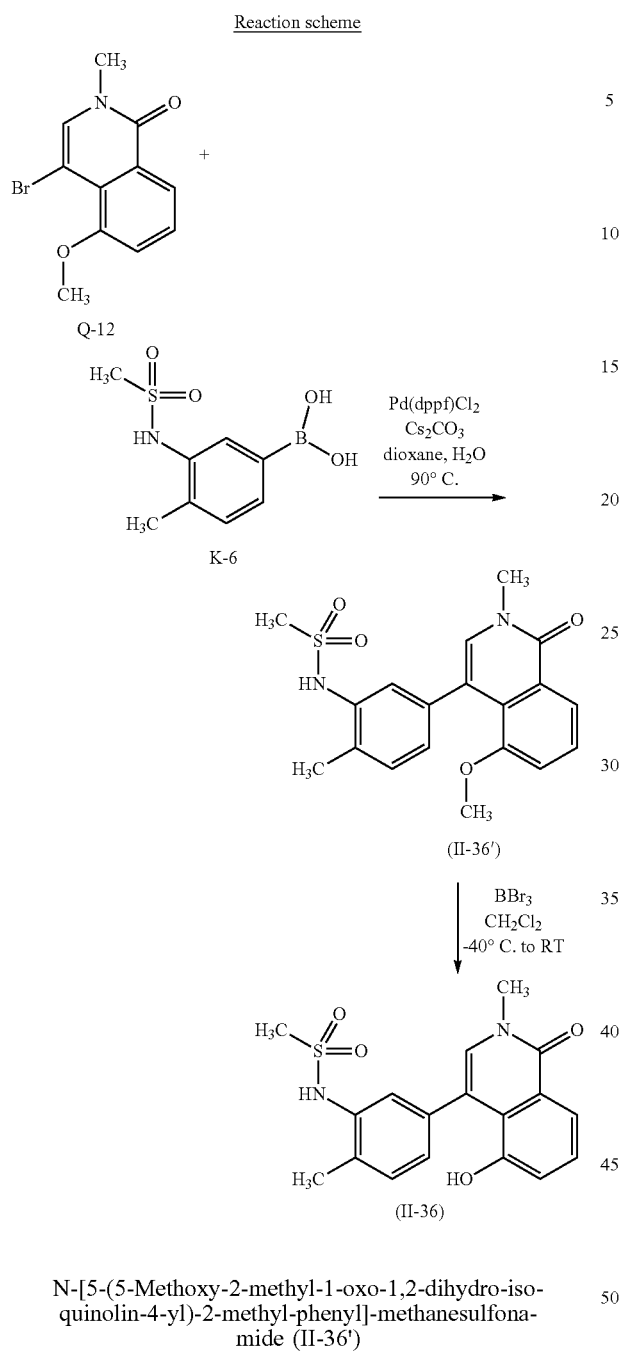

4-Bromo-5-methoxy-2-methyl-2H-isoquinolin-1-one Q-12 (0.200 g; 0.746 mmol), 3-methyl-(3-methylsulfonylamino)-phenyl boronic acid K-6 (0.171 g; 0.746 mmol) and 1,1'-bis(diphenylphosphino)ferrocenepalladium(II) dichloride (0.122 g; 0.149 mmol) are dissolved in dioxane/water 4:1 (10 mL). Caesium carbonate (0.487 g; 1.492 mmol) is added and the reaction mixture is stirred under $N_2$ at 90° C. for 2 h. The reaction mixture is poured onto ice water, extracted with ethyl acetate, the combined organic layers are washed with brine, dried and concentrated under reduced pressure and purified by prepTLC.

HPLC-MS: $(M+H)^+=373$; $t_{Ret}=2.509$ min; method M11

N-[5-(5-Hydroxy-2-methyl-1-oxo-1,2-dihydro-isoquinolin-4-yl)-2-methyl-phenyl]-methanesulfonamide (II-36)

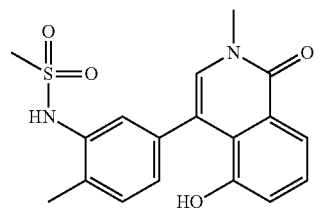 [SMILES: Cc1ccc(-c2cn(C)c(=O)c3cccc(O)c23)cc1NS(C)(=O)=O]

A solution of N-[5-(5-methoxy-2-methyl-1-oxo-1,2-dihydro-isoquinolin-4-yl)-2-methyl-phenyl]-methanesulfonamide II-36' (160.0 mg; 0.430 mmol) dissolved in DCM (11 mL) is treated with boron tribromide (2.133 mL; 22.5 mmol) at −40° C. and then stirred overnight at RT. The reaction mixture is poured onto water and extracted with ethyl acetate. The combined organic layers are dried with brine, dried, concentrated under reduced pressure and purified by HPLC.

HPLC-MS: $(M+H)^+=359$; $t_{Ret}=2.264$ min; method M11

Method 7:
Preparation of Compound II-37

N-[5-(7-Amino-2-methyl-1-oxo-1,2-dihydro-isoquinolin-4-yl)-2-methyl-phenyl]-methanesulfonamide

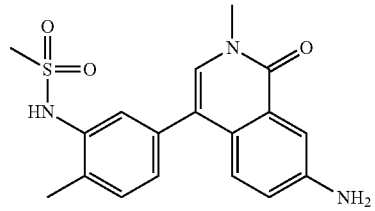

Reaction scheme

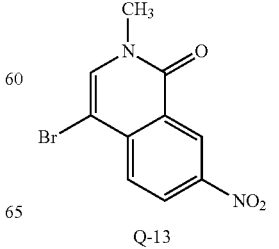

247
-continued

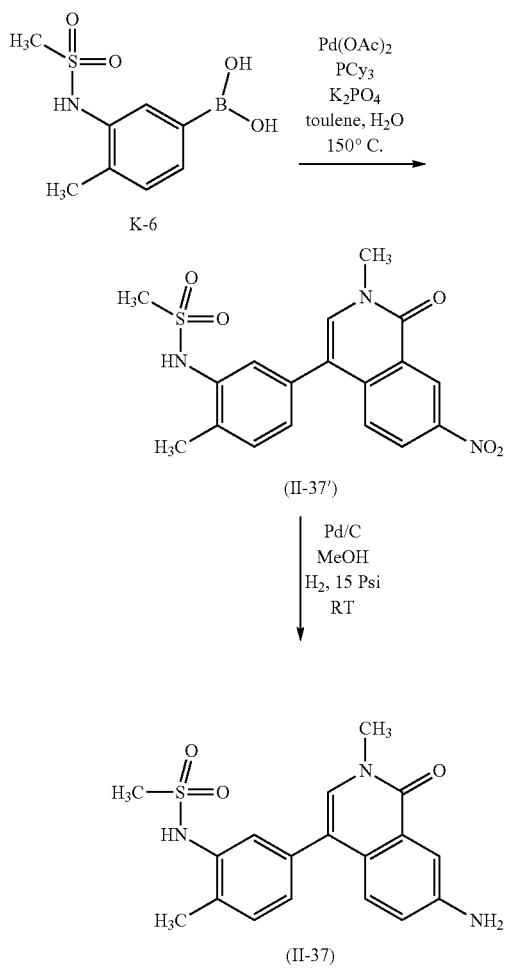

N-[2-Methyl-5-(2-methyl-7-nitro-1-oxo-1,2-dihydro-isoquinolin-4-yl)-phenyl]-methanesulfonamide (II-37')

4-Bromo-7-nitro-2H-isoquinolin-1-one Q-13 (0.050 g; 0.177 mmol), 3-methyl-(3-methylsulfonylamino)phenyl boronic acid K-6 (0.057 g; 0.249 mmol) and palladium(II) acetate (0.4 mg; 0.002 mmol), tricyclohexylphosphine (1.1 mg; 0.004 mmol) and potassium phosphate (0.056 g; 0.264 mmol) are dissolved in toluene/water 6:1 (1 mL) and stirred at 150° C. for 2 h. The reaction mixture is concentrated under reduced pressure, taken up in water and extracted with DCM. The combined organic layers are concentrated under reduced pressure and purified by HPLC.

248

N-[5-(7-Amino-2-methyl-1-oxo-1,2-dihydro-isoquinolin-4-yl)-2-methyl-phenyl]-methanesulfonamide (II-37)

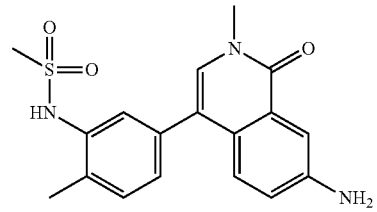 [SMILES: Cc1ccc(-c2cn(C)c(=O)c3cc([N+](=O)[O-])ccc23)cc1NS(C)(=O)=O]

N-[2-Methyl-5-(2-methyl-7-nitro-1-oxo-1,2-dihydro-isoquinolin-4-yl)-phenyl]-methanesulfonamide II-37' (14.0 mg; 0.036 mmol) is dissolved in MeOH, then Pd/C is added and the mixture is purged with $H_2$ and stirred under 15 psi $H_2$ pressure at RT. The mixture is diluted with MeOH, filtered and concentrated under reduced pressure.

Structure confirmed by $^1$H NMR

Method 8:

Preparation of Compound II-39

N-[2-Methyl-5-(2-methyl-5-methylamino-1-oxo-1,2-dihydro-isoquinolin-4-yl)-phenyl]-methanesulfonamide

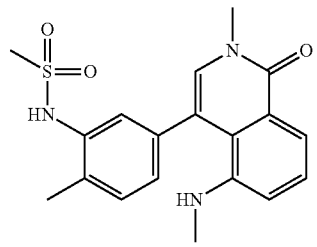 [SMILES: CNc1cccc2c(=O)n(C)cc(-c3ccc(C)c(NS(C)(=O)=O)c3)c12]

Reaction scheme

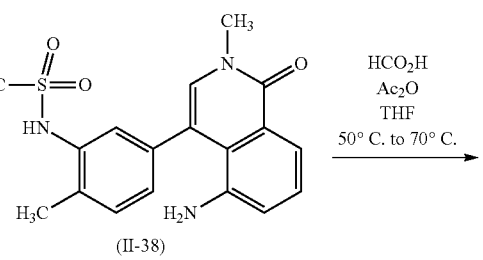

249
-continued

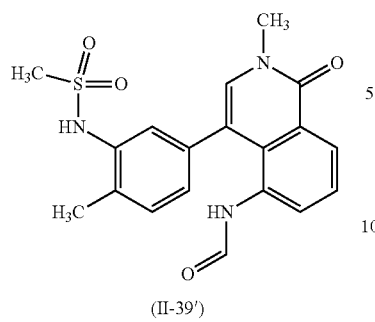
(II-39')

BH₃
THF
70° C.

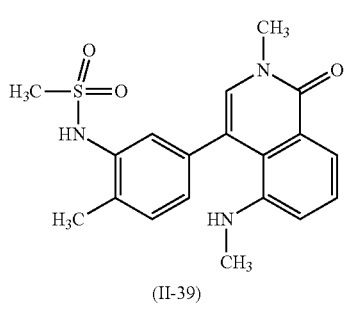
(II-39)

N-[5-(5-Formylamino-2-methyl-1-oxo-1,2-dihydro-isoquinolin-4-yl)-2-methyl-phenyl]-methanesulfonamid (II-39')

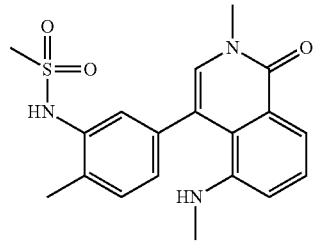 [SMILES: CNc1cccc2c(=O)n(C)cc(-c3ccc(C)c(NS(C)(=O)=O)c3)c12]

Formic acid (0.008 g; 0.174 mmol) and acetic anhydride (0.6 mg; 0.006 mmol) are stirred at 50° C. for 30 min. To this mixture N-[5-(5-amino-2-methyl-1-oxo-1,2-dihydro-isoquinolin-4-yl)-2-methyl-phenyl]-methanesulfonamide II-38 (0.020 g; 0.056 mmol) is added and the mixture is stirred at 70° C. for 12 h. The mixture is concentrated under reduced pressure and directly used in the next reaction step.

250

N-[2-Methyl-5-(2-methyl-5-methylamino-1-oxo-1,2-dihydro-isoquinolin-4-yl)-phenyl]-methanesulfonamide (II-39)

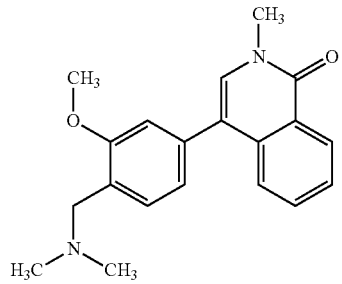 [SMILES: COc1cc(-c2cn(C)c(=O)c3ccccc23)ccc1CN(C)C]

The crude N-[5-(5-formylamino-2-methyl-1-oxo-1,2-dihydro-isoquinolin-4-yl)-2-methyl-phenyl]-methanesulfonamide II-39' (20.0 mg; 0.052 mmol) is dissolved in THF (5 mL), then borane-tetrahydrofuran complex (1M; 259 µL; 0.259 mmol) is added and the mixture is stirred at 70° C. for 12 h. The mixture is concentrated under reduced pressure and the crude product is purified by HPLC.

Method 9:
Preparation of Compound II-41

4-(4-Dimethylaminomethyl-3-methoxy-phenyl)-2-methyl-2H-isoquinolin-1-one

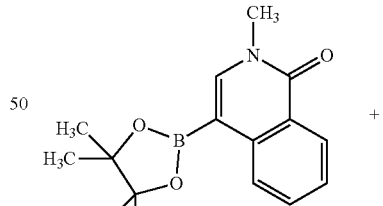

Reaction scheme

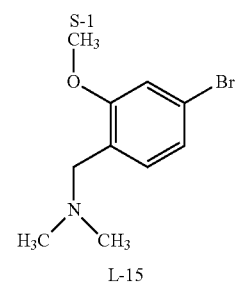

L-15

Pd(dppf)Cl₂•CH₂Cl₂
Na₂CO₃
DMF
100° C.

-continued

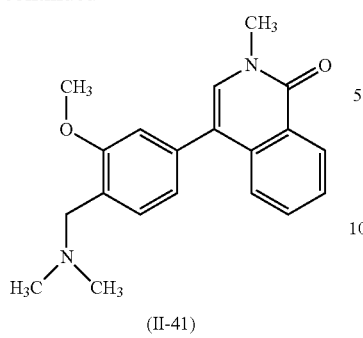

(II-41)

4-(4-Dimethylaminomethyl-3-methoxy-phenyl)-2-methyl-2H-isoquinolin-1-one (II-41)

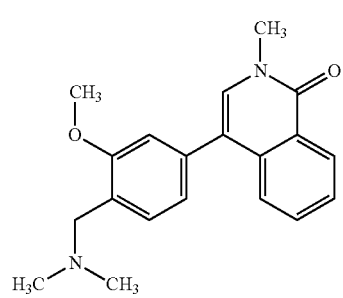

2-Methyl-4-(4,4,5,5-tetramethyl-[1,3,2]dioxaborolan-2-yl)-2H-isoquinolin-1-one S-1 (0.070 g; 0.245 mmol), (4-bromo-2-methoxy-benzyl)-dimethyl-amine L-15 (0.060 g; 0.245 mmol), 1,1'-bis(diphenylphosphino)ferrocene palladium(II) dichloride (0.020 g; 0.025 mmol) are dissolved in DMF (0.8 mL). A solution of 2N sodium bicarbonate (307 µl, 0.614 mmol) is added, the vial purged with argon, sealed and heated to 100° C. for 1 h. To the reaction mixture one drop of water is added and the mixture is filtered and purified by basic (ammonia buffer) RP HPLC (column: X-Bridge C-18 30×50 mm). The product containing fractions are concentrated under reduced pressure, taken up in acetonitrile/water 1:1 and freeze dried.

HPLC-MS: $(M+H)^+=323$; $t_{Ret}=1.10$ min; method M1

Method 10:

Preparation of Compound II-42

2-Methyl-4-[4-(piperazine-1-carbonyl)-phenyl]-2H-isoquinolin-1-one

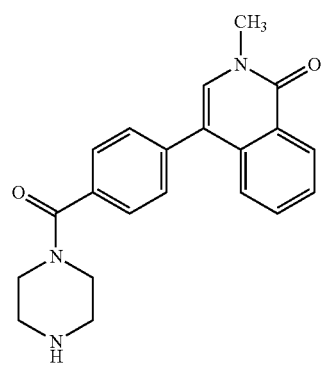 [SMILES: Cn1cc(-c2ccc(C(=O)N3CCNCC3)cc2)c2ccccc2c1=O]

Reaction scheme

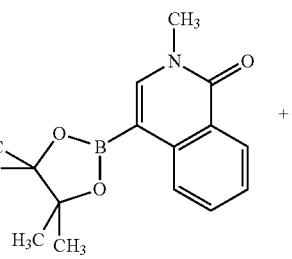

S-1

+

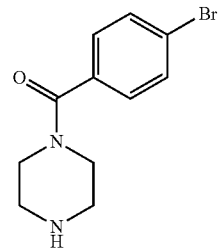

L-101

Pd(dppf)Cl$_2$
Cs$_2$CO$_3$
dioxane, H$_2$O
80° C.

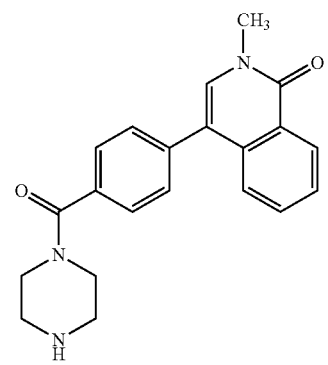

(II-42)

253

Methyl-4-[4-(piperazine-1-carbonyl)-phenyl]-2H-isoquinolin-1-one (II-42)

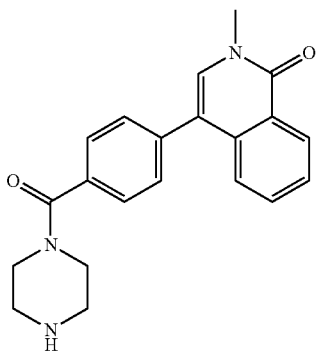 [SMILES: Cn1cc(-c2ccc(C(=O)N3CCNCC3)cc2)c2ccccc2c1=O]

2-Methyl-4-(4,4,5,5-tetramethyl-[1,3,2]dioxaborolan-2-yl)-2H-isoquinolin-1-one S-1 (0.150 g; 0.526 mmol), 1-[(4-bromophenyl)carbonyl]piperazine L-101 (0.280 g; 1.040 mmol), 1,1'-bis(diphenylphosphino)ferrocenepalladium(II) dichloride (0.080 g; 0.098 mmol) are dissolved in DMF (8 mL). A solution of 2N sodium bicarbonate (0.210 g; 1.98 mmol) is added, the vial purged with $N_2$, sealed and heated to 60° C. for 6 h. To the reaction mixture one drop of water is added and the mixture is filtered and purified by MPLC and then purified by RP HPLC. The product containing fractions are concentrated under reduced pressure.

HPLC-MS: $(M+H)^+=348$; $t_{Ret}=2.232$ min; method M10

According to the procedure of II-1, the examples II-2 to II-20 and II-50 to II-51 are synthesized. According to the procedure of II-21, the examples II-22 to II-27 are synthesized. According to the procedure of II-28, the example II-29 is synthesized. According to the procedure of II-30, the examples II-31 to I-33 are synthesized. According to the procedure of II-30 with the exception of the acidic N-Boc deprotection step, the example II-34 is synthesized. According to the procedure of II-37, the example II-38 is synthesized. According to the procedure of II-39, the example II-40 is synthesized. According to the procedure of II-42, the examples II-43 to II-49 are synthesized.

| # | Structure | MS (M + H)$^+$ | $t_{Ret.}$ HPLC [min] | HPLC-Method |
|---|---|---|---|---|
| II-1 | 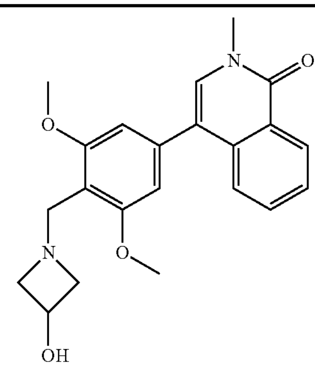 | 381 | 1.020 | M1 |
| II-2 | 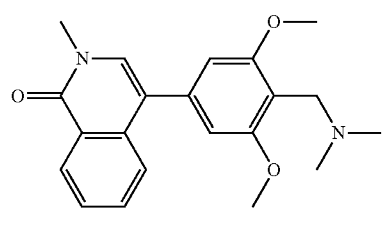 [SMILES: COc1cc(-c2cn(C)c(=O)c3ccccc23)cc(OC)c1CN(C)C] | 353 | 1.040 | M1 |
| II-3 | 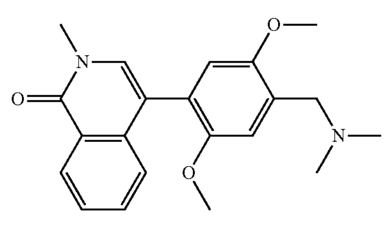 [SMILES: COc1cc(-c2cn(C)c(=O)c3ccccc23)c(OC)cc1CN(C)C] | 353 | 1.100 | M1 |
| II-4 | 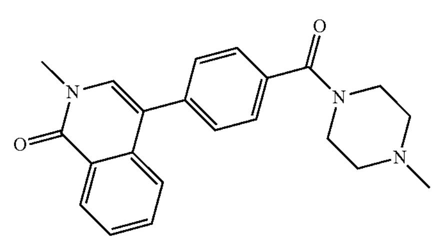 [SMILES: CN1CCN(C(=O)c2ccc(-c3cn(C)c(=O)c4ccccc34)cc2)CC1] | 362 | 0.940 | M1 |

-continued

| # | Structure | MS (M + H)+ | t_Ret. HPLC [min] | HPLC-Method |
|---|---|---|---|---|
| II-5 | 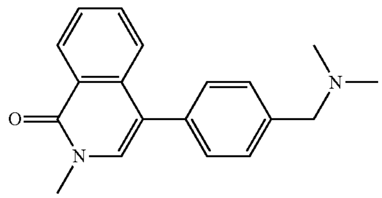 [SMILES: CN(C)Cc1ccc(-c2cn(C)c(=O)c3ccccc23)cc1] | 293 | 1.890 | M11 |
| II-6 | 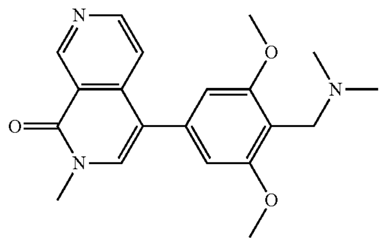 [SMILES: COc1cc(-c2cn(C)c(=O)c3cnccc23)cc(OC)c1CN(C)C] | 354 | 0.800 | M1 |
| II-7 | 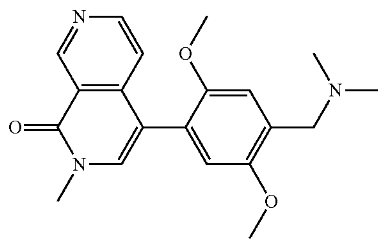 [SMILES: COc1cc(-c2cn(C)c(=O)c3cnccc23)c(OC)cc1CN(C)C] | 354 | 0.920 | M1 |
| II-8 | 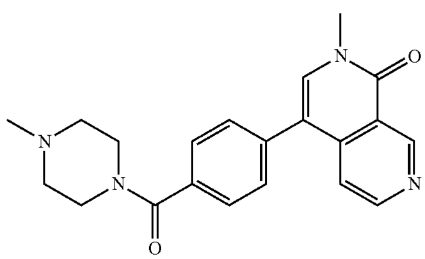 [SMILES: CN1CCN(C(=O)c2ccc(-c3cn(C)c(=O)c4cnccc34)cc2)CC1] | 363 | 0.770 | M1 |
| II-9 | 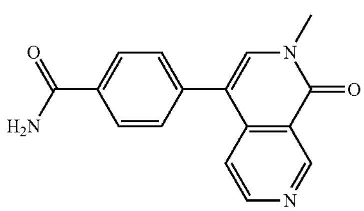 [SMILES: Cn1cc(-c2ccc(C(N)=O)cc2)c2ccncc2c1=O] | 280 | 0.480 | M1 |
| II-10 | 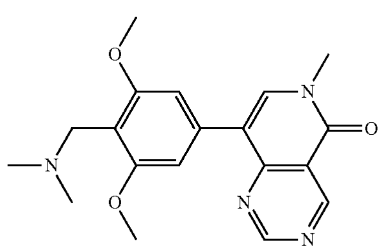 [SMILES: COc1cc(-c2cn(C)c(=O)c3cncnc23)cc(OC)c1CN(C)C] | 355 | 0.780 | M1 |

-continued

| # | Structure | MS (M + H)+ | t_Ret. HPLC [min] | HPLC-Method |
|---|---|---|---|---|
| II-11 | 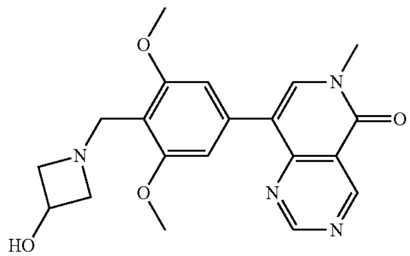 [SMILES: COc1cc(-c2cn(C)c(=O)c3cncnc23)cc(OC)c1CN1CC(O)C1] | 383 | 0.740 | M1 |
| II-12 | 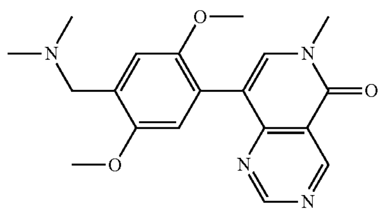 [SMILES: COc1cc(-c2cn(C)c(=O)c3cncnc23)c(OC)cc1CN(C)C] | 355 | 0.850 | M1 |
| II-13 | 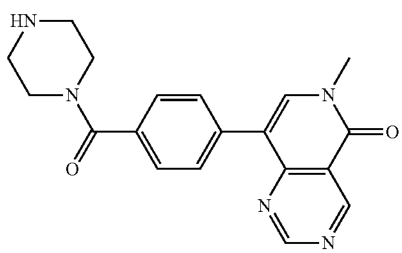 [SMILES: Cn1cc(-c2ccc(C(=O)N3CCNCC3)cc2)c2ncncc2c1=O] | 350 | 0.460 | M1 |
| II-14 | 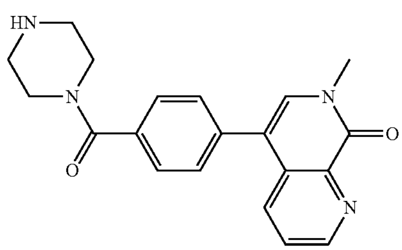 [SMILES: Cn1cc(-c2ccc(C(=O)N3CCNCC3)cc2)c2cccnc2c1=O] | 349 | 0.470 | M1 |
| II-15 | 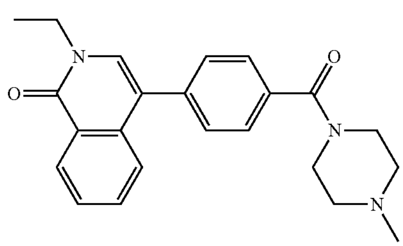 [SMILES: CCn1cc(-c2ccc(C(=O)N3CCN(C)CC3)cc2)c2ccccc2c1=O] | 376/174 | 1/0.88 | M1 |
| II-16 | 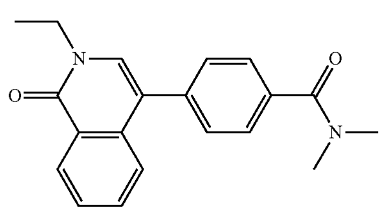 [SMILES: CCn1cc(-c2ccc(C(=O)N(C)C)cc2)c2ccccc2c1=O] | 321 | 1.020 | M1 |

-continued

| # | Structure | MS (M + H)+ | t_Ret. HPLC [min] | HPLC-Method |
|---|---|---|---|---|
| II-17 | 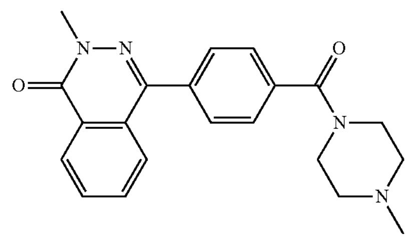 [SMILES: CN1CCN(C(=O)c2ccc(-c3nn(C)c(=O)c4ccccc34)cc2)CC1] | 363 | 0.900 | M1 |
| II-18 | 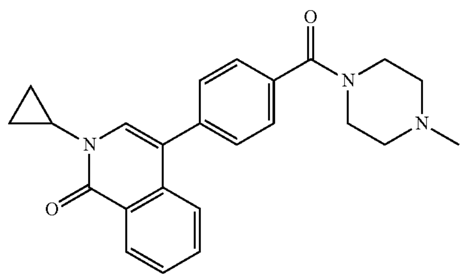 [SMILES: CN1CCN(C(=O)c2ccc(-c3cn(C4CC4)c(=O)c4ccccc34)cc2)CC1] | 388 | 1.000 | M1 |
| II-19 | 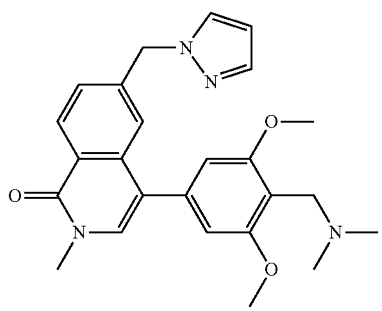 [SMILES: COc1cc(-c2cn(C)c(=O)c3ccc(Cn4cccn4)cc23)cc(OC)c1CN(C)C] | 433 | 1.010 | M1 |
| II-20 | 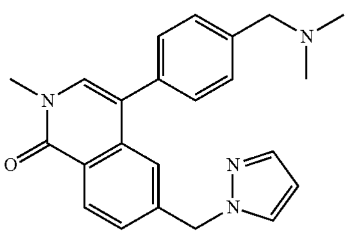 | 373 | 1.030 | M1 |
| II-21 | 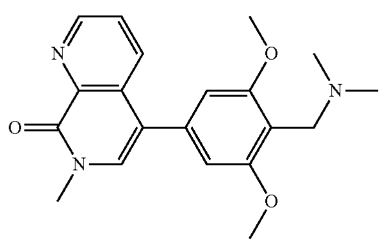 [SMILES: COc1cc(-c2cn(C)c(=O)c3ncccc23)cc(OC)c1CN(C)C] | 354 | 2.037 | M11 |
| II-22 | 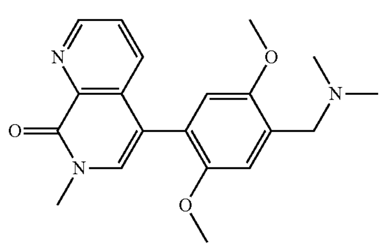 [SMILES: COc1cc(-c2cn(C)c(=O)c3ncccc23)c(OC)cc1CN(C)C] | 354 | 1.923 | M10 |

| # | Structure | MS (M + H)+ | t_Ret. HPLC [min] | HPLC-Method |
|---|---|---|---|---|
| II-23 | 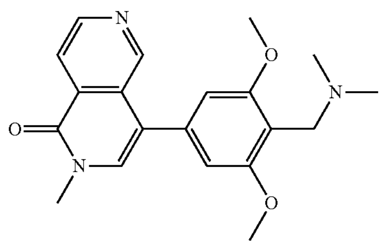 [SMILES: COc1cc(-c2cn(C)c(=O)c3ccncc23)cc(OC)c1CN(C)C] | 354 | 2.099 | M10 |
| II-24 | 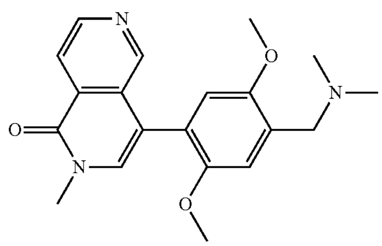 [SMILES: COc1cc(-c2cn(C)c(=O)c3ccncc23)c(OC)cc1CN(C)C] | 354 | 2.009 | M10 |
| II-25 | 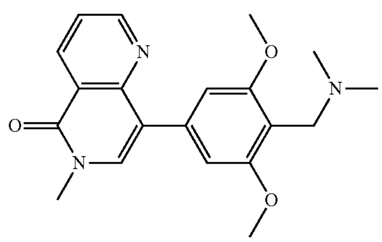 [SMILES: COc1cc(-c2cn(C)c(=O)c3cccnc23)cc(OC)c1CN(C)C] | 354 | 1.786 | M11 |
| II-26 | 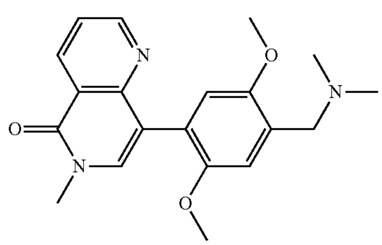 [SMILES: COc1cc(-c2cn(C)c(=O)c3cccnc23)c(OC)cc1CN(C)C] | 354 | 2.012 | M10 |
| II-27 | 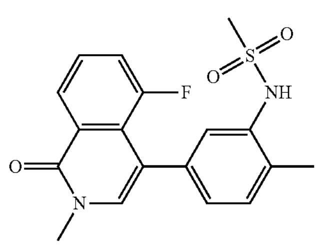 [SMILES: Cc1ccc(-c2cn(C)c(=O)c3cccc(F)c23)cc1NS(C)(=O)=O] | 361 | 2.850 | M10 |
| II-28 | 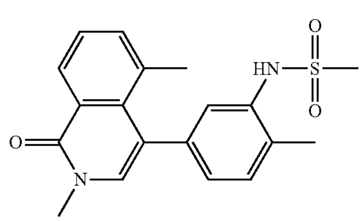 [SMILES: Cc1ccc(-c2cn(C)c(=O)c3cccc(C)c23)cc1NS(C)(=O)=O] | 357 | 2.523 | M11 |

| # | Structure | MS (M + H)+ | t_Ret. HPLC [min] | HPLC-Method |
|---|---|---|---|---|
| II-29 | 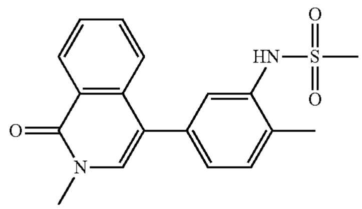 [SMILES: Cc1ccc(-c2cn(C)c(=O)c3ccccc23)cc1NS(C)(=O)=O] | 343 | NMR | |
| II-30 | 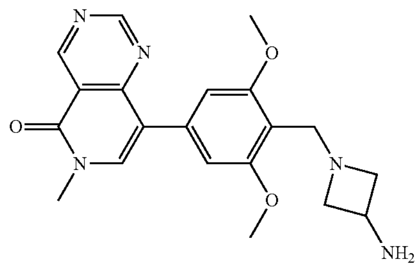 [SMILES: COc1cc(-c2cn(C)c(=O)c3cncnc23)cc(OC)c1CN1CC(N)C1] | 382 | 0.680 | M1 |
| II-31 | 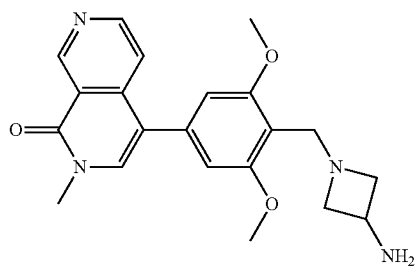 [SMILES: COc1cc(-c2cn(C)c(=O)c3cnccc23)cc(OC)c1CN1CC(N)C1] | 381 | 0.930 | M1 |
| II-32 | 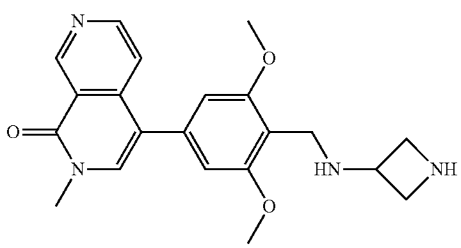 [SMILES: COc1cc(-c2cn(C)c(=O)c3cnccc23)cc(OC)c1CNC1CNC1] | 381 | 1.010 | M1 |
| II-33 | 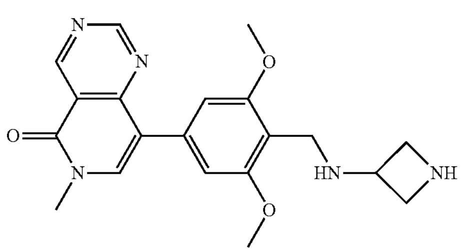 [SMILES: COc1cc(-c2cn(C)c(=O)c3cncnc23)cc(OC)c1CNC1CNC1] | 382 | 0.900 | M1 |
| II-34 | 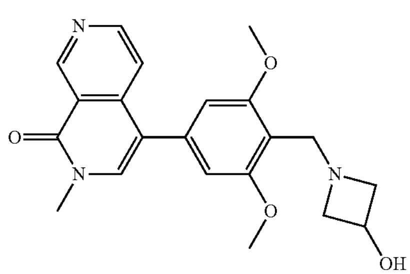 [SMILES: COc1cc(-c2cn(C)c(=O)c3cnccc23)cc(OC)c1CN1CC(O)C1] | 382 | 0.780 | M1 |

| # | Structure | MS (M + H)+ | t_Ret. HPLC [min] | HPLC-Method |
|---|---|---|---|---|
| II-35 | 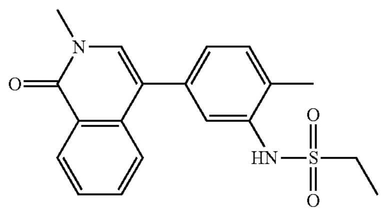 [SMILES: CCS(=O)(=O)Nc1cc(-c2cn(C)c(=O)c3ccccc23)ccc1C] | 357 | 1.130 | M1 |
| II-36 | 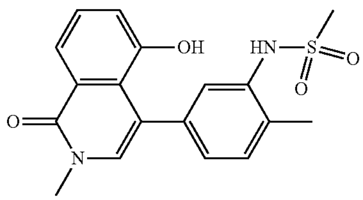 [SMILES: Cc1ccc(-c2cn(C)c(=O)c3cccc(O)c23)cc1NS(C)(=O)=O] | 359 | 2.264 | M11 |
| II-37 | 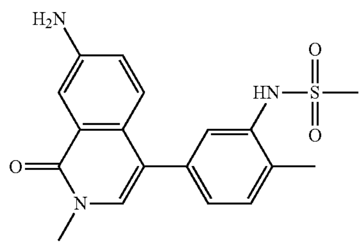 [SMILES: Cc1ccc(-c2cn(C)c(=O)c3cc(N)ccc23)cc1NS(C)(=O)=O] | 358 | NMR | |
| II-38 | 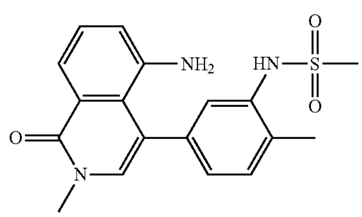 [SMILES: Cc1ccc(-c2cn(C)c(=O)c3cccc(N)c23)cc1NS(C)(=O)=O] | 358 | | |
| II-39 | 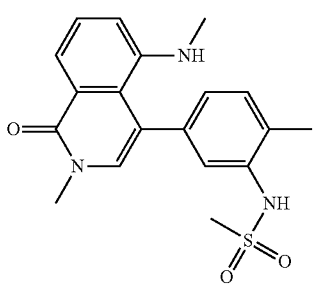 [SMILES: CNc1cccc2c(=O)n(C)cc(-c3ccc(C)c(NS(C)(=O)=O)c3)c12] | observed by TLC Rf = 0.5 (Eluent PE:EtOAc 1:1) | | |
| II-40 | 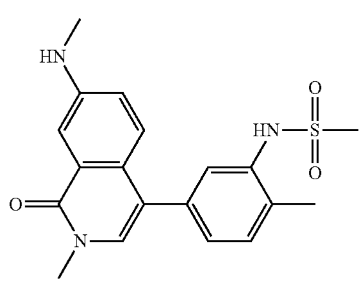 [SMILES: CNc1ccc2c(-c3ccc(C)c(NS(C)(=O)=O)c3)cn(C)c(=O)c2c1] | 372 | | |

-continued

| # | Structure | MS (M + H)+ | t_Ret. HPLC [min] | HPLC-Method |
|---|---|---|---|---|
| II-41 | 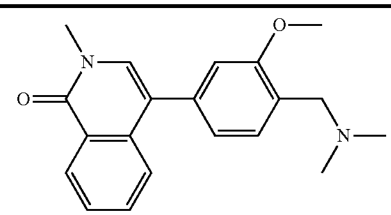 | 323 | 1.100 | M1 |
| II-42 | 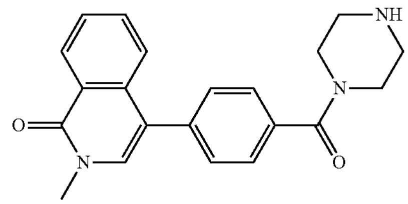 [SMILES: Cn1cc(-c2ccc(C(=O)N3CCNCC3)cc2)c2ccccc2c1=O] | 348 | 2.232 | M10 |
| II-43 | 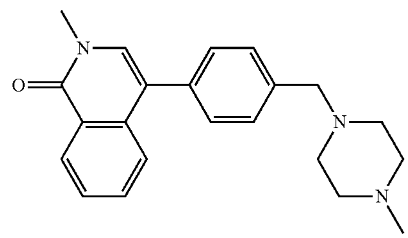 [SMILES: CN1CCN(Cc2ccc(-c3cn(C)c(=O)c4ccccc34)cc2)CC1] | 348 | 2.226 | M10 |
| II-44 | 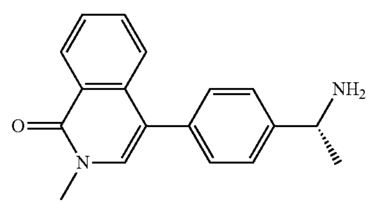 [SMILES: C[C@@H](N)c1ccc(-c2cn(C)c(=O)c3ccccc23)cc1] | 279 | 1.273, 2.732 | M11 |
| II-45 | 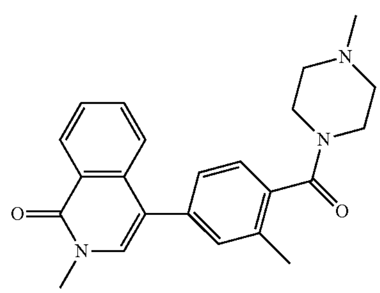 [SMILES: Cc1cc(-c2cn(C)c(=O)c3ccccc23)ccc1C(=O)N1CCN(C)CC1] | 376 | 1.927 | M11 |
| II-46 | 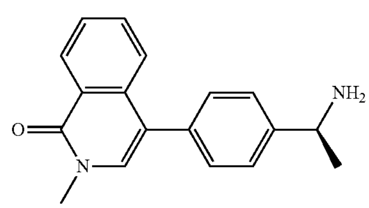 [SMILES: C[C@H](N)c1ccc(-c2cn(C)c(=O)c3ccccc23)cc1] | 279 | 2.180 | M11 |
| II-47 | 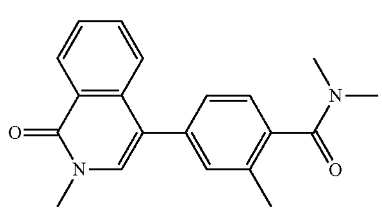 [SMILES: Cc1cc(-c2cn(C)c(=O)c3ccccc23)ccc1C(=O)N(C)C] | 321 | 2.405 | M11 |

-continued

| # | Structure | MS (M + H)+ | t_Ret. HPLC [min] | HPLC-Method |
|---|---|---|---|---|
| II-48 | 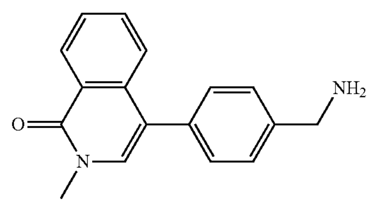 [SMILES: Cn1cc(-c2ccc(CN)cc2)c2ccccc2c1=O] | 265 | 2.104 | M11 |
| II-49 | 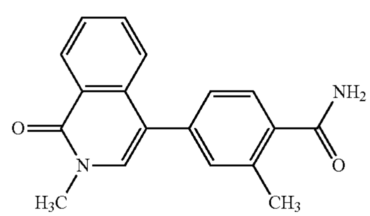 [SMILES: Cc1cc(-c2cn(C)c(=O)c3ccccc23)ccc1C(N)=O] | 293 | 2.498 | M11 |
| II-50 | 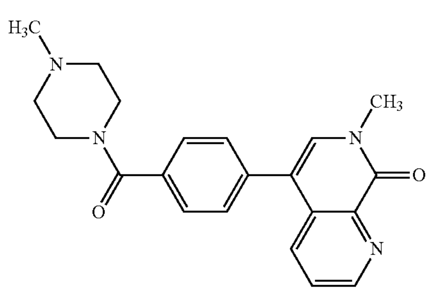 [SMILES: CN1CCN(C(=O)c2ccc(-c3cn(C)c(=O)c4ncccc34)cc2)CC1] | 363 | 0.72 | M1 |
| II-51 | 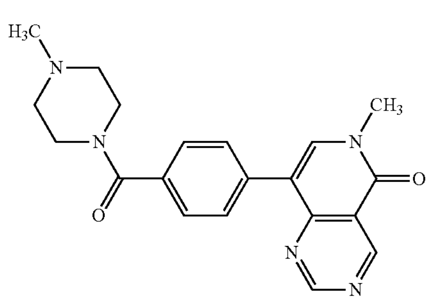 [SMILES: CN1CCN(C(=O)c2ccc(-c3cn(C)c(=O)c4cncnc34)cc2)CC1] | 364 | 0.72 | M1 |

271

Preparation of Compounds of Type III
Preparation of Intermediate W-1

4-Bromo-6-methyl-1-(toluene-4-sulfonyl)-1,6-dihydro-pyrrolo[2,3-c]pyridin-7-one

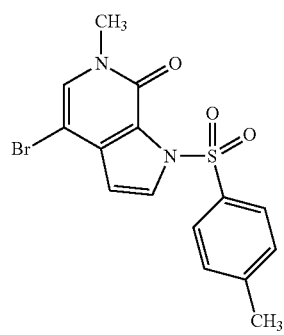 [SMILES: Cc1ccc(S(=O)(=O)n2ccc3c(Br)cn(C)c(=O)c32)cc1]

272

4-Bromo-7-methoxy-1-(toluene-4-sulfonyl)-1H-pyrrolo[2,3-c]pyridine U-1

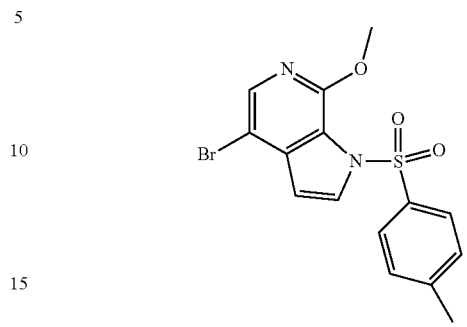

Sodium hydride (4.757 g; 60% in oil; 118.917 mmol) is carefully added at 0° C. to a solution of 4-bromo-7-methoxy-1H-pyrrolo[2,3-c]pyridine T-1 (18.000 g; 79.275 mmol) in DMF (100.0 mL). The reaction mixture is stirred 1 hour with ice cooling. 4-Methyl-benzenesulfonyl chloride (18.136 g;

Reaction scheme

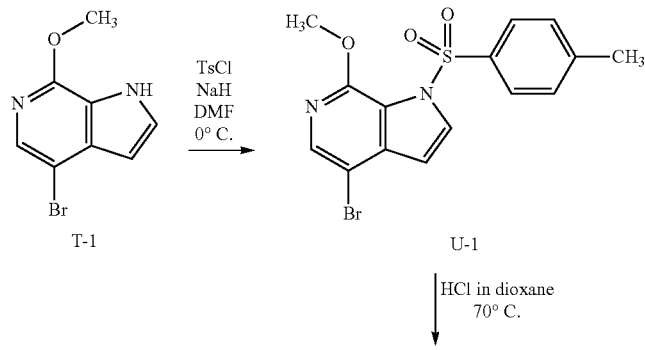

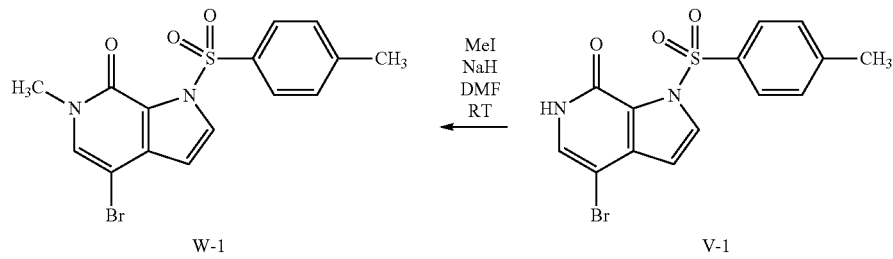

95.127 mmol) is added dropwise and the reaction mixture is stirred at 0° C. for 1 h. The reaction mixture is quenched with aq. ammonia chloride and then extracted with ethyl acetate. The organic layer is isolated and dried under reduced pressure.

HPLC-MS: (M+H)$^+$=382; $t_{Ret}$=0.935 min; method M6

4-Bromo-1-(toluene-4-sulfonyl)-1,6-dihydro-pyrrolo[2,3-c]pyridin-7-one V-1

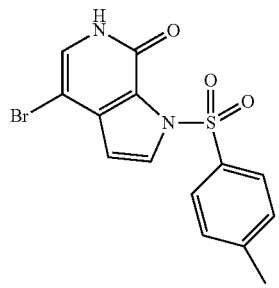 [SMILES: Cc1ccc(S(=O)(=O)n2ccc3c(Br)c[nH]c(=O)c32)cc1]

A 4M solution of HCl in 1,4-dioxane (100.0 mL; 400.000 mmol) is added to 4-bromo-7-methoxy-1-(toluene-4-sulfonyl)-1H-pyrrolo[2,3-c]pyridine U-1 (22.000 g; 57.707 mmol). The reaction mixture is stirred overnight at 70° C. The 1,4-dioxane is removed under reduced pressure.

HPLC-MS: (M+H)$^+$=367/369; $t_{Ret}$=1.267 min; method M7

4-Bromo-6-methyl-1-(toluene-4-sulfonyl)-1,6-dihydro-pyrrolo[2,3-c]pyridin-7-one W-1

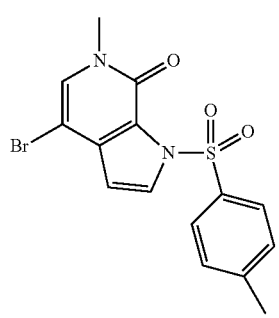 [SMILES: Cc1ccc(S(=O)(=O)n2ccc3c(Br)cn(C)c(=O)c32)cc1]

Sodium hydride (1.797 g; 60%; 44.932 mmol) is carefully added to a solution of 4-bromo-1-(toluene-4-sulfonyl)-1,6-dihydro-pyrrolo[2,3-c]pyridine-7-one V-1 (11.000 g; 29.955 mmol) in DMF (150.0 mL). The reaction mixture is stirred at RT for 0.5 h. Methyl iodide (6.378 g; 44.934 mmol) is added dropwise and the reaction is stirred at RT for 3 h. The reaction mixture is then quenched carefully with water and the precipitated product is filtered off and dried under reduced pressure at 50° C.

HPLC-MS: (M+H)$^+$=381/383; $t_{Ret}$=3.894 min; method M11

According to the procedure of W-1, the example W-2 is synthesized.

| # | Structure | MS (M + H)$^+$ | $t_{Ret.}$ HPLC [min] | HPLC-Method |
|---|---|---|---|---|
| W-1 | 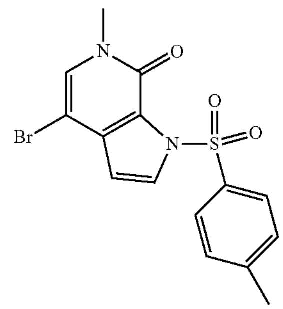 [SMILES: Cc1ccc(S(=O)(=O)n2ccc3c(Br)cn(C)c(=O)c32)cc1] | 381 | 3.403 | M11 |
| W-2 | 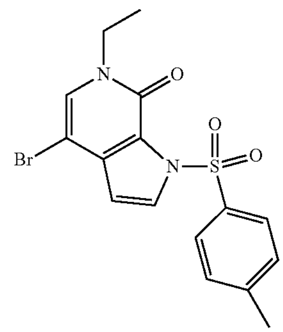 [SMILES: CCn1cc(Br)c2ccn(S(=O)(=O)c3ccc(C)cc3)c2c1=O] | 395/397 | 0.851 | M6 |

Preparation of Intermediate X-1

6-Methyl-4-(4,4,5,5-tetramethyl-[1,3,2]dioxaborolan-2-yl)-1-(toluene-4-sulfonyl)-1,6-dihydro-pyrrolo[2,3-c]pyridin-7-one

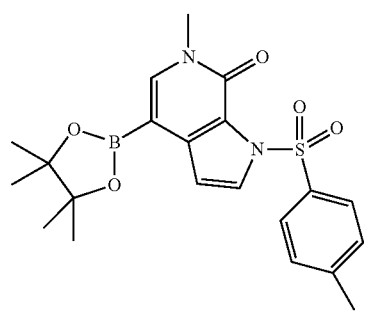 [SMILES: Cc1ccc(S(=O)(=O)n2ccc3c(B4OC(C)(C)C(C)(C)O4)cn(C)c(=O)c32)cc1]

Reaction scheme

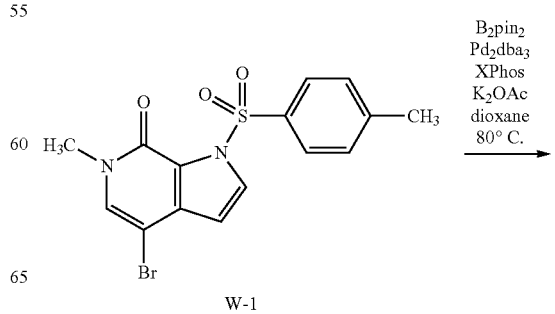

-continued

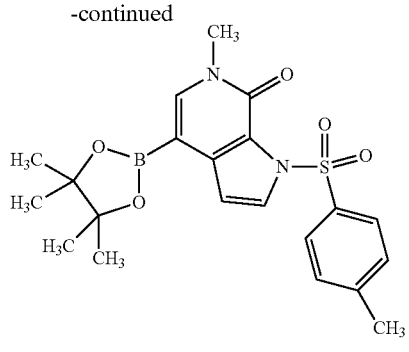

X-1

6-Methyl-4-(4,4,5,5-tetramethyl-[1,3,2]dioxaborolan-2-yl)-1-(toluene-4-sulfonyl)-1,6-dihydro-pyrrolo[2,3-c]pyridin-7-one X-1

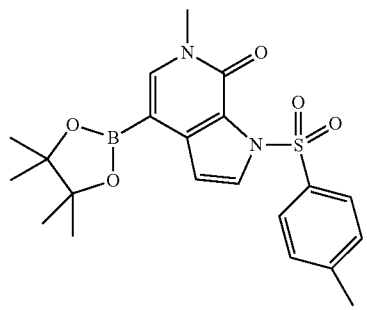 [SMILES: Cc1ccc(S(=O)(=O)n2ccc3c(B4OC(C)(C)C(C)(C)O4)cn(C)c(=O)c32)cc1]

To a solution of 4-bromo-6-methyl-1-(p-tolylsulfonyl)pyrrolo[2,3-c]pyridin-7-one W-1 (3.000 g; 7.751 mmol) in 1,4-dioxane (15.6 mL), are added bis(pinacolato)diborane (3.937 g; 15.502 mmol), tris(dibenzylideneacetone)-dipalladium(0) (180.000 mg; 0.191 mmol), potassium acetate (1.674 g; 17.052 mmol) and XPHOS/2-dicyclohexylphosphino-2',4',6'-triisopropylbiphenyl (0.369 g; 0.775 mmol), the mixture is stirred at 80° C. for 5 h. The reaction mixture is then diluted with ethyl acetate (100 mL) and extracted with water (100 mL). The organic layer is dried with Na₂SO₄, filtered and concentrated under reduced pressure. The crude product is purified by Combiflash (Column Redisep Rf, 120 g; gradient: cyclohexane/EtOAc=100%/0% to 0%/100% over 16 column volumes; flow rate=85 mL/min; detection wavelength: 230/300 nm). The product containing fractions are combined and concentrated under reduced pressure.

HPLC-MS: $(M+H)^+=429$; $t_{Ret}=1.460$ min; method M1

| # | Structure | MS $(M+H)^+$ | $t_{Ret.}$ HPLC [min] | HPLC-Method |
|---|---|---|---|---|
| X-1 | 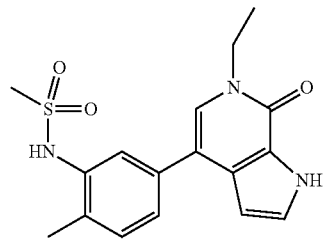 [SMILES: CCn1cc(-c2ccc(C)c(NS(C)(=O)=O)c2)c2cc[nH]c2c1=O] | 429 | 1.46 | M1 |

General Method for Preparation of Compounds of Type III
Method 1:
Preparation of Compound III-1

N-[5-(6-Ethyl-7-oxo-6,7-dihydro-1H-pyrrolo[2,3-c]pyridin-4-yl)-2-methyl-phenyl]-methanesulfonamide Reaction scheme

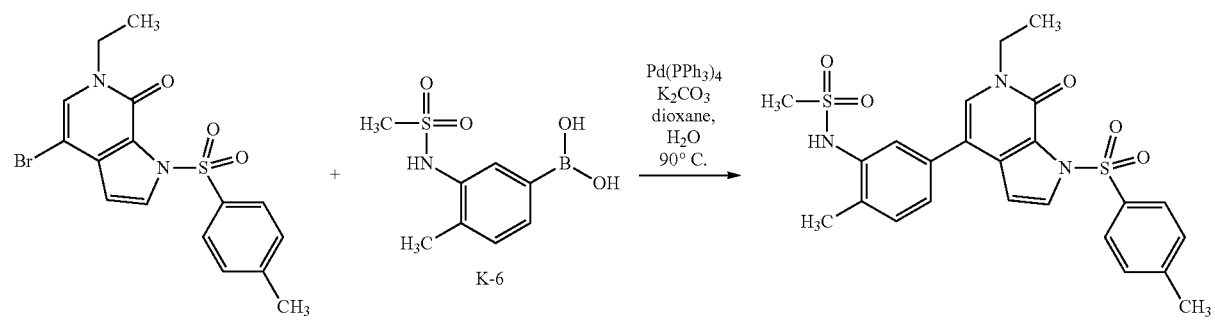

K₂CO₃
dioxane
RT

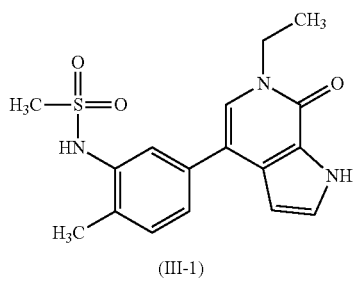

(III-1)

N-{5-[6-Ethyl-7-oxo-1-(toluene-4-sulfonyl)-6,7-dihydro-1H-pyrrolo[2,3-c]pyridin-4-yl]-2-methyl-phenyl}-methanesulfonamide (III-1')

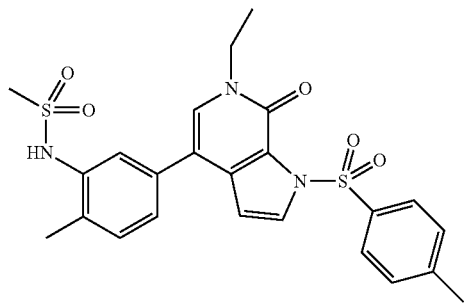

To a solution of 3-methanesulfonylamino-4-methyl-benzene boronic acid K-6 (0.450 g; 1.964 mmol) in 1,4-dioxane/water (1:1, 20 mL) is added 4-bromo-6-ethyl-1-(toluene-4-sulfonyl)-1,6-dihydro-pyrrolo[2,3-c]pyridin-7-one W-2 (0.500 g; 1.265 mmol), triphenylphosphine palladium (0) (0.300 g; 0.260 mmol) and potassium carbonate (0.360 g; 2.609 mmol). The mixture is stirred overnight at 90° C. The solvent is then evaporated under reduced pressure and the crude product is purified by silica gel chromatography.

HPLC-MS: (M+H)⁺=500; $t_{Ret}$=0.825 min; method M6

N-[5-(6-Ethyl-7-oxo-6,7-dihydro-1H-pyrrolo[2,3-c]pyridin-4-yl)-2-methyl-phenyl]-methanesulfonamide (III-1)

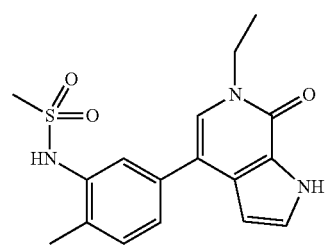 [SMILES: CCn1cc(-c2ccc(C)c(NS(C)(=O)=O)c2)c2cc[nH]c2c1=O]

To a solution of N-{5-[6-ethyl-7-oxo-1-(toluene-4-sulfonyl)-6,7-dihydro-1H-pyrrolo[2,3-c]pyridin-4-yl]-2-methyl-phenyl}-methanesulfonamide III-1' (0.400 g; 0.801 mmol) in methanol (10.0 mL) is added potassium carbonate (0.218 g; 1.580 mmol). The reaction mixture is stirred at RT for 5 h. The solvent is removed under reduced pressure. The crude product is purified by NP silica gel chromatography (Silica gel; petrol ether/ethyl acetate). The product containing fractions are combined and concentrated under reduced pressure.

HPLC-MS: (M+H)⁺=346; $t_{Ret}$=2.336 min; method M11

Method 2:

Preparation of Compound III-2

4-[3-Methoxy-4-((1R,4R)-5-methyl-2,5-diaza-bicyclo[2.2.1]hept-2-ylmethyl)-phenyl]-6-methyl-1,6-dihydro-pyrrolo[2,3-c]pyridin-7-one

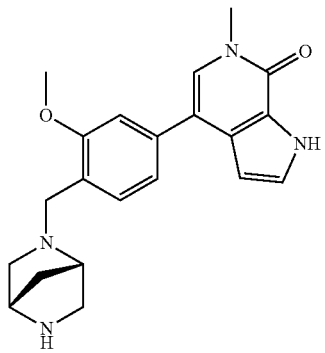 [SMILES: COc1cc(-c2cn(C)c(=O)c3[nH]ccc23)ccc1CN1C[C@@H]2C[C@H]1CN2]

Reaction scheme

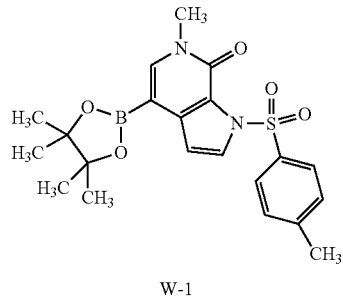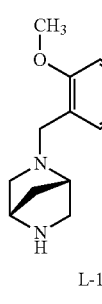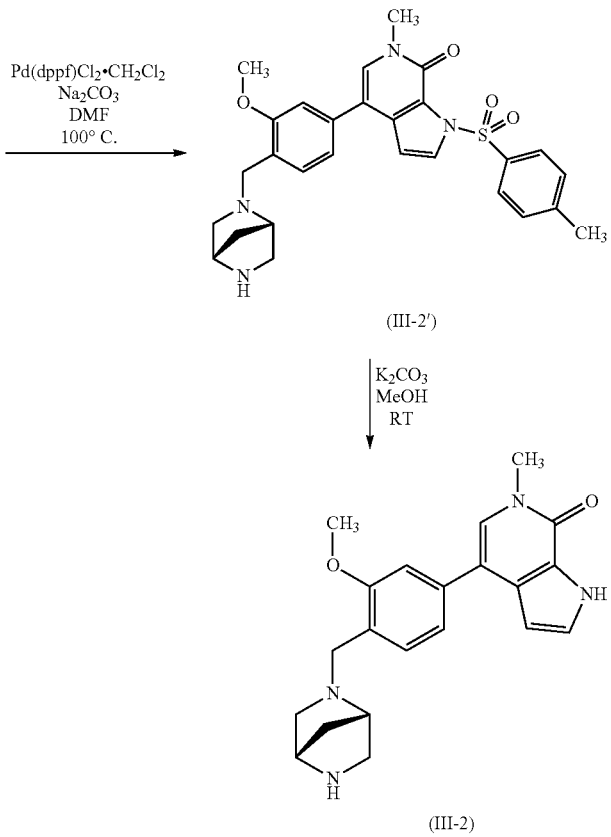

4-{4-[(S)-1-(2,5-Diaza-bicyclo[2.2.1]hept-2-yl)methyl]-3-methoxy-phenyl}-6-methyl-1-(toluene-4-sulfonyl)-1,6-dihydro-pyrrolo[2,3-c]pyridin-7-one (III-2')

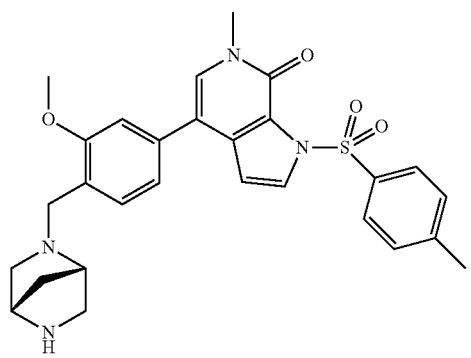 [SMILES: COc1cc(-c2cn(C)c(=O)c3c2ccn3S(=O)(=O)c2ccc(C)cc2)ccc1CN1C[C@@H]2C[C@H]1CN2]

To a solution of 6-methyl-4-(4,4,5,5-tetramethyl-[1,3,2]dioxaborolan-2-yl)-1-(toluene-4-sulfonyl)-1,6-dihydro-pyrrolo[2,3-c]pyridin-7-one W-1 (0.100 g; 0.233 mmol), (S)-2-(4-bromo-2-methoxy-benzyl)-2,5-diaza-bicyclo[2.2.1]heptane hydrochloride L-1 (0.078 g; 0.233 mmol) and 1,1'-bis-(diphenylphosphino)-ferrocenepalladium(II)dichloride dichloromethane complex (0.019 g; 0.023 mmol) in DMF (800 μL) is added an aqueous solution of sodium carbonate (0.292 mL; 2 mol/l). The reaction is stirred at 100° C. for 1 h. The reaction mixture is then purified by prep. LC-MS (column: X-Bridge C-18 30×50 mm). The product containing fractions are combined and concentrated under reduced pressure.

HPLC-MS: (M+H)$^+$=533; $t_{Ret}$=0.57 min; method M2

4-[3-Methoxy-4-((1R,4R)-5-methyl-2,5-diaza-bicyclo[2.2.1]hept-2-ylmethyl)-phenyl]-6-methyl-1,6-dihydro-pyrrolo[2,3-c]pyridin-7-one (III-2)

To a solution of 4-[3-methoxy-4-((1R,4R)-5-methyl-2,5-diaza-bicyclo[2.2.1]hept-2-ylmethyl)-phenyl]-6-methyl-1-(toluene-4-sulfonyl)-1,6-dihydro-pyrrolo[2,3-c]pyridin-7-one III-2' (0.056 g; 0.105 mmol) in methanol (1.0 mL) is added potassium carbonate (0.145 g; 1.046 mmol). The reaction mixture is stirred overnight at RT. The reaction mixture is then purified by prep. LC-MS (column: X-Bridge C-18 30×50 mm).

HPLC-MS: (M+H)$^+$=379; $t_{Ret}$=0.870 min; method M1

According to the procedure of 111-2, the examples III-3 to III-10 are synthesized.

| # | Structure | MS (M + H)+ | t_Ret. HPLC [min] | HPLC-Method |
|---|---|---|---|---|
| III-1 | 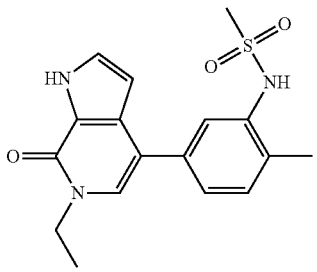 [SMILES: CCn1cc(-c2ccc(C)c(NS(C)(=O)=O)c2)c2cc[nH]c2c1=O] | 346 | 2.336 | M11 |
| III-2 | 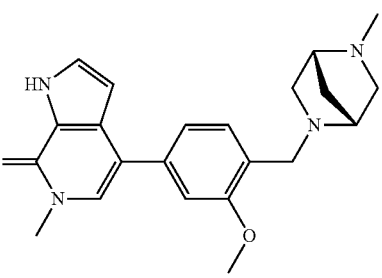 | 379 | 0.870 | M1 |
| III-3 | 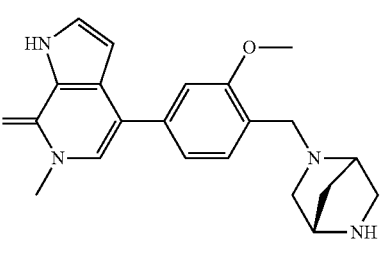 | 365 | 0.950 | M1 |
| III-4 | 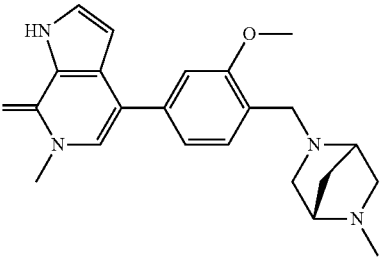 | 379 | 1.000 | M1 |
| III-5 | 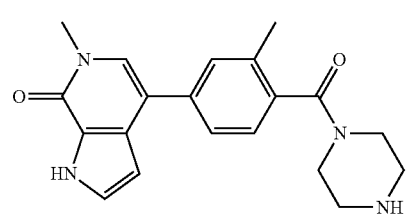 [SMILES: Cc1cc(-c2cn(C)c(=O)c3[nH]ccc23)ccc1C(=O)N1CCNCC1] | 351 | 0.680 | M1 |
| III-6 | 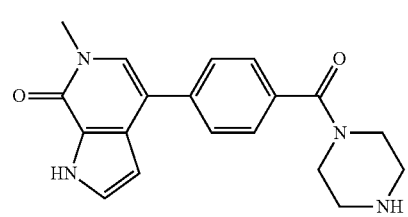 | 337 | 0.620 | M1 |

| # | Structure | MS (M + H)+ | t_Ret. HPLC [min] | HPLC-Method |
|---|---|---|---|---|
| III-7 | 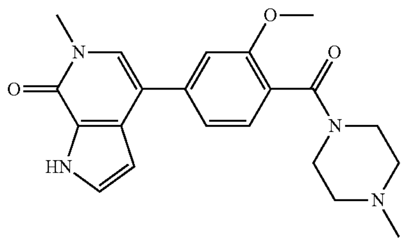 [SMILES: COc1cc(-c2cn(C)c(=O)c3[nH]ccc23)ccc1C(=O)N1CCN(C)CC1] | 381 | 0.790 | M1 |
| III-8 | 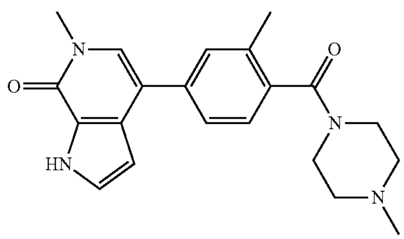 [SMILES: Cc1cc(-c2cn(C)c(=O)c3[nH]ccc23)ccc1C(=O)N1CCN(C)CC1] | 365 | 0.820 | M1 |
| III-9 | 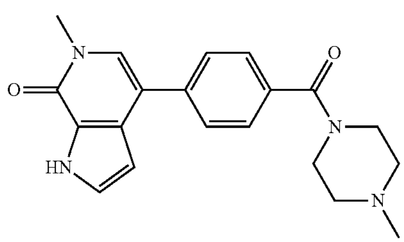 [SMILES: CN1CCN(C(=O)c2ccc(-c3cn(C)c(=O)c4[nH]ccc34)cc2)CC1] | 351 | 0.780 | M1 |
| III-10 | 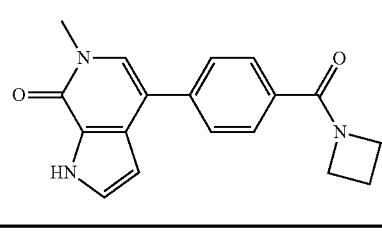 | 308 | 0.810 | M1 |

Preparation of Intermediates of Formula L
Method 1:
Preparation of Intermediate L-1

(1R,4R)-2-(4-Bromo-2-methoxy-benzyl)-5-methyl-2,5-diaza-bicyclo[2.2.1]heptane

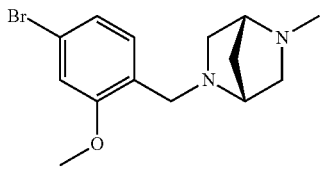 [SMILES: COc1cc(Br)ccc1CN1C[C@H]2C[C@@H]1CN2C]

boxylic acid tert-butyl ester (5.532 g; 27.901 mmol) are dissolved in dry THF (50.0 mL) and treated with sodium triacetoxyborohydride (5.913 g; 27.901 mmol) and acetic acid (0.500 mL; 8.743 mmol). The reaction is stirred at RT overnight. The reaction mixture is partitioned between dichloromethane and saturated aqueous sodium bicarbonate. The solution is dried over $Na_2SO_4$, filtered, concentrated, and purified by silica gel chromatography Combiflash (Column Redisep Rf, 40 g; gradient: DCM/MeOH=100%/0% to 90%/10% over 20 column volumes; flow rate=40 mL/min; detection wavelength: 254 nm). The product containing fractions are combined and concentrated under reduced pressure to give the expected product.

HPLC-MS: $(M+H)^+=397$; $t_{Ret}=1.46$ min; method M1

Reaction scheme

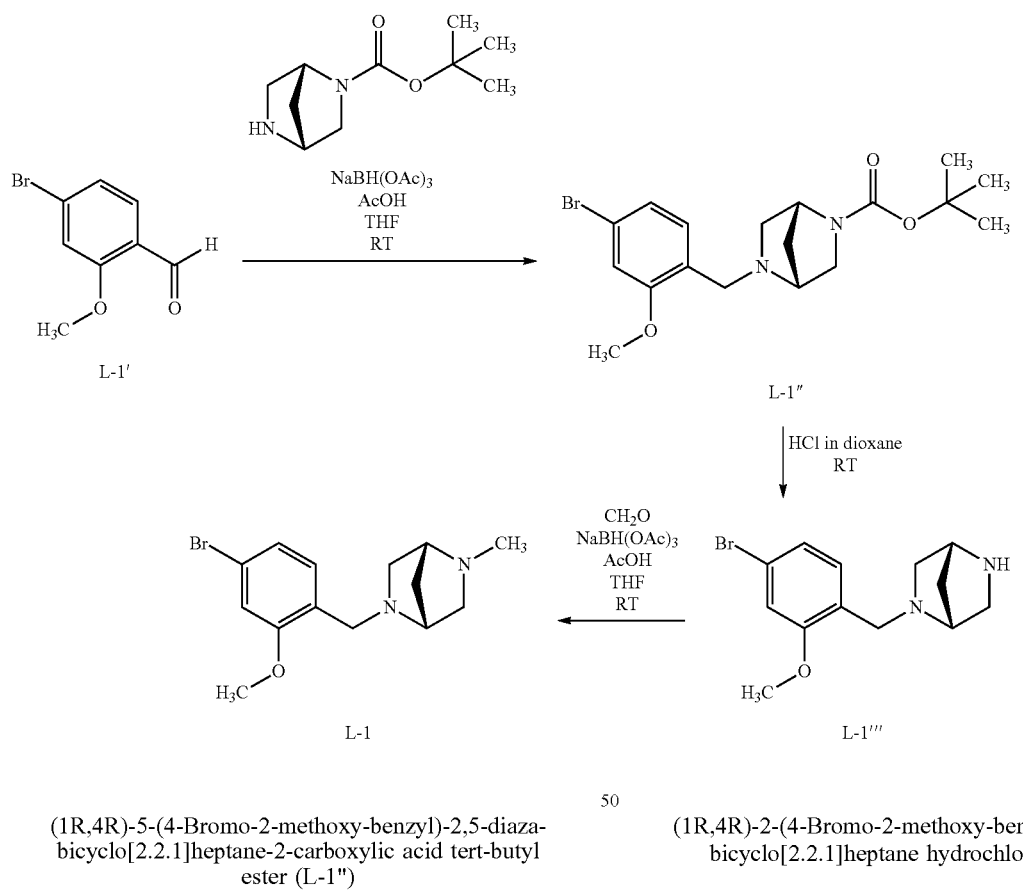

(1R,4R)-5-(4-Bromo-2-methoxy-benzyl)-2,5-diaza-bicyclo[2.2.1]heptane-2-carboxylic acid tert-butyl ester (L-1")

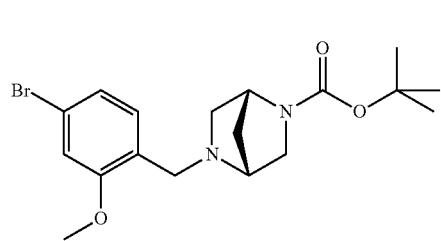 [SMILES: COc1cc(Br)ccc1CN1C[C@H]2C[C@@H]1CN2C(=O)OC(C)(C)C]

(1R,4R)-2-(4-Bromo-2-methoxy-benzyl)-2,5-diaza-bicyclo[2.2.1]heptane hydrochloride (L-1''')

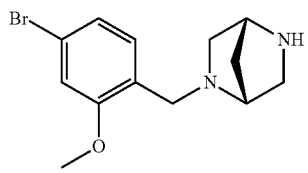 [SMILES: COc1cc(Br)ccc1CN1C[C@H]2C[C@@H]1CN2]

4-Bromo-2-methoxybenzaldehyde L-1' (2.000 g; 9.300 mmol) and (1S,4S)-2,5-diaza-bicyclo[2.2.1]heptane-2-car- (1R,4R)-5-(4-Bromo-2-methoxy-benzyl)-2,5-diaza-bicyclo[2.2.1]heptane-2-carboxylic acid tert-butyl ester L-1" (1.800 g; 4.531 mmol) is dissolved in 4M HCl in dioxane (15.0 mL; 60.000 mmol) at RT. The reaction mixture is stirred at RT overnight. The reaction mixture is concentrated under reduced pressure to give the desired product.

HPLC-MS: $(M+H)^+=297;299$; $t_{Ret}=0.45$ min; method M2

(1R,4R)-2-(4-Bromo-2-methoxy-benzyl)-5-methyl-2,5-diaza-bicyclo[2.2.1]heptane (L-1)

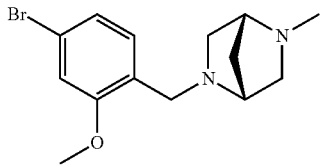 [SMILES: COc1cc(Br)ccc1CN1C[C@H]2C[C@@H]1CN2C]

(1R,4R)-2-(4-Bromo-2-methoxy-benzyl)-2,5-diaza-bicyclo[2.2.1]heptane hydrochloride L-1''' (0.500 g; 1.499 mmol) and formaldehyde (0.135 mL; 1.798 mmol) are dissolved in dry THF (50.0 mL) and treated with sodium triacetoxyborohydride (0.953 g; 4.496 mmol) and acetic acid (500 µL; 8.743 mmol). The reaction is stirred at RT overnight. The reaction mixture is partitioned between dichloromethane and saturated aqueous sodium bicarbonate. It is extracted twice with dichloromethane. The combined organic layers are dried over $Na_2SO_4$ and concentrated under reduced pressure to give the desired product.

HPLC-MS: $(M+H)^+=311$; $t_{Ret}=1.05$ min; method M1

Method 2:
Preparation of Intermediate L-16

(S)-2-(4-Bromo-2-methoxy-benzyl)-5-methyl-2,5-diaza-bicyclo[2.2.1]heptane

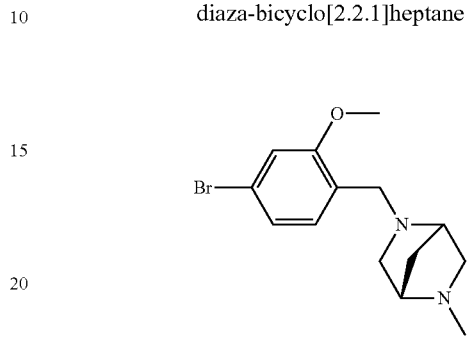

Reaction scheme

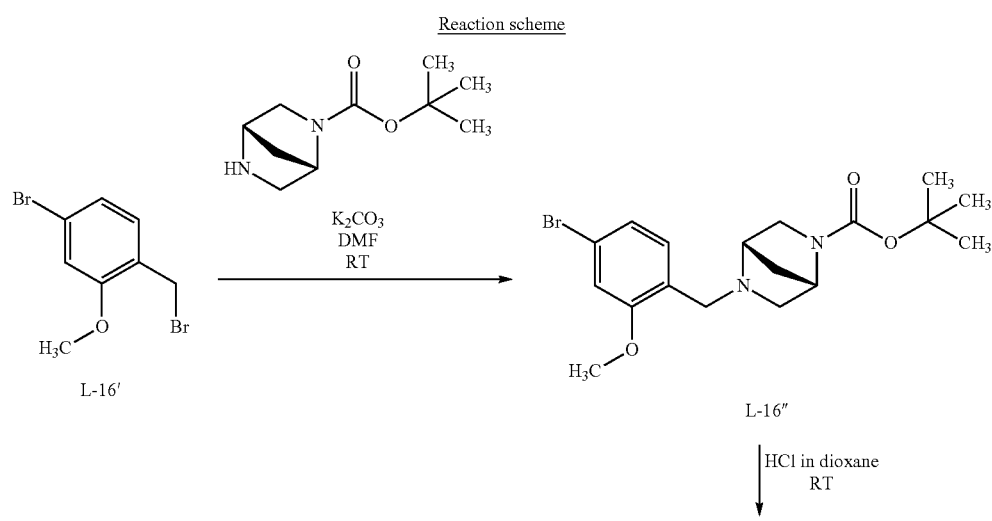

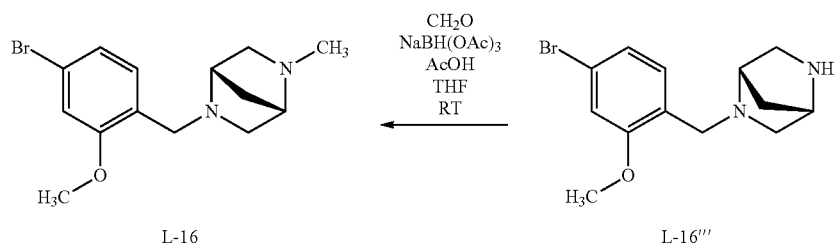

(S)-5-(4-Bromo-2-methoxy-benzyl)-2,5-diaza-bicyclo[2.2.1]heptane-2-carboxylic acid tert-butyl ester (L-16")

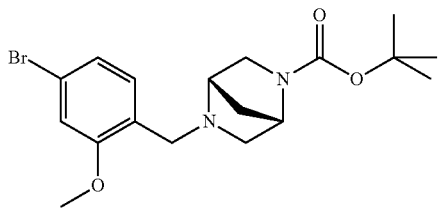 [SMILES: COc1cc(Br)ccc1CN1C[C@@H]2C[C@H]1CN2C(=O)OC(C)(C)C]

4-Bromo-1-(bromomethyl)-2-methoxybenzene L-16' (2.000 g; 7.144 mmol) and potassium carbonate (2.468 g; 17.860 mmol) are dissolved in DMF (10.0 mL). (S)-2,5-Diaza-bicyclo[2.2.1]heptane-2-carboxylic acid tert-butyl ester (1.558 g; 7.858 mmol) is added and stirred the mixture at RT for 1 h. The reaction mixture is then diluted with water (100.0 mL) and extracted with DCM (3×50.0 mL). The combined organic layers are dried over Na$_2$SO$_4$, filtered and concentrated under reduced pressure to give the product.

HPLC-MS: (M+H)$^+$=397;399; t$_{Ret}$=0.83 min; method M2

(S)-2-(4-Bromo-2-methoxy-benzyl)-2,5-diaza-bicyclo[2.2.1]heptane hydrochloride (L-16''')

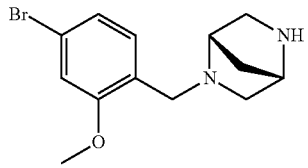 [SMILES: COc1cc(Br)ccc1CN1C[C@@H]2C[C@H]1CN2]

(S)-5-(4-Bromo-2-methoxy-benzyl)-2,5-diaza-bicyclo [2.2.1]heptane-2-carboxylic acid tert-butyl ester L-16" (2.800 g; 7.047 mmol) is dissolved in 4M HCl in dioxane (15.0 mL; 60.000 mmol) at RT. The reaction mixture is stirred at RT overnight. The reaction mixture is concentrated under reduced pressure.

HPLC-MS: (M+H)$^+$=297; 299; t$_{Ret}$=0.42 min; method M2

(S)-2-(4-Bromo-2-methoxy-benzyl)-5-methyl-2,5-diaza-bicyclo[2.2.1]heptane (L-16)

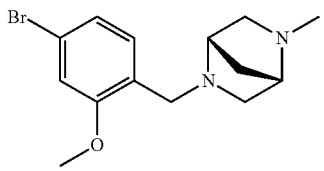 [SMILES: COc1cc(Br)ccc1CN1C[C@@H]2C[C@H]1CN2C]

(S)-2-(4-Bromo-2-methoxy-benzyl)-2,5-diaza-bicyclo [2.2.1]heptane hydrochloride L-16''' (1.000 g; 2.997 mmol) and formaldehyde (0.270 mL; 3.597 mmol) are dissolved in dry THF (50.0 mL) and treated with sodium triacetoxyborohydride (1.906 g; 8.991 mmol) and acetic acid (0.500 mL; 8.743 mmol). The reaction is stirred at RT overnight. The reaction mixture is partitioned between dichloromethane and saturated aqueous sodium bicarbonate. It is extracted twice with dichloromethane. The combined organic layers are dried over Na$_2$SO$_4$, filtered and concentrated under reduced pressure.

HPLC-MS: (M+H)$^+$=312; t$_{Ret}$=1.05 min; method M1

Method 3:
Preparation of Intermediate L-24

[1-(4-Bromo-2-methoxy-phenyl)-cyclopropyl]-dimethyl-amine

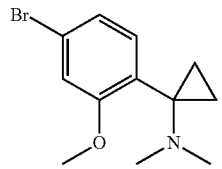

And Preparation of Intermediate L-29

1-(4-Bromo-2-ethyl-6-methoxy-phenyl)-propan-1-ol

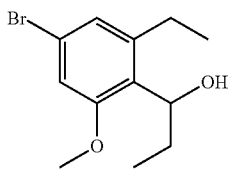

Reaction scheme

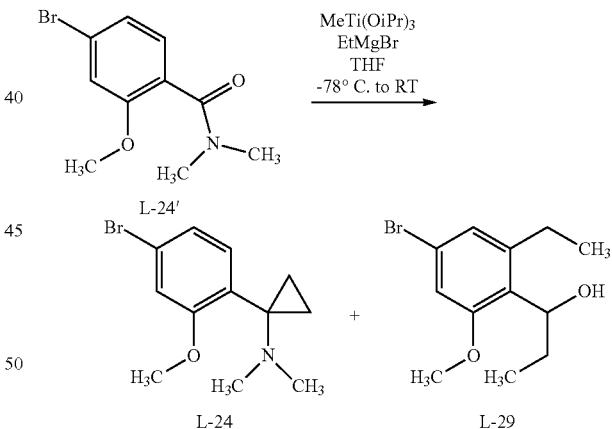

[1-(4-Bromo-2-methoxy-phenyl)-cyclopropyl]-dimethyl-amine (L-24)

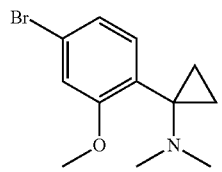

1-(4-Bromo-2-ethyl-6-methoxy-phenyl)-propan-1-ol (L-29)

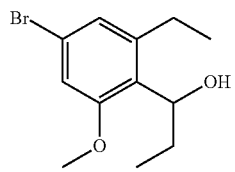

Methyltitanium triisopropoxide (1.040 g; 1.162 mmol) is dissolved in THF dry (5.0 mL) and cooled to −78° C. 1M ethylmagnesium bromide (2.325 mL; 2.325 mmol) is added dropwise at the same temperature and stirred at −78° C. for 10 min. 4-Bromo-2-methoxy-N,N-dimethyl-benzamide L-24' (200.0 mg; 0.775 mmol) dissolved in dry THF (1.0 mL) is added and resulting mixture is stirred at −78° C. for an additional 15 min. The temperature is allowed to rise up slowly to RT in the course of 1 h. The reaction is then poured into water (100 mL) and extracted with Et$_2$O (3×50 mL). Crude product is loaded onto isolute and purified by silica gel chromatography (MeOH/DCM 0 to 5%; gradient 25 min.; than isocratic 5% for 20 min; 225 nm). The product containing fractions are collected and concentrated under reduced pressure.

L-24 HPLC-MS: (M+H)$^+$=270/272; $t_{Ret}$=0.369 min; method M4

L-29 HPLC-MS: (M+H)$^+$=270; 272 (255; 257); $t_{Ret}$=0.764 min; method M2

Method 4:
Preparation of Intermediate L-31

1-(4-Bromo-benzenesulfonyl)-piperazine hydrochloride

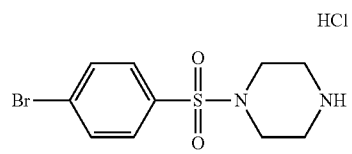 [SMILES: Cl ; O=S(=O)(c1ccc(Br)cc1)N1CCNCC1]

Reaction scheme

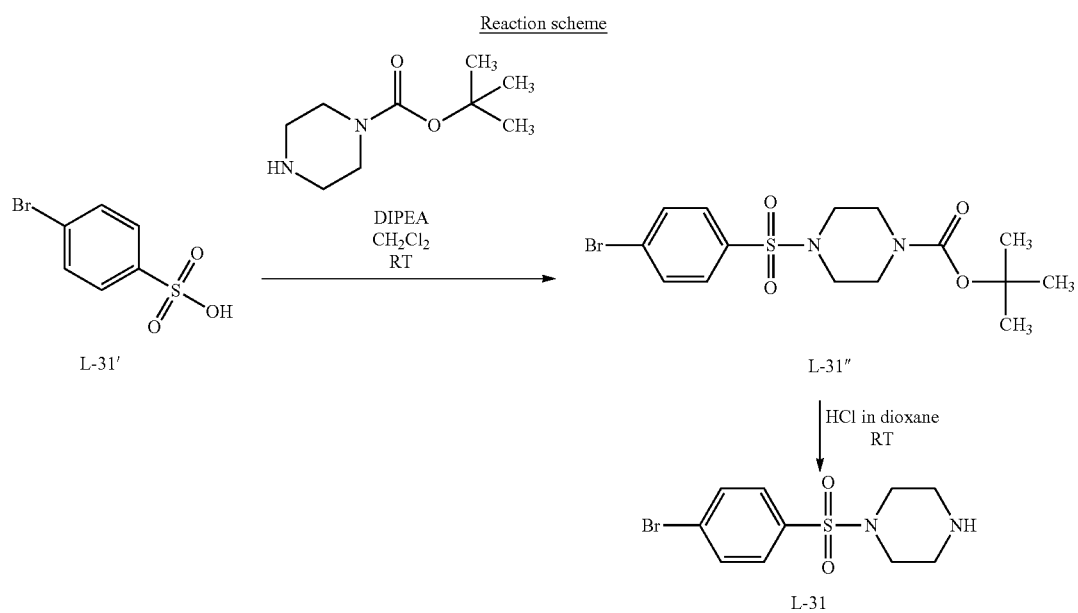

4-(4-Bromo-benzenesulfonyl)-piperazine-1-carboxylic acid tert-butyl ester (L-31')

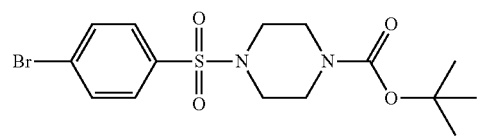 [SMILES: CC(C)(C)OC(=O)N1CCN(S(=O)(=O)c2ccc(Br)cc2)CC1]

To a solution of 4-bromobenzenesulfonyl chloride L-31' (1.000 g; 3.914 mmol) in DCM (10.0 mL), piperazine-1-carboxylic acid tert-butyl ester (0.729 g; 3.914 mmol) and DIPEA (1.347 mL; 7.827 mmol) are added and stirred at RT overnight. The reaction mixture is quenched with water and extracted with DCM (3×50.0 mL). The combined organic layers are dried over Na$_2$SO$_4$, filtered and concentrated under reduced pressure to give the expected product.

HPLC-MS: (M+H-BOC)$^+$=305; 307; $t_{Ret}$=0.77 min; method M2

293

1-(4-Bromo-benzenesulfonyl)-piperazine hydrochloride (L-31)

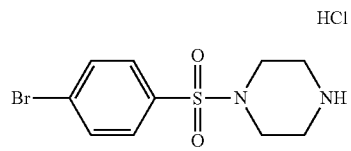 [SMILES: Cl ; O=S(=O)(c1ccc(Br)cc1)N1CCNCC1]

4-(4-Bromo-benzenesulfonyl)-piperazine-1-carboxylic acid tert-butyl ester L-31' (1.580 g; 3.898 mmol) is dissolved in 4M HCl in dioxane (15.0 mL; 60.000 mmol) and stirred at RT for 20 h. The reaction mixture is concentrated under reduced pressure.

HPLC-MS: (M+H)$^+$=305; t$_{Ret}$=0.90 min; method M1

Method 5:
Preparation of Intermediate L-54

(4-Bromo-2-methoxy-phenyl)-(S)-2,5-diaza-bicyclo[2.2.1]hept-2-yl-methanone hydrochloride

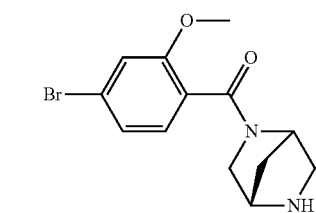

294

(4-Bromo-2-methoxy-phenyl)-(S)-2,5-diaza-bicyclo[2.2.1]hept-2-yl-methanone hydrochloride (L-54")

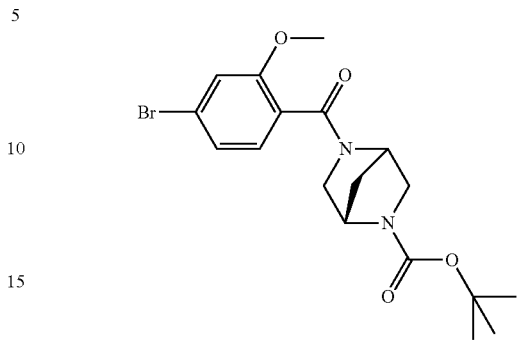

4-Bromo-2-methoxybenzoic acid L-54' (2.000 g; 8.656 mmol) is introduced into q flask. HATU (3.950 g; 10.387 mmol), DIPEA (4.196 mL; 25.969 mmol) and DMSO (800 µL) are added and the mixture is stirred for 15 min at RT. tert-Butyl (1S,4S)-(−)-2,5-diazabicyclo[2.2.1]heptane-2-carboxylate (2.574 g; 12.985 mmol) is added and stirred overnight at RT. Water and DCM are added, and the reaction mixture is extracted 3 times with DCM. The combined organic layers are dried over Na$_2$SO$_4$, filtered and concentrated under reduced pressure. The crude material is again dissolved in DMSO (5 mL), filtered and purified with the basic (ammonia buffer) RP HPLC Gilson system (column: X-Bridge C-18 50×100 mm, Flow 100 mL/min, 10 min gradient from 25-85% acetonitrile). The product containing fractions are concentrated under reduced pressure to give the expected product.

HPLC-MS: (M+H)$^+$=411; 413; t$_{Ret}$=0.65 min; method M2

Reaction scheme

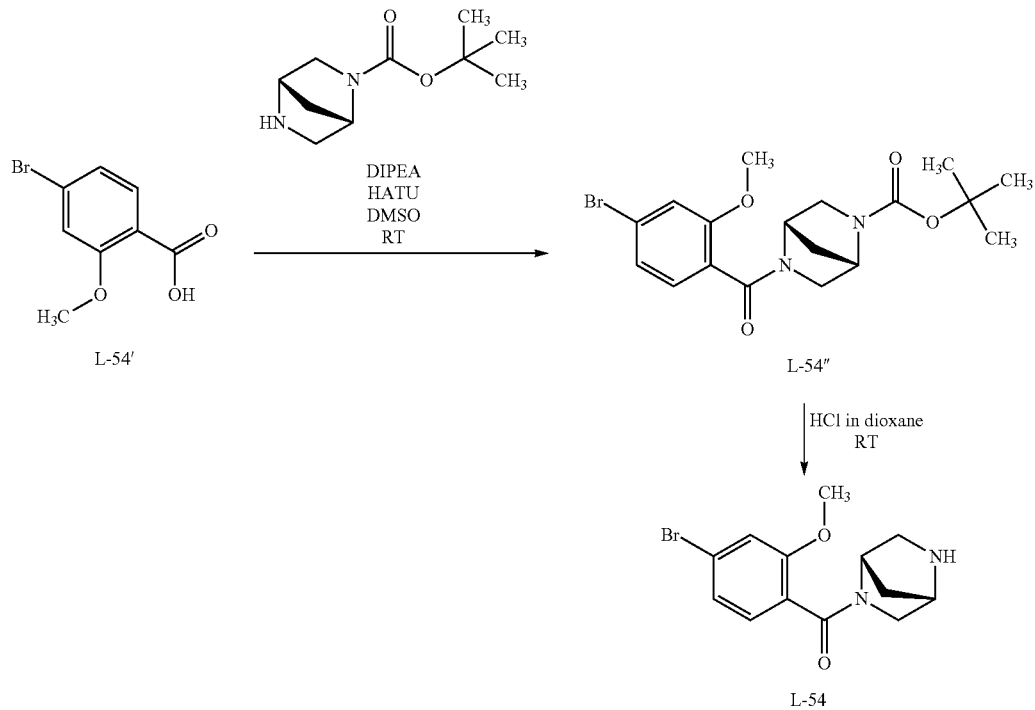

295

(4-Bromo-2-methoxy-phenyl)-(S)-2,5-diaza-bicyclo[2.2.1]hept-2-yl-methanone hydrochloride (L-54)

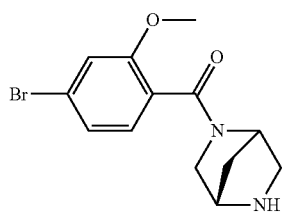

(S)-5-(4-Bromo-2-methoxy-benzoyl)-2,5-diaza-bicyclo[2.2.1]heptane-2-carboxylic acid tert-butyl ester L-54" (1.100 g; 2.675 mmol) is treated with 4M HCl in dioxane (15.0 mL; 60.000 mmol). The reaction mixture is stirred at RT overnight. The reaction mixture is concentrated under reduced pressure.

HPLC-MS: (M+H)$^+$=311; 313; $t_{Ret}$=0.34 min; method M2

Method 6:
Preparation of Intermediate L-71

4-Bromo-2-ethanesulfonylmethyl-benzoic acid methyl ester

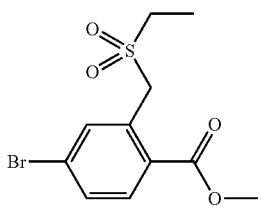

Reaction scheme

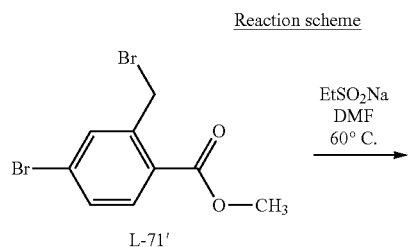

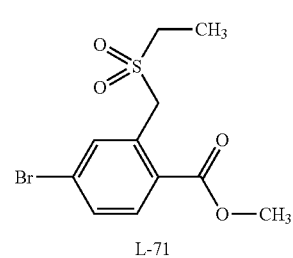

296

4-Bromo-2-ethanesulfonylmethyl-benzoic acid methyl ester (L-71)

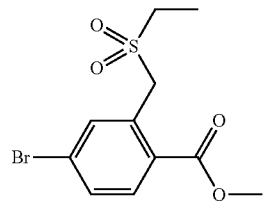 [SMILES: CCS(=O)(=O)Cc1cc(Br)ccc1C(=O)OC]

Sodium ethanesulfinate (5.279 g; 45 mmol) is added to a solution of 4-bromo-2-bromomethyl-benzoic acid methyl ester L-71' (20.0 g; 23.0 mmmol) in DMF (200 mL). The mixture is heated to 60° C. for 6 h. Ethyl acetate and water are added to the reaction mixture. The reaction mixture is extracted 3 times with ethyl acetate. The combined organic layers are dried over Na$_2$SO$_4$, filtered and concentrated under reduced pressure. The residue is purified on silica gel column chromatography.

HPLC-MS: (M+H)$^+$=321

Method 7:
Preparation of Intermediate L-73

5-Bromo-1,3-dimethoxy-2-methoxymethyl-benzene

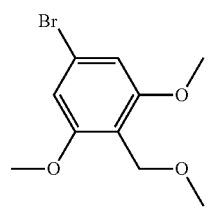

Reaction scheme

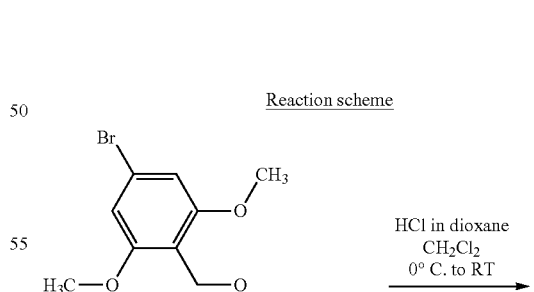

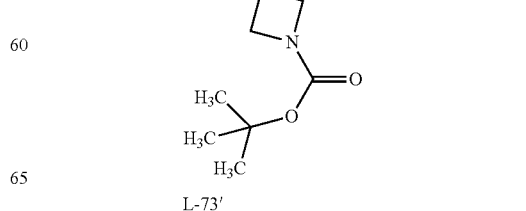

-continued

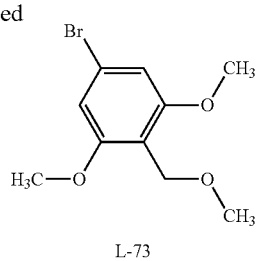

5-Bromo-1,3-dimethoxy-2-methoxymethyl-benzene (L-73)

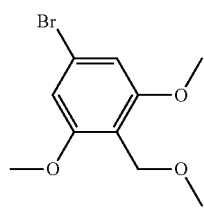

3-(4-Bromo-2,6-dimethoxy-benzyloxy)-azetidine-1-carboxylic acid tert-butyl ester L-73' (0.950 g; 2,243 mmol) is dissolved in dry DCM (20.0 mL) and the reaction is cooled to 0° C. A 4M HCl solution in dioxane (1.402 mL; 5.09 mmol) is added. The reaction mixture is stirred at RT overnight. The solvent is removed under reduced pressure. The residue is loaded onto isolute and purified on silica gel chromatography (Cyclohexane/EA o to 40%) to afford the expected product after fraction collection and evaporation.

HPLC-MS: $(M+H)^+=229$; 231; $t_{Ret}=0.66$ min; method M2

According to the procedure of L-1 with the exception of the last methylation step, the intermediate L-2 is synthesized. According to the procedure of L-1 with the exception of the 2 last steps (N-Boc deprotection and methylation step), the intermediates L-3 to L-15 are synthesized. According to the procedure of L-16 with the exception of the last methylation step, the intermediate L-17 is synthesized. According to the procedure of L-16 with the exception of the 2 last steps (N-Boc deprotection and methylation step), the intermediates L-18 to L-23 are synthesized. According to the procedure of L-24, the intermediates L-25 to L-28 are synthesized. L-29 is a side product obtained while synthesising L-24 and L-30 is a side product obtained while synthesising L-26. According to the procedure of L-31 with the exception of the last step (N-Boc deprotection), the intermediates L-32 to L-53 are synthesized. According to the procedure of L-54 with the exception of the last step (N-Boc deprotection), the intermediates L-55 to L-66 are synthesized. According to the last step of the procedure of L-1 (L-1''' to L-1), the intermediates L-67 to L-70 are synthesized. According to the procedure of L-71, the intermediate L-72 is synthesized. Intermediates L-74 to L-103 are commercially available

| # | Structure | MS (M + H)⁺ | $t_{Ret.}$ HPLC [min] | HPLC-Method |
|---|-----------|-------------|-----------------------|-------------|
| L-1 | 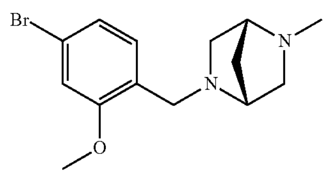 [SMILES: COc1cc(Br)ccc1CN1C[C@H]2C[C@@H]1CN2C] | 311; 313 | 0.503 | M2 |
| L-2 | 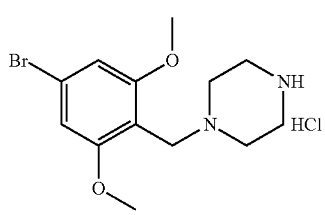 [SMILES: COc1cc(Br)cc(OC)c1CN1CCNCC1 ; Cl] | 315; 317 | 0.462 | M2 |
| L-3 | 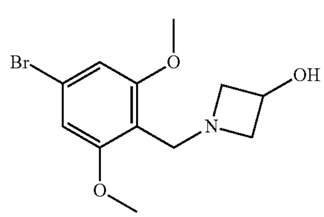 [SMILES: COc1cc(Br)cc(OC)c1CN1CC(O)C1] | 302; 304 | 0.486 | M2 |
| L-4 | 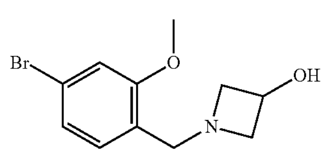 | 272; 274 | 0.441 | M2 |

| # | Structure | MS (M + H)+ | t_Ret. HPLC [min] | HPLC-Method |
|---|---|---|---|---|
| L-5 | 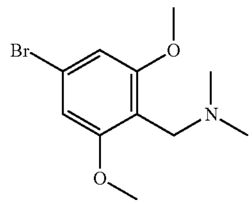 | 274; 276 | 0.517 | M2 |
| L-6 | 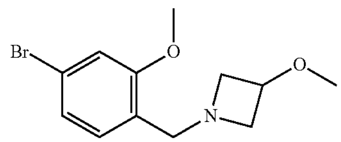 [SMILES: COc1cc(Br)ccc1CN1CC(OC)C1] | 286; 288 | 0.616 | M2 |
| L-7 | 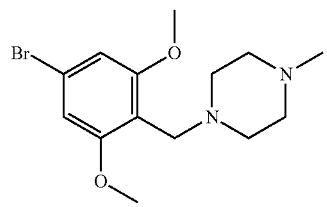 [SMILES: COc1cc(Br)cc(OC)c1CN1CCN(C)CC1] | 329; 331 | 0.536 | M2 |
| L-8 | 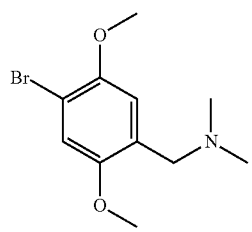 | 274; 276 | 0.313 | M4 |
| L-9 | 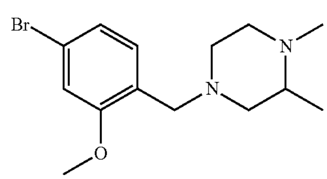 [SMILES: COc1cc(Br)ccc1CN1CCN(C)C(C)C1] | 313; 315 | 0.286 | M4 |
| L-10 | 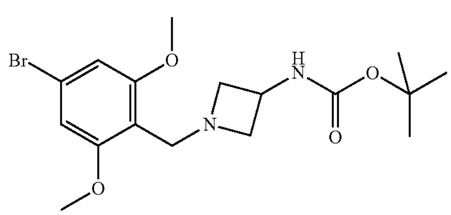 [SMILES: COc1cc(Br)cc(OC)c1CN1CC(NC(=O)OC(C)(C)C)C1] | 401; 403 | 0.708 | M2 |
| L-11 | 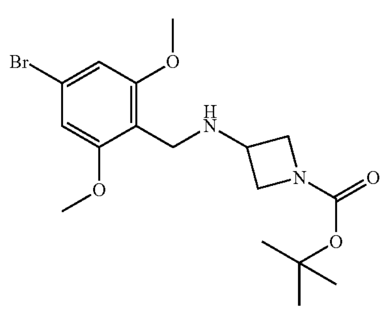 [SMILES: COc1cc(Br)cc(OC)c1CNC1CN(C(=O)OC(C)(C)C)C1] | 401; 403 | 0.773 | M2 |

-continued
| # | Structure | MS (M + H)+ | t_Ret. HPLC [min] | HPLC-Method |
|---|---|---|---|---|
| L-12 | 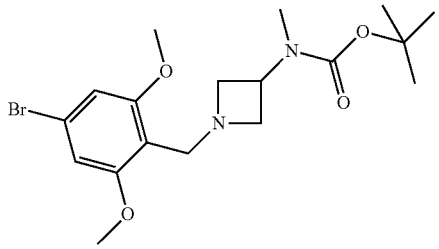 [SMILES: COc1cc(Br)cc(OC)c1CN1CC(N(C)C(=O)OC(C)(C)C)C1] | 415; 417 | 0.784 | M2 |
| L-13 | 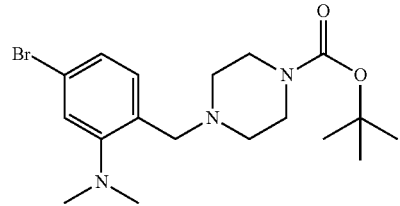 [SMILES: CN(C)c1cc(Br)ccc1CN1CCN(C(=O)OC(C)(C)C)CC1] | 398; 400 | 0.997 | M2 |
| L-14 | 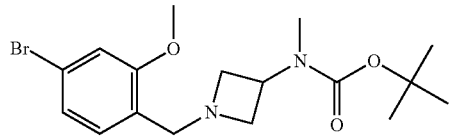 [SMILES: COc1cc(Br)ccc1CN1CC(N(C)C(=O)OC(C)(C)C)C1] | 385; 387 | 0.811 | M2 |
| L-15 | 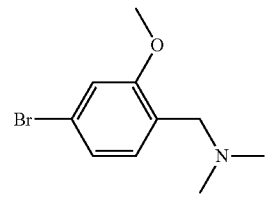 | 244; 246 | 0.570 | M2 |
| L-16 | 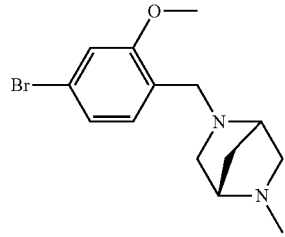 [SMILES: COc1cc(Br)ccc1CN1C[C@@H]2CC1CN2C] | 311; 313 | 0.505 | M2 |
| L-17 | 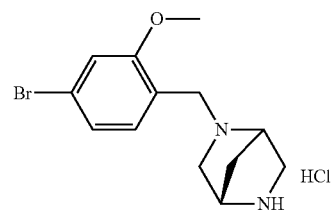 [SMILES: COc1cc(Br)ccc1CN1C[C@@H]2CC1CN2 ; Cl] | 297; 299 | 0.423 | M2 |
| L-18 | 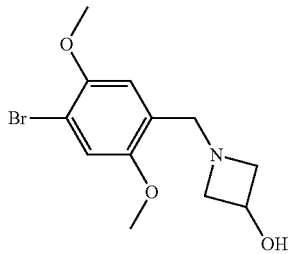 [SMILES: COc1cc(CN2CC(O)C2)c(OC)cc1Br] | 302; 304 | 0.440 | M2 |

-continued

| # | Structure | MS (M + H)+ | t_Ret. HPLC [min] | HPLC-Method |
|---|---|---|---|---|
| L-19 | 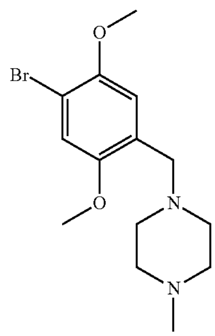 [SMILES: COc1cc(CN2CCN(C)CC2)c(OC)cc1Br] | 329; 331 | 0.540 | M2 |
| L-20 | 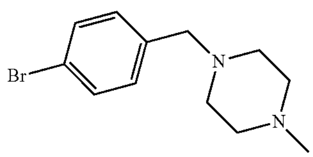 | 269; 271 | 0.551 | M2 |
| L-21 | 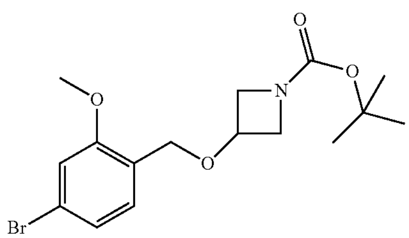 [SMILES: COc1cc(Br)ccc1COC1CN(C(=O)OC(C)(C)C)C1] | 272; 274 | 0.850 | M2 |
| L-22 | 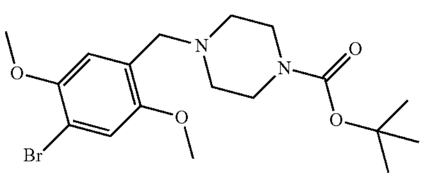 [SMILES: COc1cc(CN2CCN(C(=O)OC(C)(C)C)CC2)c(OC)cc1Br] | 415; 417 | 0.833 | M2 |
| L-23 | 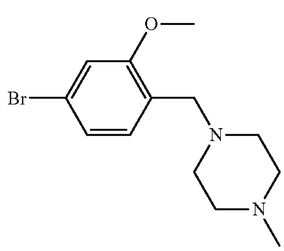 [SMILES: COc1cc(Br)ccc1CN1CCN(C)CC1] | 299; 301 | 0.561 | M2 |
| L-24 | 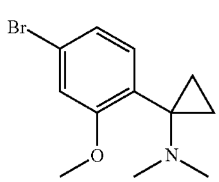 | 270; 272 | 0.369 | M4 |
| L-25 | 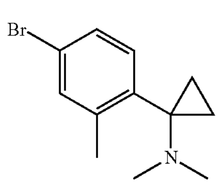 | 254; 256 | 0.830 | M2 |

-continued
| # | Structure | MS (M + H)+ | t_Ret. HPLC [min] | HPLC-Method |
|---|---|---|---|---|
| L-26 | 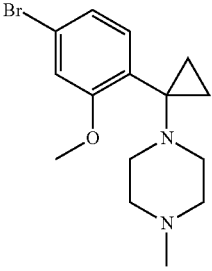 [SMILES: COc1cc(Br)ccc1C1(N2CCN(C)CC2)CC1] | 355; 357 | 0.934 | M2 |
| L-27 | 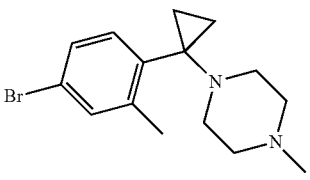 [SMILES: Cc1cc(Br)ccc1C1(N2CCN(C)CC2)CC1] | 309; 311 | 0.429 | M4 |
| L-28 | 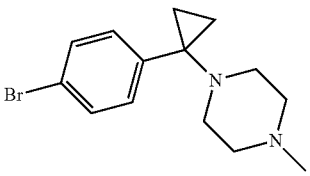 [SMILES: CN1CCN(C2(c3ccc(Br)cc3)CC2)CC1] | 295; 297 | 0.403 | M4 |
| L-29 | 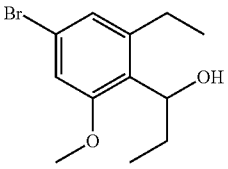 | 270; 272 | 0.369 | M4 |
| L-30 | 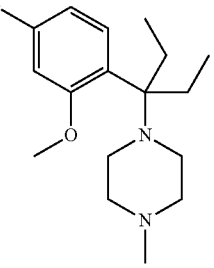 | 355; 357 | 0.521 | M4 |
| L-31 | 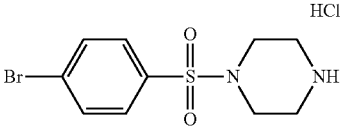 HCl | 305 | 0.90 | M1 |
| L-32 | 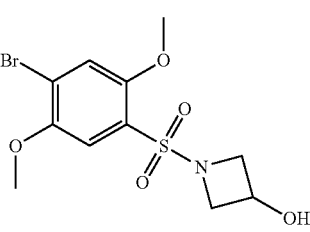 [SMILES: COc1cc(S(=O)(=O)N2CC(O)C2)c(OC)cc1Br] | 352; 354 | 0.445 | M2 |

| # | Structure | MS (M + H)+ | t_Ret. HPLC [min] | HPLC-Method |
|---|---|---|---|---|
| L-33 | 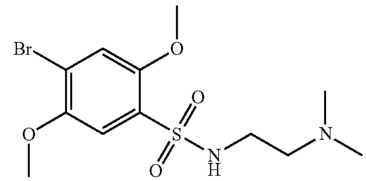 [SMILES: COc1cc(S(=O)(=O)NCCN(C)C)c(OC)cc1Br] | 367; 369 | 0.532 | M2 |
| L-34 | 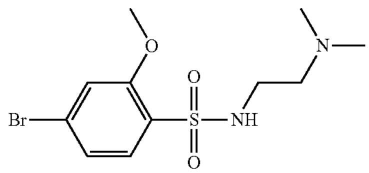 [SMILES: COc1cc(Br)ccc1S(=O)(=O)NCCN(C)C] | 337; 339 | 0.522 | M2 |
| L-35 | 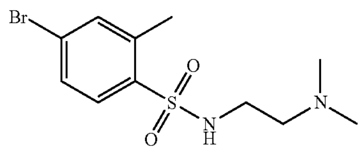 [SMILES: Cc1cc(Br)ccc1S(=O)(=O)NCCN(C)C] | 321; 323 | 0.578 | M2 |
| L-36 | 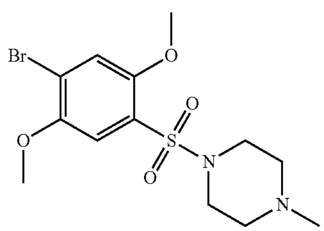 [SMILES: COc1cc(S(=O)(=O)N2CCN(C)CC2)c(OC)cc1Br] | 379; 381 | 0.530 | M2 |
| L-37 | 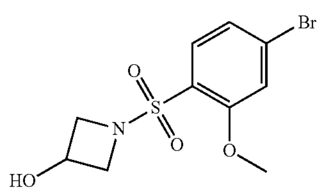 [SMILES: COc1cc(Br)ccc1S(=O)(=O)N1CC(O)C1] | 322; 324 | 0.429 | M2 |
| L-38 | 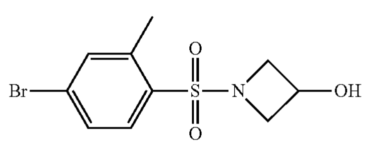 [SMILES: Cc1cc(Br)ccc1S(=O)(=O)N1CC(O)C1] | 306; 308 | 0.526 | M2 |
| L-39 | 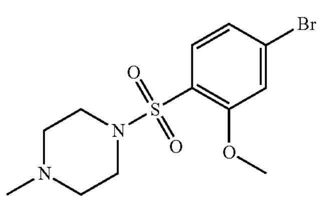 [SMILES: COc1cc(Br)ccc1S(=O)(=O)N1CCN(C)CC1] | 349; 351 | 0.519 | M2 |
| L-40 | 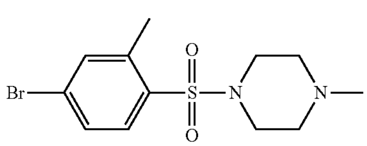 [SMILES: Cc1cc(Br)ccc1S(=O)(=O)N1CCN(C)CC1] | 333; 335 | 0.614 | M2 |

-continued

| # | Structure | MS (M + H)+ | t_Ret. HPLC [min] | HPLC-Method |
|---|---|---|---|---|
| L-50 | 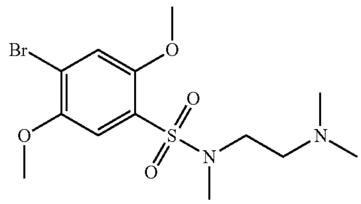 [SMILES: COc1cc(S(=O)(=O)N(C)CCN(C)C)c(OC)cc1Br] | 381; 383 | 0.577 | M2 |
| L-51 | | 365; 367 | 0.761 | M2 |
| L-51 | | 335; 337 | 0.759 | M2 |
| L-52 | 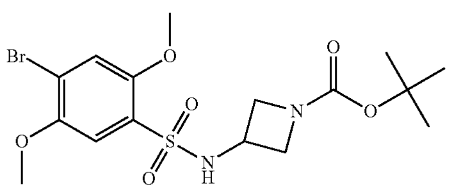 [SMILES: COc1cc(S(=O)(=O)NC2CN(C(=O)OC(C)(C)C)C2)c(OC)cc1Br] | 351; 353 | 0.699 | M2 |
| L-53 | 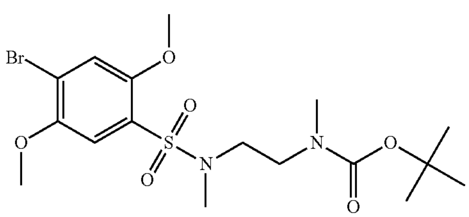 [SMILES: COc1cc(S(=O)(=O)N(C)CCN(C)C(=O)OC(C)(C)C)c(OC)cc1Br] | 367; 369 | 0.770 | M2 |
| L-54 | 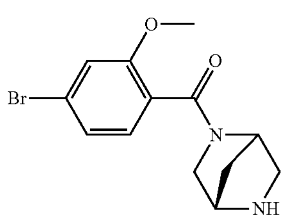 [SMILES: COc1cc(Br)ccc1C(=O)N1C[C@@H]2CC1CN2] | 311; 313 | 0.336 | M2 |
| L-55 | 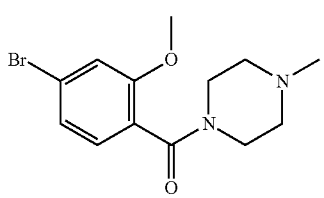 [SMILES: COc1cc(Br)ccc1C(=O)N1CCN(C)CC1] | 313; 315 | 0.440 | M2 |

-continued

| # | Structure | MS (M + H)+ | t_Ret. HPLC [min] | HPLC-Method |
|---|---|---|---|---|
| L-56 | 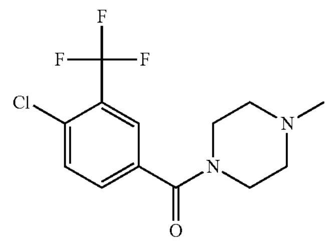 [SMILES: CN1CCN(C(=O)c2ccc(Cl)c(C(F)(F)F)c2)CC1] | 307; 309 | 0.536 | M2 |
| L-57 | 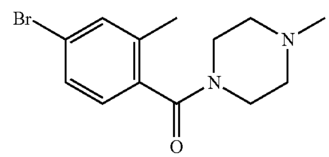 [SMILES: Cc1cc(Br)ccc1C(=O)N1CCN(C)CC1] | 297; 299 | 0.484 | M2 |
| L-58 | 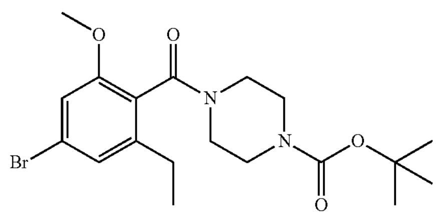 [SMILES: CCc1cc(Br)cc(OC)c1C(=O)N1CCN(C(=O)OC(C)(C)C)CC1] | 427; 429 | 1.100 | M9 |
| L-59 | 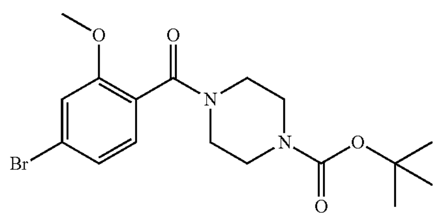 [SMILES: COc1cc(Br)ccc1C(=O)N1CCN(C(=O)OC(C)(C)C)CC1] | 399; 341 Ms-56 | 1.300 | M7 |
| L-60 | 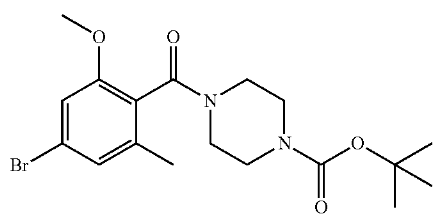 | 413; 415 | 1.388 | M7 |
| L-61 | | 397; 399 | 1.435 | M7 |
| L-61 | | 442 | 1.260 | M7 |

-continued

| # | Structure | MS (M + H)⁺ | t$_{Ret.}$ HPLC [min] | HPLC-Method |
|---|---|---|---|---|
| L-62 | 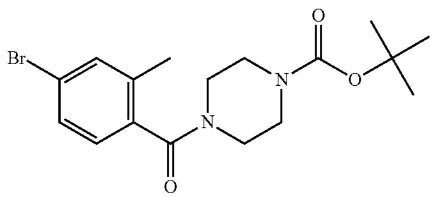 [SMILES: Cc1cc(Br)ccc1C(=O)N1CCN(C(=O)OC(C)(C)C)CC1] | 327; 329 | 0.716 | M2 |
| L-63 | 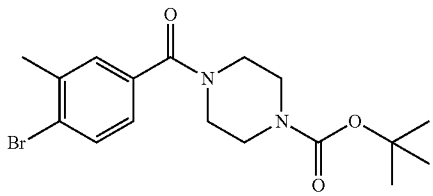 [SMILES: Cc1cc(C(=O)N2CCN(C(=O)OC(C)(C)C)CC2)ccc1Br] | 327; 329 | 1.410 | M7 |
| L-64 | 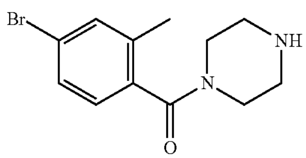 [SMILES: Cc1cc(Br)ccc1C(=O)N1CCNCC1] | 283; 285 | 0.384 | M2 |
| L-65 | 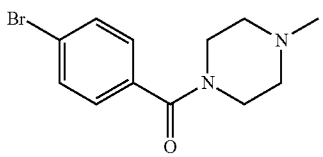 [SMILES: CN1CCN(C(=O)c2ccc(Br)cc2)CC1] | 283; 285 | 0.238 | M4 |
| L-66 | 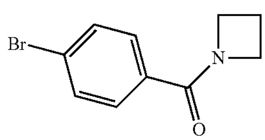 [SMILES: O=C(c1ccc(Br)cc1)N1CCC1] | 240; 242 | 0.844 | M4 |
| L-67 | 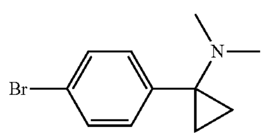 | 240; 242 | 0.292 | M4 |
| L-68 | 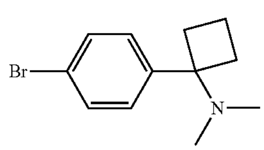 | 254; 256 | 1.230 | M4 |
| L-69 | 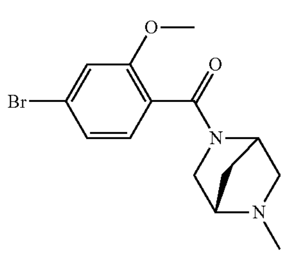 [SMILES: COc1cc(Br)ccc1C(=O)N1C[C@@H]2CC1CN2C] | 325; 327 | 0.404 | M2 |

| # | Structure | MS (M + H)+ | t_Ret. HPLC [min] | HPLC-Method |
|---|---|---|---|---|
| L-70 | 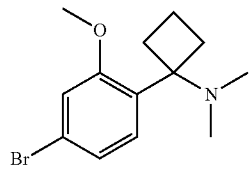 [SMILES: COc1cc(Br)ccc1C1(N(C)C)CCC1] | NMR | | |
| L-71 | 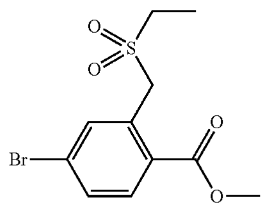 [SMILES: CCS(=O)(=O)Cc1cc(Br)ccc1C(=O)OC] | NMR | | |
| L-72 | 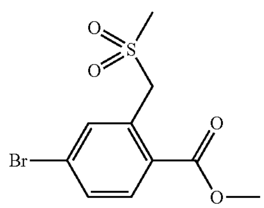 [SMILES: COC(=O)c1ccc(Br)cc1CS(C)(=O)=O] | NMR | | |
| L-73 | 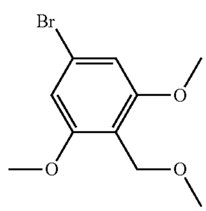 | 229; 231 | 0.659 | M2 |
| L-74 | 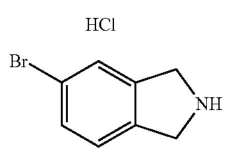 | Commercially available | | |
| L-75 | 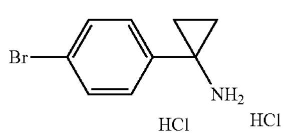 [SMILES: NC1(c2ccc(Br)cc2)CC1 ; Cl ; Cl] | Commercially available | | |
| L-76 | 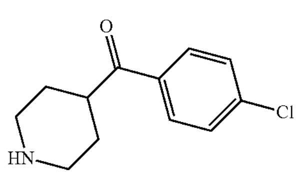 [SMILES: O=C(c1ccc(Cl)cc1)C1CCNCC1] | Commercially available | | |
| L-77 | 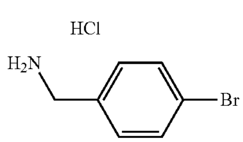 | Commercially available | | |

-continued

| # | Structure | MS (M + H)+ | t_Ret. HPLC [min] | HPLC-Method |
|---|---|---|---|---|
| L-78 | 4-chlorobenzyl piperazine | Commercially available | | |
| L-79 | 6-bromo-1,2,3,4-tetrahydroisoquinoline | Commercially available | | |
| L-80 | 3-iodobenzylamine | Commercially available | | |
| L-81 | 7-bromo-1,2,3,4-tetrahydroisoquinoline | Commercially available | | |
| L-82 | 4-bromoaniline | Commercially available | | |
| L-83 | 4-bromo-2-methylbenzylamine | Commercially available | | |
| L-84 | (R or S)-1-(4-bromophenyl)ethylamine | Commercially available | | |
| L-85 | (S or R)-1-(4-bromophenyl)ethylamine | Commercially available | | |
| L-86 | 4-bromo-2-methoxybenzylamine | Commercially available | | |
| L-87 | (4-bromophenyl)(pyrimidin-5-yl)methanone | Commercially available | | |
| L-88 | 2-(3-bromophenyl)piperidine | Commercially available | | |

| # | Structure | MS (M + H)+ | t_Ret. HPLC [min] | HPLC-Method |
|---|---|---|---|---|
| L-89 | 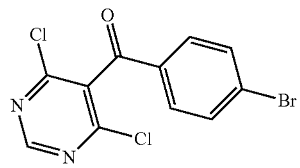 [SMILES: O=C(c1ccc(Br)cc1)c1c(Cl)ncnc1Cl] | Commercially available | | |
| L-90 | 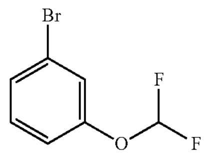 [SMILES: FC(F)Oc1cccc(Br)c1] | Commercially available | | |
| L-91 | 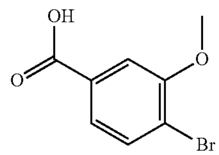 | Commercially available | | |
| L-92 | 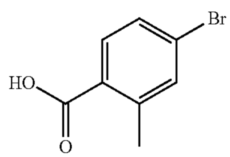 | Commercially available | | |
| L-93 | 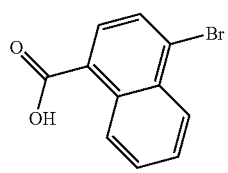 [SMILES: O=C(O)c1ccc(Br)c2ccccc12] | Commercially available | | |
| L-94 | 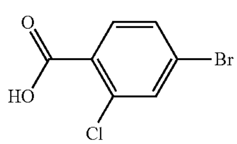 [SMILES: O=C(O)c1ccc(Br)cc1Cl] | Commercially available | | |
| L-95 | 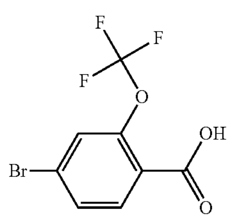 [SMILES: O=C(O)c1ccc(Br)cc1OC(F)(F)F] | Commercially available | | |
| L-96 | 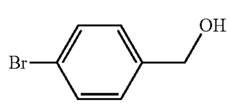 | Commercially available | | |
| L-97 | 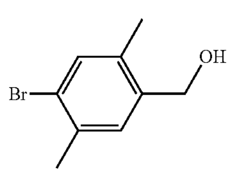 | Commercially available | | |

-continued

| # | Structure | MS (M + H)⁺ | t_Ret. HPLC [min] | HPLC-Method |
|---|---|---|---|---|
| L-98 | 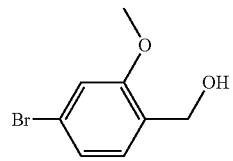 | Commercially available | | |
| L-99 | 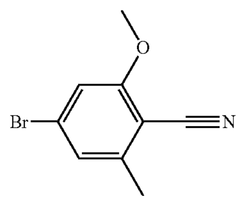 | Commercially available | | |
| L-100 | 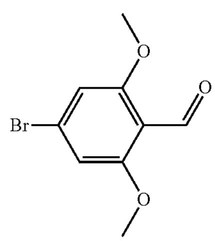 | Commercially available | | |
| L-101 | 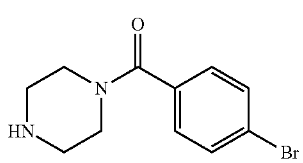 [SMILES: O=C(c1ccc(Br)cc1)N1CCNCC1] | Commercially available | | |
| L-102 | 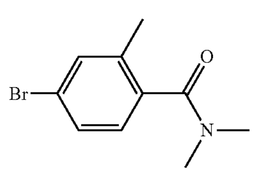 | Commercially available | | |
| L-103 | 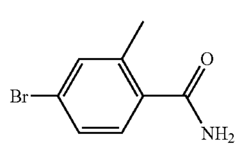 | Commercially available | | |

Preparation of Intermediates of Formula K
Method 1:
Preparation of Intermediate K-1

[2,6-Dimethoxy-4-(4,4,5,5-tetramethyl-[1,3,2]dioxaborolan-2-yl)-benzyl]-dimethyl-amine

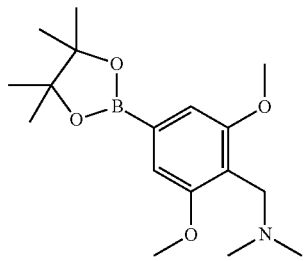

Reaction scheme

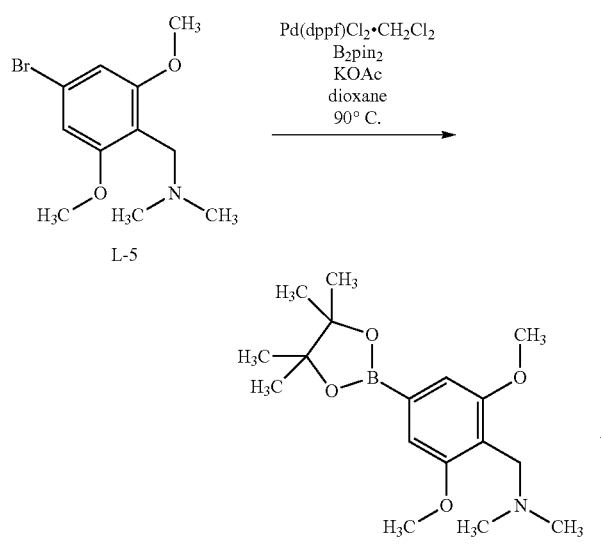

[2,6-Dimethoxy-4-(4,4,5,5-tetramethyl-[1,3,2]dioxaborolan-2-yl)-benzyl]-dimethyl-amine (K-1)

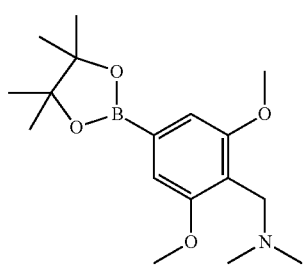

(4-Bromo-2,6-dimethoxy-benzyl)-dimethyl-amine L-5 (0.250 g; 0.885 mmol), bis(pinacolato)diboron (0.337 g; 1.327 mmol), [1,1'-bis(diphenylphosphino)-ferrocene]palladium(II) dichloride, dichloromethane (0.149 g; 0.177 mmol) and potassium acetate (0.174 g; 1.769 mmol) are weight into a round bottom flask. 1,4 Dioxane (3.0 mL) is added and the flask is flushed with argon. The reaction mixture is stirred at 90° C. overnight. The reaction mixture is cooled to RT and filtered through a plug of celite. It is washed with dioxane (2×20.0 mL), and then concentrated under reduced pressure.

HPLC-MS: (M+H)$^+$=322; t$_{Ret}$=0.50 min; method M2

Method 2:
Preparation of Intermediate K-6

N-(5-Boronic acid-2-methyl-phenyl)-methanesulfonamide

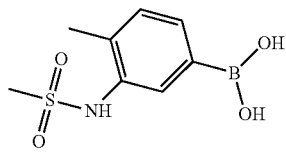

Reaction scheme

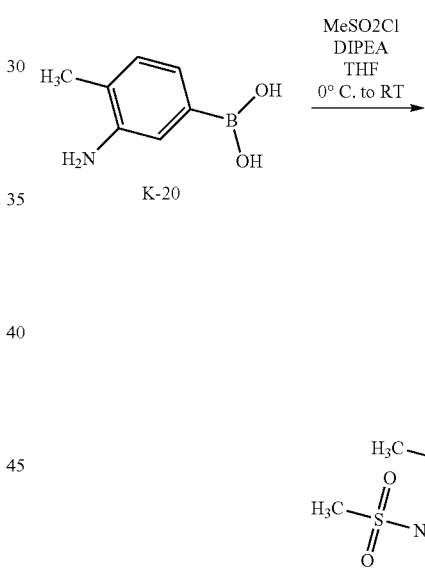

N-(5-Boronic acid-2-methyl-phenyl)-methanesulfonamide (K-6)

To a ice-cooled solution of 3-amino-4-methylphenylboronic acid K-20 (1.000 g; 6.491 mmol) in THF (50.0 mL), diisopropylethylamine is added (3.227 mL; 19.474 mmol). Methanesulfonyl chloride (0.607 mL, 7.790 mmol) is added slowly and the reaction mixture is stirred for 30 min at 0° C. and then left to warm to RT overnight. The reaction mixture is then concentrated under vacuum, then dissolve in little amount of DCM/MeOH and purified by silica gel chromatography.

HPLC-MS: (M+H)$^+$=228; t$_{Ret}$=0.24 min; method M1

Method 3:
Preparation of Intermediate K-7

4-Boronic acid-N-(1-methyl-piperidin-4-yl)-benzamide

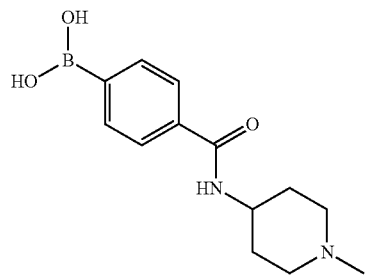 [SMILES: CN1CCC(NC(=O)c2ccc(B(O)O)cc2)CC1]

Reaction scheme

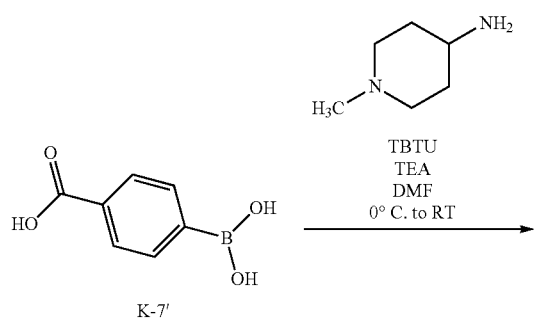

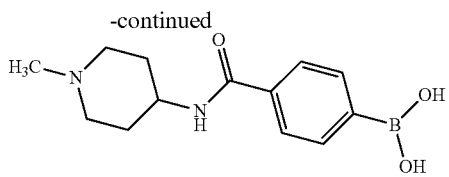

4-Boronic acid-N-(1-methyl-piperidin-4-yl)-benzamide (K-7)

TBTU (27.5 mg; 0.241 mmol) and triethylamine (19 µL; 0.140 mmol) are added to a solution of 4-carboxyphenyl-boronic acid K-7' (20.0 mg; 0.121 mmol) in DMF (500 µL). After stirring the mixture for 5 min, 1-methylpiperidin-4-amine (27.5 mg; 0.241 mmol) is added. The mixture is stirred at RT for 3 h. Then the reaction mixture is concentrated under vacuum, dissolved in DCM and mixed with water and 5% aqueous citric acid solution. The aqueous layers are washed with DCM and then neutralized and basicified. Water is then removed under reduced pressure and the residue triturated in DCM/MeOH. The precipitate is filtered off and purified by RP HPLC (Gilson).

HPLC-MS: $(M+H)^+ = 263$; $t_{Ret.} = 0.0$ min; method M1

According to the procedure of K-1, the intermediates K-2 to K-5 are synthesized. Intermediates K-8 to K- are commercially available.

| # | Structure | MS (M + H)⁺ | $t_{Ret.}$ HPLC [min] | HPLC-Method |
|---|---|---|---|---|
| K-1 | 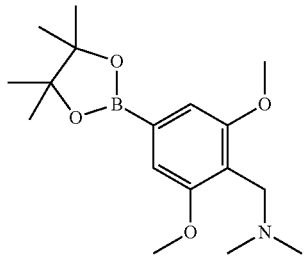 | 322 | 0.50 | M2 |
| K-2 | 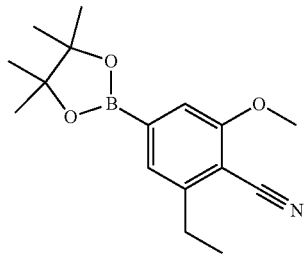 [SMILES: CCc1cc(B2OC(C)(C)C(C)(C)O2)cc(OC)c1C#N] | 288 | 1.86 | M7 |

-continued

| # | Structure | MS (M + H)+ | t_Ret. HPLC [min] | HPLC-Method |
|---|---|---|---|---|
| K-3 | 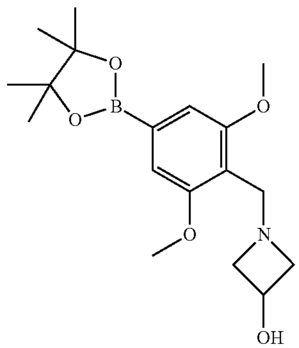 [SMILES: COc1cc(B2OC(C)(C)C(C)(C)O2)cc(OC)c1CN1CC(O)C1] | 350 | 0.544 | M2 |
| K-4 | 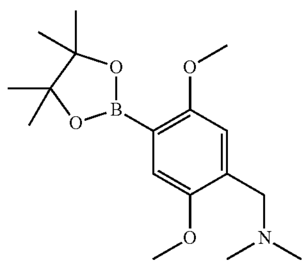 | 322 | 0.410 | M4 |
| K-5 | 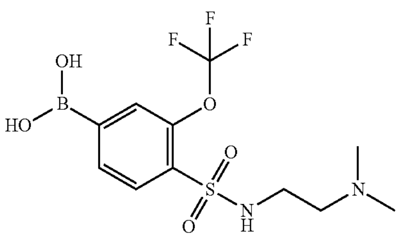 [SMILES: CN(C)CCNS(=O)(=O)c1ccc(B(O)O)cc1OC(F)(F)F] | 356 | | |
| K-6 | 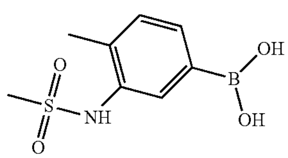 | 228 | 0.240 | M1 |
| K-7 | 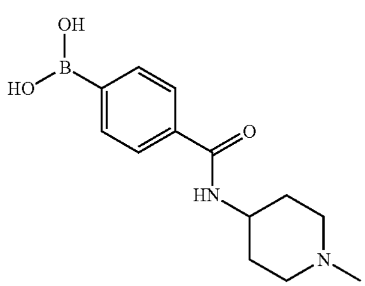 [SMILES: CN1CCC(NC(=O)c2ccc(B(O)O)cc2)CC1] | 263 | 0.000 | M1 |
| K-8 | 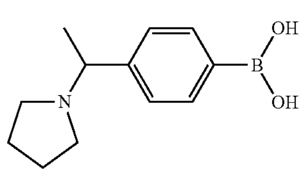 [SMILES: CC(c1ccc(B(O)O)cc1)N1CCCC1] | Commercially available | | |

-continued

| # | Structure | MS (M + H)⁺ | t$_{Ret.}$ HPLC [min] | HPLC-Method |
|---|---|---|---|---|
| K-9 | 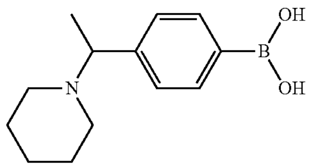 [SMILES: CC(c1ccc(B(O)O)cc1)N1CCCCC1] | Commercially available | | |
| K-10 | 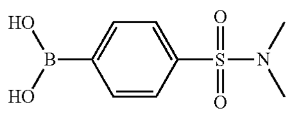 | Commercially available | | |
| K-11 | 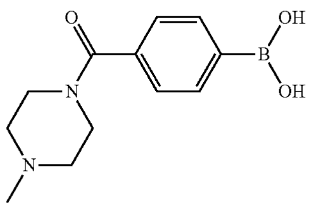 [SMILES: CN1CCN(C(=O)c2ccc(B(O)O)cc2)CC1] | Commercially available | | |
| K-12 | 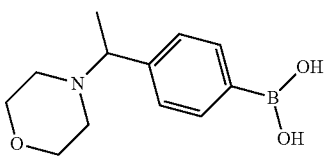 [SMILES: CC(c1ccc(B(O)O)cc1)N1CCOCC1] | Commercially available | | |
| K-13 | 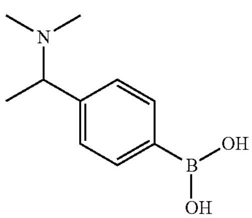 | Commercially available | | |
| K-14 | 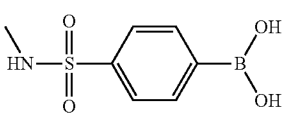 | Commercially available | | |
| K-15 | 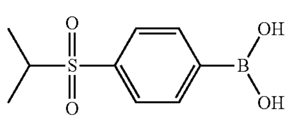 | Commercially available | | |
| K-16 | 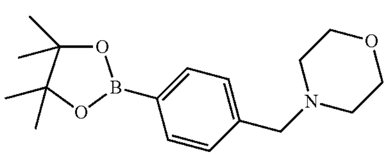 [SMILES: CC1(C)OB(c2ccc(CN3CCOCC3)cc2)OC1(C)C] | Commercially available | | |
| K-17 | 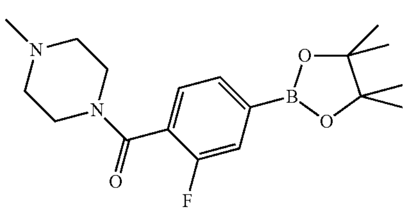 | Commercially available | | |

-continued

| # | Structure | MS (M + H)+ | t_Ret. HPLC [min] | HPLC-Method |
|---|---|---|---|---|
| K-18 | 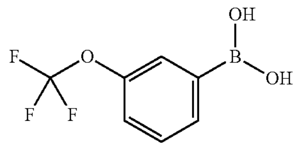 [SMILES: OB(O)c1cccc(OC(F)(F)F)c1] | Commercially available | | |
| K-19 | 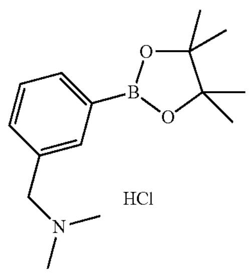 [SMILES: CN(C)Cc1cccc(B2OC(C)(C)C(C)(C)O2)c1 ; Cl] | Commercially available | | |
| K-20 | 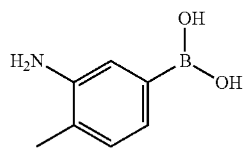 | Commercially available | | |
| K-21 | 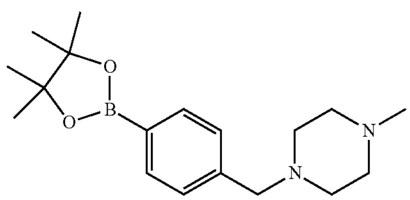 | Commercially available | | |
| K-22 | 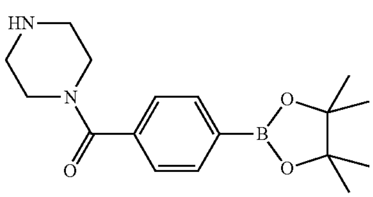 [SMILES: CC1(C)OB(c2ccc(C(=O)N3CCNCC3)cc2)OC1(C)C] | Commercially available | | |
| K-23 | 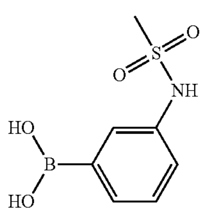 | Commercially available | | |
| K-24 | 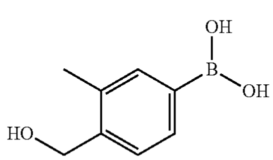 | Commercially available | | |
| K-25 | 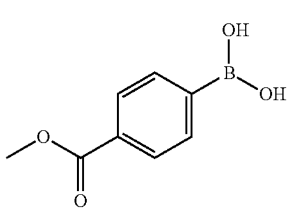 | Commercially available | | |

| # | Structure | MS (M + H)+ | $t_{Ret.}$ HPLC [min] | HPLC-Method |
|---|---|---|---|---|
| K-26 | 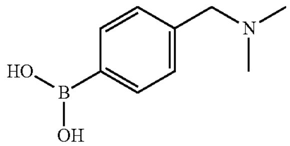 | Commercially available | | |
| K-27 | 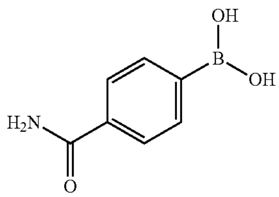 [SMILES: NC(=O)c1ccc(B(O)O)cc1] | Commercially available | | |
| K-28 | 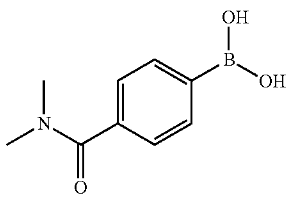 | Commercially available | | |
| K-29 | 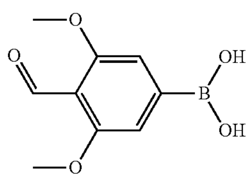 | Commercially available | | |

Biological Methods

BRD9-H3 tetra-acetylated Peptide Inhibition AlphaScreen

This assay is used to identify compounds which inhibit the interaction of the bromodomain of BRD9 with a tetra-acetylated peptide based on the sequence of histone H3 (H3 K9/14/18/23Ac (1-28)).

Reagents and Plates:

GST-Brd9:

The protein corresponding to amino acids 130-259 that contains the bromodomain of BRD9 (accession number NM_023924.4) is expressed in E. coli with an amino-terminal GST tag.

H3 K9/14/18/23Ac(1-28) Peptide:

Sequence: Biotin-ARTKQTARK(Ac)STGGK(Ac)APRK (Ac)QLATK(Ac)AARKS, MW: 3392.

AlphaScreen Beads (Perkin Elmer):

AlphaLISA Glutathione Acceptor Beads
AlphaScreen Streptavidin Donor Beads
Assay plates: Proxiplate-384 PLUS, white (PerkinElmer)

Assay Protocol:

The assay is done in a darkened room below 100 Lux.

Compounds are dispensed onto assay plates using an Access Labcyte Workstation with the Labcyte Echo 550 from a DMSO solution. For the chosen highest concentration of 100 µM, 150 nl of compound solution are transferred from a 10 mM DMSO solution. A series of 11 concentrations is transferred for each compound at which each concentration is fivefold lower than the previous one (i.e. 100 µM, 20 µM, 4 µM, 0.8 µM, etc). DMSO is added such that every well has a total of 150 nl of DMSO.

10 µl of a mix containing 6 nM GST-BRD9 protein (aa 130-259) and 18 nM biotinylated H3 K9/14/18/23Ac(1-28) peptide prepared in assay buffer (50 mM HEPES pH=7.3; 25 mM NaCl; 0.1% Tween 20; 0.1% bovine serum albumin (BSA); 2 mM dithiothreitol (DTT)) is added to 5 µl of bead mix (AlphaLISA Glutathione Acceptor Beads and AlphaScreen Streptavidin Donor Beads mixed in assay buffer at a concentration of 10 µg/mL). 15 µl of the resulting mix are added to the assay plates that contain 150 nl of the compounds. After 60 min at room temperature the signal is measured in a PerkinElmer Envision HTS Multilabel Reader using the AlphaScreen specifications from PerkinElmer.

Each plate contains negative controls where biotinylated H3 K9/14/18/23Ac(1-28) peptide and GST-BRD9 are left out and replaced by assay buffer. Negative control values are entered as low basis value when using the software Graph-Pad Prism for calculations.

Plates are kept at room temperature in a darkened incubator. Determination of IC50 values are carried out using GraphPad Prism 3.03 software (or updates thereof).

BRD9-H4 Tetraacetylated Peptide Inhibition AlphaScreen

This assay is used to identify compounds which inhibit the interaction of the bromodomain of BRD9 with a tetra-acetylated peptide based on the sequence of histone H4 (termed the "BET Bromodomain ligand" as purchased from BPS Biosciences).

Reagents and Plates:

A GST fusion protein of the bromodomain of BRD9 and an acetylated histone H4 peptide (the "BET Bromodomain Ligand" are purchased as part of the BRD9 Inhibitor Screening Assay Kit at BPS Biosciences (Cat. Number: #32519) AlphaScreen Beads (Perkin Elmer):

AlphaLISA Glutathione Acceptor Beads
AlphaScreen Streptavidin Donor Beads
Assay plates: Proxiplate-384 PLUS, white (PerkinElmer)

Assay Protocol:

The assay is done in a darkened room below 100 Lux.

Compounds are dispensed onto assay plates using an Access Labcyte Workstation with the Labcyte Echo 550 from a DMSO solution. For the chosen highest concentration of 100 µM, 150 nl of compound solution are transferred from a 10 mM DMSO solution. A series of 11 concentrations is transferred for each compound at which each concentration is five-fold lower than the previous one (i.e. 100 µM, 20 µM, 4 µM, 0.8 µM, etc). DMSO is added such that every well has a total of 150 nl of DMSO.

10 µl of a mix containing 7.5 nM GST-BRD9 and 3.75 nM of BET Bromodomain Ligand prepared in assay buffer (50 mM HEPES pH=7.3; 25 mM NaCl; 0.1% Tween 20; 0.1% bovine serum albumin (BSA); 2 mM dithiothreitol (DTT)) is added to 5 µl of bead mix (AlphaLISA Glutathione Acceptor Beads and AlphaScreen Streptavidin Donor Beads mixed in assay buffer at a concentration of 10 µg/mL). 15 µl of the resulting mix are added to the assay plates that contain 150 nl of the compounds. After 60 min at room temperature the signal is measured in a PerkinElmer Envision HTS Multi-label Reader using the AlphaScreen specifications from PerkinElmer.

Each plate contains negative controls where biotinylated BET Bromodomain Ligand and GST-BRD9 are left out and replaced by assay buffer. Negative control values are entered as low basis value when using the software GraphPad Prism for calculations. Determination of IC50 values are carried out using GraphPad Prism 3.03 software (or updates thereof).

Table summarizing the $IC_{50}$ of the compounds of the invention exemplified above

| Ex # | BRD9 - H3 assay | BRD9 - H4 assay |
|---|---|---|
| I-1 | 105 | |
| I-2 | 145 | |
| I-3 | 157 | |
| I-4 | 172 | |
| I-5 | 137 | |
| I-6 | 318 | |
| I-7 | 326 | |
| I-8 | 976 | |
| I-9 | | 172 |
| I-10 | 1075 | |
| I-11 | 1432 | |
| I-12 | 1550 | |
| I-13 | 1593 | |
| I-14 | | 109 |
| I-15 | | 279 |
| I-16 | | 568 |
| I-17 | 2540 | |
| I-18 | | 113 |
| I-19 | | 333 |
| I-20 | 50 | |
| I-21 | 1692 | |
| I-22 | 235 | |
| I-23 | | 609 |
| I-24 | | 3309 |
| I-25 | | 6580 |
| I-26 | | 2556 |
| I-27 | | 705 |
| I-28 | | 5118 |
| I-29 | | 4217 |
| I-30 | | 444 |
| I-31 | 1218 | |
| I-32 | | 2027 |
| I-33 | | 22 |
| I-34 | | 17 |
| I-35 | | 47 |
| I-36 | | 42 |
| I-37 | | 34 |
| I-38 | | 256 |
| I-39 | | 294 |
| I-40 | | 496 |
| I-41 | 179 | |
| I-42 | | 470 |
| I-43 | | 65 |
| I-44 | | 508 |
| I-45 | | 2092 |
| I-46 | 21 | |
| I-47 | 52 | |
| I-48 | 54 | |
| I-49 | 65 | |
| I-50 | 74 | |
| I-51 | 78 | |
| I-52 | 87 | |
| I-53 | 97 | |
| I-54 | 121 | |
| I-55 | 124 | |
| I-56 | 131 | |
| I-57 | 132 | |
| I-58 | 137 | |
| I-59 | 142 | |
| I-60 | 143 | |
| I-61 | 179 | |
| I-62 | 181 | |
| I-63 | 203 | |
| I-64 | 211 | |
| I-65 | 213 | |
| I-66 | 213 | |
| I-67 | 215 | |
| I-68 | 223 | |
| I-69 | | 15 |
| I-70 | 237 | |
| I-71 | 289 | |
| I-72 | 335 | |
| I-73 | 361 | |
| I-74 | 371 | |
| I-75 | 393 | |
| I-76 | 409 | |
| I-77 | 418 | |
| I-78 | | 130 |
| I-79 | | 60 |
| I-80 | 497 | |
| I-81 | 502 | |
| I-82 | 515 | |
| I-83 | 521 | |
| I-84 | 618 | |
| I-85 | 708 | |
| I-86 | 777 | |
| I-87 | 849 | |
| I-88 | | 78 |
| I-89 | | 70 |
| I-90 | 950 | |
| I-91 | | 128 |
| I-92 | 1039 | |
| I-93 | | 112 |
| I-94 | | 334 |
| I-95 | 1212 | |
| I-96 | 1252 | |
| I-97 | | 267 |
| I-98 | 2364 | |
| I-99 | | 5135 |
| I-100 | | 50 |
| I-101 | | 503 |
| I-102 | 37 | |
| I-103 | 37 | |
| I-104 | 39 | |
| I-105 | 158 | |
| I-106 | 103 | |
| I-107 | 137 | |

| Ex # | BRD9 - H3 assay | BRD9 - H4 assay |
|---|---|---|
| I-108 | 152 | |
| I-109 | 193 | |
| I-110 | 197 | |
| I-111 | 226 | |
| I-112 | 320 | |
| I-113 | 348 | |
| I-114 | 507 | |
| I-115 | 740 | |
| I-116 | 744 | |
| I-117 | 1404 | |
| I-118 | 10 | |
| I-119 | 55 | |
| I-120 | 58 | |
| I-121 | 163 | |
| I-122 | 116 | |
| I-123 | 118 | |
| I-124 | 144 | |
| I-125 | 166 | |
| I-126 | 167 | |
| I-127 | 198 | |
| I-128 | 222 | |
| I-129 | 284 | |
| I-130 | 302 | |
| I-131 | 303 | |
| I-132 | 322 | |
| I-133 | 387 | |
| I-134 | 394 | |
| I-135 | 851 | |
| I-136 | 1923 | |
| I-137 | 834 | |
| I-138 | 1259 | |
| I-139 | 1382 | |
| I-140 | 880 | |
| I-141 | 1862 | |
| I-142 | 1959 | |
| I-143 | 9 | |
| I-144 | 26 | |
| I-145 | 32 | |
| I-146 | 33 | |
| I-147 | 126 | |
| I-148 | 144 | |
| I-149 | 160 | |
| I-150 | 298 | |
| I-151 | 26 | |
| I-152 | 145 | |
| I-153 | 29 | |
| I-154 | 38 | |
| I-155 | 128 | |
| I-156 | 1775 | |
| I-157 | 89 | |
| I-158 | | 19 |
| I-159 | 167 | |
| I-160 | | 33 |
| I-161 | | 32 |
| I-162 | | 33 |
| I-163 | 550 | |
| I-164 | 64 | |
| I-165 | 79 | |
| I-166 | 230 | |
| I-167 | 41 | |
| I-168 | 40 | |
| I-169 | | 29 |
| I-170 | | 29 |
| I-171 | | 103 |
| I-172 | | 294 |
| I-173 | | 151 |
| I-174 | | 106 |
| I-175 | | 135 |
| I-176 | | 204 |
| I-177 | 1325 | |
| I-178 | 38 | |
| I-179 | 187 | |
| I-180 | 870 | |
| I-181 | 1002 | |
| I-182 | 1050 | |
| I-183 | 1147 | |
| I-184 | 1324 | |
| I-185 | 1550 | |
| I-186 | 967 | |
| I-187 | 4302 | |
| I-188 | | 270 |
| I-189 | | 23 |
| I-190 | | 21 |
| I-191 | | 3 |
| I-192 | | 33 |
| I-193 | 510 | |
| I-194 | 458 | |
| I-195 | 369 | |
| I-196 | 1009 | |
| I-197 | 468 | |
| I-198 | 71 | |
| I-199 | 55 | |
| I-200 | 132 | |
| I-201 | 163 | |
| I-202 | 268 | |
| I-203 | 704 | |
| I-204 | 231 | |
| I-205 | 69 | |
| I-206 | 479 | |
| I-207 | 93 | |
| I-208 | 114 | |
| I-209 | 218 | |
| I-210 | 302 | |
| I-211 | 468 | |
| I-212 | 750 | |
| I-213 | 5316 | |
| I-214 | 3211 | |
| I-215 | 9203 | |
| II-1 | 8 | |
| II-2 | 29 | |
| II-3 | 134 | |
| II-4 | | 86 |
| II-5 | 916 | |
| II-6 | 26 | |
| II-7 | 75 | |
| II-8 | 953 | |
| II-9 | 1404 | |
| II-10 | 37 | |
| II-11 | 42 | |
| II-12 | 344 | |
| II-13 | 589 | |
| II-14 | 1382 | |
| II-15 | | 398 |
| II-16 | | 983 |
| II-17 | 16317 | |
| II-18 | | 984 |
| II-19 | 31 | |
| II-20 | 178 | |
| II-21 | 250 | |
| II-22 | 2138 | |
| II-23 | 128 | |
| II-24 | 609 | |
| II-25 | 154 | |
| II-26 | 630 | |
| II-27 | | 1165 |
| II-28 | | 923 |
| II-29 | | 239 |
| II-30 | 5 | |
| II-31 | 11 | |
| II-32 | 24 | |
| II-33 | 23 | |
| II-34 | 8 | |
| II-35 | | 293 |
| II-36 | | 5247 |
| II-37 | | 2690 |
| II-38 | | 8422 |
| II-39 | | 7826 |
| II-40 | | 5439 |
| II-41 | 126 | |
| II-42 | 439 | |
| II-43 | 890 | |
| II-44 | 917 | |
| II-45 | 981 | |
| II-46 | 1006 | |

| Ex # | BRD9 - H3 assay | BRD9 - H4 assay |
| --- | --- | --- |
| II-47 | 1189 | |
| II-48 | 1549 | |
| II-49 | 3142 | |
| II-50 | 4852 | |
| II-51 | 5274 | |
| III-1 | | 645 |
| III-2 | 39 | |
| III-3 | 46 | |
| III-4 | 62 | |
| III-5 | 68 | |
| III-6 | 81 | |
| III-7 | 95 | |
| III-8 | 340 | |
| III-9 | 391 | |
| III-10 | 487 | |

On the basis of their biological properties the compounds of general formula (1) according to the invention, their tautomers, racemates, enantiomers, diastereomers, mixtures thereof and the salts of all the above-mentioned forms are suitable for treating diseases characterised by virus infection, inflammatory diseases and abnormal cell proliferation, such as cancer.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma (MM)), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (A ML); chronic leukaemias such as chronic lymphatic leukaemia (CLL), chronic myeloid leukaemia (C ML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are hematopoietic malignancies (including but not limited to A ML, MM), as well as solid tumors including but not limited to lung, liver, colon, brain, thyroid, pancreas, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992 (afatinib), BIBF 1120 (Vargatef™), bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, mlN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI1166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, Volasertib (or other polo-like kinae inhibitors), xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c, i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

A)

| A) Tablets | per tablet |
|---|---|
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| B) Tablets | per tablet |
|---|---|
| active substance according to formula (I) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (I) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. Compound

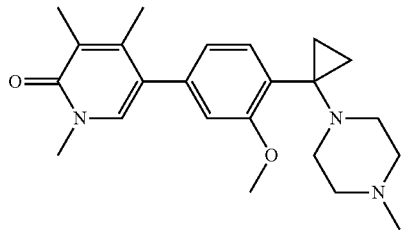

or its salts.

2. A pharmaceutical preparation containing as active substance the compound of claim 1 or a pharmaceutically acceptable salt thereof—optionally in combination with conventional excipients and/or carriers.

3. Compound

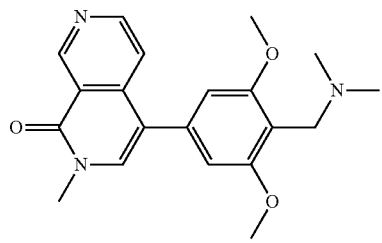 [SMILES: COc1cc(-c2cn(C)c(=O)c3cnccc23)cc(OC)c1CN(C)C]

or its salts.

4. Compound

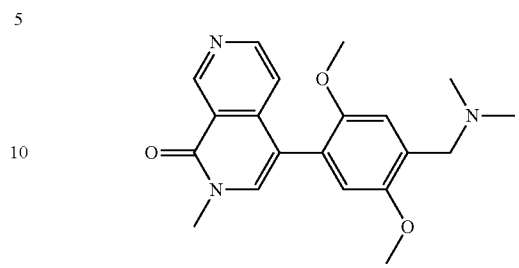

or its salts.

5. A pharmaceutical preparation containing as active substance the compound of claim 3 or a pharmaceutically acceptable salt thereof—optionally in combination with conventional excipients and/or carriers.

6. A pharmaceutical preparation containing as active substance the compound of claim 4 or a pharmaceutically acceptable salt thereof—optionally in combination with conventional excipients and/or carriers.

* * * * *